United States Patent
Ecker et al.

(10) Patent No.: US 10,913,952 B2
(45) Date of Patent: Feb. 9, 2021

(54) ENVIRONMENTAL STRESS RESPONSE TRANSCRIPTIONAL REGULATORY NETWORK

(71) Applicant: Salk Institute for Biological Studies, La Jolla, CA (US)

(72) Inventors: Joseph R. Ecker, Carlsbad, CA (US); Liang Song, La Jolla, CA (US)

(73) Assignee: Salk Institute for Biological Studies, La Jolla, CA (US)

( * ) Notice: Subject to any disclaimer, the term of this patent is extended or adjusted under 35 U.S.C. 154(b) by 180 days.

(21) Appl. No.: 15/795,104

(22) Filed: Oct. 26, 2017

(65) Prior Publication Data

US 2018/0112228 A1    Apr. 26, 2018

Related U.S. Application Data

(60) Provisional application No. 62/413,349, filed on Oct. 26, 2016.

(51) Int. Cl.
*C12N 15/82* (2006.01)

(52) U.S. Cl.
CPC ..... *C12N 15/8218* (2013.01); *C12N 15/8213* (2013.01); *C12N 15/8243* (2013.01); *C12N 15/8245* (2013.01); *C12N 15/8247* (2013.01); *C12N 15/8251* (2013.01); *C12N 15/8261* (2013.01); *C12N 15/8271* (2013.01); *C12N 15/8273* (2013.01); *C12N 15/8274* (2013.01); *C12N 15/8279* (2013.01); *C12N 15/8281* (2013.01); *C12N 15/8282* (2013.01); *C12N 15/8283* (2013.01); *C12N 15/8285* (2013.01); *C12N 15/8286* (2013.01); *C12N 15/8289* (2013.01); *C12N 15/8293* (2013.01)

(58) Field of Classification Search
None
See application file for complete search history.

(56) References Cited

U.S. PATENT DOCUMENTS

| | | | | |
|---|---|---|---|---|
| 2003/0236208 A1* | 12/2003 | Kmiec | ................ | C12N 15/102 514/44 R |
| 2006/0150283 A1* | 7/2006 | Alexandrov | ......... | C07K 14/415 800/288 |
| 2007/0039067 A1* | 2/2007 | Feldmann | ............ | C07K 14/415 800/278 |

OTHER PUBLICATIONS

GenBank Accession XM 013853315, dated Aug. 31, 2015. (Year: 2015).*
Kodahl, et al. (Plant Science 252 (2016): 22-29) . (Year: 2016).*
Distelfeld et al. (Plant Mol Biol (2012) 78:515-524). (Year: 2012).*
GenBank Accession BT025864, dated Jun. 7, 2006. (Year: 2006).*
Liu et al. (Nature biotechnology 21.10 (2003): 1222). (Year: 2003).*
Fujita et al., "Three SnRK2 Protein Kinases are the Main Positive Regulators of Abscisic Acid Signaling in Response to Water Stress in *Arabidopsis*," *Plant Cell Physiol.* 50: 2123-2132, 2009.
Tian et al., "A novel family of transcription factors conserved in angiosperms is required for ABA signalling," *Plant Cell Environ.* 40:2958-2971, 2017.
Alonso et al., "Genome-Wide Insertional Mutagenesis of *Arabidopsis thaliana*," *Science* 301:653-657, 2003.
O'Malley et al., "An adapter ligation-mediated PCR method for high-throughput mapping of T-DNA inserts in the *Arabidopsis* genome," *Nat Protoc.* 2:2910-2917, 2007.
Song et al., "A transcription factor hierarchy defines an environmental stress response network," *Science*, vol. 354, Issue 6312, Nov. 4, 2016.

* cited by examiner

*Primary Examiner* — Charles Logsdon
(74) *Attorney, Agent, or Firm* — Klarquist Sparkman, LLP

(57) ABSTRACT

This disclosure provides methods of downregulating or eliminating gene expression of one or more Dynamic Influencer of Gene expression (DIG) and/or one or more DIG-like (DIL) sequences in plants and plant cells, as well as constructs and compositions useful in such methods. Such recombinant plants can have decreased abscisic acid (ABA) sensitivity, decreased salt sensitivity, or both.

26 Claims, 40 Drawing Sheets

Specification includes a Sequence Listing.

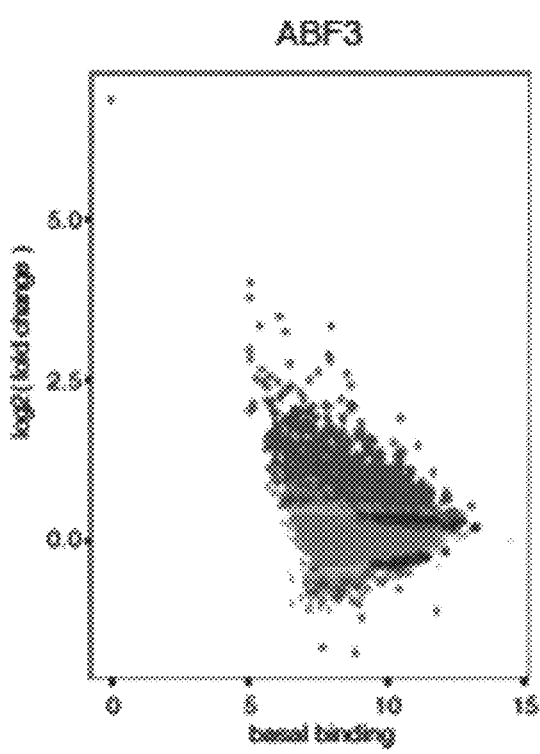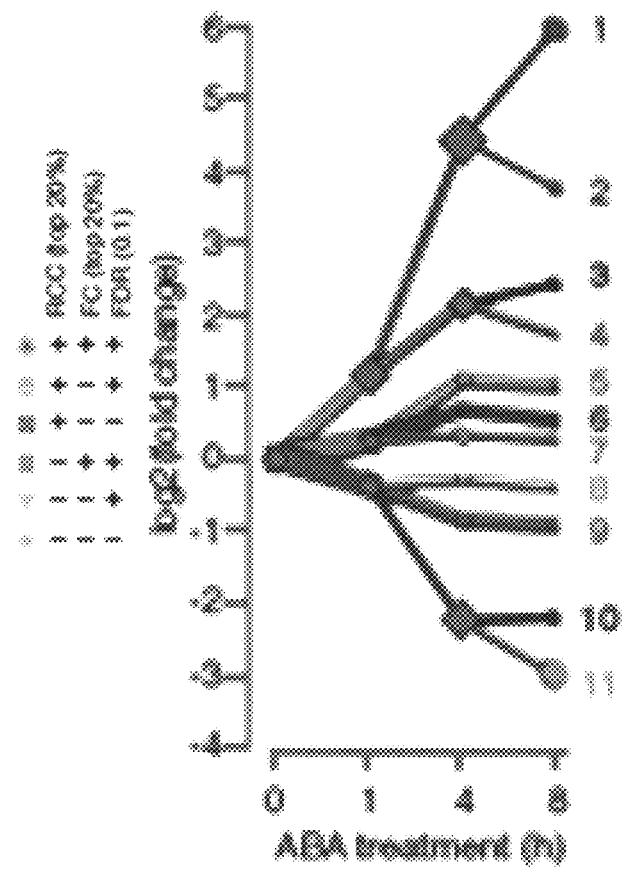
FIG. 5B
FIG. 5C

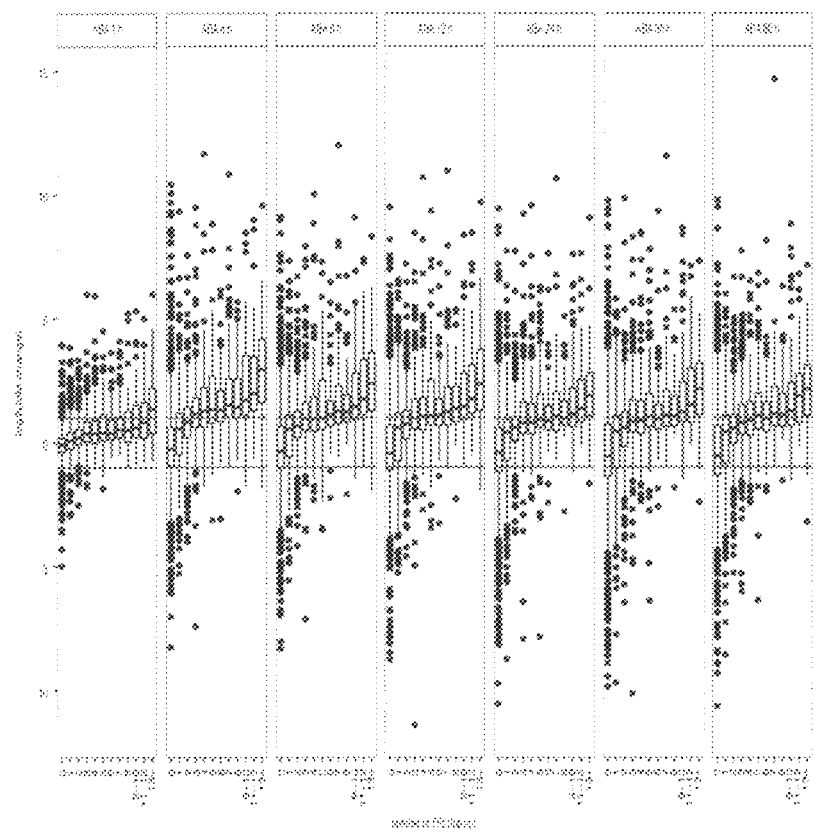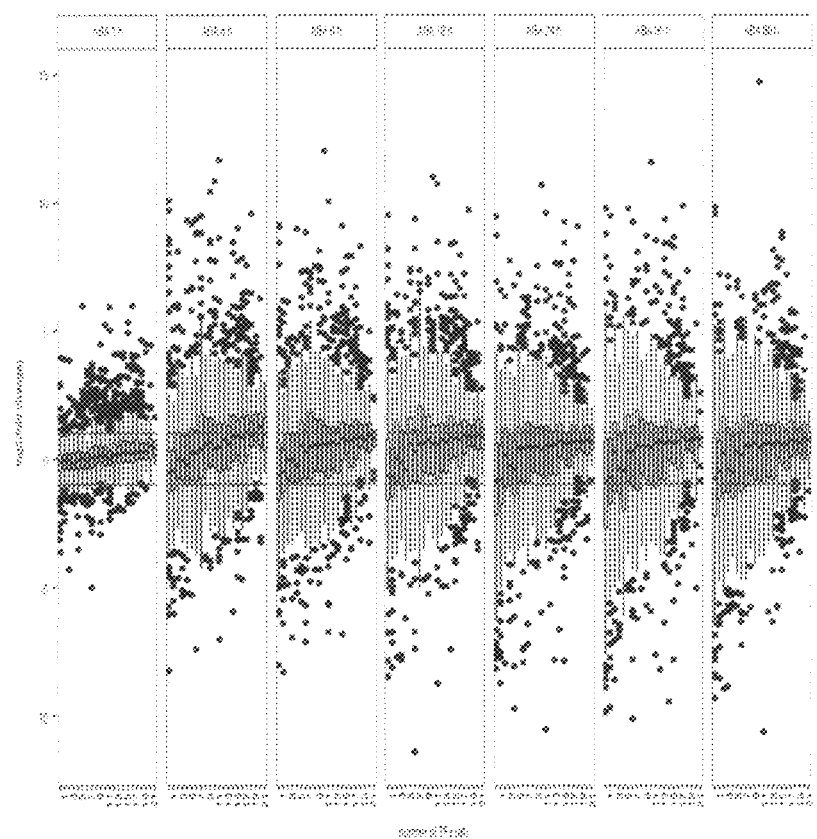
FIG. 8

FIG. 15A *RGL3*
FIG. 15B *ACS2*
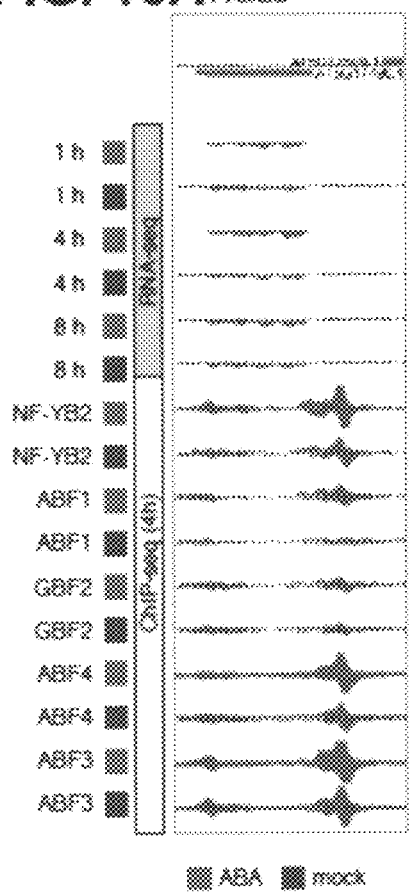
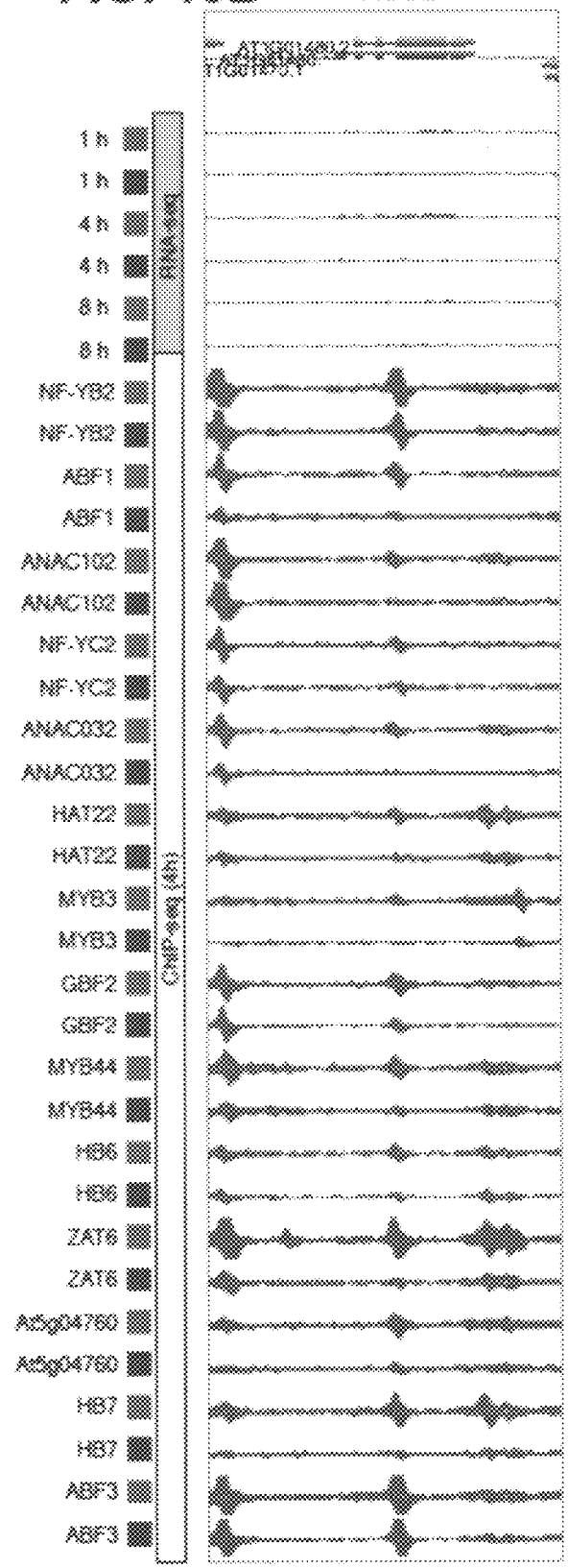

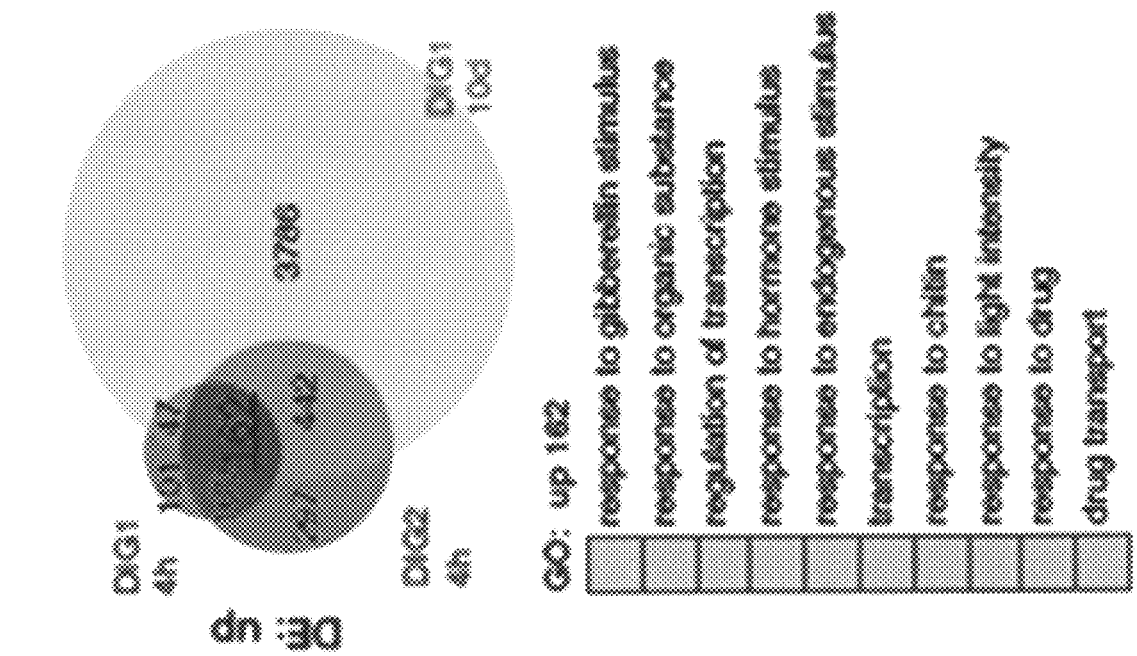
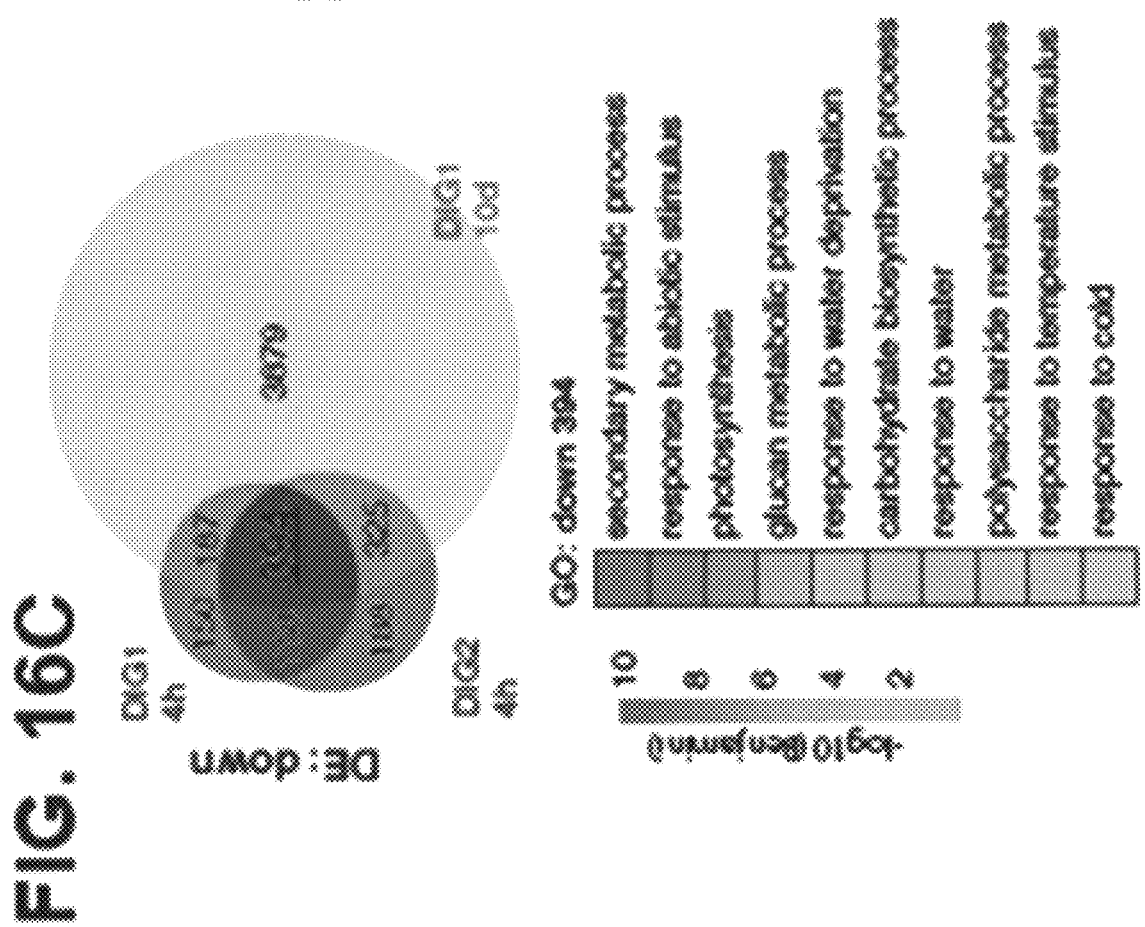
FIG. 16C

FIG. 20

ENVIRONMENTAL STRESS RESPONSE TRANSCRIPTIONAL REGULATORY NETWORK

CROSS-REFERENCE TO RELATED APPLICATION

This application claims priority to U.S. Provisional Application No. 62/413,349 filed Oct. 26, 2016, herein incorporated by reference in its entirety.

ACKNOWLEDGMENT OF GOVERNMENT SUPPORT

This invention was made with government support under MCB1024999 awarded by NSF. The government has certain rights in the invention.

FIELD

This disclosure relates to methods of downregulating or eliminating gene expression of one or more Dynamic Influencer of Gene expression (DIG) sequences and/or one or more DIG-like (DIL) sequences in plants, as well as constructs and compositions useful in such methods.

BACKGROUND

Transcription is a key step in gene expression. There have been concerted efforts to map functional elements in human, fly and worm (1-3), including a large number of cis-regulatory elements identified by profiling transcription factor (TF) binding using chromatin immunoprecipitation sequencing (ChIP-seq). One area that remains largely unexplored is how stimulus modulates TF binding and subsequent transcriptome changes. Furthermore, compared to studies in animals, very few comprehensive in vivo TF binding datasets are available for the Plantae kingdom.

To address this knowledge gap, the inventors generated more than 100 ChIP-seq and time-series RNA-seq datasets to characterize a stimulus-influenced transcriptional network and map functional cis-regulatory elements in the reference plant Arabidopsis thaliana, focused on the phytohormone abscisic acid (ABA). The response to ABA provides a model for the examination of stimulus-influenced transcriptional regulation. ABA triggers differential expression (DE) of thousands of genes including many TFs, providing a robust response that enables modeling of complex gene regulatory networks. Moreover, ABA's role in a variety of plant processes is of significant importance to both fundamental biology and agriculture (4, 5).

ABA plays a pivotal role in optimizing water use in plants and is required for both seed development and responses to multiple environmental stresses such as drought and high salinity. In Arabidopsis thaliana, ABA is recognized by the PYR/PYL/RCAR receptor proteins (6-8). Binding of ABA triggers the interaction of PYR/PYL/RCARs with group A PP2C protein phosphatases and de-represses the SnRK2 protein kinases (7, 9). SnRK2s subsequently activate substrates such as transcription factors (TFs) and elicit ABA responses (10, 11). While many TFs are contribute to the ABA responses (8), little is known about their target genes and the way these targets are combinatorially regulated. In vitro approaches including the recently described Arabidopsis cistrome dataset have enabled identification of DNA motifs and inference of the associated TFs (13-17). However, accurate predictions are still challenging due to many large, multi-member TF families. Furthermore, it is difficult to establish a direct link between TF binding and transcriptome changes or to address the dynamics of TF regulation through in vitro assays. Therefore, ChIP-seq was used to identify TF targets, examine stimulus-influenced TF binding dynamics and link them to subsequent transcriptome changes.

SUMMARY

Environmental stresses are universally encountered by microbes, plants and animals. Yet systematic studies of stress-responsive transcription factor (TF) networks in multi-cellular organisms have been limited. The phytohormone abscisic acid (ABA) influences the expression of thousands of genes, allowing us to characterize complex stress-responsive regulatory networks. Using chromatin immunoprecipitation sequencing, the inventors identified genome-wide targets of 21 ABA-related TFs to construct a comprehensive regulatory network in Arabidopsis thaliana. Determinants of dynamic TF binding and a hierarchy among TFs were defined, illuminating the relationship between differential gene expression patterns and ABA pathway feedback regulation. By extrapolating regulatory characteristics of observed canonical ABA pathway components, a new family of transcriptional regulators modulating ABA and salt responsiveness was identified, and their utility to modulate plant resilience to osmotic stress demonstrated.

Based on these observations, methods of decreasing abscisic acid (ABA) sensitivity, decreasing salt sensitivity, or both, in a plant cell or plant, are provided. For example, such phenotypes can be obtained by decreasing or eliminating expression of 1, 2, 3, 4, 5 or 6 of DIG1, DIG2, DIL1, DIL2, DIL3, and DIL4, such as decreasing or eliminating expression of a nucleic acid molecule having at least 80%, at least 85%, at least 90%, at least 95%, at least 96%, at least 97%, at least 98%, at least 99%, or 100% sequence identity to 1, 2, 3, 4, 5 or 6 of SEQ ID NO: 1, 3, 5, 7, 9 or 11, or decreasing or eliminating expression of a protein having at least 80%, at least 85%, at least 90%, at least 95%, at least 96%, at least 97%, at least 98%, at least 99%, or 100% sequence identity to 1, 2, 3, 4, 5 or 6 of SEQ ID NO: 2, 4, 6, 8, 10 or 12. Also provided are nucleic acid molecules that can be used in such methods.

In one example, an inhibitory RNA (RNAi) molecule specific for DIG1 (SEQ ID NO: 1), DIG2 (SEQ ID NO: 3), DIL1 (SEQ ID NO: 5), DIL2 (SEQ ID NO: 7), DIL3 (SEQ ID NO: 9), and/or DIL4 (SEQ ID NO: 11) is provided which can be used in these methods. Examples of RNAi molecules include but are not limited to an antisense molecule, small inhibitory RNA (siRNA), trans-acting small interfering RNA (tasiRNA), microRNA (miRNA), or an artificial micro RNA (amiRNA). Specific exemplary amiRNA sequences that can be used include the following 21-nt sequences (based on the prediction of the WMD3 server, Ossowski et al., Plant J. 53(4):674-90, 2008): TCACACAT-CACACGGCGCCGA (SEQ ID NO: 33) for AT3G27250, AT5G40790, AT5G40800, AT5G63350; and TGA-TATAAAACCAGGACACGT (SEQ ID NO: 34) for AT3G48510, AT5G40800, AT5G50360, AT5G63350.

In one example, a guide nucleic acid (e.g., guide RNA) specific for DIG1 (SEQ ID NO: 1), DIG2 (SEQ ID NO: 3), DIL1 (SEQ ID NO: 5), DIL2 (SEQ ID NO: 7), DIL3 (SEQ ID NO: 9), and/or DIL4 (SEQ ID NO: 11) is provided which can be used in these methods. Exemplary guide RNA sequences for each of the six genes are as follows (three gRNAs for each gene) AT3G27250 (DIL4): ATC- CAACGGCGAGTACTCAC (SEQ ID NO: 13); ATGGAT-CAAGATGACTGGTT (SEQ ID NO: 14); and AACTT-TATCCTGCGCCTTAC (SEQ ID NO: 15); AT3G48510 (DIG1): CTATCGCCGCTAGTTATCTC (SEQ ID NO: 16); TAATGACGCGTATCGGAAGA (SEQ ID NO: 17); and ATTAGCACTGCCGTGAACGA (SEQ ID NO: 18); AT5G40790 (DIL2): TGCGGTGACGTGCAGGGTTA (SEQ ID NO: 19); CCATGCGGCCTAGCTGCTCC (SEQ ID NO: 20); and TTATAAGCAAGATAATGCAA (SEQ ID NO: 21); AT5G40800 (DIL3): GACGACTACTGGT-CAACCAT (SEQ ID NO: 22); CTACTGCAGCTT-TAACTCTT (SEQ ID NO: 23); and TTT-TACGTGTAAGGTGAGAA (SEQ ID NO: 24); AT5G50360 (DIG2): TGAGTGACGGTGGCTTTGCG (SEQ ID NO: 25); TAGGGTGTACGGACGAGGAG (SEQ ID NO: 26); and GTTGAAGGCTAAGGCGGCGC (SEQ ID NO: 27); AT5G63350 (DIL1): GATAT-CACGAAGGACGGTGG (SEQ ID NO: 28); ACGTGT-CAAGATCGAGAAAG (SEQ ID NO: 29); and CCACCGTCGCTGGCCGGTTT (SEQ ID NO: 30). In one example, the guide RNA used to decrease expression of DItL1 is GCTCCTAAACCGGCCAGCGA (SEQ ID NO: 57) and GTTCCGGTGGGAACTCCCGA (SEQ ID NO: 58).

In one example, a transfer DNA (T-DNA) specific for DIG1 (SEQ ID NO: 1), DIG2 (SEQ ID NO: 3), DIL1 (SEQ ID NO: 5), DIL2 (SEQ ID NO: 7), DIL3 (SEQ ID NO: 9), and/or DIL4 (SEQ ID NO: 11) is provided which can be used in these methods. Exemplary T-DNA junction sequences that can be for dig1: SALK_128578; dig2: SALKseq_057406.2; and dil1: SALK_130501 are provided in SEQ ID NOS: 50-53.

The RNAi, guide nucleic acid, and T-DNA can be operably linked to a promoter (e.g., constitutive promoter, an inducible promoter, a tissue specific promoter, a ubiquitous promoter or a combination thereof), and can be part of an expression vector. In one example, a guide nucleic acid molecule is expressed via a DNA polymerase III promoter.

Transgenic plant cells that include the RNAi, guide nucleic acid, and/or T-DNA specific for 1, 2, 3, 4, 5 or 6 of DIG1 (SEQ ID NO: 1), DIG2 (SEQ ID NO: 3), DIL1 (SEQ ID NO: 5), DIL2 (SEQ ID NO: 7), DIL3 (SEQ ID NO: 9), and/or DIL4 (SEQ ID NO: 11 (which can be part of a vector) are provided. In some examples, such plant cells have decreased expression of one or more of DIG1, DIG2, DIL1, DIL2, DIL3, and DIL4. Such transgenic plant cells can have decreased abscisic acid (ABA) sensitivity, decreased salt sensitivity, or both. In some examples, the transgenic plant cell further includes an exogenous nucleic acid molecule (e.g., transgene) that confers a desired trait into the plant cell. In some examples, the plant cell is a corn, wheat, soybean, canola, rice, or cotton plant cell.

Also provided are transgenic plants that include such transgenic cells. For example, the transgenic cells can be grown into a transgenic plant. Such transgenic plants can have decreased ABA sensitivity, decreased salt sensitivity, or both. In some examples, the transgenic plant has accelerated cotyledon greening and increased lateral root growth. In some examples, the transgenic plant further includes an exogenous nucleic acid molecule (e.g., transgene) that confers a desired trait into the plant, such as one or more of herbicide tolerance, drought tolerance, heat tolerance, low or high soil pH level tolerance, salt tolerance, resistance to an insect, resistance to a bacterial disease, resistance to a viral disease, resistance to a fungal disease, resistance to a nematode, resistance to a pest, male sterility, site-specific recombination; abiotic stress tolerance, modified phosphorus characteristics, modified antioxidant characteristics; modified essential seed amino acid characteristics, decreased phytate, modified fatty acid metabolism, and modified carbohydrate metabolism.

Also provided are methods of inhibiting expression and/or activity of 1, 2, 3, 4, 5 or 6 of DIG1, DIG2, DIL1, DIL2, DIL3, and DIL4 in a plant cell. Such methods can include introducing into the plant cell (e.g., by transformation) an RNAi, guide nucleic acid, and/or T-DNA specific for 1, 2, 3, 4, 5 or 6 of DIG1 (SEQ ID NO: 1), DIG2 (SEQ ID NO: 3), DIL1 (SEQ ID NO: 5), DIL2 (SEQ ID NO: 7), DIL3 (SEQ ID NO: 9), and/or DIL4 (SEQ ID NO: 11) (which can be part of a vector). The RNAi, guide nucleic acid, T-DNA, or expression vector, is expressed by the cell, thereby inhibiting one or more of DIG1, DIG2, DIL1, DIL2, DIL3, and DIL4 in the plant cell.

In one example, the method of inhibiting expression and/or activity of 1, 2, 3, 4, 5 or 6 of DIG1, DIG2, DIL1, DIL2, DIL3, and DIL4 includes introducing one or more guide nucleic acids specific for 1, 2, 3, 4, 5 or 6 of DIG1 (SEQ ID NO: 1), DIG2 (SEQ ID NO: 3), DIL1 (SEQ ID NO: 5), DIL2 (SEQ ID NO: 7), DIL3 (SEQ ID NO: 9), and/or DIL4 (SEQ ID NO: 11) and introducing a Cas9 protein or a Cas9 encoding nucleic acid into the cell, thereby inhibiting one or more 1, 2, 3, 4, 5 or 6 of DIG1, DIG2, DIL1, DIL2, DIL3, and DIL in the plant cell.

The foregoing and other objects and features of the disclosure will become more apparent from the following detailed description, which proceeds with reference to the accompanying figures.

BRIEF DESCRIPTION OF THE DRAWINGS

FIGS. 5A-5F. Dynamic TF binding triggered by ABA treatment correlates with gene function and expression. (A) Genes targeted by higher number of TFs with dynamic binding events (x-axis) have higher percentage overlap (y-axis) with genes annotated with ABA and ABA-related GO terms, but not with GO terms specific to other hormones. This positive correlation is stronger for target genes associated with stronger dynamics (different color lines). (B) Hormone-dependent, locus-specific TF binding dynamics vary greatly across the genome. Log 2 (fold change) of TF binding upon ABA treatment (y-axis) was plotted against basal binding measured as log 2 (normalized read counts) under mock treatment (x-axis). Peaks were classified by three criteria: read count change (RCC, within top 20%), fold change (FC, within top 20%), and DiffBind FDR (less than 0.1). Peaks satisfying all three criteria were designated as top dynamic (+++) and those failing all three were designated as static (---). The remaining peaks were designated as moderately dynamic. (C) DREM analysis shows 11 paths of DE genes after 8 hours of ABA treatment. (D) Each DREM path is enriched for specific GO terms. (E) Level of DE is correlated with multi-TF dynamic binding. (F) Ridge regression model for differential expression at 4 hour using binding strength in both ABA- and mock-treated condition includes contribution from multiple TF in both conditions. Regression coefficients are plotted as relative importance of the binding features.

FIG. 8. "Top up" binding by TFs 4 hours post ABA dose indicates DE of target genes across multiple time points. Log 2(fold change) of DE genes plotted against count of targeting TFs through "top up" binding (upper panel) or "all" binding (lower panel).

FIGS. 15A-15B. ABA network analysis reveals mechanisms of hormone crosstalk. (A-B) A master regulator of gibberellin response (A) and a biosynthesis gene of the ethylene pathway (B) are DEed by ABA treatment. Genome browser shots show TFs targeting via "top up" binding. Dynamic binding is mainly contributed by the bZIP and NF-Y factors to the promoter of RGL3, and by a diverse family of TFs to the gene body of ACS2.

FIGS. 16A-16I. Network analysis identifies new transcriptional regulators of ABA response. (A) Expression and functional composition of DE grouped by the number of targeting TFs through "top up" binding. Number of genes in each bin is shown in black. The bins to which the DIG/DIL genes belong are indicated on the right, with number of targeting TFs shown in parentheses. (B) DIG/DILs are regulated by multiple ABA-responsive TFs. Left panel: a phylogram of *Arabidopsis* DIG/DIL proteins. Right panel: TFs targeting the DIG/DIL genes. (C) DEX-induction of DIGs results in DE of stress- and water-related genes. Upper panels: DE genes by DIGs after indicated period of DEX treatment. Lower panels: top GO terms enriched in DIG DE genes. (D) Confocal imaging of 9-day-old DEX-treated transgenic seedlings shows DIG1 is nuclear localized. (E-F) Metagene profiles (E) and heatmaps (F) of normalized ChIP-seq read counts surrounding DIG DE genes. Down-regulated genes are often associated with strong DIG binding in their promoters. (G) Empirical cumulative distributions of −log 10(p-value) of ChIP-seq peaks of DIG1 show it bound more strongly to DIG down-regulated genes than to up-regulated or non-DE genes. (H) A CCAAT(n)$_8$ ABRE motif is strongly enriched near DIG1 binding sites residing within 1 kb of DIG down-regulated genes. Either a weaker motif or no similar motif is enriched in the corresponding regions of non-DE genes or DIG up-regulated genes. (I) Induction of DIGs results in DE of ABA- and developmental-related TFs.

FIG. 20. Epitope tags of the ChIPped TFs. Nucleotide sequences of 3×FLAG-YPet (SEQ ID NO: 55) for N-terminus tagging and YPet-6×His-3×FLAG (SEQ ID NO: 56) for C-terminus tagging were colored by the indicated features.

SEQUENCE LISTING

Figure 1A:
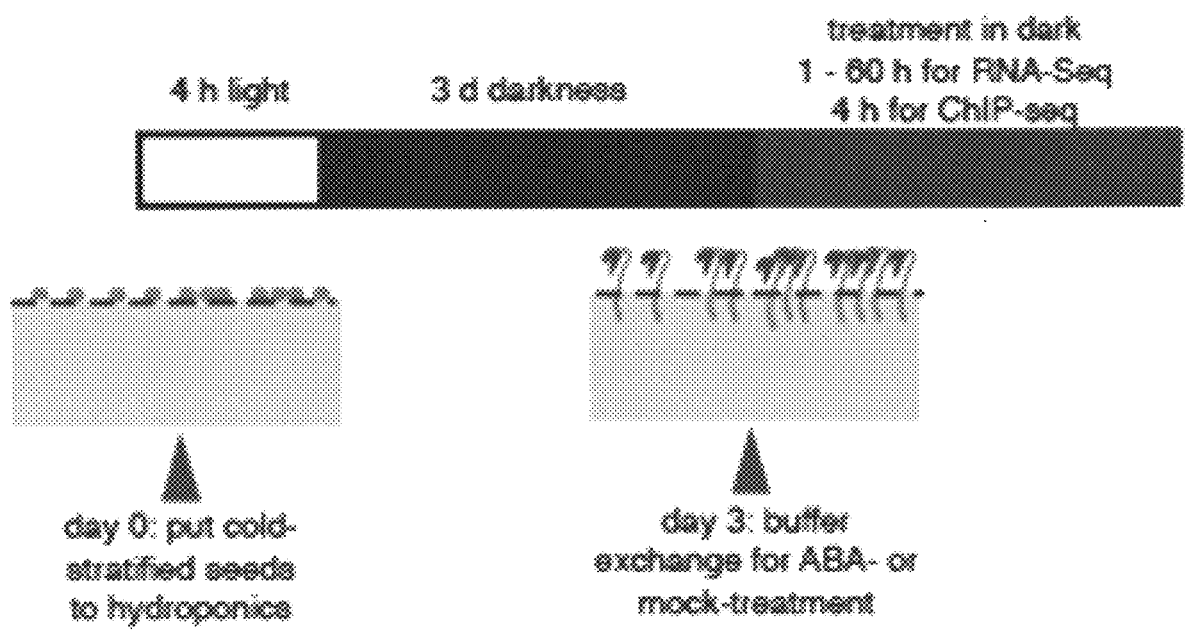
FIGS. 1A-1E. TF identity and hormone treatment determine genome-wide binding profiles. (A) Growing *Arabidopsis thaliana* in hydroponics allows convenient buffer exchange for hormone treatment. (B) DREM reconstructed RNA expression paths 60 hours post ABA exposure. Each path corresponds to a set of genes that are co-expressed. Split nodes (green diamonds) represent a temporal event where a group of genes co-expressed up to that point diverge in expression, most likely due to regulatory events. Most splits are observed up to and including the 4 h time point, indicating that the majority of regulatory events occur at the first 4 hours. (C) The number of ChIP-seq peaks varies greatly between TFs and treatment conditions. (D) ABA mediated differential gene expression and altered dynamics of TF binding as exemplified by CYP707A1 and HAI2 genes. (E) Comparison of binding correlations based on normalized ChIP-seq read counts near binding sites shows that TFs from same family often have similar binding profiles. TF-TF interaction (bZIPs and NF-Y, black dashed box) and hormone treatment (RD26 and ANAC032, dotted boxes A and M for ABA- and mock-treatment) also contribute to binding profile similarities between TFs.

The nucleic acid sequences listed below are shown using standard letter abbreviations for nucleotide bases, as defined in 37 C.F.R. § 1.822. Only one strand of each nucleic acid sequence is shown, but the complementary strand is understood as included in embodiments where it would be appropriate. The sequence listing generated on Oct. 26, 2017, 112 kb, and filed herewith, is incorporated by reference. In the accompanying sequence listing:

SEQ ID NOS: 1 and 2: DIG1 (At3g48510.1) nucleic acid and protein sequence, respectively.

SEQ ID NOS: 3 and 4: DIG2 (At5g50360.1) nucleic acid and protein sequence, respectively.

SEQ ID NOS: 5 and 6: DIL1 (At5g63350.1) nucleic acid and protein sequence, respectively.

SEQ ID NOS: 7 and 8: DIL2 (At5g40790.1) nucleic acid and protein sequence, respectively.

SEQ ID NOS: 9 and 10: DIL3 (At5g40800.1) nucleic acid and protein sequence, respectively.

SEQ ID NOS: 11 and 12: DIL4 (At3g27250.1) nucleic acid and protein sequence, respectively.

SEQ ID NOS: 13-15 are exemplary guide RNAs specific for DIL4.

SEQ ID NOS: 16-18 are exemplary guide RNAs specific for DIG1.

SEQ ID NOS: 19-21 are exemplary guide RNAs specific for DIL2.

SEQ ID NOS: 22-24 are exemplary guide RNAs specific for DIL3.

SEQ ID NOS: 25-27 are exemplary guide RNAs specific for DIG2.

SEQ ID NOS: 28-30 are exemplary guide RNAs specific for DIL1.

SEQ ID NOS: 31 and 32 are primer sequences.

SEQ ID NOS: 33 and 34 are exemplary amiRNA sequences.

SEQ ID NO: 35: a DIG-related protein from tomato (Solyc03g111100.1).

SEQ ID NO: 36: a DIG-related protein from tomato (Solyc02g093890.1).

SEQ ID NO: 37: a DIG-related protein from tomato (Solyc02g068030.1).

SEQ ID NO: 38: a DIG-related protein from soybean (GLYMA19G22560.1).

SEQ ID NO: 39: a DIG-related protein from soybean (GLYMA17G13720.1).

SEQ ID NO: 40: a DIG-related protein from soybean (GLYMA06G18060.1).

SEQ ID NO: 41: a DIG-related protein from soybean (GLYMA05G06810.1).

SEQ ID NO: 42: a DIG-related protein from soybean (GLYMA05G03080.1).

SEQ ID NO: 43: a DIG-related protein from soybean (GLYMA04G36920.1).

SEQ ID NO: 44: a DIG-related protein from rice (Os12g0242500-01).

SEQ ID NO: 45: a DIG-related protein from maize (GRMZM2G084005_P01).

SEQ ID NO: 46: a DIG-related protein from *Arabidopsis thaliana* (At1g27461.1).

SEQ ID NO: 47: a DIG-related protein from rice (Os07g0585700-01 Sdr4).

SEQ ID NO: 48: a DIG-related protein from maize (GRMZM2G396402_P01).

SEQ ID NO: 49: a DIG-related protein from maize (GRMZM2G105302_P01).

SEQ ID NOS: 50-51 are T-DNA junction sequences for SALK_128578, chromosome 3, COOR C/17967613-17967922,17968310-17968369.

SEQ ID NO: 52 is a T-DNA junction sequence for SALKseq_057406.2, chromosome 5, COOR W/20505825-20505825.

SEQ ID NO: 53 is a T-DNA junction sequence for SALK_130501, chromosome 5, COOR C/25380458-25380504.

SEQ ID NO: 54: a nucleic acid sequence for vector pROK2 that can be used with T-DNA to generate insertion mutants using method provided herein.

SEQ ID NO: 55: a nucleotide sequence of 3×FLAG-YPet for N-terminus tagging. 3×FLAG is nt 1-66, Protease 3C cleavage site is nt 67 to 90, YPet (A206K) nt 91 to 804; FRT is nt 807 to 840.

SEQ ID NO: 56: a nucleotide sequence of YPet-6×His-3×FLAG for C-terminus tagging. YPet (A206K) nt 19 to 732; FRT is nt 734 to 768, and 6× is nt 787 to 804; Protease 3C cleavage site nt 805 to 828; and 3×FLAG is nt 829-894.

SEQ ID NOS: 57-58 are exemplary guide RNAs specific for DIL1.

DETAILED DESCRIPTION

The following explanations of terms and methods are provided to better describe the present disclosure and to guide those of ordinary skill in the art in the practice of the present disclosure. The singular forms "a," "an," and "the" refer to one or more than one, unless the context clearly dictates otherwise. For example, the term "comprising a protein" includes single or plural proteins and is considered equivalent to the phrase "comprising at least one protein." The term "or" refers to a single element of stated alternative elements or a combination of two or more elements, unless the context clearly indicates otherwise. As used herein, "comprises" means "includes." Thus, "comprising A or B," means "including A, B, or A and B," without excluding additional elements. Dates of GenBank® Accession Nos. referred to herein are the sequences available at least as early as Oct. 26, 2016. All references and GenBank® Accession numbers cited herein are incorporated by reference in their entirety.

Unless explained otherwise, all technical and scientific terms used herein have the same meaning as commonly understood to one of ordinary skill in the art to which this disclosure belongs. Although methods and materials similar or equivalent to those described herein can be used in the practice or testing of the present disclosure, suitable methods and materials are described below. The materials, methods, and examples are illustrative only and not intended to be limiting.

In order to facilitate review of the various embodiments of the disclosure, the following explanations of specific terms are provided:

Agronomic trait: Characteristic of a plant, which characteristics include, but are not limited to, plant morphology, physiology, growth and development, yield, nutritional enhancement, disease or pest resistance, or environmental or chemical tolerance are agronomic traits. In the plants and plant cells of this disclosure, the expression of nucleic acid molecule(s) that decrease or eliminate expression of 1, 2, 3, 4, 5 or 6 of DIG1, DIG2, DIL1, DIL2, DIL3, and DIL4, confers one or more agronomically desirable traits, e.g. decreased abscisic acid (ABA) sensitivity, decreased salt sensitivity, or both. Such plants can have other enhanced agronomic traits (e.g., a measurable improvement in an agronomic trait including, but not limited to, yield increase, including increased yield under non-stress conditions and increased yield under environmental stress conditions), for example due to the presence of one or more other transgens that confer such traits. Stress conditions may include, for example, drought, shade, fungal disease, viral disease, bacterial disease, insect infestation, nematode infestation, cold temperature exposure, heat exposure, osmotic stress, reduced nitrogen nutrient availability, reduced phosphorus nutrient availability and high plant density. "Yield" can be affected by many properties including without limitation, plant height, pod number, pod position on the plant, number of internodes, incidence of pod shatter, grain size, efficiency of nodulation and nitrogen fixation, efficiency of nutrient assimilation, resistance to biotic and abiotic stress, carbon assimilation, plant architecture, resistance to lodging, percent seed germination, seedling vigor, and juvenile traits. Yield can also affected by efficiency of germination (including germination in stressed conditions), growth rate (including growth rate in stressed conditions), ear number, seed number per ear, seed size, composition of seed (starch, oil, protein) and characteristics of seed fill. Increased yield may result from improved utilization of key biochemical compounds, such as nitrogen, phosphorous and carbohydrate, or from improved responses to environmental stresses, such as cold, heat, drought, salt, and attack by pests or pathogens. The recombinant nucleic acid molecules that decrease or eliminate expression of 1, 2, 3, 4, 5 or 6 of DIG1, DIG2, DIL1, DIL2, DIL3, and DIL4 can to provide plants having improved growth and development, and ultimately increased yield.

Altering level of production or expression: Changing, either by increasing or decreasing, the level of production or expression of a nucleic acid sequence or an amino acid sequence (for example a protein, an siRNA, a miRNA, an mRNA, a gene), as compared to a control level of production or expression.

Antisense, Sense, and Antigene: DNA has two antiparallel strands, a 5'→3' strand, referred to as the plus strand, and a 3'→5' strand, referred to as the minus strand. Because RNA polymerase adds nucleic acids in a 5'→3' direction, the minus strand of the DNA serves as the template for the RNA during transcription. Thus, an RNA transcript will have a sequence complementary to the minus strand, and identical to the plus strand (except that U is substituted for T).

Antisense molecules are molecules that are specifically hybridizable or specifically complementary to either RNA or the plus strand of DNA. Sense molecules are molecules that are specifically hybridizable or specifically complementary to the minus strand of DNA. Antigene molecules are either antisense or sense molecules directed to a DNA target (such as DIG1, DIG2, DIL1, DIL2, DIL3, or DIL4). An antisense RNA (asRNA) is a molecule of RNA complementary to a sense (encoding) nucleic acid molecule (such as DIG1, DIG2, DIL1, DIL2, DIL3, or DIL4).

Binding or stable binding: An oligonucleotide binds or stably binds to a target nucleic acid (such as DIG1, DIG2, DIL1, DIL2, DIL3, and/or DIL4) if a sufficient amount of the oligonucleotide forms base pairs or is hybridized to its target nucleic acid, to permit detection of that binding. Binding can be detected by either physical or functional properties of the target:oligonucleotide complex. Binding between a target and an oligonucleotide can be detected by any procedure known to one skilled in the art, including both functional and physical binding assays. For instance, binding can be detected functionally by determining whether binding has an observable effect upon a biosynthetic process such as expression of a gene, DNA replication, transcription, translation and the like.

Physical methods of detecting the binding of complementary strands of DNA or RNA are known, and include such methods as DNase I or chemical footprinting, gel shift and affinity cleavage assays, Northern blotting, dot blotting and light absorption detection procedures. For example, one method involves observing a change in light absorption of a solution containing an oligonucleotide (or an analog) and a target nucleic acid at 220 to 300 nm as the temperature is slowly increased. If the oligonucleotide or analog has bound to its target, there is a sudden increase in absorption at a characteristic temperature as the oligonucleotide (or analog) and the target disassociate from each other, or melt.

The binding between an oligomer and its target nucleic acid is frequently characterized by the temperature ($T_m$) at which 50% of the oligomer is melted from its target. A higher ($T_m$) means a stronger or more stable complex relative to a complex with a lower ($T_m$).

Cas9: An RNA-guided RNA endonuclease enzyme that can cut DNA. Cas9 has two active cutting sites (HNH and RuvC), one for each strand of the double helix. Catalytically inactive (deactivated) Cas9 (dCas9) as also encompassed by this disclosure. In some examples, a dCas9 includes one or more of the following point mutations: D10A, I1840A, N863A.

Cas9 sequences are publicly available. For example, GenBank® Accession Nos. nucleotides 796693 . . . 800799 of CP012045.1 and nucleotides 1100046 . . . 1104152 of CP014139.1 disclose Cas9 nucleic acids, and GenBank® Accession Nos. NP_269215.1, AMA70685.1 and AKP81606.1 disclose Cas9 proteins. In some examples, the Cas9 is a deactivated form of Cas9 (dCas9), such as one that is nuclease deficient (e.g., those shown in GenBank® Accession Nos. AKA60242.1 and KR011748.1). In certain examples, Cas9 has at least 80% sequence identity, for example at least 85%, 90%, 95%, 98%, or 99% sequence identity to such sequences.

Complementarity and percentage complementarity: Molecules with complementary nucleic acids form a stable duplex or triplex when the strands bind, or hybridize, to each other by forming Watson-Crick, Hoogsteen or reverse Hoogsteen base pairs. Stable binding occurs when an oligonucleotide remains detectably bound to a target nucleic acid sequence under the required conditions.

Complementarity is the degree to which bases in one nucleic acid strand base pair with (are complementary to) the bases in a second nucleic acid strand. Complementarity is conveniently described by the percentage, i.e., the proportion of nucleotides that form base pairs between two strands or within a specific region or domain of two strands. For example, if 10 nucleotides of a 15-nucleotide oligonucleotide form base pairs with a targeted region of a DNA molecule, that oligonucleotide is said to have 66.67% complementarity to the region of DNA targeted.

Sufficient complementarity means that a sufficient number of base pairs exist between the oligonucleotide and the target sequence (such as DIG1, DIG2, DIL1, DIL2, DIL3, and/or DIL4) to achieve detectable binding, and disrupt or reduce expression of the gene product(s) encoded by that target sequence. When expressed or measured by percentage of base pairs formed, the percentage complementarity that fulfills this goal can range from as little as about 50% complementarity to full, (100%) complementary. In some embodiments, sufficient complementarity is at least about 50%, about 75% complementarity, or at least about 90% or 95% complementarity. In particular embodiments, sufficient complementarity is 98%, 99%, or 100% complementarity.

Control level: The amount of a molecule, such as a polypeptide or nucleic acid molecule, normally found in nature under a certain condition and/or in a specific genetic background. In certain embodiments, a control level of a molecule can be measured in a cell or specimen that has not been subjected, either directly or indirectly, to a treatment (e.g., introduction of an RNAi molecule or guide sequence). A control level is also referred to as a wildtype or a basal level.

Control plant: A control plant, i.e. a plant that does not contain a recombinant nucleic acid molecule that confers (for instance) an enhanced agronomic trait in a transgenic plant, is used as a baseline for comparison to identify an enhanced agronomic trait in the transgenic plant. A suitable control plant may be a non-transgenic plant of the parental line used to generate a transgenic plant. A control plant may in some cases be a transgenic plant line that comprises an empty vector or marker gene, but does not contain the recombinant nucleic acid, or does not contain all of the recombinant nucleic acid molecules in the test plant.

CRISPRs (clustered regularly interspaced short palindromic repeats): DNA loci containing short repetitions of base sequences. Each repetition is followed by short segments of "spacer DNA" from previous exposures to a virus. CRISPRs are found in approximately 40% of sequenced bacteria genomes and 90% of sequenced archaea. CRISPRs are often associated with cas genes that code for proteins related to CRISPRs. The CRISPR/Cas system is a prokaryotic immune system that confers resistance to foreign genetic elements such as plasmids and phages and provides a form of acquired immunity. CRISPR spacers recognize and cut these exogenous genetic elements in a manner analogous to RNAi in eukaryotic organisms. The CRISPR/Cas system can be used for gene editing (adding, disrupting or changing the sequence of specific genes) and gene regulation. By delivering the Cas9 protein and appropriate guide RNAs into a cell, the organism's genome can be cut at any desired location.

Downregulated or knocked down: When used in reference to the expression of a molecule, such as a gene or a protein (e.g., a target gene, such as DIG1, DIG2, DIL1, DIL2, DIL3, and/or DIL4), refers to any process which results in a decrease in production of a gene product, but in some examples not complete elimination of the gene product or gene function. In one example, downregulation or knock down does not result in complete elimination of detectable expression or activity. A gene product can be RNA (such as mRNA, rRNA, tRNA, and structural RNA) or protein. Therefore, downregulation or knock down includes processes that decrease transcription of a gene or translation of mRNA and thus decrease the presence of proteins or nucleic acids. RNAi and CRISPR/Cas9 systems can be used to downregulate any target of interest.

Examples of processes that decrease transcription include those that facilitate degradation of a transcription initiation complex, those that decrease transcription initiation rate, those that decrease transcription elongation rate, those that decrease processivity of transcription and those that increase transcriptional repression. Gene downregulation can include reduction of expression above an existing level. Examples of processes that decrease translation include those that decrease translational initiation, those that decrease translational elongation and those that decrease mRNA stability.

Downregulation or knock down includes any detectable decrease in the production of a gene product. In certain examples, detectable target protein or nucleic acid expression in a cell (such as DIG1, DIG2, DIL1, DIL2, DIL3, and/or DIL4) decreases by at least 20%, at least 30%, at least 40%, at least 50%, at least 60%, at least 70%, at least 75%, at least 80%, at least 90%, at least 95%, at least 96%, at least 97%, at least 98%, or at least 99% (such as a decrease of 40% to 90%, 40% to 80% or 50% to 95%) as compared to a control (such an amount of protein or nucleic acid expression detected in a corresponding normal or wild-type cell or plant). In one example, a control is a relative amount of expression in a non-recombinant plant cell.

Encode: A polynucleotide is said to encode a polypeptide if, in its native state or when manipulated by methods well known to those skilled in the art, it can be transcribed and/or translated to produce the mRNA for and/or the polypeptide or a fragment thereof. The anti-sense strand is the complement of such a nucleic acid, and the encoding sequence can be deduced therefrom.

Expression: The process by which a gene's coded information is converted into the structures present and operating in the cell. Expressed genes include those that are transcribed into mRNA and then translated into protein and those that are transcribed into RNA but not translated into protein (for example, siRNA, transfer RNA and ribosomal RNA). Thus, expression of a target sequence, such as a gene or a promoter region of a gene, can result in the expression of an mRNA, a protein, or both. The expression of the target sequence can be inhibited or enhanced (decreased or increased).

Gene Editing: A type of genetic engineering in which a nucleic acid molecule, such as DNA, is inserted, deleted or replaced in the genome of an organism using engineered nucleases, which create site-specific double-strand breaks (DSBs) at desired locations in the genome. The induced double-strand breaks are repaired through nonhomologous end-joining (NHEJ) or homologous recombination (HR), resulting in targeted mutations or repairs. CRISPR/Cas9 methods can be used to edit the sequence of one or more target genes, such as DIG1, DIG2, DIL1, DIL2, DIL3, and/or DIL4. Gene editing can also be used to mutate a gene in a test organism, such as a plant.

Gene Silencing: A specific type of gene regulation, namely significantly reducing (e.g., a reduction of at least 90%, at least 95%, or at least 99%) or preventing expression of a gene (such as DIG1, DIG2, DIL1, DIL2, DIL3, and/or DIL4). Can also be referred to as knocking out gene expression, when the gene is completely silenced. Methods of gene silencing include RNAi methods, as well as gene editing methods such as CRISPR-Cas9.

Guide sequence: A polynucleotide sequence having sufficient complementarity with a target polynucleotide sequence (such as DIG1, DIG2, DILL DIL2, DIL3, and/or DIL4) to hybridize with the target sequence and direct sequence-specific binding of a Cas9 to the target sequence. In some examples, the guide sequence is RNA. In some examples, the guide sequence is DNA. The guide nucleic acid can include modified bases or chemical modifications (e.g., see Latorre et al., Angewandte Chemie 55:3548-50, 2016). In some embodiments, the degree of complementarity between a guide sequence and its corresponding target sequence, when optimally aligned using a suitable alignment algorithm, is about or more than about 50%, 60%, 75%, 80%, 85%, 90%, 95%, 97.5%, 99%, or more. Optimal alignment may be determined with the use of any suitable algorithm for aligning sequences, non-limiting example of which include the Smith-Waterman algorithm, the Needleman-Wunsch algorithm, algorithms based on the Burrows-Wheeler Transform (e.g., the Burrows Wheeler Aligner), ClustalW, Clustal X, BLAT, Novoalign (Novocraft Technologies, ELAND (Illumina, San Diego, Calif.), SOAP (available at soap.genomics.org.cn), and Maq (available at maq.sourceforge.net). In some embodiments, a guide sequence is about, or at least about, 5, 10, 11, 12, 13, 14, 15, 16, 17, 18, 19, 20, 21, 22, 23, 24, 25, 26, 27, 28, 29, 30, 35, 40, 45, 50, 75, or more nucleotides in length. In some embodiments, a guide sequence is less than about 75, 50, 45, 40, 35, 30, 25, 20, 15, 12, or fewer nucleotides in length. In some embodiments, a guide sequence is 15-25 nucleotides (such as 18-22 or 18 nucleotides).

The ability of a guide sequence to direct sequence-specific binding of a CRISPR complex to a target sequence may be assessed by any suitable assay. For example, the components of a CRISPR system sufficient to form a CRISPR complex, including the guide sequence to be tested, may be provided to a host cell having the corresponding target sequence, such as by transfection with vectors encoding the components of the CRISPR sequence, followed by an assessment of preferential cleavage within the target sequence, such as by Surveyor assay as described herein. Similarly, cleavage of a target polynucleotide sequence may be evaluated in a test tube by providing the target sequence, components of a CRISPR complex, including the guide sequence to be tested and a control guide sequence different from the test guide sequence, and comparing binding or rate of cleavage at the target sequence between the test and control guide sequence reactions. Other assays are possible, and will occur to those skilled in the art.

Heterologous: A type of sequence that is not normally (i.e. in the wild-type sequence) found adjacent to a second sequence. In one embodiment, the sequence is from a different genetic source, such as a virus or organism, than the second sequence.

Hybridization: Oligonucleotides and their analogs hybridize by hydrogen bonding, which includes Watson-Crick, Hoogsteen or reversed Hoogsteen hydrogen bonding, between complementary bases. Generally, nucleic acid consists of nitrogenous bases that are either pyrimidines (cytosine (C), uracil (U), and thymine (T)) or purines (adenine (A) and guanine (G)). These nitrogenous bases form hydrogen bonds between a pyrimidine and a purine, and the bonding of the pyrimidine to the purine is referred to as base pairing. More specifically, A will hydrogen bond to T or U, and G will bond to C. In RNA molecules, G also will bond to U. Complementary refers to the base pairing that occurs between two distinct nucleic acid sequences or two distinct regions of the same nucleic acid sequence.

Hybridization conditions resulting in particular degrees of stringency will vary depending upon the nature of the hybridization method of choice and the composition and length of the hybridizing nucleic acid sequences. Generally, the temperature of hybridization and the ionic strength (especially the $Na^+$ concentration) of the hybridization buffer will determine the stringency of hybridization, though waste times also influence stringency. Calculations regarding hybridization conditions required for attaining particular degrees of stringency are discussed by Sambrook et al. (ed.), *Molecular Cloning: A Laboratory Manual*, 2nd ed., vol. 1-3, Cold Spring Harbor Laboratory Press, Cold Spring Harbor, N.Y., 1989, chapters 9 and 11, herein incorporated by reference.

The following is an exemplary set of hybridization conditions and is not meant to be limiting.

Very High Stringency (Detects Sequences that Share 90% Sequence Identity)
Hybridization: 5×SSC at 65° C. for 16 hours
Wash twice: 2×SSC at room temperature (RT) for 15 minutes each
Wash twice: 0.5×SSC at 65° C. for 20 minutes each
High Stringency (Detects Sequences that Share 80% Sequence Identity or Greater)
Hybridization: 5×-6×SSC at 65° C.-70° C. for 16-20 hours
Wash twice: 2×SSC at RT for 5-20 minutes each
Wash twice: 1×SSC at 55° C.-70° C. for 30 minutes each
Low Stringency (Detects Sequences that Share Greater than 50% Sequence Identity)
Hybridization: 6×SSC at RT to 55° C. for 16-20 hours
Wash at least twice: 2×-3×SSC at RT to 55° C. for 20-30 minutes each Interfering with or inhibiting (expression of a target sequence): Refers to the ability of an agent, such as those used with RNAi or CRISPR-Cas9, to measurably reduce the expression and/or stability of molecules carrying the target sequence (such as DIG1, DIG2, DIL1, DIL2, DIL3, and/or DIL4). "Interfering with or inhibiting" expression contemplates reduction of the end-product of the gene or sequence, e.g., the expression or function of the encoded protein or a protein, nucleic acid, other biomolecule, or biological function influenced by the target sequence, and thus includes reduction in the amount or longevity of the mRNA transcript or other target sequence. In some embodiments, the small RNA or other molecule guides chromatin modifications which inhibit the expression of a target sequence. It is understood that the phrase is relative, and does not require absolute inhibition (suppression) of the sequence. Thus, in certain embodiments, interfering with or inhibiting expression of a target sequence requires that, following application of the small RNA or other molecule (such as a vector or other construct encoding one or more small RNAs), the sequence is expressed at least 5% less than prior to application, at least 10% less, at least 15% less, at least 20% less, at least 25% less, or even more reduced. Thus, in some particular embodiments, application of a small RNA or other molecule reduces expression of the target sequence by about 30%, about 40%, about 50%, about 60%, or more. In specific examples, where the small RNA or other molecule is particularly effective, expression is reduced by 70%, 80%, 85%, 90%, 95%, or even more.

Isolated: A biological component (such as a nucleic acid molecule, protein or organelle) that has been substantially separated or purified away from other biological components in the cell of the organism in which the component naturally occurs, i.e., other chromosomal and extra-chromosomal DNA and RNA, proteins and organelles. Nucleic acids and proteins that have been isolated include nucleic acids and proteins purified by standard purification methods. The term also embraces nucleic acids and proteins prepared by recombinant expression in a host cell as well as chemically synthesized nucleic acids.

MicroRNA (miRNA): Small, non-coding RNA gene products of approximately 21 nucleotides long and found in diverse organisms, including animals and plants. miRNAs structurally resemble siRNAs except that they arise from structured, foldback-forming precursor transcripts derived from miRNA genes. Primary transcripts of miRNA genes form hairpin structures that are processed by the multidomain RNaseIII-like nuclease DICER and DROSHA (in animals) or DICER-LIKE1 (DCL1; in plants) to yield miRNA duplexes. The mature miRNA is incorporated into RISC complexes after duplex unwinding. Plant miRNAs interact with their RNA targets with perfect or near perfect complementarity.

Operably linked: A first nucleic acid sequence is operably linked with a second nucleic acid sequence when the first nucleic acid sequence is placed in a functional relationship with the second nucleic acid sequence. For instance, a promoter is operably linked to a sequence if the promoter affects the transcription or expression of the sequence). Generally, operably linked nucleic acid sequences are contiguous and, where necessary to join two protein coding regions, in the same reading frame.

Post-Transcriptional Gene Silencing (PTGS): A form of gene silencing in which the inhibitory mechanism occurs after transcription. This can result in either decreased steady-state level of a specific RNA target or inhibition of translation (Tuschl, *ChemBiochem*, 2:239-245, 2001). In the literature, the terms RNA interference (RNAi) and posttranscriptional cosuppression are often used to indicate posttranscriptional gene silencing.

Promoter: An array of nucleic acid control sequences which direct transcription of a nucleic acid. A promoter includes necessary nucleic acid sequences near the start site of transcription, such as, in the case of a polymerase II type promoter, a TATA element. A promoter also optionally includes distal enhancer or repressor elements which can be located as much as several thousand base pairs from the start site of transcription.

Purified: The term purified does not require absolute purity; rather, it is intended as a relative term. Thus, for example, a purified protein preparation is one in which the protein referred to is more pure (has fewer impurities) than the protein in its natural environment within a cell.

Recombinant: A recombinant nucleic acid molecule is one that has a sequence that is not naturally occurring or has a sequence that is made by an artificial combination of two otherwise separated segments of sequence. This artificial combination can be accomplished by routine methods, such as chemical synthesis or by the artificial manipulation of isolated segments of nucleic acids, such as by genetic engineering techniques. Similarly, a recombinant protein is one encoded by a recombinant nucleic acid molecule. Similarly, a recombinant or transgenic cell is one that contains a recombinant nucleic acid molecule and expresses a recombinant protein.

Regulatable promoter: A promoter whose activity is regulated by an agent, such as a transcription factor, a chemical compound, or a nucleic acid molecule.

Regulating gene expression: The process of controlling the expression of a gene by increasing or decreasing the expression, production, or activity of an agent that affects gene expression. The agent can be a protein, such as a transcription factor, or a nucleic acid molecule, such as a miRNA or an siRNA molecule, which when in contact with the gene or its upstream regulatory sequences, or a mRNA encoded by the gene, either increases or decreases gene expression.

RNA interference (RNAi): Gene silencing mechanisms that involve small RNAs (including miRNA and siRNA) are frequently referred to under the broad term RNAi. Natural functions of RNAi include protection of the genome against invasion by mobile genetic elements such as transposons and viruses, and regulation of gene expression.

RNA interference results in the inactivation or suppression of expression of a gene within a cell or organism. RNAi can be triggered by one of two general routes. First, it can be triggered by direct cellular delivery of short-interfering RNAs (siRNAs, usually ~21 nucleotides in length and delivered in a dsRNA duplex form with two unpaired nucleotides at each 3' end), which have sequence complementarity to a RNA that is the target for suppression (e.g., DIG1, DIG2, DIL1, DIL2, DIL3, and/or DIL4). Second, RNAi can be triggered a method in which siRNAs are formed in vivo from various types of designed, expressed genes. These genes typically express RNA molecules that form intra- or inter-molecular duplexes (dsRNA) which are processed by natural enzymes (DICER or DCL) to form siRNAs. In some cases, these genes express "hairpin"-forming RNA transcripts with perfect or near-perfect base-pairing; some of the imperfect hairpin-forming transcripts yield a special type of small RNA, termed microRNA (miRNA). In either general method, the siRNAs (or miRNAs) function as "guide sequences" to direct an RNA-degrading enzyme (termed RISC) to cleave or silence the target RNA. In some cases, an RNAi-inducing gene is integrated into the genome of a transgenic cell. An example would be a plant that is modified to suppress a specific gene by an RNAi-inducing transgene. In some examples, RNAi is triggered in transgenic plants by transgenes that express a dsRNA (either intramolecular or hairpin, or intermolecular in which two transcripts anneal to form dsRNA).

RNA silencing: A general term that is used to indicate RNA-based gene silencing or RNAi.

Sequence identity: The similarity between amino acid (or nucleotide) sequences is expressed in terms of the similarity between the sequences, otherwise referred to as sequence identity. Sequence identity is frequently measured in terms of percentage identity (or similarity or homology); the higher the percentage, the more similar the two sequences are. Homologs or variants of a polypeptide will possess a relatively high degree of sequence identity when aligned using standard methods.

Methods of alignment of sequences for comparison are well known in the art. Various programs and alignment algorithms are described in: Smith and Waterman, *Adv. Appl. Math.* 2:482, 1981; Needleman and Wunsch, *J. Mol. Biol.* 48:443, 1970; Pearson and Lipman, *Proc. Natl. Acad. Sci. U.S.A.* 85:2444, 1988; Higgins and Sharp, *Gene* 73:237, 1988; Higgins and Sharp, *CABIOS* 5:151, 1989; Corpet et al., *Nucleic Acids Research* 16:10881, 1988; and Pearson and Lipman, *Proc. Natl. Acad. Sci. U.S.A.* 85:2444, 1988. Altschul et al., *Nature Genet.* 6:119, 1994, presents a detailed consideration of sequence alignment methods and homology calculations.

The NCBI Basic Local Alignment Search Tool (BLAST) (Altschul et al., *J. Mol. Biol.* 215:403, 1990) is available from several sources, including the National Center for Biotechnology Information (NCBI, Bethesda, Md.) and on the internet, for use in connection with the sequence analysis programs blastp, blastn, blastx, tblastn, and tblastx. A description of how to determine sequence identity using this program is available on the NCBI website on the internet.

Variants of the DIG1, DIG2, DIL1, DIL2, DIL3, and/or DIL4 nucleic acid and protein sequences disclosed herein are typically characterized by possession of at least about 80%, at least 90%, at least 95%, at least 96%, at least 97%, at least 98% or at least 99% sequence identity counted over the full length alignment with the amino acid sequence using the NCBI Blast 2.0, gapped blastp set to default parameters. For comparisons of amino acid sequences of greater than about 30 amino acids, the Blast 2 sequences function is employed using the default BLOSUM62 matrix set to default parameters, (gap existence cost of 11, and a per residue gap cost of 1). When aligning short peptides (fewer than around 30 amino acids), the alignment should be performed using the Blast 2 sequences function, employing the PAM30 matrix set to default parameters (open gap 9, extension gap 1 penalties). Proteins with even greater similarity to the reference sequences will show increasing percentage identities when assessed by this method, such as at least 95%, at least 98%, or at least 99% sequence identity. When less than the entire sequence is being compared for sequence identity, homologs and variants will typically possess at least 80% sequence identity over short windows of 10-20 amino acids, and may possess sequence identities of at least 85% or at least 90% or at least 95% depending on their similarity to the reference sequence. Methods for determining sequence identity over such short windows are available at the NCBI website on the internet. One of skill in the art will appreciate that these sequence identity ranges are provided for guidance only; it is entirely possible that strongly significant homologs could be obtained that fall outside of the ranges provided.

Thus, a DIG1, DIG2, DIL1, DIL2, DIL3, or DIL4 protein provided herein can share at least 80%, at least 85%, at least 90%, at least 91%, at least 92%, at least 95%, at least 96%, at least 97%, at least 98% or at least 99% sequence identity to any one of SEQ ID NOS: 2, 4, 6, 8, 10, or 12 respectively. In addition, a DIG1, DIG2, DIL1, DIL2, DIL3, or DIL4 nucleic acid molecule can have at least 80%, at least 85%, at least 90%, at least 92%, at least 95%, at least 96%, at least 97%, at least 98% or at least 99% sequence identity to any one of SEQ ID NOS: 1, 3, 5, 7, 9, or 11, respectively. In some examples, a DIG/DIL related protein has at least 80%, at least 85%, at least 90%, at least 92%, at least 95%, at least 96%, at least 97%, at least 98% or at least 99% sequence identity to any one of SEQ ID NOS:35, 36, 37, 38, 39, 40, 41, 42, 43, 44, 45, 46, 47, 48 and 49.

Silencing agent or molecule: A specific molecule, which can exert an influence on a cell in a sequence-specific manner to reduce or silence the expression or function of a target, such as a target gene or protein (such as DIG1, DIG2, DIL1, DIL2, DIL3, and/or DIL4). Examples of silencing agents include nucleic acid molecules such as naturally occurring or synthetically generated small interfering RNAs (siRNAs), naturally occurring or synthetically generated microRNAs (miRNAs), naturally occurring or synthetically generated dsRNAs, and antisense sequences (including antisense oligonucleotides, hairpin structures, and antisense expression vectors), as well as constructs that code for any one of such molecules.

Small interfering RNA (siRNA): RNA of approximately 21-25 nucleotides that is processed from a dsRNA by a DICER enzyme (in animals) or a DCL enzyme (in plants). The initial DICER or DCL products are double-stranded, in which the two strands are typically 21-25 nucleotides in length and contain two unpaired bases at each 3' end. The individual strands within the double stranded siRNA structure are separated, and typically one of the siRNAs then are associated with a multi-subunit complex, the RNAi-induced silencing complex (RISC). A typical function of the siRNA is to guide RISC to the target based on base-pair complementarity.

Target nucleic acid (to be inhibited): A nucleic acid molecule whose expression is to be decreased or eliminated, for example decreased by at least 80% or at least 90%. In some examples, such a target can interact with an RNAi molecule (e.g., miRNA or siRNA) or a guide sequence. In specific examples, the target is 1, 2, 3, 4, 5 or 6 of DIG1, DIG2, DIL1, DIL2, DIL3, and DIL4).

Trans-acting siRNAs (tasiRNAs): A subclass of siRNAs that function like miRNAs to repress expression of target genes, yet have unique biogenesis requirements. Trans-acting siRNAs form by transcription of ta-siRNA-generating genes, cleavage of the transcript through a guided RISC mechanism, conversion of one of the cleavage products to dsRNA, and processing of the dsRNA by DCL enzymes. A ta-siRNA precursor is any nucleic acid molecule, including single-stranded or double-stranded DNA or RNA, which can be transcribed and/or processed to release a ta-siRNA.

Transcriptional gene silencing (TGS): A phenomenon that is triggered by the formation of dsRNA that is homologous with gene promoter regions and sometimes coding regions. TGS results in DNA and histone methylation and chromatin remodeling, thereby causing transcriptional inhibition rather than RNA degradation. Both TGS and PTGS depend on dsRNA, which is cleaved into small (e.g., 20-25 nucleotides) interfering RNAs (Eckhardt, *Plant Cell,* 14:1433-1436, 2002; Aufsatz et al., *Proc. Natl. Acad. Sci. U.S.A.,* 99:16499-16506, 2002).

Transgenic: This term refers to a plant or plant cell that contains recombinant genetic material not normally found in entities of this type (such as a transgene) and which has been introduced into the entity in question (or into progenitors of the entity) by for example, human manipulation. Thus, a plant that is grown from a plant cell into which recombinant DNA is introduced by transformation is a transgenic plant, as are all offspring of that plant that contain the introduced transgene (whether produced sexually or asexually).

Transduced and Transformed: A virus or vector "transduces" a cell when it transfers nucleic acid into the cell. A cell is "transformed" or "transfected" by a nucleic acid transduced into the cell when the DNA becomes stably replicated by the cell, either by incorporation of the nucleic acid into the cellular genome, or by episomal replication.

These terms encompasses all techniques by which a nucleic acid molecule can be introduced into such a cell, including transfection with viral vectors, transformation with plasmid vectors, transformation with *Agrobacterium tumefaciens*, and introduction of naked DNA by electroporation, lipofection, particle gun acceleration and other methods in the art. In some example the method is a chemical method (e.g., calcium-phosphate transfection), physical method (e.g., electroporation, microinjection, particle bombardment), fusion (e.g., liposomes), receptor-mediated endocytosis (e.g., DNA-protein complexes, viral envelope/capsid-DNA complexes) and biological infection by viruses such as recombinant viruses Vector: A vector can include nucleic acid sequences that permit it to replicate in a host cell, such as an origin of replication. A vector can also include one or more selectable marker genes and other genetic elements known in the art. An integrating vector is capable of integrating itself into a host nucleic acid. An expression vector is a vector that contains the necessary regulatory sequences to allow transcription and translation of inserted gene or genes.

One type of vector is a "plasmid," which refers to a circular double stranded DNA loop into which additional DNA segments can be inserted, such as by standard molecular cloning techniques. Another type of vector is a viral vector, wherein virally-derived DNA or RNA sequences are present in the vector for packaging into a virus (e.g., retroviruses, replication defective retroviruses, adenoviruses, replication defective adenoviruses, and adeno-associated viruses). Viral vectors also include polynucleotides carried by a virus for transfection into a host cell.

Certain vectors are capable of autonomous replication in a host cell into which they are introduced (e.g., bacterial vectors having a bacterial origin of replication). Other vectors (e.g., non-episomal mammalian vectors) are integrated into the genome of a host cell upon introduction into the host cell, and thereby are replicated along with the host genome.

Certain vectors are capable of directing the expression of genes to which they are operatively-linked. Such vectors are referred to herein as "expression vectors." Common expression vectors of utility in recombinant DNA techniques are often in the form of plasmids. Recombinant expression vectors can comprise a nucleic acid (such as a guide RNA or RNAi) in a form suitable for expression of the nucleic acid in a host cell, which means that the recombinant expression vectors include one or more regulatory elements, which may be selected on the basis of the host cells to be used for expression, that is operatively-linked to the nucleic acid sequence to be expressed. Within a recombinant expression vector, "operably linked" is intended to mean that the nucleotide sequence of interest is linked to the regulatory element(s) in a manner that allows for expression of the nucleotide sequence (e.g., in an in vitro transcription/translation system or in a host cell when the vector is introduced into the host cell). It will be appreciated by those skilled in the art that the design of the expression vector can depend on such factors as the choice of the host cell to be transformed, the level of expression desired, etc.

Overview

A systematic study of a transcriptional network was performed by combining dynamic binding data of 21 TFs and time series RNA-seq data in response to a stimulus by the plant hormone ABA. It was observed that dynamic TF binding measured at a single time point correlated with the transcriptome changes over a prolonged span of time. Consistent with yeast and animals (2, 3, 39, 40), transcription of genes in *Arabidopsis* are often subject to a complex regulation of multiple TFs. It was further demonstrated that dynamic binding, especially by multiple TFs, is more functionally relevant than static TF binding in correlation with differential gene expression. This may be because an expression scheme with coordinated changes in the binding dynamics of multiple TFs would ensure robust responsiveness of target genes to a stimulus. This observation has a broad application to plants and other species, including prioritizing studies of 1) TF binding events and cis-regulatory elements, 2) functionally unknown genes in a pathway.

In plants, studies of transcriptional regulation are often focused on master regulators (33, 41, 42). The data herein confirm the importance of master regulators in plants. For instance, it was observed that ABFs and a physical interactor NF-YB2 ranked as top contributors to explain gene expression. In addition, the primary binding motif of ABFs also enhances the binding dynamics of many other ABA-responsive TFs. However, more than just the master regulators are needed to attain complex transcriptome changes to a stimulus, as many ABA-responsive genes are dynamically targeted by multiple TFs. Therefore, ABA response can be viewed as orchestrated by a handful of master regulators and facilitated by other TFs, where coordinated signaling and regulatory response lead to a rapid elicitation of transcriptome changes.

As indicated by GO annotation, network analyses recovered genes affecting all aspects of ABA-related processes such as seed development and response to osmotic stresses. In planta ectopic expression of several members of a newly discovered family of transcriptional regulators also exhibited altered response to both ABA and high salinity. Therefore, although the experiments were performed using seedlings, the discoveries are applicable to a broader range of development stages and stress scenarios. Emerging technologies to optimize plant water use have been developed based on the in-depth characterization of ABA perception (43). Knowledge derived from the genes identified herein are valuable to global agriculture, for example enabling new strategies for plants to respond to the challenges of ongoing drought and groundwater depletion in changing environments.

Based on these observations, methods of decreasing abscisic acid (ABA) sensitivity, decreasing salt sensitivity, or both, in a plant cell or plant, are provided. For example, such phenotypes can be obtained by decreasing or eliminating expression of 1, 2, 3, 4, 5 or 6 of DIG1, DIG2, DIL1, DIL2, DIL3, and DIL4 (and/or a DIG related gene). Thus, in some examples, expression of any one of SEQ ID NOS: 1-12 or 35-49, or a sequence having (such as one, at least 2, at least 3, at least 4, at least 5 or at least 6 of such molecules, such as 1, 2, 3, 4, 5 or 6 of SEQ ID NO: 1, 2, 3, 4, 5, 6, 7, 8, 9, 10, 11, 12, 35, 36, 37, 38, 39, 40, 41, 42, 43, 44, 45, 46, 47, 48 or 49), is reduced or eliminated in a plant cell or plant, resulting in decreased abscisic acid sensitivity, decreased salt sensitivity, or both, of the cell or plant. In one example, such phenotypes are obtained by decreasing or eliminating expression of a DIL gene or protein, DIG gene or protein, or a DIG related gene or protein, such as decreasing or eliminating expression of at least one gene or protein sequence (such as at least 2, at least 3, at least 4, at least 5 or at least 6) having at least at least 80%, at least 90%, at least 95%, at least 98%, at least 99%, or 100% sequence identity to any of SEQ ID NOS: 1, 2, 3, 4, 5, 6, 7, 8, 9, 10, 11, 12, 35, 36, 37, 38, 39, 40, 41, 42, 43, 44, 45, 46, 47, 48 and 49. Thus, in some examples, expression of any one of SEQ ID NOS: 1-12 or 35-49 (such as one, at least 2, at least 3, at least 4, at least 5 or at least 6 of such molecules, such as 1, 2, 3, 4, 5 or 6 of SEQ ID NO: 1, 2, 3, 4, 5, 6, 7, 8, 9, 10, 11, 12, 35, 36, 37, 38, 39, 40, 41, 42, 43, 44, 45, 46, 47, 48 or 49), is reduced or eliminated in a plant cell or plant, resulting in decreased abscisic acid sensitivity, decreased salt sensitivity, or both, of the cell or plant.

Also provided are nucleic acid molecules that can be used in such methods. In some examples, expression and/or activity of DIG1 (such as reducing expression of a nucleic acid molecule having at least 80%, at least 85%, at least 90%, at least 92%, at least 95%, at least 96%, at least 97%, at least 98% or at least 99% sequence identity to SEQ ID NO: 1 or reducing expression of a protein having at least 80%, at least 85%, at least 90%, at least 92%, at least 95%, at least 96%, at least 97%, at least 98% or at least 99% sequence identity to SEQ ID NO: 2) is reduced in the transgenic plant or transgenic plant cell by at least 50%, at least 60%, at least 70%, at least 80%, at least 90%, at least 95%, at least 98%, at least 99%, or 100% (for example as compared to the same plant that has a native or wild-type DIG1 sequence).

In some examples, expression and/or activity of DIG2 (such as reducing expression of a nucleic acid molecule having at least 80%, at least 85%, at least 90%, at least 92%, at least 95%, at least 96%, at least 97%, at least 98% or at least 99% sequence identity to SEQ ID NO: 3 or reducing expression of a protein having at least 80%, at least 85%, at least 90%, at least 92%, at least 95%, at least 96%, at least 97%, at least 98% or at least 99% sequence identity to SEQ ID NO: 4) in the transgenic plant or transgenic plant cell is reduced by at least 50%, at least 60%, at least 70%, at least 80%, at least 90%, at least 95%, at least 98%, at least 99%, or 100% (for example as compared to the same plant that has a native or wild-type DIG2 sequence).

In some examples, expression and/or activity of DIL1 (such as reducing expression of a nucleic acid molecule having at least 80%, at least 85%, at least 90%, at least 92%, at least 95%, at least 96%, at least 97%, at least 98% or at least 99% sequence identity to SEQ ID NO: 5 or reducing expression of a protein having at least 80%, at least 85%, at least 90%, at least 92%, at least 95%, at least 96%, at least 97%, at least 98% or at least 99% sequence identity to SEQ ID NO: 6) is reduced in the transgenic plant or transgenic plant cell by at least 50%, at least 60%, at least 70%, at least 80%, at least 90%, at least 95%, at least 98%, at least 99%, or 100% (for example as compared to the same plant that has a native or wild-type DIL1 sequence).

In some examples, expression and/or activity of DIL2 (such as reducing expression of a nucleic acid molecule having at least 80%, at least 85%, at least 90%, at least 92%, at least 95%, at least 96%, at least 97%, at least 98% or at least 99% sequence identity to SEQ ID NO: 7 or reducing expression of a protein having at least 80%, at least 85%, at least 90%, at least 92%, at least 95%, at least 96%, at least 97%, at least 98% or at least 99% sequence identity to SEQ ID NO: 8) is reduced in the transgenic plant or transgenic plant cell by at least 50%, at least 60%, at least 70%, at least 80%, at least 90%, at least 95%, at least 98%, at least 99%, or 100% (for example as compared to the same plant that has a native or wild-type DIL2 sequence).

In some examples, expression and/or activity of DIL3 (such as reducing expression of a nucleic acid molecule having at least 80%, at least 85%, at least 90%, at least 92%, at least 95%, at least 96%, at least 97%, at least 98% or at least 99% sequence identity to SEQ ID NO: 9 or reducing expression of a protein having at least 80%, at least 85%, at least 90%, at least 92%, at least 95%, at least 96%, at least 97%, at least 98% or at least 99% sequence identity to SEQ ID NO: 10) is reduced in the transgenic plant or transgenic plant cell by at least 50%, at least 60%, at least 70%, at least 80%, at least 90%, at least 95%, at least 98%, at least 99%, or 100% (for example as compared to the same plant that has a native or wild-type DIL3 sequence).

In some examples, expression and/or activity of DIL4 (such as reducing expression of a nucleic acid molecule having at least 80%, at least 85%, at least 90%, at least 92%, at least 95%, at least 96%, at least 97%, at least 98% or at least 99% sequence identity to SEQ ID NO: 11 or reducing expression of a protein having at least 80%, at least 85%, at least 90%, at least 92%, at least 95%, at least 96%, at least 97%, at least 98% or at least 99% sequence identity to SEQ ID NO: 12) is reduced in the transgenic plant or transgenic plant cell by at least 50%, at least 60%, at least 70%, at least 80%, at least 90%, at least 95%, at least 98%, at least 99%, or 100% (for example as compared to the same plant that has a native or wild-type DIL4 sequence). In some examples, combinations of these effects are achieved.

In one example, one or more inhibitory RNA (RNAi) molecules specific for DIG1 (SEQ ID NO: 1, a nucleic acid molecule having at least 80%, at least 85%, at least 90%, at least 92%, at least 95%, at least 96%, at least 97%, at least 98% or at least 99% sequence identity to SEQ ID NO: 1), DIG2 (SEQ ID NO: 3, or a nucleic acid molecule having at least 80%, at least 85%, at least 90%, at least 92%, at least 95%, at least 96%, at least 97%, at least 98% or at least 99% sequence identity to SEQ ID NO: 3), DIL1 (SEQ ID NO: 5, or a nucleic acid molecule having at least 80%, at least 85%, at least 90%, at least 92%, at least 95%, at least 96%, at least 97%, at least 98% or at least 99% sequence identity to SEQ ID NO: 5), DIL2 (SEQ ID NO: 7; or a nucleic acid molecule having at least 80%, at least 85%, at least 90%, at least 92%, at least 95%, at least 96%, at least 97%, at least 98% or at least 99% sequence identity to SEQ ID NO: 7), DIL3 (SEQ ID NO: 9, or a nucleic acid molecule having at least 80%, at least 85%, at least 90%, at least 92%, at least 95%, at least 96%, at least 97%, at least 98% or at least 99% sequence identity to SEQ ID NO: 9), and/or DIL4 (SEQ ID NO: 11, or a nucleic acid molecule having at least 80%, at least 85%, at least 90%, at least 92%, at least 95%, at least 96%, at least 97%, at least 98% or at least 99% sequence identity to SEQ ID NO: 11) are provided which can be used in these methods. Examples of RNAi molecules include but are not limited to an antisense molecule, small inhibitory RNA (siRNA), trans-acting small interfering RNA (tasiRNA), microRNA (miRNA), or an artificial micro RNA (amiRNA).

In one example, one or more guide nucleic acids (e.g., guide RNA) specific for DIG1 (e.g., SEQ ID NO: 1), DIG2 (e.g., SEQ ID NO: 3), DIL1 (e.g., SEQ ID NO: 5), DIL2 (e.g., SEQ ID NO: 7), DIL3 (e.g., SEQ ID NO: 9), and/or DIL4 (e.g., SEQ ID NO: 11) are provided which can be used in these methods.

In one example, one or more transfer DNAs (T-DNA) specific for DIG1 (e.g., SEQ ID NO: 1), DIG2 (e.g., SEQ ID NO: 3), DIL1 (e.g., SEQ ID NO: 5), DIL2 (e.g., SEQ ID NO: 7), DIL3 (e.g., SEQ ID NO: 9), and/or DIL4 (e.g., SEQ ID NO: 11) are provided which can be used in these methods. T-DNA knock out mutants, such as the SALK lines provided herein, were made by inserting a long external DNA sequence from a binary vector into the plant genome. Upon insertion into the target gene, expression of the gene is reduced or inhibited. This is how SALK_128578, SALKseq_057406.2, and SALK_130501 provided herein disrupt the expression of DIG1, DIG2, and DIL1 respectively. In one example, the PROK2 vector is used for T-DNA insertion (see SEQ ID NO: 54). But other vectors can be used.

The RNAi, guide nucleic acid, and T-DNA can be operably linked to a promoter (e.g., constitutive promoter, an inducible promoter, a tissue specific promoter, a ubiquitous promoter or a combination thereof), and can be part of an expression vector. Exemplary promoters and vectors are provided herein. In some examples, the promoter is codon optimized for expression in plant cells.

Transgenic plant cells that include the RNAi, guide nucleic acid, and/or T-DNA specific for 1, 2, 3, 4, 5 or 6 of DIG1 (e.g., SEQ ID NO: 1), DIG2 (e.g., SEQ ID NO: 3), DIL1 (e.g., SEQ ID NO: 5), DIL2 (e.g., SEQ ID NO: 7), DIL3 (e.g., SEQ ID NO: 9), and/or DIL4 (e.g., SEQ ID NO: 11 (which can be part of a vector) are provided. In some examples, such plant cells have decreased expression of one or more of DIG1, DIG2, DIL1, DIL2, DIL3, and DIL4. Such transgenic plant cells can have decreased abscisic acid (ABA) sensitivity, decreased salt sensitivity, or both. In some examples, the transgenic plant cell further includes an exogenous nucleic acid molecule (e.g., transgene) that confers a desired trait into the plant cell. In some examples, the plant cell is a corn, wheat, soybean, canola, rice, peanut, or cotton plant cell.

Also provided are transgenic plants that include such transgenic cells. For example, the transgenic cells can be grown into a transgenic plant. Such transgenic plants can have decreased ABA sensitivity, decreased salt sensitivity, or both. In some examples, the transgenic plant has accelerated cotyledon greening and increased lateral root growth. In some examples, the transgenic plant has decreased ABA sensitivity, such as a decrease of at least 10%, at least 20%, at least 50%, at least 75%, at least 90%, or at least 95%, as compared to the same plant that is not transgenic (when grown in the same conditions). In some examples, the transgenic plant has decreased salt sensitivity, such as a decrease of at least 10%, at least 20%, at least 50%, at least 75%, at least 90%, or at least 95%, as compared to the same plant that is not transgenic (when grown in the same conditions). In some examples, the transgenic plant has accelerated cotyledon greening, such as an acceleration of at least 10%, at least 20%, at least 50%, or at least 75% earlier than the same plant that is not transgenic (when grown in the same conditions). In some examples, the transgenic plant has increased lateral root growth, such as an increase of at least 10%, at least 20%, at least 50%, or at least 75% as compared to the same plant that is not transgenic (when grown in the same conditions). In some examples, combinations of these effects are observed. In some examples, the transgenic plant further includes an exogenous nucleic acid molecule (e.g., transgene) that confers a desired trait into the plant.

Exemplary additional desired traits that can be present in the transgenic plant or plant cell, include one or more of herbicide tolerance, drought tolerance, heat tolerance, low or high soil pH level tolerance, salt tolerance, resistance to an insect, resistance to a bacterial disease, resistance to a viral disease, resistance to a fungal disease, resistance to a nematode, resistance to a pest, male sterility, site-specific recombination; abiotic stress tolerance, modified phosphorus characteristics, modified antioxidant characteristics; modified essential seed amino acid characteristics, decreased phytate, modified fatty acid metabolism, and modified carbohydrate metabolism. In some examples, the modified fatty acid metabolism or modified carbohydrate metabolism is produced by introducing a gene encoding one or more of glutenins, gliadins, phytase, fructosyltransferase, levansucrase, a-amylase, invertase and starch branching enzyme, or encoding an antisense of stearyl-ACP desaturase. In some examples, the resistance to an insect or pest is conferred by a transgene encoding a *Bacillus thuringiensis* (Bt) endotoxin. In some examples, the herbicide tolerance includes tolerance to an herbicide comprising glyphosate, sulfonylurea, imidazolinone, dicamba, glufosinate, phenoxy proprionic acid, L-phosphinothricin, cyclohexone, cyclohexanedione, triazine, benzonitrile, broxynil, chlorophenoxy acetic acid or combinations thereof.

Also provided are methods of inhibiting expression and/or activity of 1, 2, 3, 4, 5 or 6 of DIG1, DIG2, DIL1, DIL2, DIL3, and DIL4 in a plant cell. Such methods can include introducing into the plant cell (e.g., by transformation) an RNAi, guide nucleic acid, and/or T-DNA specific for 1, 2, 3, 4, 5 or 6 of DIG1 (e.g., SEQ ID NO: 1), DIG2 (e.g., SEQ ID NO: 3), DIL1 (e.g., SEQ ID NO: 5), DIL2 (e.g., SEQ ID NO: 7), DIL3 (e.g., SEQ ID NO: 9), and/or DIL4 (e.g., SEQ ID NO: 11) (which can be part of a vector). The RNAi, guide nucleic acid, T-DNA, or expression vector, is expressed by the plant cell, thereby inhibiting one or more of DIG1, DIG2, DIL1, DIL2, DIL3, and DIL4 in the plant cell. Such transgenic plant cells can be grown into transgenic plants.

In one example, the method of inhibiting expression and/or activity of 1, 2, 3, 4, 5 or 6 of DIG1, DIG2, DIL1, DIL2, DIL3, and DIL4 includes introducing one or more guide nucleic acids specific for 1, 2, 3, 4, 5 or 6 of DIG1 (e.g., SEQ ID NO: 1), DIG2 (e.g., SEQ ID NO: 3), DIL1 (e.g., SEQ ID NO: 5), DIL2 (e.g., SEQ ID NO: 7), DIL3 (e.g., SEQ ID NO: 9), and/or DIL4 (e.g., SEQ ID NO: 11) and introducing a Cas9 protein or a Cas9 encoding nucleic acid into the cell, thereby inhibiting one or more 1, 2, 3, 4, 5 or 6 of DIG1, DIG2, DIL1, DIL2, DIL3, and DIL4 in in the plant cell. Such transgenic plant cells can be grown into transgenic plants.

Both monocotyledonous and dicotyledonous plants can be manipulated to generate plants in which 1, 2, 3, 4, 5 or 6 of DIG1, DIG2, DIL1, DIL2, DIL3, and DIL4 are downregulated or inhibited. Representative, non-limiting example plants include *Arabidopsis*; field crops (e.g. alfalfa, barley, bean, clover, corn, cotton, flax, lentils, maize, pea, rape/canola, rice, rye, safflower, sorghum, soybean, sunflower, tobacco, and wheat); vegetable crops (e.g. asparagus, beet, *brassica* generally, broccoli, Brussels sprouts, cabbage, carrot, cauliflower, celery, cucumber (cucurbits), eggplant, lettuce, mustard, onion, pepper, potato, pumpkin, radish, spinach, squash, taro, tomato, and zucchini); fruit and nut crops (e.g. almond, apple, apricot, banana, blackberry, blueberry, cacao, cassava, cherry, citrus, coconut, cranberry, date, hazelnut, grape, grapefruit, guava, kiwi, lemon, lime, mango, melon, nectarine, orange, *papaya*, passion fruit, peach, peanut, pear, pineapple, pistachio, plum, raspberry, strawberry, tangerine, walnut, and watermelon); tree woods and ornamentals (e.g. alder, ash, aspen, azalea, birch, boxwood, *camellia*, carnation, *chrysanthemum*, elm, fir, ivy, jasmine, juniper, oak, palm, poplar, pine, redwood, *rhododendron*, rose and rubber).

Examples of ornamental plants, such as those grown for visual display, that can be modified to downregulate or inhibit expression of 1, 2, 3, 4, 5 or 6 of DIG1, DIG2, DIL1, DIL2, DIL3, and DIL4 include, for example, indoor or outdoor nursery plants, house and garden plants, and florist crops, each of which may include without limitation trees, shrubs, perennials, bulbs, annuals, groundcovers, turf grasses, herbs, or native plants.

Reducing Gene Expression

Any method in the art can be used to reduce or eliminate expression of 1, 2, 3, 4, 5, or all 6 of DIG1, DIG2, DIL1, DIL2, DIL3, and DIL4 (or a DIG related sequence, such as those shown in SEQ ID NOS: 35-49) in a plant or plant cell. For example, inhibitory RNA molecules, such as antisense molecules, siRNAs, microRNAs (miRNAs), artificial microRNAs (amiRNAs), and trans-acting small interfering RNAs (tasiRNAs) can be used, as can T-DNA insertion mutation methods and CRISPR-Cas9 methods. Thus, small RNA-directed gene silencing (e.g., using amiRNAs, syntasiRNAs, hairpin-based RNA interference, virus-induced gene silencing, and transcriptional silencing) can be used to selectively reduce or eliminate expression of 1, 2, 3, 4, 5, or all 6 of DIG1, DIG2, DIL1, DIL2, DIL3, and DIL4 in a plant or plant cell.

In some examples, a plurality of methods are used to reduce or eliminate expression of 1, 2, 3, 4, 5, or all 6 of DIG1, DIG2, DIL1, DIL2, DIL3, and DIL4 in a plant or plant cell, such as combinations of RNAi, T-DNA, and CRISPR-Cas9 methods. In one example, T-DNA mutants are used to decrease or eliminate expression of DIG1, DIG2, and/or DIL1 and CRISPR/Cas9 mutagenesis is used to decrease or eliminate expression of DIL2, DIL3, and/or DIL4.

Specific gene suppressive elements can be designed that are specific for the target sequences (e.g., 1, 2, 3, 4, 5, or all 6 of DIG1, DIG2, DIL1, DIL2, DIL3, and DIL4) to be suppressed. Gene suppressive elements (usually about 21-nucleotides in length), complementary to a target (e.g., gene transcript) to be suppressed, can be provided as an RNAi-triggering cassette, in register, in either sense or antisense orientation starting from the initiation cleavage site.

RNA Interference (RNAi)

RNAi gene silencing methods can be used to reduce or eliminate expression of 1, 2, 3, 4, 5, or all 6 of DIG1, DIG2, DIL1, DIL2, DIL3, and DIL4 (or a DIG related sequence, such as those shown in SEQ ID NOS: 35-49) in a plant or plant cell. Examples of RNAi molecules that can be used to decrease or reduce such expression include antisense molecules, siRNAs, microRNAs (miRNAs), artificial microRNAs (amiRNAs), and trans-acting small interfering RNAs (tasiRNAs). Such molecules can be generated using genetic engineering techniques or using in vitro chemical synthesis, such as the phosphoramidite method.

Antisense molecules are molecules that are specifically hybridizable or specifically complementary to either RNA or the plus strand of DNA. In one example, one or more antisense molecules are used to reduce or eliminate expression of 1, 2, 3, 4, 5, or all 6 of DIG1, DIG2, DIL1, DIL2, DIL3, and DIL4 in a plant or plant cell. For example, one or more antisense molecules specific for 1, 2, 3, 4, 5, 6 of DIG1, DIG2, DIL1, DIL2, DIL3, and DIL4 (or a DIG related sequence, such as those shown in SEQ ID NOS: 35-49) can be used.

siRNAs are a class of RNA molecules about 20-25 bp (such as 20, 21, 22, 23, 24 or 25 bp) in length. siRNA interferes with the expression of a target genes with complementary nucleotide sequences by degrading mRNA after transcription resulting in reduced or no translation. In one example, siRNA is used to reduce or eliminate expression of 1, 2, 3, 4, 5, or all 6 of DIG1, DIG2, DIL1, DIL2, DIL3, and DIL4 (or a DIG/related sequence, such as those shown in SEQ ID NOS: 35-49) in a plant or plant cell. For example, one or more siRNAs that are about 20-25 nucleotides and specific for 1, 2, 3, 4, 5, 6 of DIG1, DIG2, DIL1, DIL2, DIL3, and DIL4 (or a DIG related sequence, such as those shown in SEQ ID NOS: 35-49) can be used.

MicroRNAs (miRNAs) and trans-acting small interfering RNAs (tasiRNAs) are two classes of plant small RNAs that act in posttranscriptional RNA silencing pathways to silence target RNA transcripts with sequence complementarity. In one example, miRNA is used to reduce or eliminate expression of 1, 2, 3, 4, 5, or all 6 of DIG1, DIG2, DIL1, DIL2, DIL3, and DIL4 in a plant or plant cell. For example, one or more miRNAs that are about 22 nucleotides and specific for 1, 2, 3, 4, 5, 6 of DIG1, DIG2, DIL1, DIL2, DIL3, and DIL4 (or a DIG related sequence, such as those shown in SEQ ID NOS: 35-49) can be used. In one example, tasiRNA is used to reduce or eliminate expression of 1, 2, 3, 4, 5, or all 6 of DIG1, DIG2, DIL1, DIL2, DIL3, and DIL4 (or a DIG related sequence, such as those shown in SEQ ID NOS: 35-49) in a plant or plant cell. For example, one or more tasiRNAs that are about 21 nucleotides and specific for 1, 2, 3, 4, 5, 6 of DIG1, DIG2, DIL1, DIL2, DIL3, and DIL4 (or a DIG related sequence, such as those shown in SEQ ID NOS: 35-49) can be used.

amiRNA-mediated gene silencing is a type of homology-based gene silencing that can be used to repress or eliminate gene expression (see for example, Tiwari et al., *Plant Mol. Biol.* 86:1-18, 2014 and Carbonell et al., *Plant Physiol* 165:15-29, 2014). Similar to microRNAs, amiRNAs are single-stranded, approximately 21 nt long, and designed by replacing the mature miRNA sequences of duplex within pre-miRNAs. These amiRNAs are processed via small RNA biogenesis and silencing machinery and deregulate target expression. In one example, amiroRNA is used to reduce or eliminate expression of 1, 2, 3, 4, 5, or all 6 of DIG1, DIG2, DIL1, DIL2, DIL3, and DIL4 (or a DIG related sequence, such as those shown in SEQ ID NOS: 35-49) in a plant or plant cell.

RNAi sequences specific for 1, 2, 3, 4, 5 or 6 of DIG1, DIG2, DIL1, DIL2, DIL3, and DIL4 (or a DIG related sequence, such as those shown in SEQ ID NOS: 35-49) can be generated using routine methods, based on the sequences provided herein. The RNAi sequence can be operably linked to a promoter or other regulatory sequence which governs transcription of the RNAi. In some examples, the RNAi sequence is part of a vector. Other construct components may include additional regulatory elements, such as 5' introns for enhancing transcription, 3' untranslated regions (such as polyadenylation signals and sites), DNA for transit or signal peptides.

Vectors suitable for stable transformation of culturable cells are known. Typically, such vectors include a multiple-cloning site suitable for inserting a cloned nucleic acid molecule, such that it will be under the transcriptional control of 5' and 3' regulatory sequences. In addition, transformation vectors include one or more selectable markers; such as an antibiotic resistance gene. Such plant expression vectors also can contain a promoter regulatory region (e.g., a regulatory region controlling inducible or constitutive, environmentally- or developmentally-regulated, or cell- or tissue-specific expression), a transcription initiation start site, a ribosome binding site, an RNA processing signal, a transcription termination site, and/or a polyadenylation signal. A number of vectors suitable for stable transformation of plant cells or for the establishment of transgenic plants have been described in, e.g., Pouwels et al. (*Cloning Vectors: A Laboratory Manual,* 1985, Suppl., 1987), Weissbach and Weissbach (*Meth. Plant Mol. Bio.*, Academic Press, 1989) and Gelvin et al. (*Plant Molecular Biology Manual*, Kluwer Academic Publishers, 1990).

CRISPR-Cas9 and Other Nuclease Systems

Nucleases can be targeted to a specific nucleic acid sequence (such as 1, 2, 3, 4, 5 or 6 of DIG1, DIG2, DIL1, DIL2, DIL3, and DIL4, or a DIG related sequence, such as those shown in SEQ ID NOS: 35-49) to generate DNA strand breaks for the purposes of gene editing. CRISPR-Cas9 systems, transcription activator-like effector nucleases (TALENs), zinc finger nucleases (ZFNs), and FokI restriction enzymes are some of the sequence-specific nucleases that have been used as gene editing tools. These enzymes target their nuclease activities to desired target loci through interactions with guide regions engineered to recognize sequences of interest. Thus, any of these systems can be used in the disclosed methods to decrease expression of 1, 2, 3, 4, 5, or 6 of DIG1, DIG2, DIL1, DIL2, DIL3, and DIL4 (or a DIG related sequence, such as those shown in SEQ ID NOS: 35-49).

Clustered regularly interspaced short palindromic repeats (CRISPRs) and CRISPR associated genes (cas) are components of nucleic acid-based adaptive immune systems that are widespread in bacteria and archaea (Sorek et al., Annu. Rev. Biochem. 2013 Mar. 11; 82:237-266). Foreign genetic material from a virus or a plasmid is acquired by and stored in a CRISPR complex, and this information is used to recognize and degrade complementary nucleic acids upon subsequent invasion. Each CRISPR locus includes of a series of short repeats separated by non-repetitive spacer sequences. The non-repetitive spacer sequences are acquired from foreign genetic elements such as viruses and plasmids. Transcription of CRISPR loci generates a library of CRISPR-derived RNAs (crRNAs) containing sequences complementary to previously encountered invading nucleic acids (Haurwitz et al., Science. 2012:329; 1355). In general, a crRNA (e.g., a guide sequence) can be designed to target any nucleotide sequence (such as 1, 2, 3, 4, 5, or 6 of DIG1, DIG2, DIL1, DIL2, DIL3, and DIL4, or a DIG related sequence, such as those shown in SEQ ID NOS: 35-49). crRNA are incorporated into a ribonucleoprotein complex containing CRISPR-associated (Cas) proteins which scans the intracellular environment for invading nucleic acid sequences complementary to the crRNA spacer (Wiedenheft et al., PNAS 2011; 108:10092-10097; Rollins et al., Nucl. Acids Res. 8 Feb. 2015; published online. doi: 10.1093/nar/gkv094).

Efficient detection of invading nucleic acids (e.g., DNA) relies on complementary base pairing between the target and the guide sequence, in addition to recognition of a short sequence motif immediately adjacent to the target (i.e., a protospacer-adjacent motif (PAM)) (Jore et al., Nat. Struct. Mol. Biol. 2011 May; 18:529-536; Westra et al., PLoS Genet 2013 Sep. 5; 9:e1003742; Semenova et al. PNAS 2011; Rollins et al., NAR 2015). Target recognition by guide sequence (e.g., DNA or RNA) occurs through complementary base pairing with target sequence (e.g., DNA or RNA), which directs cleavage of foreign sequences by means of Cas proteins. This target nucleotide recognition mechanism allows for CRISPR technology to be repurposed for sequence-specific genome editing.

Three main CRISPR system types (Type I, II, and III) and numerous subtypes that encode distinct guide surveillance complexes have been identified (Makarova et al., Nat Rev Microbiol. 2011 May 9; 9(6):467-477). Type II systems rely on a single protein (Cas9) and a single guide sequence (e.g., sgRNA) for recognition of invading DNA (Sternberg et al., Nature. 2014 Mar. 6; 507:62-67). Most CRISPR systems use short CRISPR-derived RNAs (crRNAs) to target invading nucleic acid, and many of these nucleic acid targeting systems rely on sophisticated multi-subunit complexes. Some of the multi-subunit crRNA-guided complexes (e.g., Cascade, Csm, Cmr, and Csy) have longer guide sequences that can be exploited to increase the accuracy of target recognition. For example, the type I-F CRISPR-mediated adaptive immune system known as Csy consists of a nine protein subunit ribonucleoprotein complex and a 60 nucleotide (nt) crRNA region that participates in target recognition (Wiedenheft, Proc. Natl. Acad. Sci. USA. 2011; 108:10092-10097). Target recognition by CRISPR-Csy is initiated by detection of a double-stranded PAM located adjacent to the complementary DNA target (Rollins et al., Nucl. Acids Res. 8 Feb. 2015; published online. doi: 10.1093/nar/gkv094).

Thus, the CRISPR/Cas9 system can be used for gene editing in a cell, such as a plant cell, to decrease expression of 1, 2, 3, 4, 5 or 6 of DIG1, DIG2, DIL1, DIL2, DIL3, and DIL4 (or a DIG related sequence, such as those shown in SEQ ID NOS: 35-49). Generally, the CRISPR/Cas9 system includes (1) a Cas9 protein and (2) single guide nucleic acid molecule, such as RNA (sgRNA or gRNA), which is operably linked downstream of a target sequence and upstream of a promoter (such as the U6 promoter). When introduced into cells (for example as part of a single vector or plasmid or divided into multiple vectors or plasmids), the guide nucleic acid molecule guides the Cas9 to the locus and Cas9 cuts the target site. Cas9 unwinds the DNA duplex and cleaves one or both strands upon recognition of a target sequence by the guide nucleic acid molecule, but only if the correct protospacer-adjacent motif (PAM) is present at the 3' end. Non-homologous end joining (NHEJ) repair of this cut will result in small insertions and deletions (indels), so the technique can be used to knockout genes. If short, homologous DNA is also included in the transfection, the technique can also be used to insert this DNA into the cut site through HDR. Using this system, DNA sequences within the endogenous genome and their functional outputs are easily edited or modulated.

In some examples a plurality of different guide nucleic acid molecules (e.g., gRNAs), one for each target (such as 1, 2, 3, 4, 5, or 6 of DIG1, DIG2, DIL1, DIL2, DIL3, and DIL4, or a DIG related sequence, such as those shown in SEQ ID NOS: 35-49), are used, and can be present on a single plasmid or multiple plasmids. In some examples, a plurality of different guide nucleic acid molecules (e.g., gRNAs) are used for each target (such as DIG1, DIG2, DIL1, DIL2, DIL3, or DIL4) and can be present on a single plasmid or multiple plasmids.

The Cas9 protein and the guide nucleic acid molecule(s) specific for the target gene(s) (such as 1, 2, 3, 4, 5, or 6 of DIG1, DIG2, DIL1, DIL2, DIL3, and DIL4, or a DIG related sequence, such as those shown in SEQ ID NOS: 35-49) can be introduced into a target cell directly, or expressed recombinantly (e.g., from one or more vectors).

In one example, the Cas9 protein is expressed from a nucleic acid molecule introduced into the target cells containing a target gene whose expression is desired to be controlled, for example as a plasmid DNA, mRNA, or stably integrated copies into the target genome. In one example, the guide molecule(s) (e.g., gRNA) specific for the target whose expression is to be controlled is expressed from plasmid DNA or stably integrated copies into the target genome. The nucleic acid molecules expressed in the target cell can be under the control of a promoter (such as CMV, H1, U6, EC1.2 and YAO, for example such as EC1.2 or YAO to express Cas9, and U6 promoter to express gRNA) and contain one or more selection markers (such as antibiotic resistance).

In one example, multiple plasmids or vectors are used for the gene editing. The nucleic acid molecule encoding Cas9 can be provided for example on one vector or plasmid, and the guide nucleic acid molecule (e.g., gRNA) on yet another plasmid or vector. Multiple plasmids can be mixed and transfected into cells at the same time, for example using *Agrobacterium*-mediated transformation, floral dip methods, or callus formation. In some examples, multiple nucleic acid molecules are expressed from a single vector or plasmid. For example, a single plasmid can include the nucleic acid molecule encoding the Cas9 and the guide nucleic acid molecule(s).

In some examples, the Cas9 protein and/or the guide nucleic acid molecule(s) are introduced as separate components into the target plant cell. In other examples, the purified Cas9 protein is charged with the guide nucleic acid (e.g., gRNA), and this complex is introduced into target cells (e.g., using transfection or injection). Once the Cas9 protein and guide nucleic acid molecule are in the cell, gene expression can be controlled.

T-DNA Insertion Mutation

*Agrobacterium* transfer DNA (T-DNA) is an effective plant mutagen that has been used to create sequence-indexed T-DNA insertion (see for example O'Malley et al., Nat. Protocols 2:2910-7, 2007 and Alonso et al., Science 301: 653-7, 2003, herein incorporated by reference in their entireties). Thus, T-DNA insertion mutation methods can be used in the disclosed methods to decrease expression of 1, 2, 3, 4, 5, or 6 of DIG1, DIG2, DIL1, DIL2, DIL3, and DIL4 (or a DIG related sequence, such as those shown in SEQ ID NOS: 35-49).

Directed mutagenesis can be performed using Ti plasmid containing the pYAO:hSpCas9-U6:target-sgRNA cassette according to Yan et al. (*Mol Plant* 8:1820-3, 2015). Plants can be transformed with an appropriate T-DNA as follows. Seeds of the desired plant can be germinated, and when the inflorescences reach approximately 10 cm, plants can be vacuum-infiltrated using *Agrobacterium tumefaciens* (such as strain C58) that harbors the appropriate vector(s). Floral stems can be submerged in the *Agrobacterium*-containing infiltration media.

Exemplary Promoters

The methods of reducing or inhibiting expression of 1, 2, 3, 4, 5, or all 6 of DIG1, DIG2, DIL1, DIL2, DIL3, and DIL4 (or a DIG related sequence, such as those shown in SEQ ID NOS: 35-49) can utilize a promoter, for example operably linked to an RNAi or guide nucleic acid molecule. Such a construct can be part of a vector. Promoters are nucleic acid control sequences which direct transcription of a nucleic acid. A promoter includes necessary nucleic acid sequences near the start site of transcription, such as, in the case of an RNA polymerase II type promoter, a TATA element. Optionally, a promoter may include an enhancer and/or a repressor element. Enhancer and repressor elements can be located adjacent to, or distal to the promoter, and can be located as much as several thousand base pairs from the start site of transcription. Examples of promoters that can be used in the present disclosure include, but are not limited to the Cauliflower mosaic virus 35S promoter, SV40 promoter, the CMV enhancer-promoter, the CMV enhancer/β-actin promoter, DNA polymer II promoter, and the tissue-specific promoter probasin. Other promoter sequences that can be used to construct nucleic acids and practice methods disclosed herein include, but are not limited to: the lac system, the trp system, the tac system, the trc system, major operator and promoter regions of phage lambda, the control region of fd coat protein, the early and late promoters of SV40, promoters derived from polyoma, adenovirus, retrovirus, baculovirus and simian virus, the promoter for 3-phosphoglycerate kinase, the promoters of yeast acid phosphatase, the promoter of the yeast alpha-mating factors, any retroviral LTR promoter such as the RSV promoter; inducible promoters, such as the MMTV promoter; the metallothionein promoter; heat shock promoters; the albumin promoter; the histone promoter; the α-actin promoter; TK promoters; B19 parvovirus promoters; the SV10 late promoter; the ApoAI promoter and combinations thereof.

In certain embodiments, a promoter is a strong promoter, which promotes transcription of RNA at high levels, for example at levels such that the transcriptional activity of the promoter generally accounts for about 5% or more of the transcriptional activity of all transcription within a cell. The strength of a promoter is often tissue-specific and thus may vary from one cell type to another. Examples of strong promoters include, but are not limited to: viral promoters (such as CaMV 35S or CoYMV), ubiquitin promoter (such as Ubi-1 from maize), actin promoter (e.g, Act from rice), nopaline synthase promoter, and the octopine synthase promoter, pEMU promoter, MAS promoter, or a H3 histone promoter.

In another embodiment, a promoter is a tissue-specific, cell-specific, or developmental stage-specific promoter, which promotes transcription in a single cell or tissue type, a narrow range of cells or tissues, or in one or more specific developmental stages, or at least promotes measurable more transcription in such. Examples of such promoters include, but are not limited to: anther-specific, embryo-specific, endosperm-specific, floral-specific, leaf-specific, meristem-specific, nodule-specific, phloem-specific, seed-specific, stem-specific, stomata-specific, trichome-specific, root-specific, tapetum-specific, and xylem-specific promoters. See, for instance, Carpenter et al., *The Plant Cell* 4:557-571, 1992, Denis et al., *Plant Physiol.* 101:1295-1304 1993, Opperman et al., *Science* 263:221-223, 1993, Stockhause et al., *The Plant Cell* 9:479-489, 1997; Roshal et al., *EMBO J.* 6:1155, 1987; Schernthaner et al., *EMBO J.* 7:1249, 1988; and Bustos et al., *Plant Cell* 1:839, 1989.

Inducible promoters or gene-switches are used to both spatially and temporally regulate gene expression. By allowing the time and/or location of gene expression to be precisely regulated, gene-switches or inducible promoters may control deleterious and/or abnormal effects caused by overexpression or non-localized gene expression. Thus, for a typical inducible promoter in the absence of the inducer, there would be little or no gene expression while, in the presence of the inducer, expression should be high (i.e., off/on). Examples of stimulus-responsive promoters include, but are not limited to hormone-responsive promoters (e.g., ethanol inducible alcR-encoded transcriptional activator (ALCR), a promoter derived from alcA), light-inducible promoters (such as a rbcS promoter), metal-inducible promoters, heat-shock promoters, wound-inducible and stress-inducible (e.g., drought stress, salt stress, shear stress, nutrient stress) promoters. Others are activated by chemical stimuli, such as IPTG or Tetracycline (Tet), or galactose. Other promoters are responsive to pathogen infection or insect damage.

Controllable gene expression systems are known, including those regulated by light (e.g., the pea rbcS-3A promoter, Kuhlemeier et al., The *Plant Cell,* 1:471-478, 1989, and the maize rbcS promoter, Schaffner and Sheen, *Plant Cell* 3:997, 1991), heat (Callis et al., *Plant Physiol.* 88:965, 1988; Ainley and Key, *Plant Mol. Biol.,* 14:949-967, 1990; Holtorf et al., *Plant Mol. Biol.* 29:637-646, 1995), pathogens (PR1-a; Williams et al., *Biotechnology* 10:540-543, 1992; Gatz, *Annu. Rev. Plant Physiol. Plant Mol. Biol.* 48:89-108, 1997), herbicide safeners (In2-2, GST-27; De Veylder et al., *Plant Cell Physiol.* 38:568-577, 1997), light (Kuhlemeier et al., *Plant Cell* 1:471-478, 1989), wounding (Firek et al. *Plant Mol. Biol.* 22:129-212, 1993), ethanol (Salter et al., *Plant J.* 16:127-132, 1998), phytohormones (Li et al., *Plant Cell* 3:1167-1175, 1991), steroids (Aoyama and Chua, *Plant J.,* 11:605-612, 1997), wounding (e.g., wunI, Siebertz et al., *Plant Cell* 1:961, 1989), hormones, such as abscisic acid (Marcotte et al., *Plant Cell* 1:969, 1989); chemicals such as methyl jasminate or salicylic acid (see Gatz et al., *Ann. Rev. Plant Physiol. Plant Mol. Biol.* 48:89-108 1997), and tetracycline (Gatz et al., *Plant J.* 2:397-404, 1992; Weinmann et al., *Plant J.,* 5:559-569, 1994; Sommer et al., *Plant Cell Rep.* 17:891-896, 1998) (from Granger & Cyr, *Plant Cell Reports* 20:227-234, 2001).

Promoters that can be used with the methods and vectors provided herein include promoters present in plant genomes as well as promoters from other sources, including nopaline synthase (nos) promoter and octopine synthase (ocs) promoters carried on tumor-inducing plasmids of *Agrobacterium tumefaciens*, caulimovirus promoters such as the cauliflower mosaic virus or figwort mosaic virus promoters. For instance, see U.S. Pat. Nos. 5,322,938 and 5,858,742 which disclose versions of the constitutive promoter derived from cauliflower mosaic virus (CaMV35S), U.S. Pat. No. 5,378,619 which discloses a Figwort Mosaic Virus (FMV) 35S promoter, U.S. Pat. No. 5,420,034 which discloses a napin promoter, U.S. Pat. No. 6,437,217 which discloses a maize RS81 promoter, U.S. Pat. No. 5,641,876 which discloses a rice actin promoter, U.S. Pat. No. 6,426,446 which discloses a maize RS324 promoter, U.S. Pat. No. 6,429,362 which discloses a maize PR-1 promoter, U.S. Pat. No. 6,232,526 which discloses a maize A3 promoter, U.S. Pat. No. 6,177,611 which discloses constitutive maize promoters, U.S. Pat. No. 6,433,252 which discloses a maize L3 oleosin promoter, U.S. Pat. No. 6,429,357 which discloses a rice actin 2 promoter and intron, U.S. Pat. No. 5,837,848 which discloses a root specific promoter, U.S. Pat. No. 6,084,089 which discloses cold inducible promoters, U.S. Pat. No. 6,294,714 which discloses light inducible promoters, U.S. Pat. No. 6,140,078 which discloses salt inducible promoters, U.S. Pat. No. 6,252,138 which discloses pathogen inducible promoters, U.S. Pat. No. 6,175,060 which discloses phosphorus deficiency inducible promoters, U.S. Pat. No. 6,635,806 which discloses a coixin promoter, U.S. 2002/0192813 A1 which discloses 5', 3' and intron elements useful in the design of effective plant expression vectors, U.S. 2004/0216189 A1 which discloses a maize chloroplast aldolase promoter, and U.S. 2004/0123347 A1 which discloses water-deficit inducible promoters, all of which are incorporated herein by reference. These and numerous other promoters that function in plant cells are known to those skilled in the art and available for use in recombinant polynucleotides of the present disclosure to provide for expression of desired genes in transgenic plant cells.

Furthermore, the promoters may be altered to contain multiple "enhancer sequences" to assist in elevating gene expression. Such enhancers are known in the art. By including an enhancer sequence with such constructs, the expression of the selected protein may be enhanced. These enhancers often are found 5' to the start of transcription in a promoter that functions in eukaryotic cells, but can often be inserted upstream (5') or downstream (3') to the coding sequence. In some instances, these 5' enhancing elements are introns. Exemplary enhancers are the 5' introns of the rice actin 1 (see U.S. Pat. No. 5,641,876) and rice actin 2 genes, the maize alcohol dehydrogenase gene intron, the maize heat shock protein 70 gene intron (U.S. Pat. No. 5,593,874) and the maize shrunken 1 gene.

In other aspects, sufficient expression in plant seed tissues is desired to effect improvements in seed composition. Exemplary promoters for use for seed composition modification include promoters from seed genes such as napin (U.S. Pat. No. 5,420,034), maize L3 oleosin (U.S. Pat. No. 6,433,252), zein Z27 (Russell et al. (1997) *Transgenic Res.* 6(2):157-166), globulin 1 (Belanger et al (1991) *Genetics* 129:863-872), glutelin 1 (Russell (1997) supra), and peroxiredoxin antioxidant (Per1) (Stacy et al. (1996) *Plant Mol Biol.* 31(6):1205-1216).

Recombinant Constructs and Vectors

The methods of reducing or inhibiting expression of 1, 2, 3, 4, 5, or all 6 of DIG1, DIG2, DIL1, DIL2, DIL3, and DIL4 (or a DIG related sequence, such as those shown in SEQ ID NOS: 35-49) can utilize a recombinant RNAi or guide nucleic acid molecule, which can be part of a vector. Recombinant nucleic acid constructs prepared in accordance with this disclosure can include a 3' element that typically contains a polyadenylation signal and site, especially if the recombinant nucleic acid is intended for protein expression as well as gene suppression. 3' elements include those from *Agrobacterium tumefaciens* genes such as nos 3', tml 3', tmr 3', tms 3', ocs 3', tr7 3', e.g. disclosed in U.S. Pat. No. 6,090,627, incorporated herein by reference; 3' elements from plant genes such as wheat (*Triticum aesevitum*) heat shock protein 17 (Hsp17 3'), a wheat ubiquitin gene, a wheat fructose-1,6-biphosphatase gene, a rice glutelin gene a rice lactate dehydrogenase gene and a rice beta-tubulin gene, all of which are disclosed in U.S. published patent application 2002/0192813 A1, incorporated herein by reference; and the pea (*Pisum sativum*) ribulose biphosphate carboxylase gene (rbs 3'), and 3' elements from the genes within the host plant.

Constructs and vectors may also include a transit peptide for targeting of a gene target to a plant organelle, e.g., to a chloroplast, leucoplast or other plastid organelle. For descriptions of the use of chloroplast transit peptides see U.S. Pat. Nos. 5,188,642 and 5,728,925, incorporated herein by reference. For description of the transit peptide region of an *Arabidopsis* EPSPS gene see Klee et al., (MGG 210:437-442, 1987).

Plant expression vectors optionally include RNA processing signals, e.g., introns, which may be positioned upstream or downstream of a polypeptide-encoding sequence in the transgene. In addition, the expression vectors may also include additional regulatory sequences from the 3'-untranslated region of plant genes, e.g., a 3' terminator region to increase mRNA stability of the mRNA, such as the PI-II terminator region of potato or the octopine or nopaline synthase 3' terminator regions.

Such vectors also generally include one or more dominant selectable marker genes, including genes encoding antibiotic resistance (e.g., resistance to hygromycin, kanamycin, bleomycin, G418, streptomycin, paromomycin, or spectinomycin) and herbicide-resistance genes (e.g., resistance to phosphinothricin acetyltransferase or glyphosate) to facilitate manipulation in bacterial systems and to select for transformed plant cells.

Screenable markers are also used for cell transformation including color markers such as genes encoding ß-glucuronidase (gus) or anthocyanin production, or fluorescent markers such as genes encoding luciferase or green fluorescence protein (GFP).

Delivery of Constructs to Target Cells

Once a nucleic acid molecule (e.g., synthetic construct) for use in RNAi, CRISPR-Cas9, or T-DNA mutation methods is generated, standard techniques may be used to express the encoded molecule(s) (e.g., guide RNA, siRNA, amiRNA) in a transgenic cell, transgenic seed or transgenic plant. The basic approach is to clone, for instance, the synthetic construct into a transformation vector, such that it is operably linked to control sequences (e.g., a promoter) that direct expression of the nucleic acid in target plant cells. The transformation vector is then introduced into the target cells and progeny containing the introduced nucleic acid construct are selected. In some embodiments, all or part of the transformation vector will stably integrate into the genome of the target plant cell. That part of the transformation vector that integrates into the target plant cell and that contains the introduced RNAi, CRISPR-Cas9, or T-DNA construct and associated sequences for controlling expression (the introduced "transgene") can be referred to as the recombinant expression cassette. Selection of progeny plants containing the introduced transgene may be based upon the detection of an altered phenotype (e.g., decreased ABA sensitivity, decreased salt sensitivity, or both). Such a phenotype may result directly from the synthetic construct cloned into the transformation vector or may be manifested as enhanced (or reduced) resistance to a chemical agent (such as an antibiotic) as a result of the inclusion of a selectable marker gene incorporated into the transformation vector.

Transformation and regeneration of both monocotyledonous and dicotyledonous plant cells is routine. Suitable methods may include, but are not limited to: electroporation of plant protoplasts; liposome-mediated transformation; polyethylene glycol (PEG) mediated transformation; transformation using viruses; micro-injection of plant cells; microprojectile bombardment of plant cells; vacuum infiltration; and *Agrobacterium tumefaciens* (AT) mediated transformation.

Following transformation and regeneration of plants with the transformation vector, transformed plants may be selected using a dominant selectable marker incorporated into the transformation vector. Such a marker can confer antibiotic or herbicide resistance on the seedlings of transformed plants, and selection of transformants can be accomplished by exposing the seedlings to appropriate concentrations of the antibiotic or herbicide.

After transformed plants are selected and grown to maturity, they can be assayed using the methods described herein, and other methods appropriate to the synthetic construct of the transgene, to determine whether the introduced nucleic acid molecules are being produced, and/or whether the target gene(s) (e.g., 1, 2, 3, 4, 5, or all 6 of DIG1, DIG2, DIL1, DIL2, DIL3, and DIL4, or a DIG related sequence, such as those shown in SEQ ID NOS: 35-49) are measurably inhibited as a result of the introduced transgene.

Numerous methods for transforming plant cells with recombinant DNA are known in the art. Two commonly used methods for plant transformation are *Agrobacterium*-mediated transformation and microprojectile bombardment. Microprojectile bombardment methods are illustrated in U.S. Pat. No. 5,015,580 (soybean); U.S. Pat. No. 5,550,318 (corn); U.S. Pat. No. 5,538,880 (corn); U.S. Pat. No. 5,914, 451 (soybean); U.S. Pat. No. 6,160,208 (corn); U.S. Pat. No. 6,399,861 (corn) and 6,153,812 (wheat) and *Agrobacterium*-mediated transformation is described in U.S. Pat. No. 5,159,135 (cotton); U.S. Pat. No. 5,824,877 (soybean); U.S. Pat. No. 5,591,616 (corn); and 6,384,301 (soybean), all of which are incorporated herein by reference. For *Agrobacterium tumefaciens* based plant transformation system, additional elements present on transformation constructs will include T-DNA left and right border sequences to facilitate incorporation of the recombinant polynucleotide into the plant genome.

Transformation methods can be practiced in tissue culture on media and in a controlled environment. "Media" refers to the numerous nutrient mixtures that are used to grow cells in vitro, that is, outside of the intact living organism. Recipient cell targets0 include, but are not limited to, meristem cells, callus, immature embryos and gametic cells such as microspores, pollen, sperm and egg cells. It is contemplated that any cell from which a fertile plant may be regenerated is useful as a recipient cell. Callus may be initiated from tissue sources including, but not limited to, immature embryos, seedling apical meristems, microspores and the like. Cells capable of proliferating as callus are also recipient cells for genetic transformation. Practical transformation methods and materials for making transgenic plants, e.g. various media and recipient target cells, transformation of immature embryos and subsequent regeneration of fertile transgenic plants are disclosed in U.S. Pat. Nos. 6,194,636 and 6,232,526, which are incorporated herein by reference.

The seeds of transgenic plants can be harvested from fertile transgenic plants and be used to grow progeny generations of transformed plants including hybrid plants line for screening of plants having an enhanced agronomic trait (e.g., decreased ABA sensitivity, decreased salt sensitivity, or both). In addition to direct transformation of a plant with a recombinant nucleic acid molecule (such as DNA or RNA), transgenic plants can be prepared by crossing a first plant having a recombinant nucleic acid molecule with a second plant lacking the nucleic acid molecule. For example, recombinant nucleic acid molecule(s) can be introduced into first plant line that is amenable to transformation to produce a transgenic plant which can be crossed with a second plant line to introgress the recombinant nucleic acid molecule into the second plant line. A transgenic plant with recombinant nucleic acid molecule providing an enhanced agronomic trait, e.g. decreased ABA sensitivity, decreased salt sensitivity, or both, can be crossed with transgenic plant line having other recombinant nucleic acid molecule that confers another desirable agronomic trait, e.g. herbicide resistance or pest resistance, to produce progeny plants having recombinant nucleic acid molecule that confers both traits. Typically, in such breeding for combining traits the transgenic plant donating the additional trait is a male line and the transgenic plant carrying the base traits is the female line. The progeny of this cross will segregate such that some of the plants will carry the DNA for both parental traits and some will carry DNA for one parental trait; such plants can be identified by markers associated with parental recombinant DNA Progeny plants carrying DNA for both parental traits can be crossed back into the female parent line multiple times, e.g. usually 6 to 8 generations, to produce a progeny plant with substantially the same genotype as one original transgenic parental line but for the recombinant DNA of the other transgenic parental line Marker genes provide an efficient system for identification of those cells that are stably transformed by receiving and integrating a transgenic nucleic acid molecule construct into their genomes. Exemplary marker genes provide selective markers which confer resistance to a selective agent, such as an antibiotic or herbicide. Any of the herbicides to which plants may be resistant are useful agents for selective markers. Potentially transformed cells are exposed to the selective agent. In the population of surviving cells will be those cells where, generally, the resistance-conferring gene is integrated and expressed at sufficient levels to permit cell survival. Cells may be tested further to confirm stable integration of the exogenous nucleic acid molecule. Commonly used selective marker genes include those conferring resistance to antibiotics such as kanamycin and paromomycin (nptII), hygromycin B (aph IV) and gentamycin (aac3 and aacC4) or resistance to herbicides such as glufosinate (bar or pat) and glyphosate (aroA or EPSPS). Examples of such selectable are illustrated in U.S. Pat. Nos. 5,550,318; 5,633,435; 5,780,708 and 6,118,047, all of which are incorporated herein by reference. Screenable markers which provide an ability to visually identify transformants can also be employed, e.g., a gene expressing a colored or fluorescent protein such as a luciferase or green fluorescent protein (GFP) or a gene expressing a beta-glucuronidase or uidA gene (GUS) for which various chromogenic substrates are known.

Cells that survive exposure to the selective agent, or cells that have been scored positive in a screening assay, may be cultured in regeneration media and allowed to mature into plants. Developing plantlets can be transferred to plant growth mix, and hardened off, e.g., in an environmentally controlled chamber at about 85% relative humidity, 600 ppm $CO_2$, and 25-250 microeinsteins $m^{-2}$ $s^{-1}$ of light, prior to transfer to a greenhouse or growth chamber for maturation. Plants are regenerated from about 6 weeks to 10 months after a transformant is identified, depending on the initial tissue. Plants may be pollinated using conventional plant breeding methods known to those of skill in the art and seed produced, e.g. self-pollination is commonly used with transgenic corn. The regenerated transformed plant or its progeny seed or plants can be tested for expression of the recombinant DNA and screened for the presence of enhanced agronomic trait.

Transgenic Plants and Seeds

Transgenic plant seeds provided herein are grown to generate transgenic plants having decreased ABA sensitivity, decreased salt sensitivity, or both as compared to a control plant (such as a plant with a native or wild-type DIG1, DIG2, DIL1, DIL2, DIL3, DIL4, or DIG-related sequence). Seed for plants with decreased ABA sensitivity, decreased salt sensitivity, or both is identified by screening transformed plants, progeny, or progeny seed for the enhanced trait(s). A screening program can be used to evaluate multiple transgenic plants (events) comprising the recombinant DNA, e.g. multiple plants from 2 to 20 or more transgenic events.

Transgenic plants grown from transgenic seed provided herein demonstrate improved agronomic traits, such as decreased ABA sensitivity, decreased salt sensitivity, or both that contribute to accelerated cotyledon greening, increased lateral root growth, or both. In some examples, such plants have enhanced yield resulting from improved plant growth and development, stress tolerance, improved seed development, higher light response, improved flower development, or improved carbon and/or nitrogen metabolism Some transgenic events which survive to fertile transgenic plants that produce seeds and progeny plants will not exhibit decreased ABA sensitivity, decreased salt sensitivity, or both. Screening can be used to identify the transgenic plant having decreased ABA sensitivity, decreased salt sensitivity, or both from populations of plants transformed as described herein by evaluating ABA sensitivity, salt sensitivity, or both in a variety of assays to detect the agronomic trait.

The following examples are provided to illustrate certain particular features and/or embodiments. These examples should not be construed to limit the invention to the particular features or embodiments described.

Example 1

Materials and Methods

This example describes the materials and methods used to obtain the results discussed in Examples 2-5 below. Additional information can be found in Song et al., "A transcription factor hierarchy defines an environmental stress response network," *Science*, Vol. 354, Issue 6312, 4 Nov. 2016, herein incorporated by reference in its entirety.
Plant Materials Recombineering lines for the ChIP-seq experiments were generated as previously described (19) with minor modifications. A YPet-6×His-3×FLAG tag and a 3×FLAG-YPet tag were designed for C-terminus and N-terminus fusion to the TFs of interest (Table 2, FIG. 20). To abolish weak dimerization of YPet (45), an A206K point mutation was introduced by primers 5'-ATCCTTGAAGAGCTTA-GACTGGTAAGA-3' (SEQ ID NO: 31) and 5'-TCT-TACCAGTCTAAGCTCTTCAAGGAT-3' (SEQ ID NO: 32). After floral dip of wild-type Col-0 plants, T1 seeds were pooled and transgenic plants were selected on plates containing 1× Linsmaier and Skoog (LS) pH buffered basal salts, pH 5.7 (Caisson laboratories, UT, USA, cat. #LSP03-1LT) with 0.7% agar and 15 µg/ml glufosinate ammonium (Fisher Scientific, NH, USA, cat. #N-12111-250MG). Single-insertional transgenic lines were selected by Chi-square test from T2 plants on 1× LS plates containing 15 µg/ml glufosinate ammonium. The expression of the tagged TFs was confirmed by western blotting. Homozygous transgenic lines were selected from the subsequent generation for bulking seeds. DEX-inducible lines for the functional characterization of DIGs were generated by cloning the coding sequence of DIGs into p35S::LhGR-p6xOP::mGFP-attL1-ccdB-attR1 cassette by LR combination. After floral dip of wild-type Col-0 plants, T1 seeds were pooled and transgenic plants were selected by hygromycin.
ChIP-Seq Experiments and Analysis 0.4 g seeds were surface sterilized by 50% bleach+0.05% Triton-X100 for 10 minutes. After 4 days of stratification at 4° C., seeds were spread on nylon mesh (Component Supply, FL, USA, cat. #U-CMN-215) in 6 hydroponics (Sigma-Aldrich, MO, USA, cat. #P1552) containing 1× pH buffered LS basal salts. After exposure under light for 4 hours to enhance germination, seeds were grown in dark at 22° C. for 3 days. Etiolated seedlings were then switched to 1× LS buffer containing either (+/−)-ABA (MP biomedicals LLC, CA, USA, cat. #190673) dissolved in 100% ethanol at a final concentration of 10 µM or ethanol alone as mock and treated for 4 hours in dark before ChIP as previously described (46). Briefly, harvested seedlings were cross-linked by 1% formaldehyde solution (Sigma-Aldrich, cat. #F8775) under vacuum for 20 minutes. After nuclei isolation, chromatin was sonicated to 100-400 bp fragments. Tagged TFs in the transgenic lines were immunoprecipitated by a rabbit polyclonal anti-GFP antibody (Thermo Fisher Scientific, MA, USA, cat. #A11122). After elution, reverse crosslinking and DNA purification, Illumina TruSeq libraries were constructed according to manufacturer's protocols. All ChIP-seq experiments in both ABA and ethanol mock-treatment conditions were done with biological replicates. Uniquely mapped sequencing reads to the TAIR10 genome assembly (Bowtie v0.12.7) (47, 48) were used to call peaks by the IDR pipeline utilizing MACS2 (49) with mock IP of wild-type Col-0 ChIPped by the anti-GFP antibody as a control. Peaks with a p-value<=1e-16 were kept and differential binding of TFs were analyzed by DiffBind (v1.10.1 with edgeR 3.0.8) (23). To calculate TF binding similarity in FIG. 1E, the center of peaks (termed "summits") of all ChIPped TFs were pooled together to create a union list. Sequencing coverage within 50 base pairs of summits in the union list was counted and normalized by deepTools (v1.5.8) (50). Pairwise Pearson correlation between samples was used as entries in the distance matrix to plot the heat map in FIG. 1E. Hierarchy height of ChIPped TFs was calculated as described (40):

$$h=(O-I)/(O+I)$$

where O and I are out-degree and in-degree of examined TF through top-ranked dynamic binding. Peaks in each dynamic binding categories were associated to TAIR10 annotated genes within 1000 bp from the summit of the peaks, using the R BioConductor package ChIPpeakAnno (v2.12.1) (51).
Motif Discovery and Modeling the Contribution of Individual Motif to TF Binding Dynamics De novo motif discovery was carried out by meme-chip (meme 4.9.1) using a background file calculated from TAIR10 intergenic sequences (47). Top five enriched motifs identified within 50 base pairs of the summits were filtered at e-value cutoff of 1e-05. To model the contribution of individual features, a set of non-redundant sequence features were selected to represent the overall motif diversity. To do this we first assembled a set of 135 motifs in our dataset, consisted of the two most enriched motifs in the top 600 peaks in ABA- and mock-treated conditions for each TF, as well as top five motifs enriched in dynamic and static peaks for all TFs. The motifs were clustered by applying hierarchical clustering using motif distances calculated by Pearson Correlated Coefficients as column comparison metric and Ungapped Smith-Waterman alignment method (52, 53). Dynamic tree cut of the clustering dendrogram (54) identified 19 major clusters (color of dendrogram branch and the left of the annotation tracks in FIG. 11). As several of the clusters contain similar motifs (for example, the G-boxes and the AG-rich motifs are split into multiple clusters), we selected 11 sequence features to capture the diversity in this set of motifs indicated by dark red color of motif name and dark red color in the right annotation track in FIG. 11. Basal binding was measured as log 2(normalized read counts) under mock treatment and occurrences of motifs were assessed by FIMO (55) at the p-value cutoff of 0.0004. These features were used to fit log 2(fold change) of the binding of indicated TFs in FIG. 5D between ABA- and mock treatment. Relative changes of explained variability was calculated as:

$$(R^{2'}-R^2)/R^2$$

where $R^{2'}$ and $R^2$ are the adjusted $R^2$ from lm( ) output that includes and excludes Cluster II or Cluster III motif as a feature, respectively.
RNA-Seq Experiments and Analysis For ABA time series experiments, two biological replicates of 3-day-old etiolated, hydroponic-grown wild-type Col-0 seedlings were treated either by 10 µM (+/−)-ABA (MP biomedicals LLC, cat. #190673) dissolved in ethanol or ethanol-only mock control for 1, 4, 8, 12, 24, 36, and 60 hours. For DEX treatment, short term experiment was carried out by treating 3-day-old etiolated, DEX-inducible GFP-DIG1, GFP-DIG2 or GFP lines with 10 μM DEX (Sigma Aldrich, cat. #D9184); long term experiment was carried out by growing the same lines of plants containing 500 nM DEX for 10 days. Total RNA was isolated using the RNeasy Plant Mini Kit (Qiagen, CA, USA, Cat. #74903), and cDNA libraries were constructed using the TruSeq Stranded Total RNA LT Sample Prep Kit (Illumina, CA, USA, Cat. #15032611) according to manufacturers' instructions. Single-end reads were generated by the HiSeq 2500 Sequencing System (Illumina) and mapped to TAIR10 genome assembly using TopHat 2 (v2.0.8) (56). Mapped reads with mapping score equal to or larger than 10 were counted by HTSeq (v0.5.4) (57) and analyzed by edgeR (v3.6.2) (18) to identify differentially expressed genes using contrasts between ABA- and mock-treated samples at each time point and false discovery rate 0.01 or 0.05 as thresholds.

DREM

Figure 7:
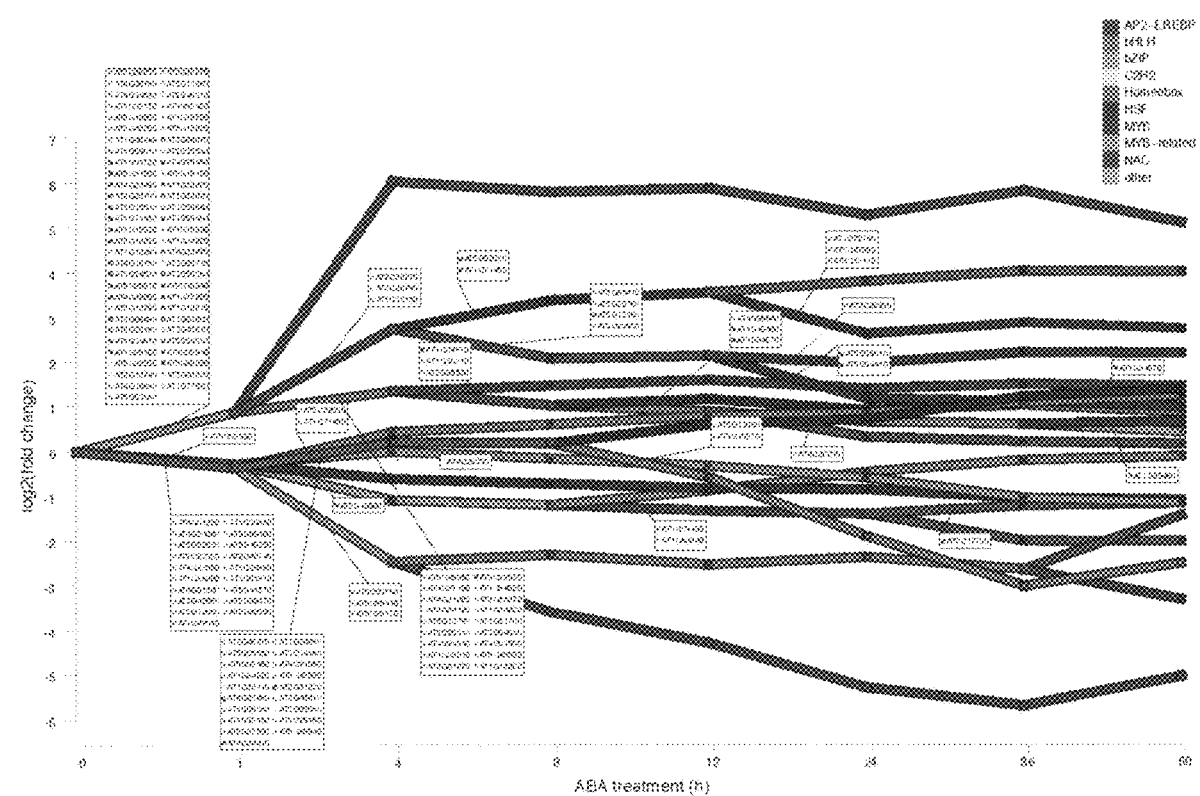
FIG. 7. DREM model recovered most families of the 21 ChIPped TFs. DREM reconstructed expression profiles for the 60-hour ABA treatment time series from a collection of TF-gene interaction data from the AGRIS database (26), PBM (13) and DAP-seq (15) data. Each path corresponds to a set of genes that are co-expressed. Split nodes (green diamonds) represent a temporal event where a group of genes co-expressed up to that point diverge in expression, most likely due to regulatory events. While the overlap between the TFs covered by AGRIS, PBM and DAP-seq and the TFs studied by ChIP-seq is limited, the family of TFs predicted to be active are similar. The DREM model identified TFs from all ChIPped families except for CCAAT-HAP3 and CCAAT-HAP5, which do not bind DNA in in vitro assays as a monomer (27).

The Dynamic Regulatory Events Miner (DREM) (25, 58), integrates TF-gene interactions from ChIP-seq experiments with time series gene expression data to identify patterns of temporal gene expression, the associated regulators and the dynamics of the interactions. Splits in the reconstructed network (green nodes in FIGS. 1B, 5C, 2, 7) represent divergence of genes that are co-regulated up to that point and can be annotated by DREM with the TFs that are predicted to regulate them, allowing us to associate the temporal information (the timing of the splits) with the interaction information either directly measured by ChIP-seq (FIG. 2) or inferred from the AGRIS database (26), PBM (13) and DAP-seq (15) data (FIG. 7). The analysis performed here used the log fold change of 3061 DE genes (see Table 1 of U.S. Provisional Application No. 62/413,349 and Table S1 of Song et al., "A transcription factor hierarchy defines an environmental stress response network," Science, Vol. 354, Issue 6312, 4 Nov. 2016, both herein incorporated by reference) identified in the ABA time series RNA-seq data. DREM paths were created using all DE genes without further filtering.

For GO enrichment in DE genes targeted by categories of dynamic binding peaks (FIG. 5D), we defined the genes in distinct DREM paths as foreground, and all expressed genes as background, and retrieved the Functional Annotation Chart with EASE score (modified p-value) threshold of 0.1 and count threshold of 2, using functionalities provided by the R BioConductor package RDAVIDWebService (59) to query the DAVID web service (60). The GO terms in GO_TERM_BP_FAT with FDR<=1% from all target gene sets are combined, and the enrichment p-values of these terms are retrieved for each gene set to create the heatmap in FIG. 5D. If a term is not reported to be significant for a target set, its p-value is set to 0.1 (the p-value threshold).

Modeling the Contribution of Individual TF to Gene Expression

An approach was adopted that is similar to previous regression-based models that relate gene expression to TF binding (61, 62). We first defined TF affinity score (TFAS), $A_{ij}$, for TF j on gene i, using the peak closest to the TSS of the gene:

$$A_{ij} = ge^{-\frac{d}{d_0}},$$

where g is the log 2 TMM normalized read counts of the peak, d is the distance of the peak summit to TSS. $d_0$ is set to 1000. For N genes and M TF, we constructed one N×M TFAS matrix for the ABA treatment and one for the ethanol mock treatment, and concatenated these two matrices horizontally to create a final N×2M matrix A. We centered and scaled each column of A and fit a log-linear model:

$$\log Y_i = \Sigma_{j=1}^{2M} \beta_j A_{ij} + \epsilon_i,$$

where $Y_i$ is the fold change in expression of gene i at 4 h ABA treatment compared to mock. The model training and testing were limited to genes that are differentially expressed at 4 h with FDR<=0.01 and those are not differentially expressed at all time points (FDR>0.7). A glmnet regression model (63) was trained on 75% of the genes by 5 repeats of 10-fold cross-validation using the caret package in R (64) with tuning metric set to RMSE and the elastic net mixing parameter α=0 to allow selection correlated TFAS features. The "best" rule was used to choose a value for the tuning parameter (in this case, the regularization parameter λ), i.e., a value that minimized the average RMSE of the regression on the 50 resampling of the training set. The glmnet model was then fitted using the chosen λ value to arrive at the regression coefficients in the final model. The unscaled coefficients of the TFAS features are plotted as binding feature importance in FIG. 5F.

Confocal Imaging

Nine-day-old DEX inducible GFP and GFP-DIG1 seedlings grown on 1× LS plates containing 200 nM DEX and 300 nM ABA were imaged by Zeiss 710 confocal microscope under an Argon laser at 488 nm. GFP signal was captured within the 493-548 nm emission window and was pseudo-colored in green. Auto-fluorescence from chloroplasts was captured within the 569-695 nm emission window and was pseudo-colored in red.

Sequence Analysis of DIGs and their Homologs

Protein sequence of DIG1 was used as a query to search for homologous protein sequences in *Arabidopsis thaliana* by the BLASTP search tool on EnsemblPlants (65). The resulting six protein sequences (Q9FK36, Q9SMP6, Q9FGW7, Q9LK28, Q9FKS6, Q9FKS7) were used to query *Arabidopsis thaliana, Glycine max, Solanum lycopersicum, Oryza sativa japonica* and *Zea mays* by BLASP, resulting in 21 homologous sequences. These sequences were aligned by MEGA6 (66) using distance-based maximum likelihood method, and bootstrap values were generated from 1000 replications.

Chlorophyll Measurement

Chlorophyll content was determined as previously described (67). Briefly, each sample consisting of ca. 50 seeds were germinated and grown on LS plates supplemented with or without ABA and DEX for eight days. The seedlings were collected and ground in liquid nitrogen. Chlorophyll were extracted by 80% acetone until pellets were almost white. Absorbance was measured at 647 and 664 nm in a DU-730 spectrophotometer (Beckman Coulter, CA, USA). Chlorophyll content was determined as $chl\ a+b = 17.76*A647 + 7.34*A664$ Chlorophyll content of each transgenic line was then normalized by the corresponding seedlings grown on LS plates containing no DEX or ABA. The 95% confidence interval around the mean estimate was calculated from 3 biological replicates.

Example 2

ChIP-Seq Analyses of ABA Responses

Figure 1B:
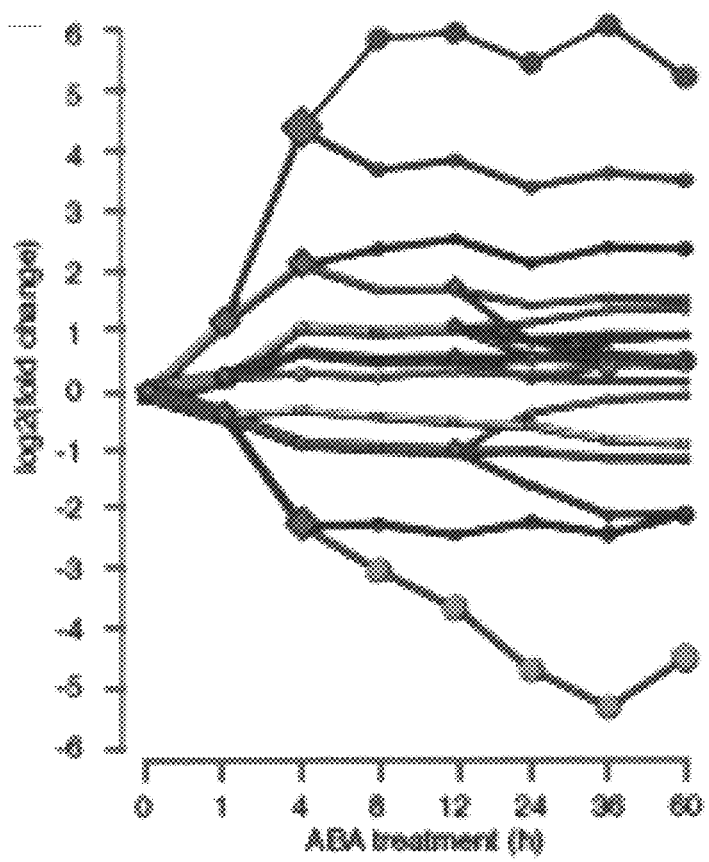
Figure 2:
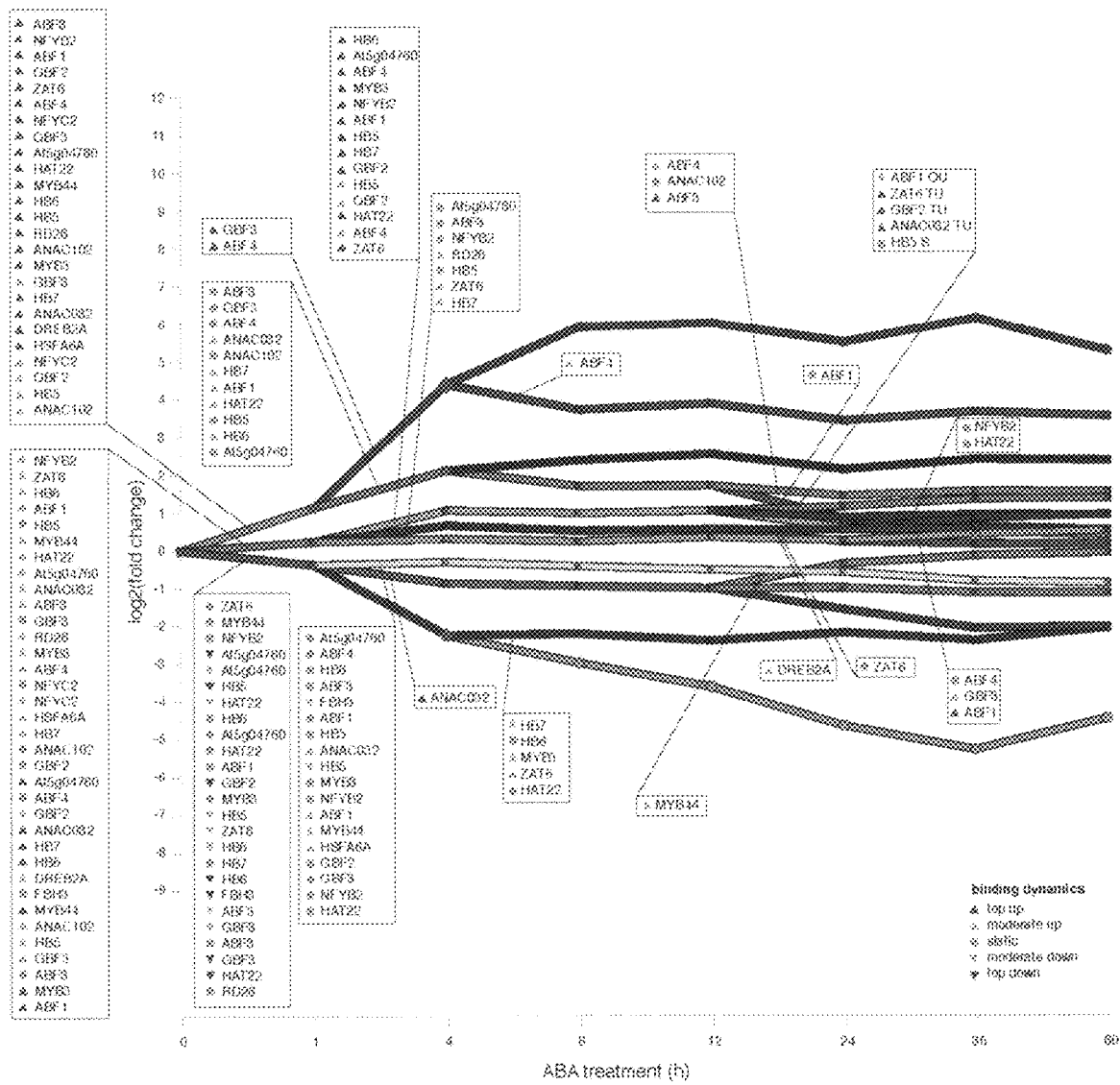
FIG. 2. Dynamic TF regulatory network controls ABA response. DREM reconstructed expression profiles for the 60-hour experiment. Each path corresponds to a set of genes that are co-expressed. Split nodes (green diamonds) represent a temporal event where a group of genes co-expressed up to that point diverge in expression, most likely due to regulatory events. TF-target gene interactions are categorized by TF binding dynamics (FIGS. 5B, 6). TFs whose target genes are enriched in a path are ranked by the significance of association with the path.

The genome-wide binding dynamics of a diverse collection of TFs was profiled using ChIP-seq to develop an in planta ABA transcriptional regulatory network. ABA-responsive transcripts were first surveyed in *Arabidopsis thaliana*, by generating strand-specific RNA-seq libraries from 3-day-old etiolated whole seedlings treated with either 10 uM (+/−)-ABA or an ethanol-containing mock for 1, 4, 8, 12, 24, 36 and 60 hours (FIG. 1A). Among 18,310 expressed genes, 3,061 are DE (FDR<0.01, Table 1) (18) for at least one time point. One hour of ABA treatment leads to moderate DE of many genes, and most transcriptional responses plateau after 8 hours (FIGS. 1B, 2). On the basis of gene expression data, we performed ChIP-seq experiments at four hours post ABA dose. TFs were selected based on responsiveness to ABA and published evidence, aiming to provide a good representation of TF families (FIG. 3; Tables 1 and 2). In general, highly expressed and responsive TFs were chosen in each representative TF family because in the context of an in planta experimental framework, the impact of these TFs on gene expression can be more effectively investigated compared with their weakly expressed homologs. All TF genes were epitope tagged by a recombineering-based approach (19), mostly with large DNA transformable artificial chromosomes, allowing the TFs to be expressed under their native promoters and genomic context (Table 2). The final dataset consisted of one hundred and twenty-two ChIP-seq experiments of 21 TFs from 11 families, including mock- and ABA-treated conditions.

TABLE 1

TFs selected for ChIP

| TF family | TF | Literature curated link to ABA response | RNA-seq evidence |
|---|---|---|---|
| ANAC | RD26 (ANAC072) | Overexpression of RD26 leads to increased ABA responses in terms of stronger inhibition of root growth than wild type plants on ABA plate, and better drought tolerance (70, 71). Roots growth of plants overexpressing the RD26-EAR motif fusion protein is less inhibited by ABA than wild type controls (70). The protein interacts with ABI5 in Y2H assays (32). | up regulated by 10 uM ABA treatment for 4 hours. |
| ANAC | ANAC032 | ANAC032 belongs to the same stress-responsive clade of NACs as RD26 (72). The protein interacts with ABA signaling components such as ABI1, AHG3, HAI1, PYL4, SnRK3.15 and ABI5 in Y2H assays (32). | up regulated by 10 uM ABA treatment for 4 hours. |
| ANAC | ANAC102 | ANAC102 belongs to the same stress-responsive clade of NACs as RD26 (72). | up regulated by 10 uM ABA treatment for 4 hours. |
| AP2/EREBP | DREB2A | The expression of the DREB2A gene is strongly induced by drought and high salinity stress (73). The protein functions synergistically with ABF4 to transactivate a reporter driven by the RD29A promoter fragment in protoplasts (74). The protein also physically interacts with ABF2 and ABF4 in Y2H assays, and can be pulled down in vitro by ABF2 (75). | up regulated by 10 uM ABA treatment for 4 hours. |
| bHLH | FBH3 | The FBH3 protein is a direct substrate of ABA signaling components SnRK2.2/SnRK2.3/SnRK2.6 (76). Phosphorylation of FBH3 has been linked to regulation of stomata aperture (77). Overexpression of FBH3 leads to better germination and cotyledon greening than wild type plants on plates containing high salt concentrations. The overexpressors are also more drought resistant (78). | up regulated by 10 uM ABA treatment for 4 hours. |
| bZIP, clade A | ABF1 | ABF1 is a close homolog of ABF3. Both ABF1 and ABF3 are substrates of the E3 ubiquitin ligase KEG, and ABA treatment stabilizes both ABFs (79). ABF1 interacts with ABI3 in Y2H assays (80). | up regulated by 10 uM ABA treatment for 4 hours. |
| bZIP, clade A | ABF3 | ABF3 is one of the master TFs in ABA signaling. The root growth of abf3 single loss of function (lof) mutant and abf2abf3abf4 triple mutant are significantly less inhibited by ABA than wild type controls (33). The triple mutant exhibits greatly reduced drought resistance, whereas ABF3 overexpressor has increased drought tolerance (33, 81). | up regulated by 10 uM ABA treatment for 4 hours. |
| bZIP, clade A | ABF4 | Similar to ABF3, ABF4 is one of the master TFs in ABA signaling, except that the root growth of abf4 single lof mutant and wild type controls are comparably inhibited by ABA (33). ABF4 overexpressor has increased drought tolerance (81). | up regulated by 10 uM ABA treatment for 4 hours. |

TABLE 1-continued

TFs selected for ChIP

| TF family | TF | Literature curated link to ABA response | RNA-seq evidence |
|---|---|---|---|
| bZIP, clade G | GBF2 | | up regulated by 10 uM ABA treatment for 4 hours. |
| bZIP, clade G | GBF3 | The GBF3 protein is capable of binding to the promoter of cold and dehydration responsive Adh gene in vitro (82). | up regulated by 10 uM ABA treatment for 4 hours. |
| C2H2 ZF | ZAT6 | ZAT6 has a close homolog ZAT10 (83). ZAT6 interacts with drought-responsive MPK6 in transient expression assays, and can be phosphorylated by MPK6 in vitro (84). Overexpression of either ZAT6 or ZAT10 leads to enhanced osmotic stress tolerance (84, 85). However, RNAi or lof mutant lines of ZAT10 also improves tolerance to osmotic stress. ZAT10 functions as a transcription represser in transient reporter assays (86). Both ZAT6 and ZAT10 contain EAR motifs and interact with transcriptional corepressor TPL in Y2H screens (87, 88). | up regulated by 10 uM ABA treatment for 4 hours. |
| HD-ZIP I | HB5 | HB5 is in the same subclade as HB6 (89). The two proteins are capable of dimerizing in vitro, and recognizing the same dyad-symmetric binding site in electrophoretic mobility shift assays (90). | |
| HD-ZIP I | HB6 | HB6 interacts with ABI1 in Y2H assays. The protein also has ABI1 dependent transactivating activity in protoplasts. HB6 overexpressors are less responsive to ABA during germination. In addition, the detached leaves of the of the OE plants experience faster water loss than wild type controls (91). | up regulated by 10 uM ABA treatment for 4 hours. |
| HD-ZIP II | HAT22 | HAT22 contains an EAR motif and interacts with transcriptional corepressor TPL in Y2H screens (87, 88). Leaf senescence, a phenomenon commonly seen in plants undergo drought stress, can be triggered by overexpresson of HAT22 (92, 93). | up regulated by 10 uM ABA treatment for 4 hours. |
| HSF | HSFA6A | Overexpression of HSFA6A leads to enhanced ABA responses in terms of a stronger inhibition of seed germination than wild type plants on ABA plate, and better drought tolerance (94). | up regulated by 10 uM ABA treatment for 4 hours. |
| NFYB/ HAP3 | NF-YB2 | NFYs are known to promote chromatin accessibility thus facilitate the binding of other TFs in mammals (27). Overexpression of NF-YB2 results in a stronger inhibition of germination than wild type controls on ABA plates. NF-YB2 interacts with ABF3 but not with the other ABFs in Y2H assays (22). The nf-yb2 lof mutants have much delayed flowering time compared to wild-type controls when growing under osmotic stress (95). | up regulated by 10 uM ABA treatment for 4 hours. |
| NFYC/ HAP5 | NF-YC2 | | up regulated by 10 uM ABA treatment for 4 hours. |
| R2R3 MYB | MYB3 | | up regulated by 10 uM ABA treatment for 4 hours. |
| R2R3 MYB | MYB44 | Overexpression of MYB44 leads to increased ABA responses in terms of a stronger inhibition of seed germination than wild type plants on ABA plate, and better drought tolerance (96). MYB44 contains an LxLxL EAR motif and interacts with trascriptional corepressor TPR1 and TPR3 in Y2H screens (87, 88). | up regulated by 10 uM ABA treatment for 4 hours. |

TABLE 2

Transgenic lines for ChIP

| transgene | Genetic Background | vector | tag | tagPosition | promoter |
|---|---|---|---|---|---|
| ABF1 | Col-0 | TAC:JAtY62D20 | FY | N | native |
| ABF3 | Col-0 | plasmid:pMDC123 | FY | N | native |
| ABF4 | Col-0 | TAC:JAtY60O20 | FY | N | native |
| GBF2 | Col-0 | TAC:JAtY57G14 | YHF | C | native |
| GBF3 | Col-0 | TAC:JAtY66N23 | YHF | C | native |
| ANAC032 | Col-0 | TAC:JAtY50N03 | YHF | C | native |
| ANAC102 | Col-0 | TAC:JAtY49D11 | YHF | C | native |
| RD26 | Col-0 | TAC:JAtY76M07 | YHF | C | native |
| NFYB2 | Col-0 | TAC:JAtY63D09 | YHF | C | native |
| NFYC2 | Col-0 | TAC:JAtY80H06 | YHF | C | native |
| HSFA6A | Col-0 | TAC:JAtY57L24 | FY | N | native |
| DREB2A | Col-0 | TAC:JAtY68D04 | YHF | C | native |
| HAT22 | Col-0 | TAC:JAtY77C04 | YHF | C | native |
| HB5 | Col-0 | TAC:JAtY58F22 | YHF | C | native |
| HB6 | Col-0 | TAC:JAtY79K18 | YHF | C | native |
| HB7 | Col-0 | TAC:JAtY67K15/ JAtY67E11 | YHF | C | native |
| MYB3 | Col-0 | TAC:JAtY71B10 | YHF | C | native |
| MYB44 | Col-0 | TAC:JAtY56M19 | YHF | C | native |
| ZAT6 | Col-0 | TAC:JAtY70O03 | FY | N | native |
| At5g04760 | Col-0 | TAC:JAtY60K23 | YHF | C | native |
| FBH3 | Col-0 | TAC:JAtY61G02 | YHF | C | native |
| DTAF1 | Col-0 | plasmid:pDEX1MX | GFP | N | 6xOP |
| DTAF2 | Col-0 | plasmid:pDEX1MX | GFP | N | 6xOP |

Figure 1C:
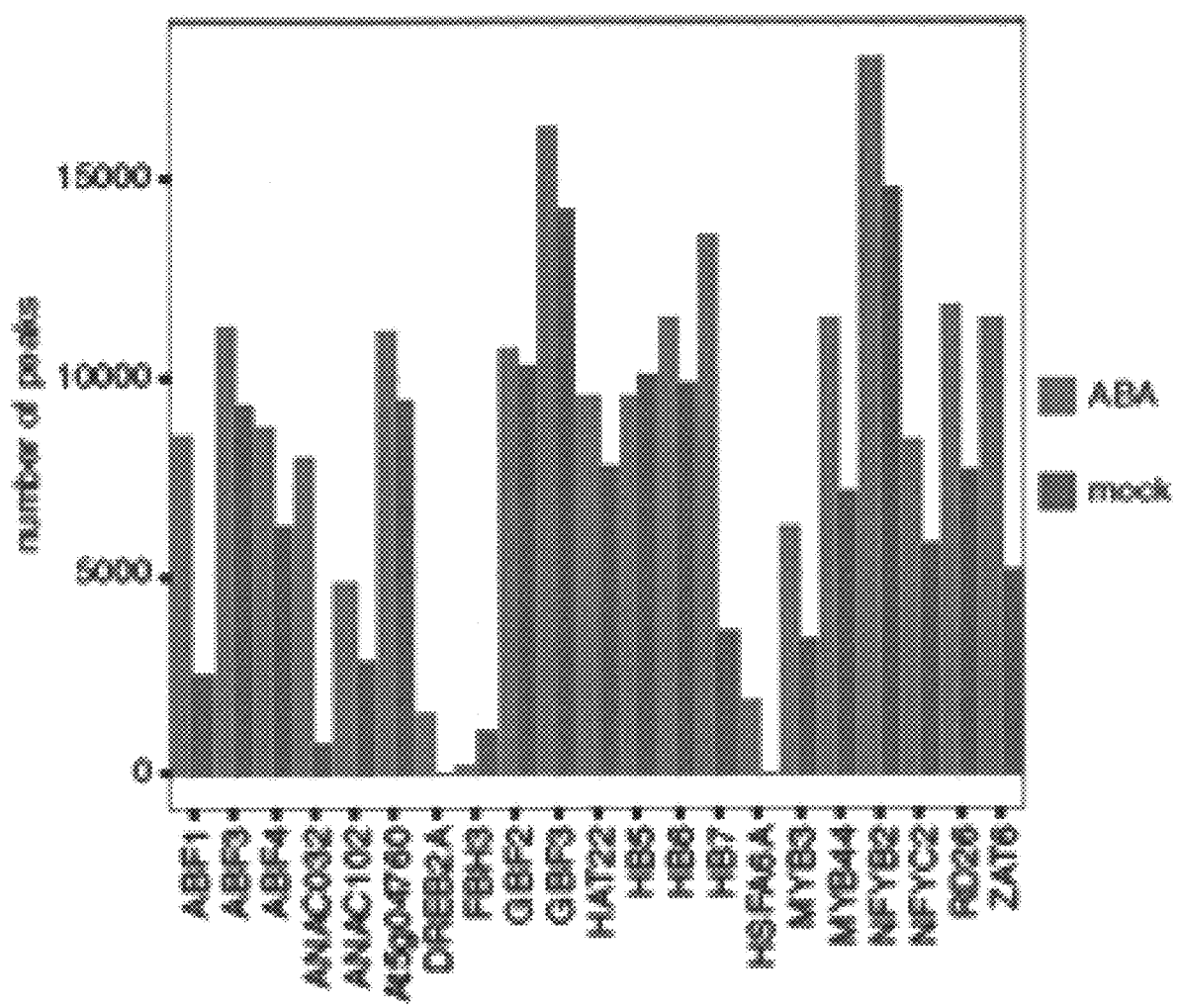
Figure 1D:
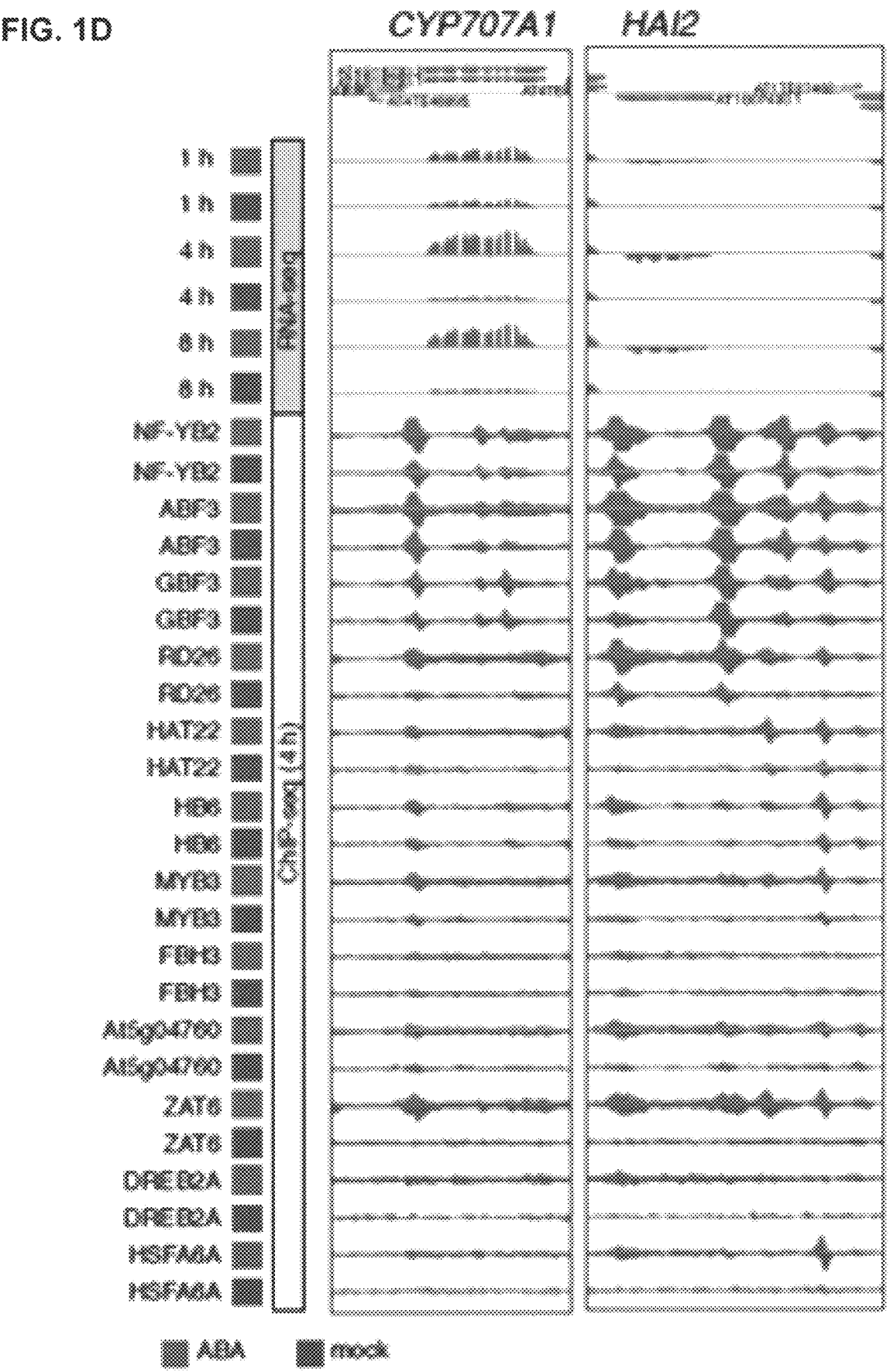
Figure 1E:
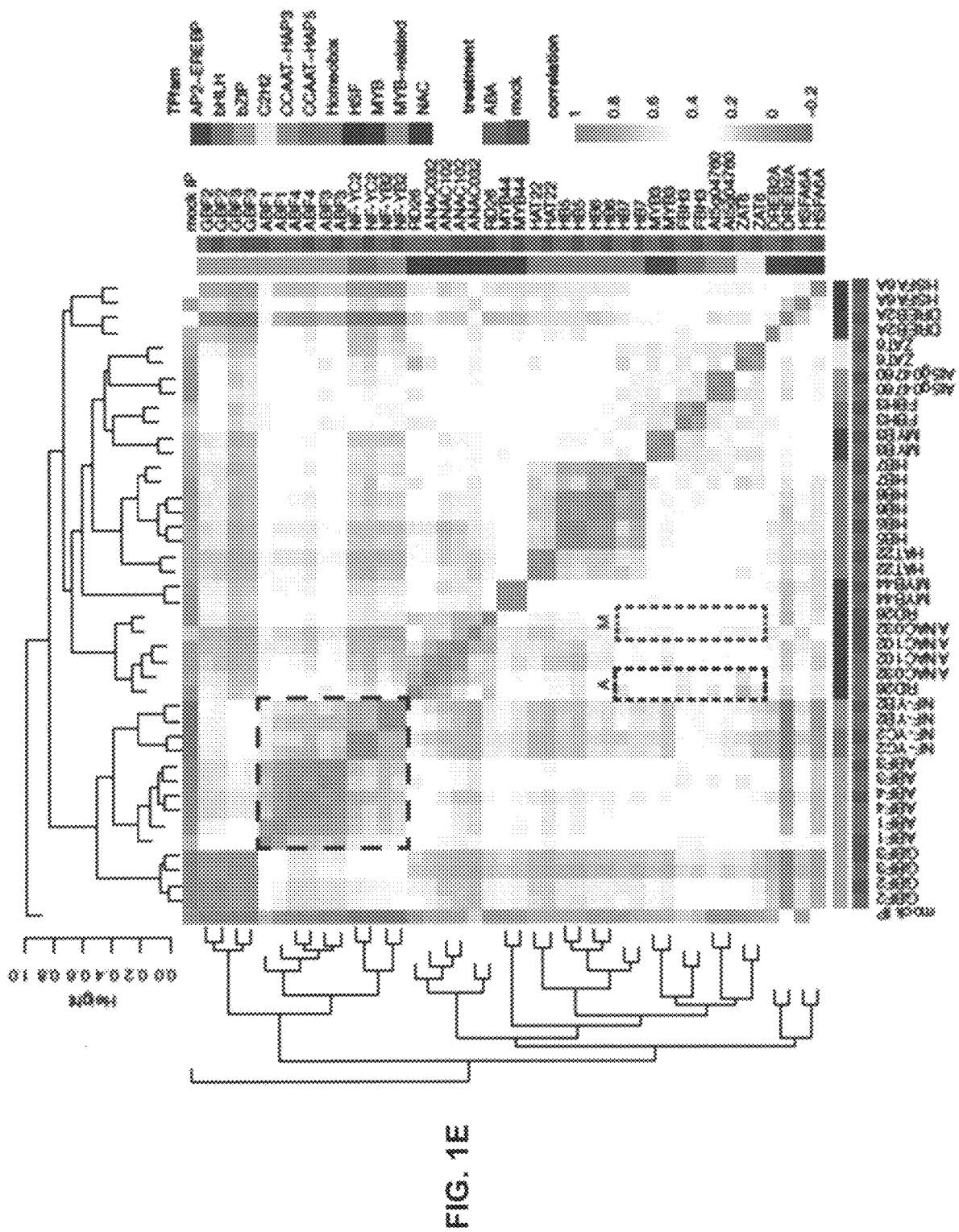
Figure 3:
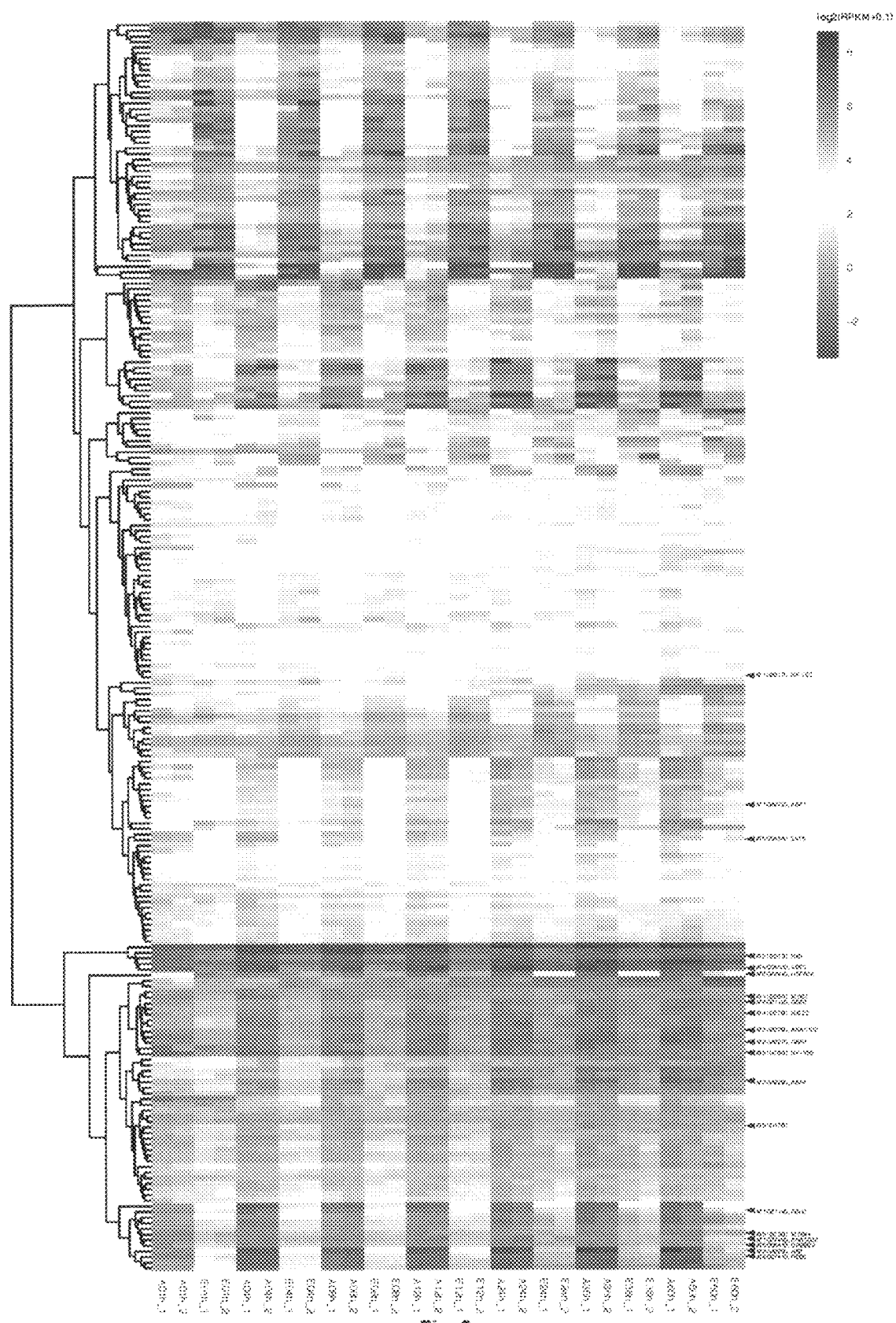
FIG. 3 ABA triggers differential expression of hundreds of TFs. Differential expressed TFs by ABA were identified by edgeR using an FDR threshold of 0.05. Two hundred and twenty-two TFs that are differentially expressed for the first 1, 4 or 8 hours of ABA treatment were grouped based on log 2(RPKM+0.1) using the McQuitty's hierarchical clustering method. ChIPped TFs were labeled by black arrowheads.
Figure 4:
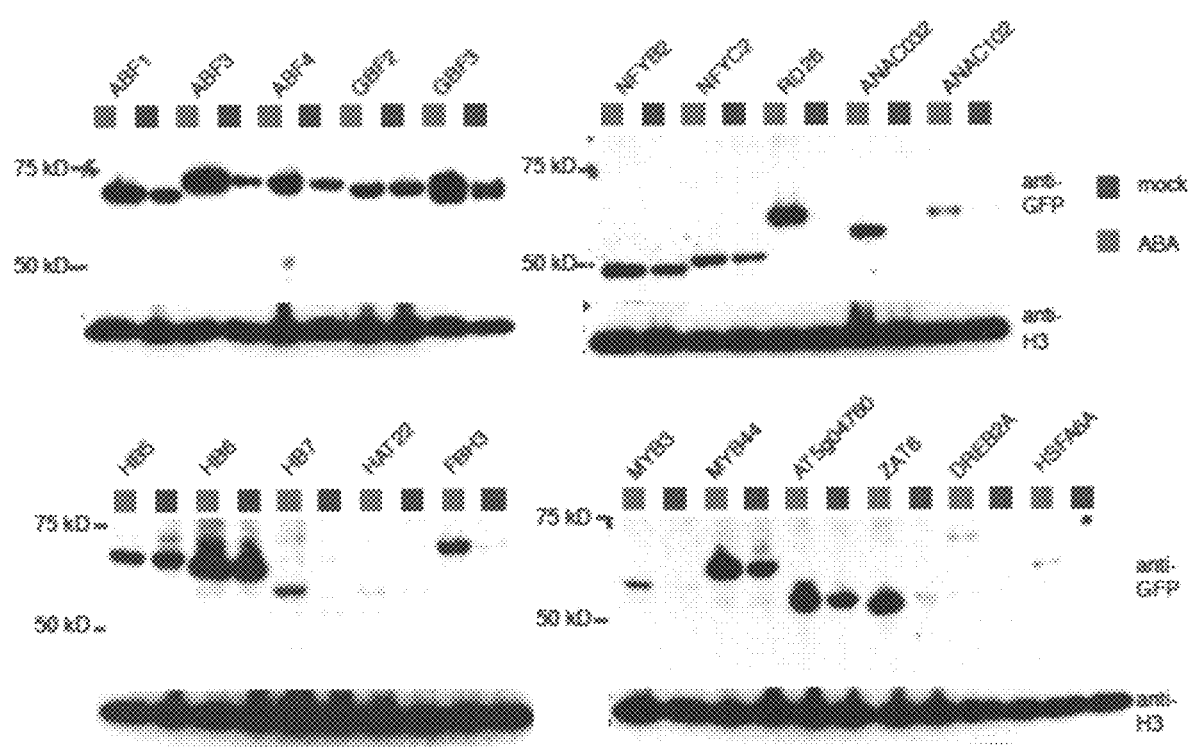
FIG. 4. ChIPped TFs respond to ABA at the protein level. Western blots show that the protein abundance of most TFs were elevated by ABA. H3 detected by anti-histone H3 antibody used as a loading control.

Overall, the number of binding sites (termed "peaks") varies greatly across TFs and between treatments (FIG. 1C). Most TFs gain bindings sites across the genome after ABA treatment (FIG. 1C), consistent with the fact that these TFs are induced by ABA at both the transcript and protein level (FIGS. 1D, 3, 4). As exemplified by CYP707A1 and HAI2 (20, 21), two important genes regulating ABA catabolism and signaling, respectively, the dynamic binding of TFs elicited by ABA is often accompanied by altered transcript abundance of the target genes (FIG. 1D). Comparing the genome wide binding profiles of these TFs, taking into account the binding location and strength, revealed that the TFs are generally grouped by family and known physical interactions (FIG. 1E) (22). Interestingly, the binding profiles between NAC and other TF families become more similar after ABA treatment (FIG. 1E, box A vs. M), indicating ABA prompts coordinated regulation of target genes by these TFs.

Example 3

Hormonal Effects on TF Binding and Expression of Target Genes

Dramatic changes in TF binding at promoter regions of several known components of ABA signaling pathway were observed (FIG. 1D), so it was determined whether dynamic binding may predict genes function in the ABA pathway.

To quantify hormone-dependent, locus-specific change of TF binding, ChIP-seq peaks of each TF between ABA- and mock-treated conditions were compared by performing differential binding analysis of the sequencing reads under the peaks (23). Three measures of differential binding were calculated for each peak: 1) normalized read count change (RCC) that measures absolute changes of binding, 2) fold change (FC) that measures relative changes of binding, and 3) statistically significant differential binding (FDR). Since there are limited down-regulated binding events in the dataset, up-regulated binding was focused on to determine the optimal cutoff of RCC, FC and FDR to define the relationship between dynamic binding targets and genes involved in ABA response. Three groups of Arabidopsis thaliana genes were extracted (see Table 4 of U.S. Provisional Application No. 62/413,349 and Table S4 of Song et al., "A transcription factor hierarchy defines an environmental stress response network," Science, Vol. 354, Issue 6312, 4 Nov. 2016, both herein incorporated by reference) based on gene ontology (GO) annotation (24).

Figure 5A:
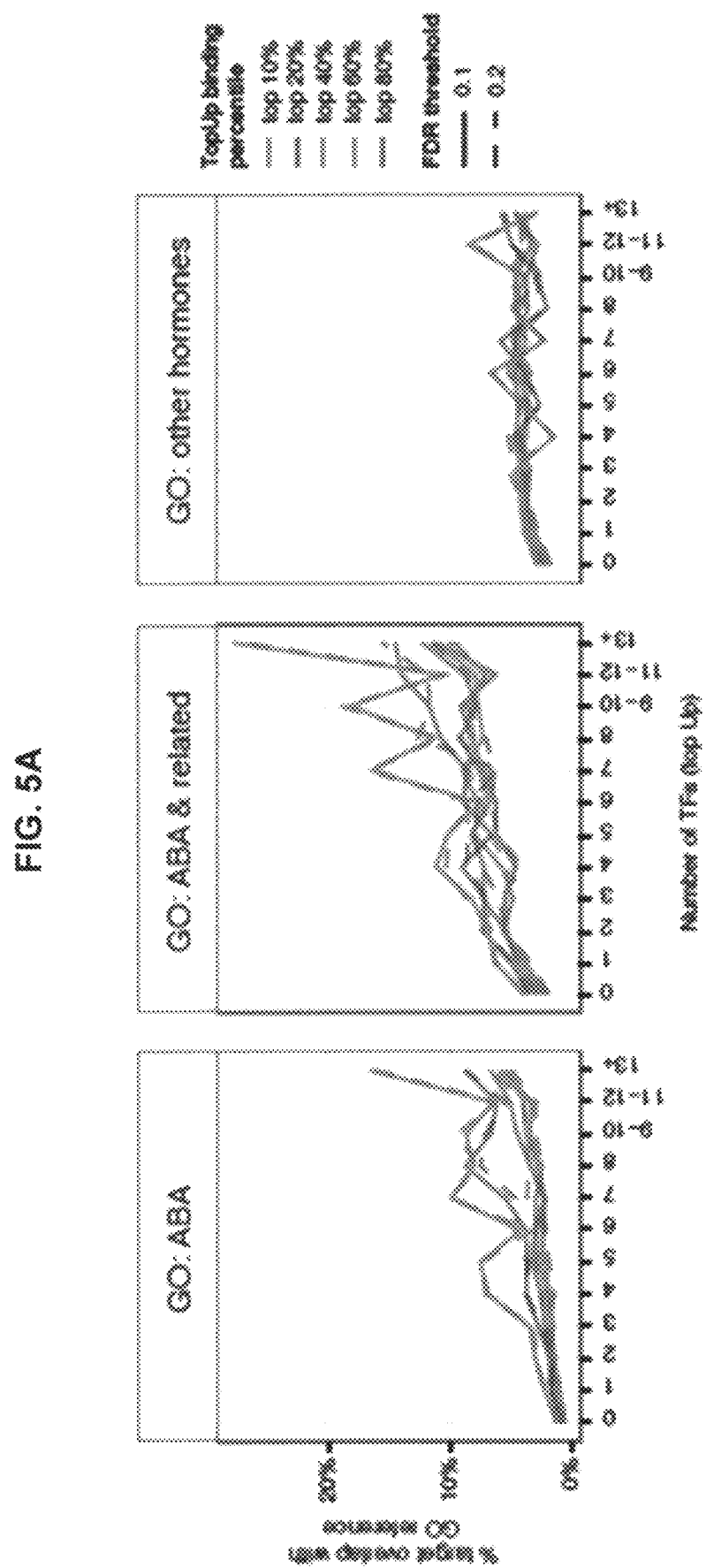

Group 1 contains 493 genes involved in ABA response, Group 2 contains 1452 genes involved in responses to either ABA or other related processes such as water deprivation, osmotic stress, salt stress, cold, seed development and stomatal movement. Group 3 contains 999 genes involved in responses to other hormones after excluding genes shared with Group 2. Three observations emerged from comparing these lists to the TF target gene lists defined by various thresholds on RCC, FC and FDR. First, when Group 1 and 2 genes were used as a reference set, the percentage of TF targets overlapping with the set increases with the number of bound TFs (FIG. 5A, panels 1-2). By contrast, there is very little, if any, increase when Group 3 (other hormone genes) was used as the reference (FIG. 5A, panel 3). Second, an increase of RCC and FC threshold beyond top 20% boosted the percentage of target genes involved in ABA-related responses but not genes-related to other hormones (FIG. 5A, panel 3). This improvement is even more obvious for genes targeted by multiple TFs. Lastly, FDR thresholds of 0.1 and 0.2 show little differences across all analyses. These results support the premise that dynamic binding by multiple TFs is an important feature to specifically recover genes involved in ABA-related responses.

Figure 6:
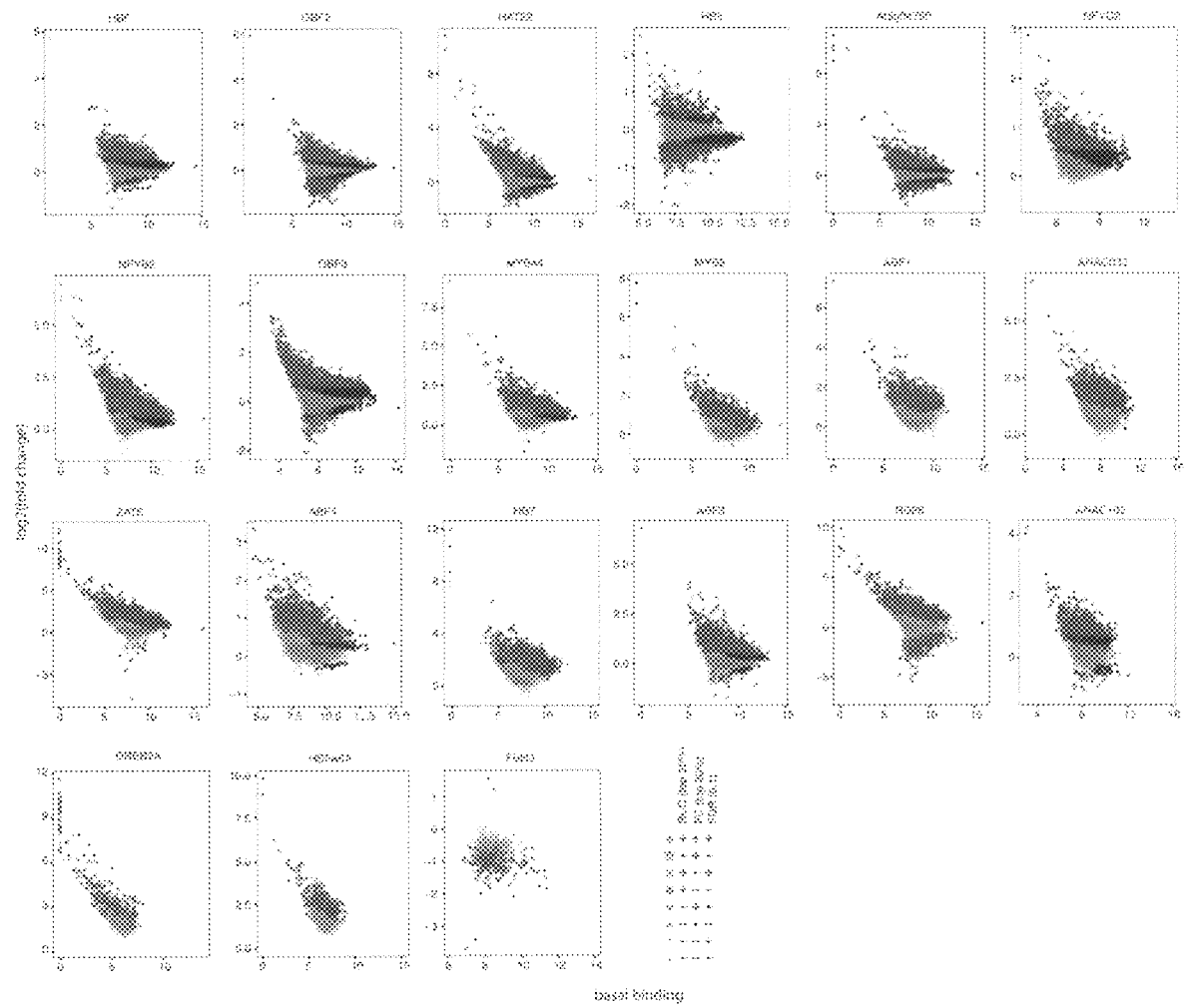
FIG. 6. ChIPped TFs exhibit locus-specific binding dynamics across the genome in response to ABA treatment. Log 2(fold change) of TF binding upon ABA treatment was plotted against basal binding measured as log 2(normalized read counts) under mock treatment. Peaks were classified into eight categories by three criteria: read count change (RCC, within top 20%), fold change (FC, within top 20%), and DiffBind FDR (less than 0.1). +++ and --- were designated as top dynamic and static respectively. The remaining were designated as moderately dynamic.

The top 20% RCC and FC and FDR 0.1 were selected as the cutoff for follow-up analyses. As shown in FIGS. 5B and 6, peaks passing all three thresholds were designated as top-ranked up- ("top up") or down-regulated ("top down") whereas those failing all thresholds were designated as static; all remaining peaks were classified as moderately up—("moderate up") or down-regulated ("moderate down"). For all tested TFs except FBH3 and HB5, peaks tend to gain binding instead of maintaining or losing binding after ABA treatment.

Figure 5D:
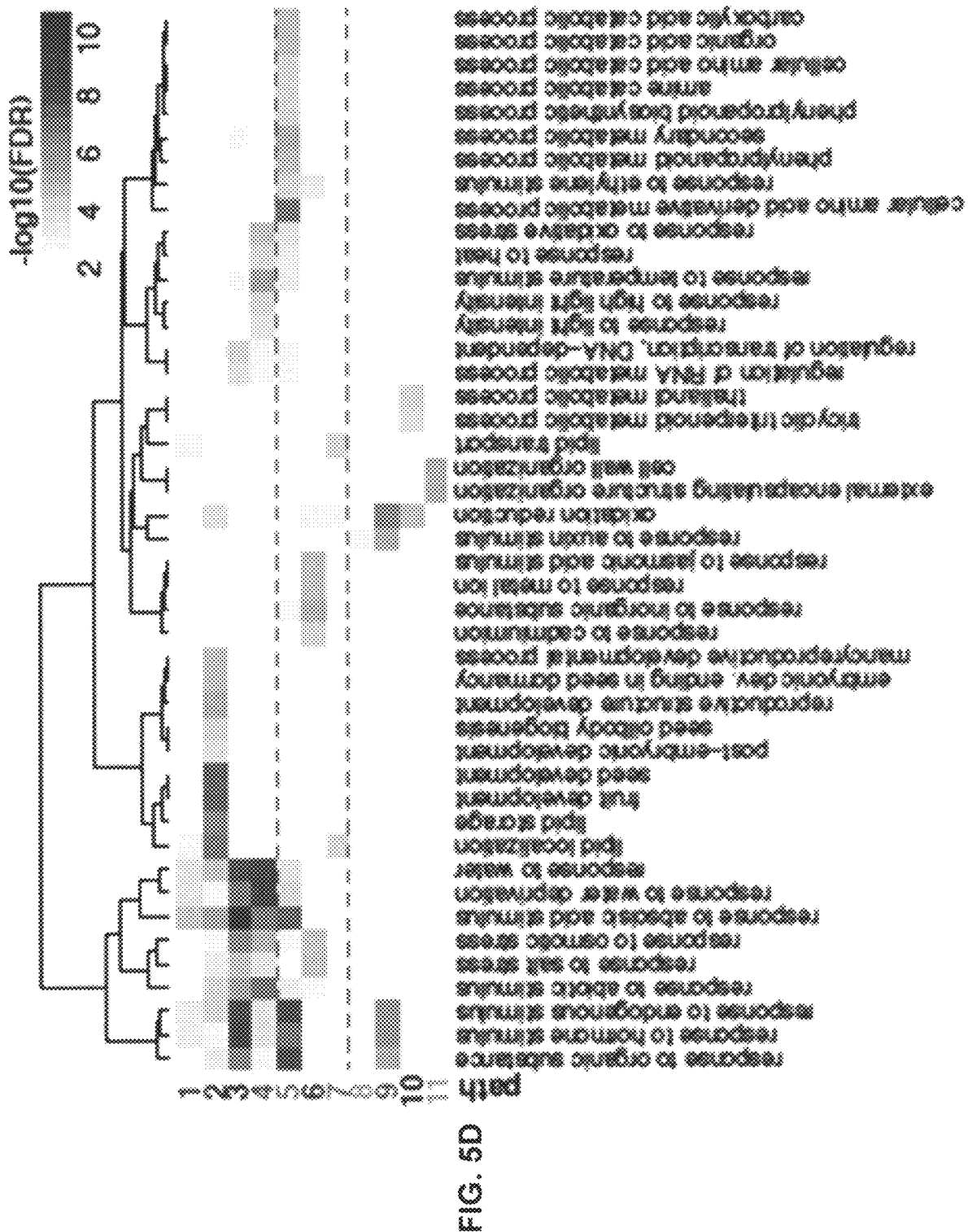
Figure 5F:
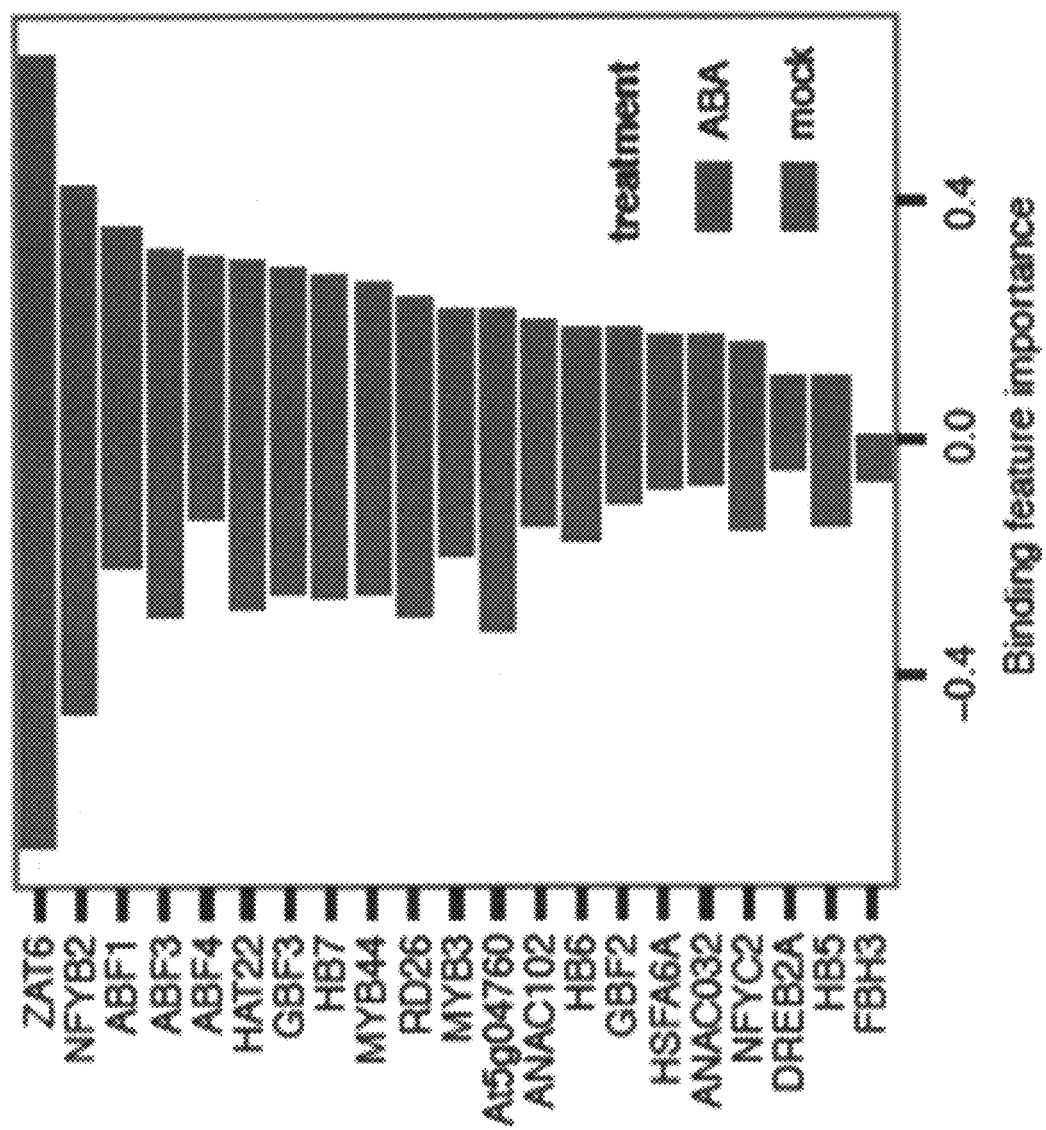
Figure 5E:
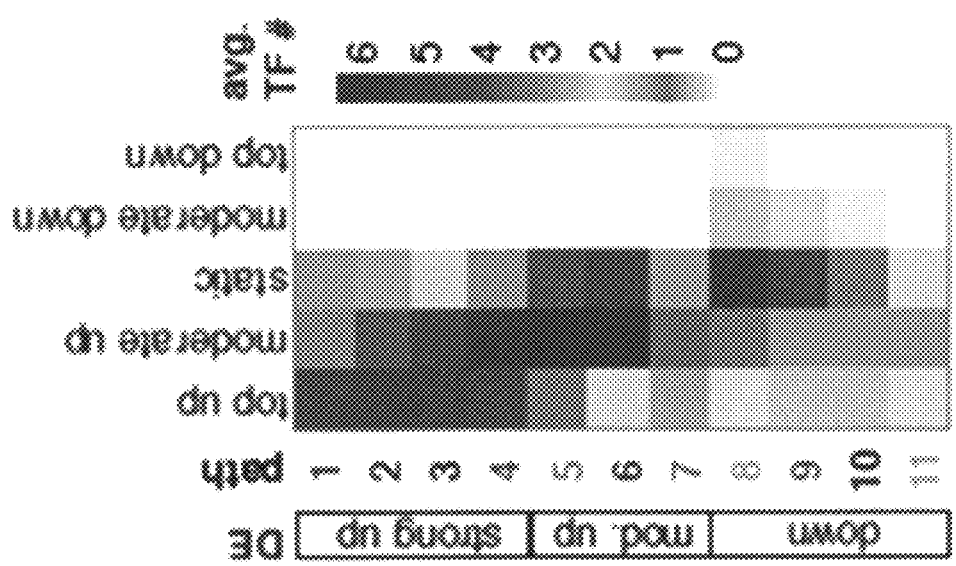

The relationship between dynamic TF binding triggered by ABA treatment and gene expression was determined. The Dynamic Regulatory Event Miner (DREM) (25) reports 11 paths of DE genes for the first 8 hours of ABA treatment (FIG. 5C). As shown in FIG. 7, combining DREM with DNA motifs from PBM, AGRIS and DAP-seq databases recovered few TFs in the dataset, likely due to a low overlap of these TFs with the databases (13, 15, 26). The DREM model identified TFs from all ChIPped families except for CCAAT-HAP3 and CCAAT-HAP5, which do not bind DNA in in vitro assays as a monomer (27). In addition, although TF binding was examined at the single time point, a positive correlation was observed between the number of dynamically bound TF and the magnitude of DE across all time points (FIG. 8), suggesting TF binding data at 4 hour post ABA dose can explain a broad temporal span of gene expression. ABA-related GO terms such as seed development and response to salt/osmotic stress/water deprivation were enriched in up-regulated genes, whereas a few growth-related terms such as response to auxin stimulus and cell wall organization were enriched in down-regulated genes (FIG. 5D). We observed a distinct distribution of dynamic binding category across DREM paths (FIGS. 2, 5E, Table 3). The extent of multi-TF dynamic binding is associated with the magnitude of differential gene expression. For example, highly up-regulated genes are often targeted by multiple TFs through "top up" binding. Moderately up-regulated genes are more commonly targeted by multiple TFs through "moderate up" binding. Down-regulated genes are rarely associated with "top up" binding. Instead, these genes are predominantly associated with either static binding by multiple TFs or down-regulated TF binding.

capture the diversity of motifs. These sequence features were selected from major clusters of all the motifs found in the strongest 600 peaks (Cluster A-I motifs) and the dynamic and static peaks (Cluster 1 to 3 motifs) (FIG. 11). Examining the p-values of the regression coefficients (FIG. 10B) suggests that the primary motifs of ABF (which also represent cluster 3 motifs) and ANAC TFs are associated with

TABLE 3

Distribution of dynamic binding categories across DREM paths

| #note | sumTopUp | sumOtherUp | sumStatic | sumOtherDn | sumTopDn | numGenesInClade |
|---|---|---|---|---|---|---|
| clade 01 | 392 | 271 | 126 | 5 | 0 | 86 |
| clade 02 | 864 | 701 | 293 | 6 | 2 | 178 |
| clade 03 | 920 | 845 | 429 | 23 | 1 | 189 |
| clade 04 | 1137 | 1498 | 792 | 30 | 5 | 259 |
| clade 05 | 1867 | 3480 | 2226 | 107 | 23 | 538 |
| clade 06 | 1117 | 3302 | 2477 | 113 | 22 | 507 |
| clade 07 | 285 | 640 | 494 | 27 | 9 | 170 |
| clade 08 | 114 | 996 | 1654 | 183 | 88 | 286 |
| clade 09 | 307 | 1644 | 2515 | 267 | 122 | 561 |
| clade 10 | 100 | 475 | 551 | 55 | 42 | 164 |
| clade 11 | 54 | 192 | 261 | 20 | 14 | 123 | total number of binding events associated with indicated DREM clades are shown in columns 2 to 6.
chi-square test was carried out between dynamic binding and static binding, p-value is shown in the pv.ChiSquare row.
NA*: chi-square test was not performed for sumTopDn because the small number of DB events associated to top DREM clades violates the sample size assumption of chi-square test.

Figure 9:
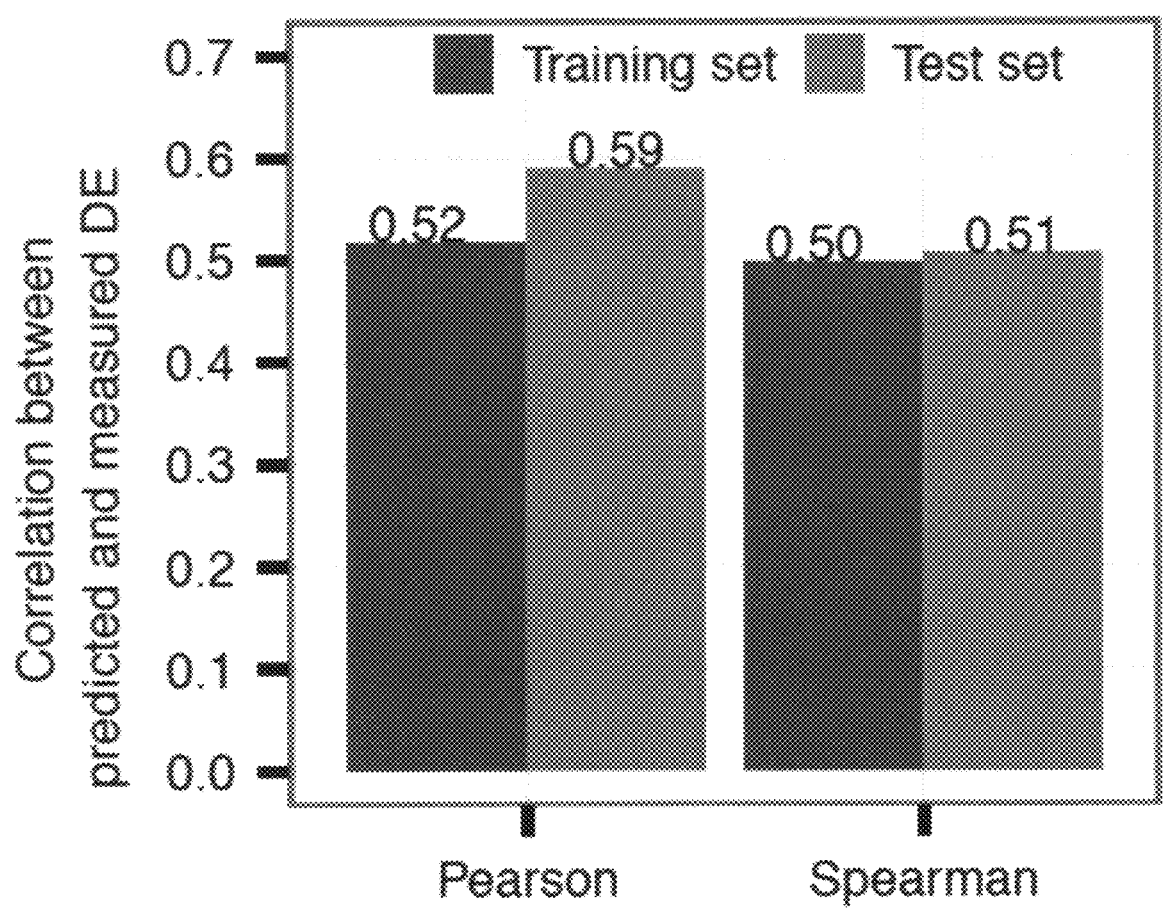
FIG. 9. Performance of ridge regression model of differential gene expression using TF binding strength as features. Parameter tuning was performed by 10-fold cross-validation repeated 5 times on 75% of the genes as training set and the remaining as test set.

These data indicate that DE at the whole seedling level is often subject to a combinatorial regulation by multiple TFs. As an independent validation, a regression model of differential expression was built using peak signals in ABA and mock-treated conditions as features without hard thresholds for the level of dynamic binding. The resulting model reveals that multiple TF binding features such as ZAT6, NF-YB2 and ABF factors in both ABA- and mock-treated conditions contribute to differential expression of target genes (FIGS. 5F, 9).

Example 4

Determinants of Differential Transcription Factor Binding

With the discovery of tens of thousands of differential binding events, whether features that may predict binding dynamics was determined. Motif discovery by MEME-ChIP (28) was used to identify enriched motifs of all 21 ChIPped TFs from the strongest 600 peaks after either ABA or mock hormone treatment. A complete collection of the motifs is available on line.

Figure 10A:
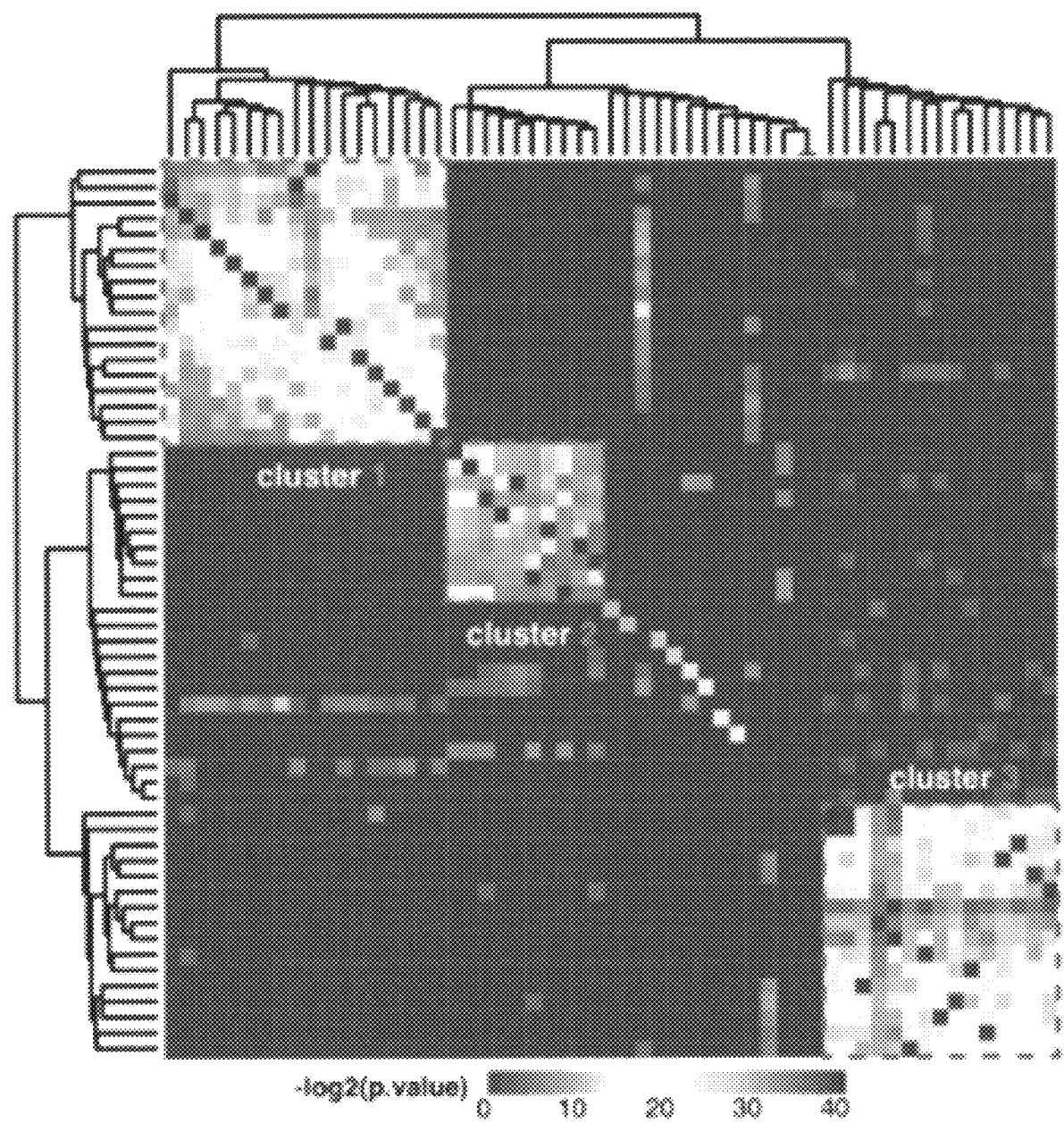
FIGS. 10A-10C. Determinants of TF binding dynamics. (A) Hierarchical clustering of motifs enriched in dynamic and static peaks revealed three clusters. Each entry in the distance matrix is -log 2(p-value) of motif similarity reported by Tomtom (44). (B) Linear regression of differential binding using basal binding and non-redundant sequence features identified positive and negative determinants of dynamic TF binding. Heatmap colors map to two-tailed t-test p-values on the regression coefficients for the null hypothesis that the coefficient is zero. The sequence features were selected from motifs enriched in the strongest peaks in ABA- and mock-treated conditions as well as dynamic and static peaks (FIG. 11). (C) Scatter plots on the left: basal binding of TFs quantified by normalized read count in the peak (x-axis) against log 2(fold change) of TF binding after ABA treatment (y-axis), with color of each dot mapped to the number of indicated motifs in the same peak. The occurrence of Cluster 3 and Cluster 2 motifs over the distributions of log 2 (fold change) of binding are shown in histograms on the right, with the same color code as the scatter plot. Proportion of peaks containing Cluster 3 motif increases along with log 2(fold change) of TF binding for the indicated TFs, whereas proportion of peaks containing Cluster 2 motif are negatively correlated with log 2(fold change) of TF binding.

To investigate whether there are additional motifs that correlated with TF binding dynamics, motif discovery on both dynamic and static peaks was also performed for a handful of TFs. These factors, NF-YB2, ABF1, ABF4, FBH3, MYB3, RD26, ZAT6 and HB7, were selected to represent a variety of TF families. Pairwise comparison of primary and secondary motifs discovered from dynamic and static peaks across the selected TFs revealed three major clusters (FIG. 10A). Cluster 1 motifs are composed of (AG)n repeats. Cluster 2 motifs contain a (A/G)G(A/C)CC (A/C) consensus sequence, whereas Cluster 3 comprises G-box motifs (FIG. 10B).

Figure 10B:
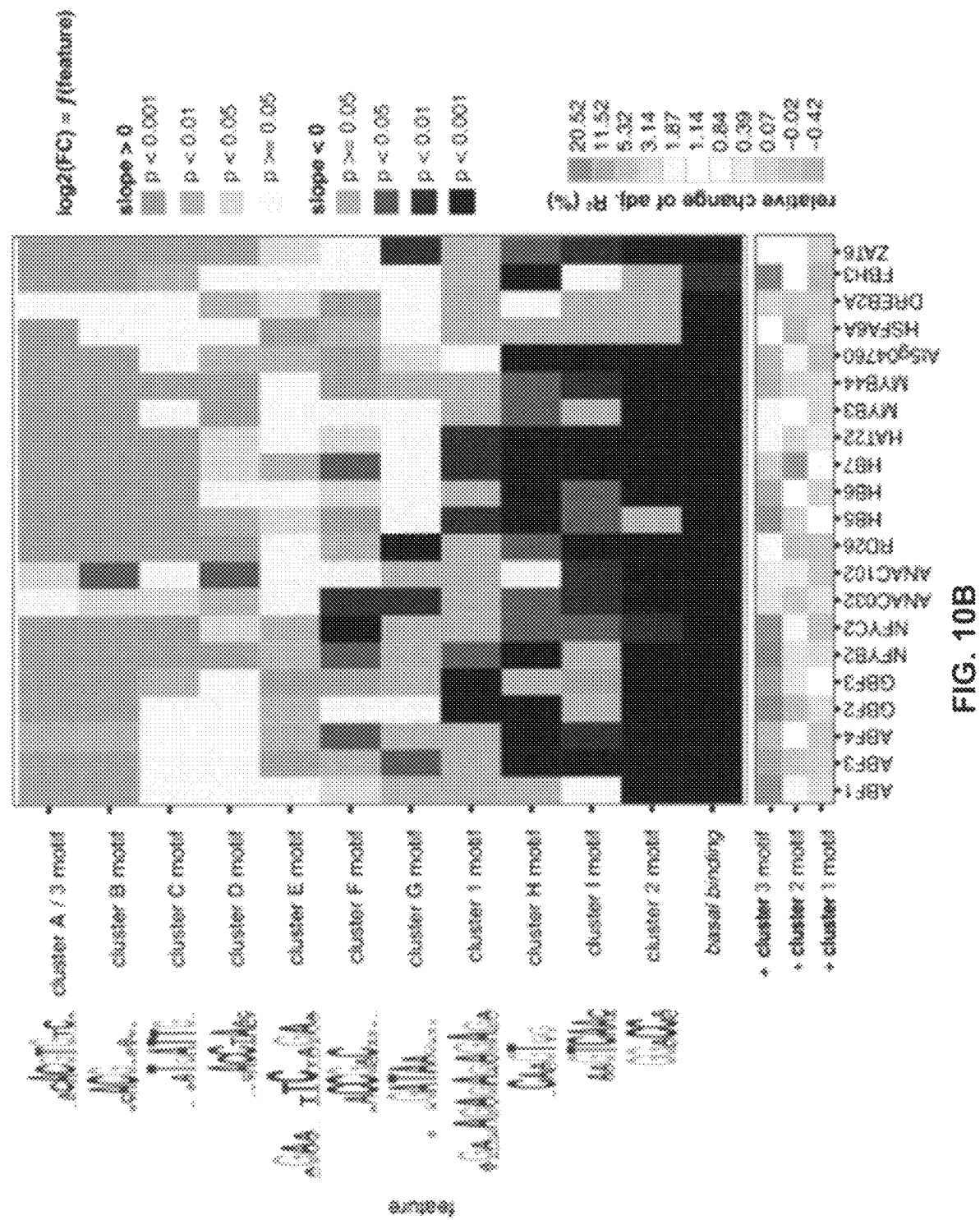
Figure 11:
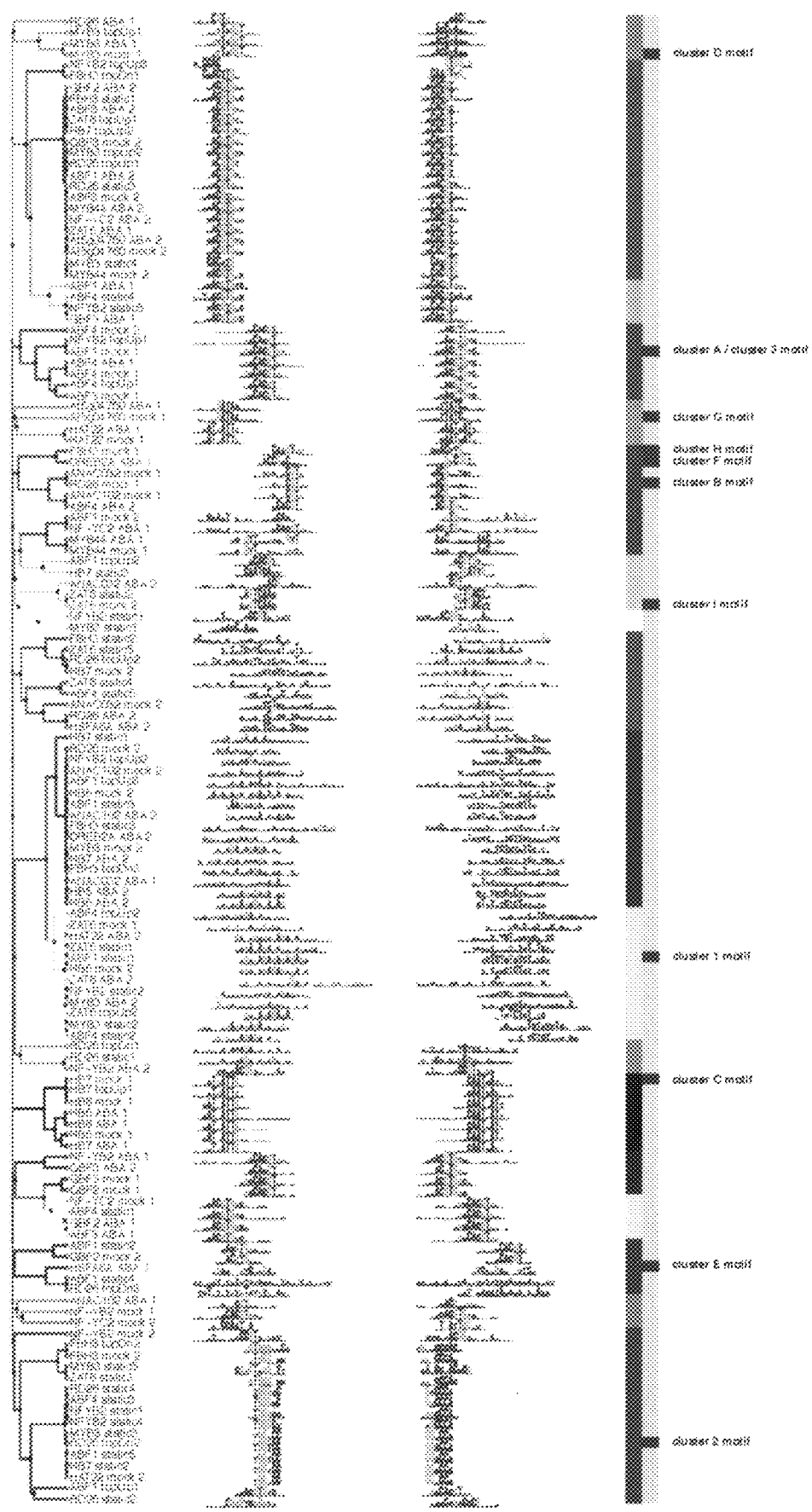
FIG. 11. Hierarchical clustering of motifs identified major groups of sequence features in the strongest ChIP-seq peaks or in the dynamic or static peaks. A set of 135 motifs were identified from the top 600 peaks of all TFs in ABA- or mock-treated conditions (TFname_C_i, where C is ABA or mock, and i corresponds to the rank of enrichment of the motifs), as well as from dynamic and static peaks (TFname_Di where D is topUp, topDn or static).

To examine the contributors to binding dynamics, linear regression was used to model the fold change of binding as a function of variables including basal binding of the TF (under mock treatment) and the number of occurrences (counts) of a set of non-redundant sequence features that enhanced dynamic binding, whereas basal binding and Cluster 2 motifs are associated with a negative impact on binding dynamics for a broad range of TFs (FIG. 10B, see Table 6 of U.S. Provisional Application No. 62/413,349 and Table S6 of Song et al., "A transcription factor hierarchy defines an environmental stress response network," Science, Vol. 354, Issue 6312, 4 Nov. 2016, both herein incorporated by reference). Including Cluster 3 or Cluster 1 motifs in the regression results increases the explained variability by up to 20% (FIG. 10B).

Figure 10C:
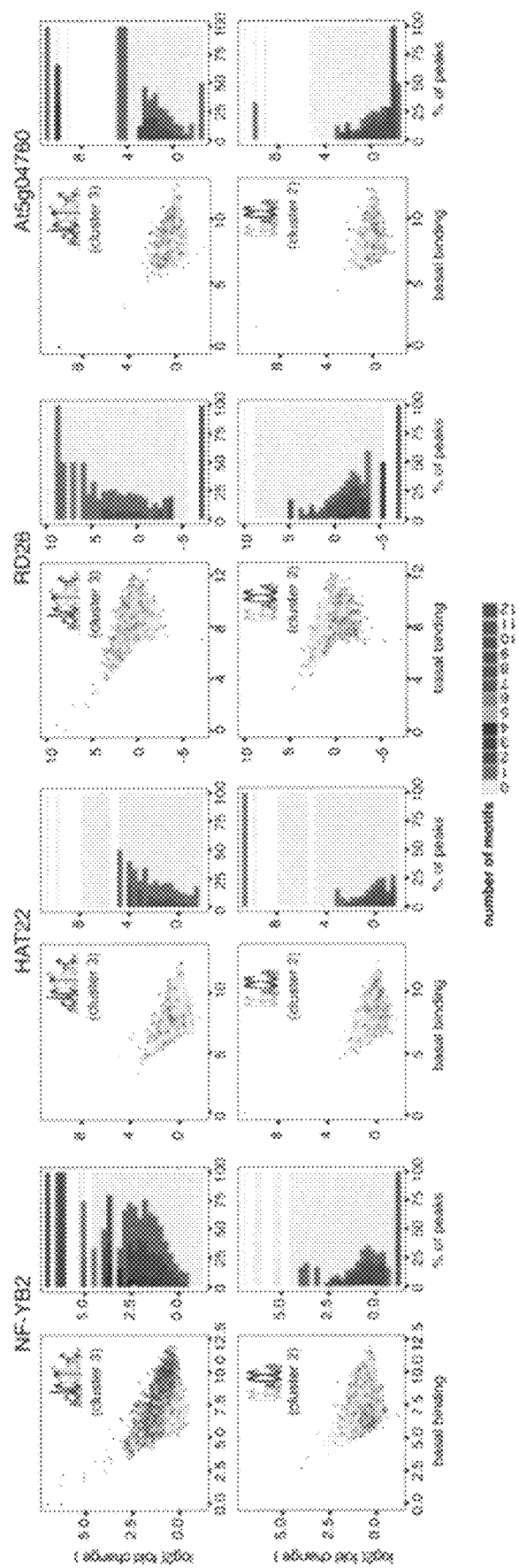

To visualize the impact of Cluster 3 G-box motif and Cluster 2 motif at the resolution of individual peaks, we plotted basal binding of TFs quantified by normalized read count against log 2 fold change of binding after ABA treatment and assigned a color to individual binding events on the basis of the count of motifs in the same peak (FIG. 10C). The proportion of peaks containing Cluster 3 motif increases along with log 2 fold change of binding, whereas the proportion of peaks containing Cluster 2 common motif are negatively correlated with log 2 fold change of binding. These data indicate that the binding of a TF to Cluster 3 motif (likely the ABFs) and the binding of an unknown family of TFs to Cluster 2 motif, positively and negatively regulate the binding dynamics of neighboring TFs.

Example 5

Construction of an ABA Response Network

Figure 12A:
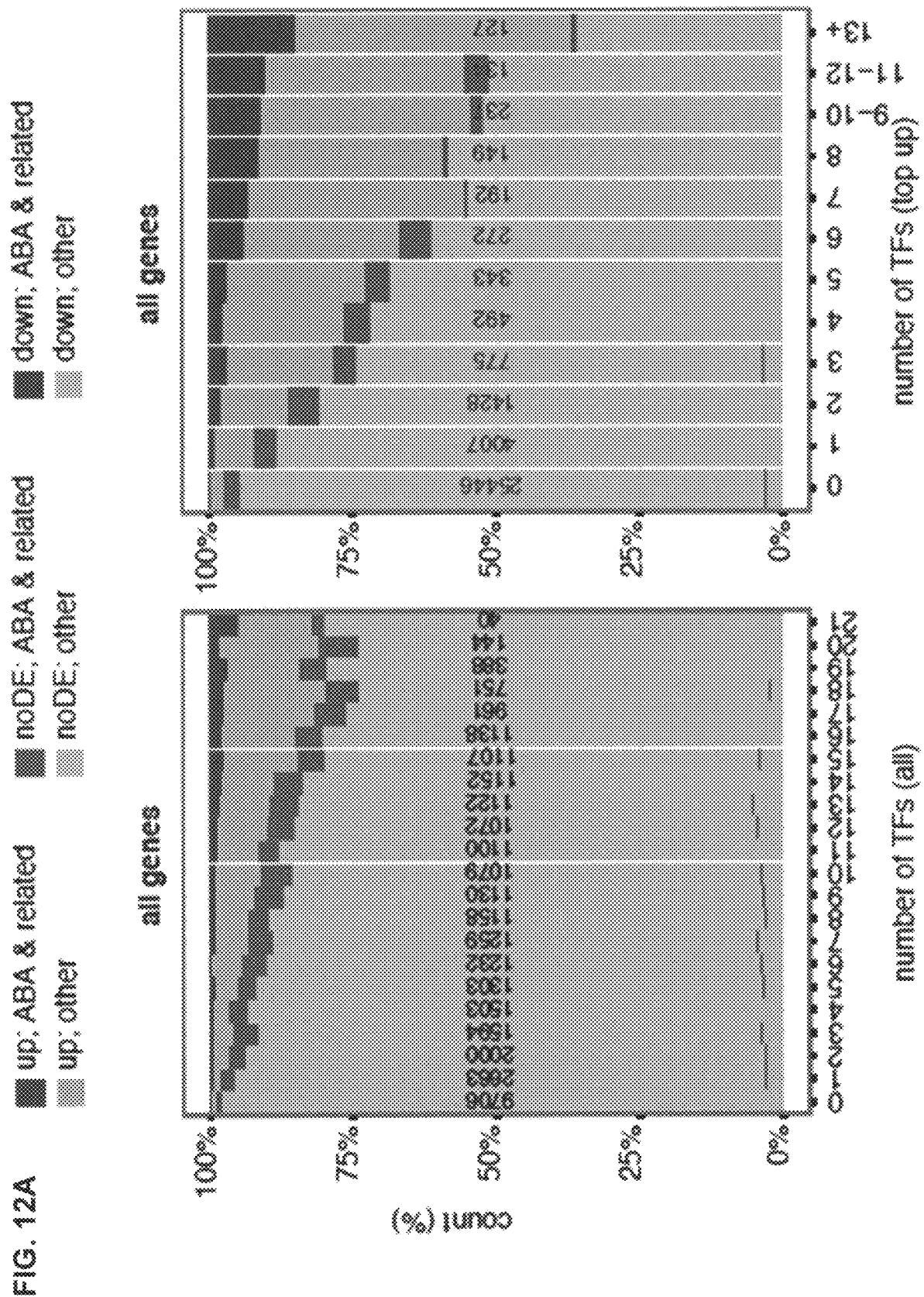
FIGS. 12A-12C. TF network integrates expression and connectivity features of genes in ABA response. (A-B) Expression and functional composition of all genes (A) and TF genes (B) are grouped by the number of targeting TFs through either any kind of binding or "top up" binding. "Top up" binding is a better predictor for both ABA-related BP functions and DE than "all" binding. The number of genes in each bin is shown in black. The bins to which of the TFs included in this study belong are indicated at the top of (B). (C) ABA pathway genes are subject to extensive feedback regulations and multi-TF dynamic binding. ChIPped TFs are arranged in three tiers by normalized hierarchy height. Target genes are grouped by function. Node color depicts changes of transcript abundance after 4 hours of ABA treatment. Edge color corresponds to TF binding dynamic categories.
Figure 12B:
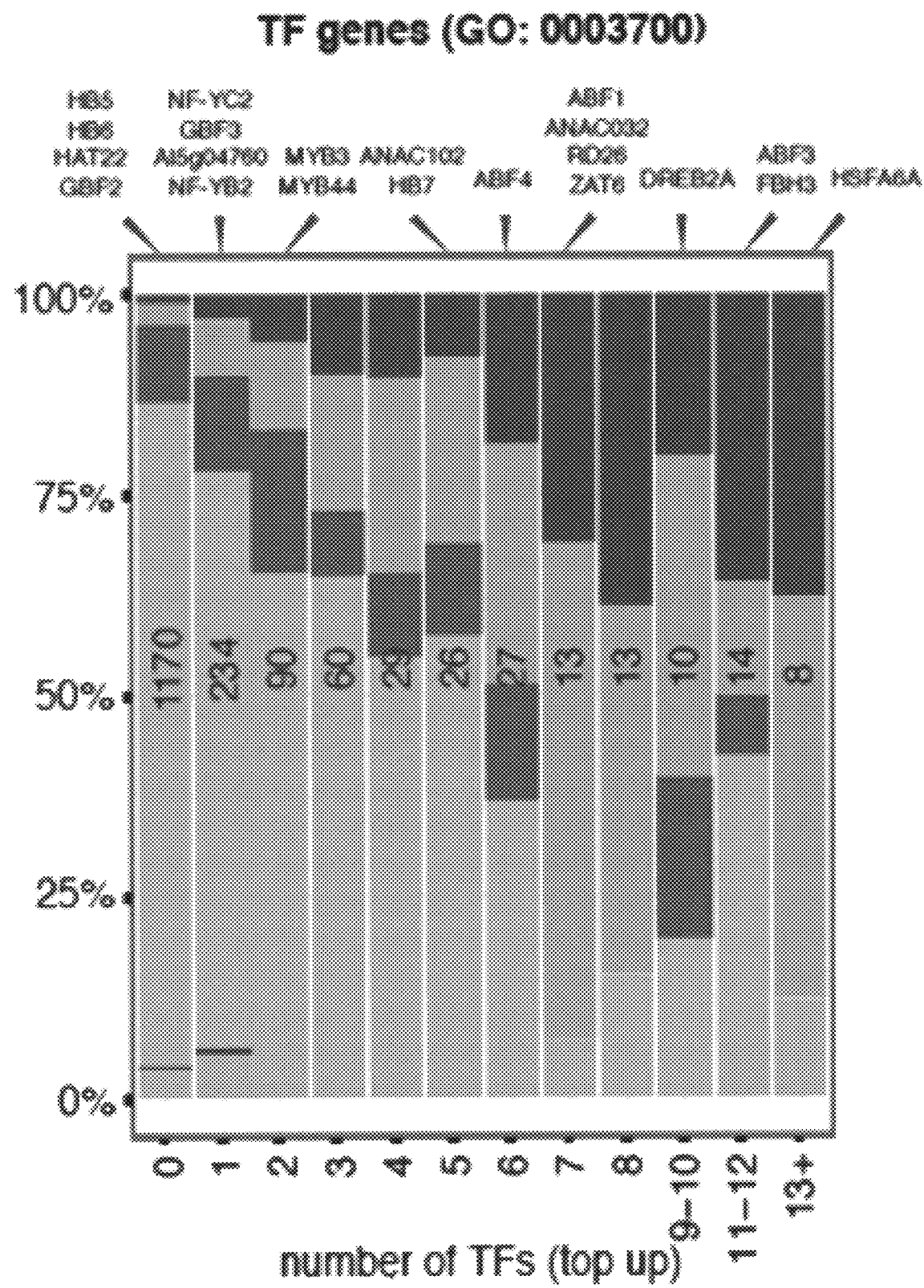
Figure 12C:
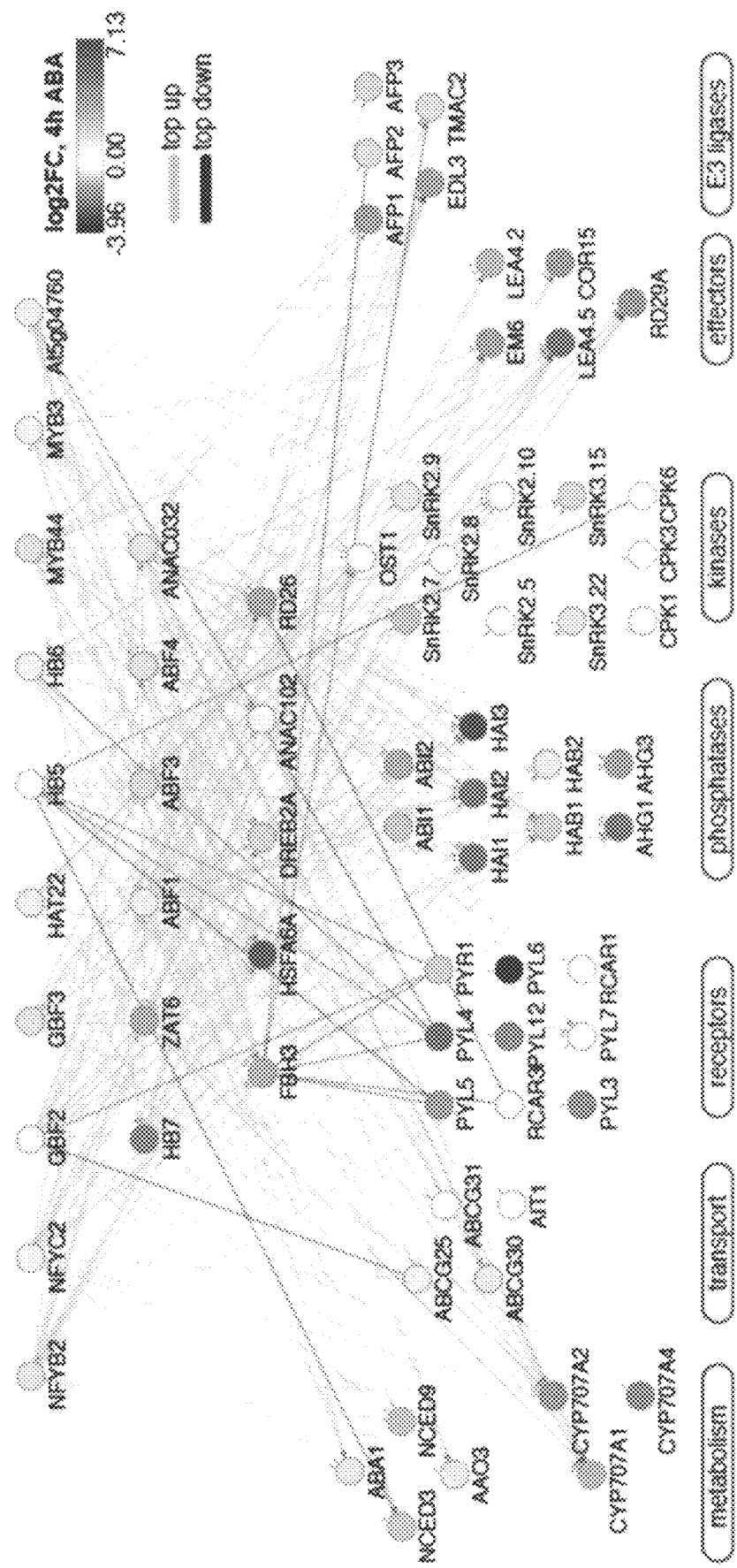
Figure 13A:
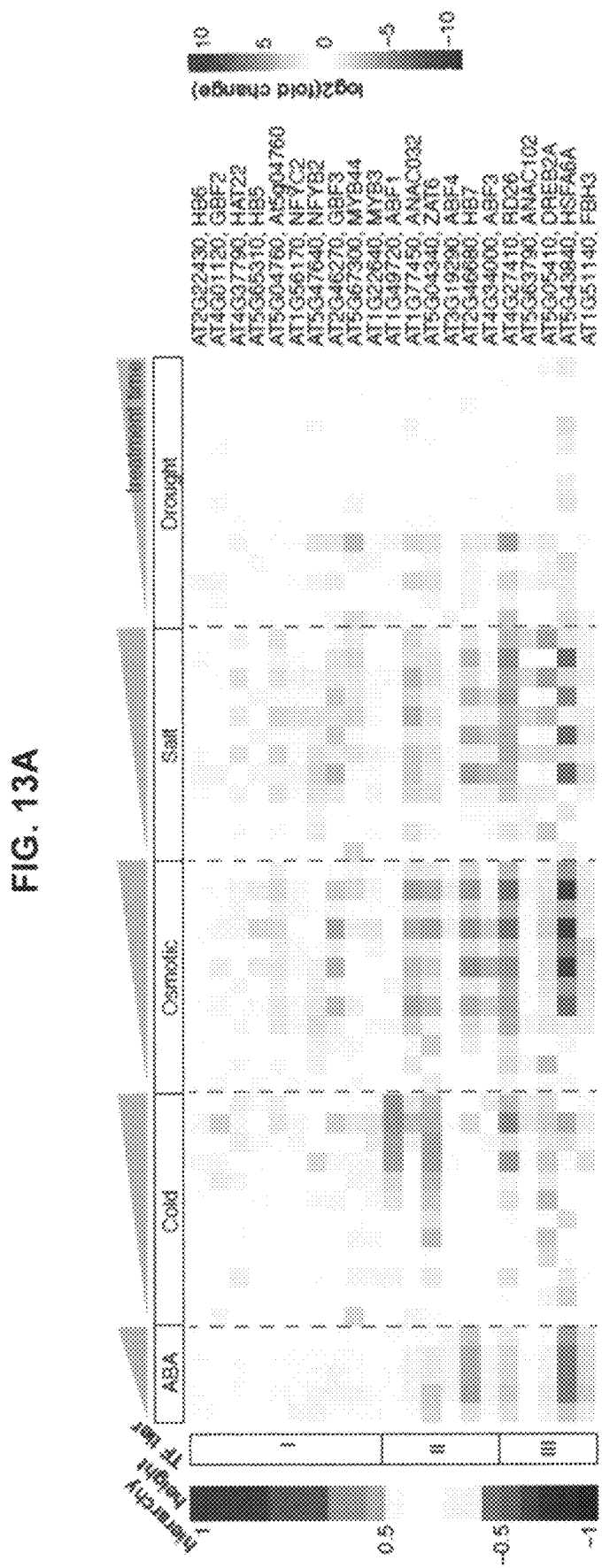
FIGS. 13A-13C. The hierarchical organization of TF network escalates the binding dynamics of lower tier TFs. (A) Log 2(fold change) of TF binding upon ABA treatment was plotted against basal binding measured as log 2(normalized read counts) under mock treatment. Peaks were classified into eight categories by three criteria: read count change (RCC, within top 20%), fold change (FC, within top 20%), and DiffBind FDR (less than 0.1). +++ and --- were designated as top dynamic and static respectively. The remaining were designated as moderately dynamic. Panels were arranged by the hierarchy height of TFs shown in FIG. 4. (B) Top tier TFs often have more static binding than lower tier TFs. (C) Western blots show that the protein abundance of most TFs were elevated by ABA. H3 detected by anti-histone H3 antibody used as a loading control.
Figure 13B:
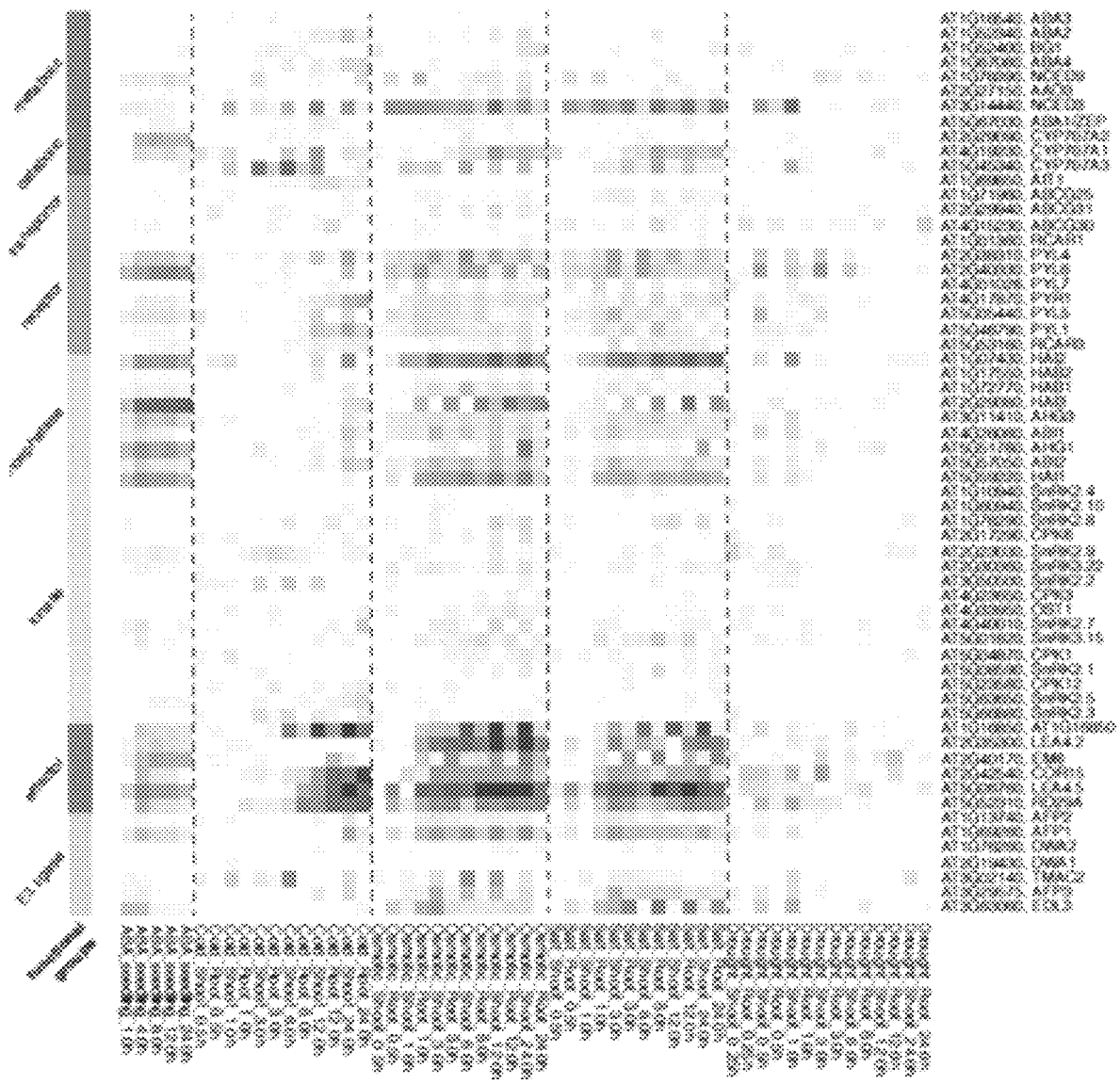
Figure 13C:
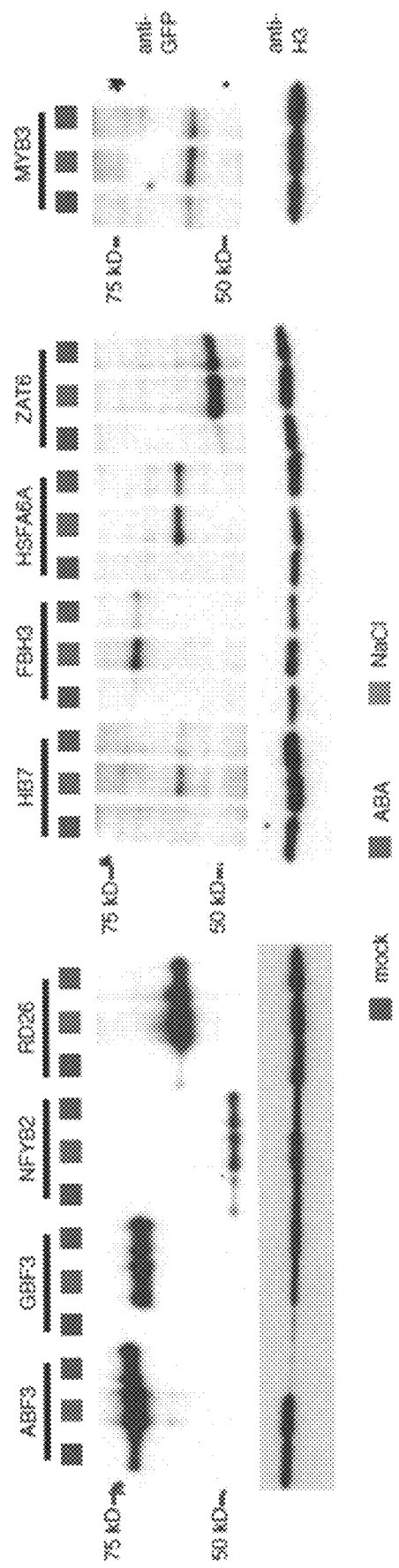

To confirm that dynamic binding is more robust than total binding in predicting gene expression and genes involved in ABA and related responses, the expression and functional composition of genes grouped by the number of targeting TFs through either any type of binding or "top up" binding was compared (FIG. 12A). Representation of both genes associated with ABA-related GO terms and ABA up-regulated genes increase more rapidly with the increase number of TFs that have "top up" binding. Therefore, top-ranked dynamic TF binding triggered by ABA treatment was used to demonstrate the wiring of this ABA network using the core ABA metabolic and signaling genes and to calculate the hierarchical height of TFs in the network (FIGS. 12B-12C, 13A). TFs in the network are organized into three tiers by their hierarchical height (FIG. 4C, 13A). The level of DE of lower tier TFs is often amplified compared to upper tier TFs, which results in greater changes in binding dynamics likely as a result of greater protein accumulation (FIGS. 4, 12A-C, 13A). Negative regulators of ABA response, including genes encoding ABA catabolic enzymes, protein phosphatase 2Cs and E3 ligases, are often induced by ABA and are heavily targeted by multiple TFs through highly up-regulated TF binding (FIG. 12C). By contrast, positive regulators of ABA response can either be up-regulated due to increased TF binding, or down-regulated due to reduced TF binding (FIG. 4C). These results point to a transcriptional feedback strategy in ABA response, presumably to allow rapid restoration of normal growth once stress is lifted. Because some transcriptional responses triggered by ABA are similar to those triggered by natural stresses (FIGS. 13A-13B) such as high saline conditions, we also expect to see a similar organization of regulatory networks for other osmotic-related stresses.

Figure 14:
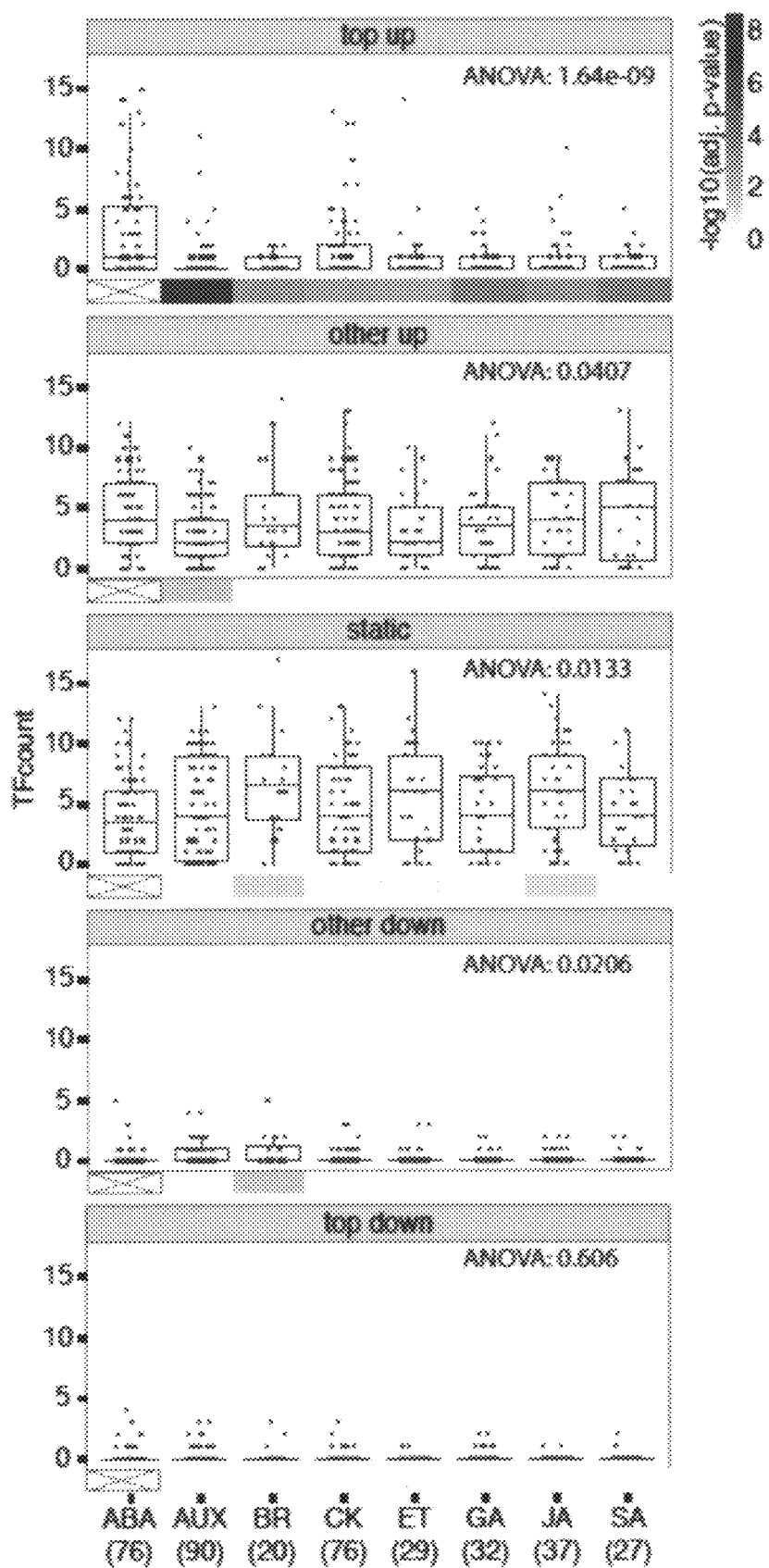
FIG. 14. "Top up" binding is a strong feature to distinguish genes related to ABA from those related to other hormones. The number of TFs targeting core hormone genes were counted for the indicated dynamic binding groups. Boxplot shows distribution of the number of associated TFs for genes related to the indicated hormone, overlaid by individual genes in red points. Blue blocks reflect statistical difference (Tukey HSD test) between the indicated hormone and ABA.

Extensive targeting by ABA-responsive TFs appears to be specific to the ABA pathway, as the core ABA genes are targeted by significantly more TFs through "top up" binding than genes from other plant hormones (FIG. 14, see Table 7 of U.S. Provisional Application No. 62/413,349 and Table S7 of Song et al., "A transcription factor hierarchy defines an environmental stress response network," Science, Vol. 354, Issue 6312, 4 Nov. 2016, both herein incorporated by reference). However, instances of hormone crosstalk can be observed in dynamically targeted DE genes. For example, both RGA-like 3 (RGL3), a master regulator of gibberellin response, and ACC synthase 2 (ACS2), an ethylene biosynthesis gene, were reported to be ABA-responsive (29, 30). It was observed that dynamic binding is mainly contributed by the bZIP and the NF-Y factors to the promoter of RGL3, and by a diverse family of TFs to the gene body of ACS2 (FIGS. 15A-15B). These results demonstrate the utility of these data to pinpoint regulatory regions that might modulate the expression of genes in one hormone response pathway by another.

Figure 16A:
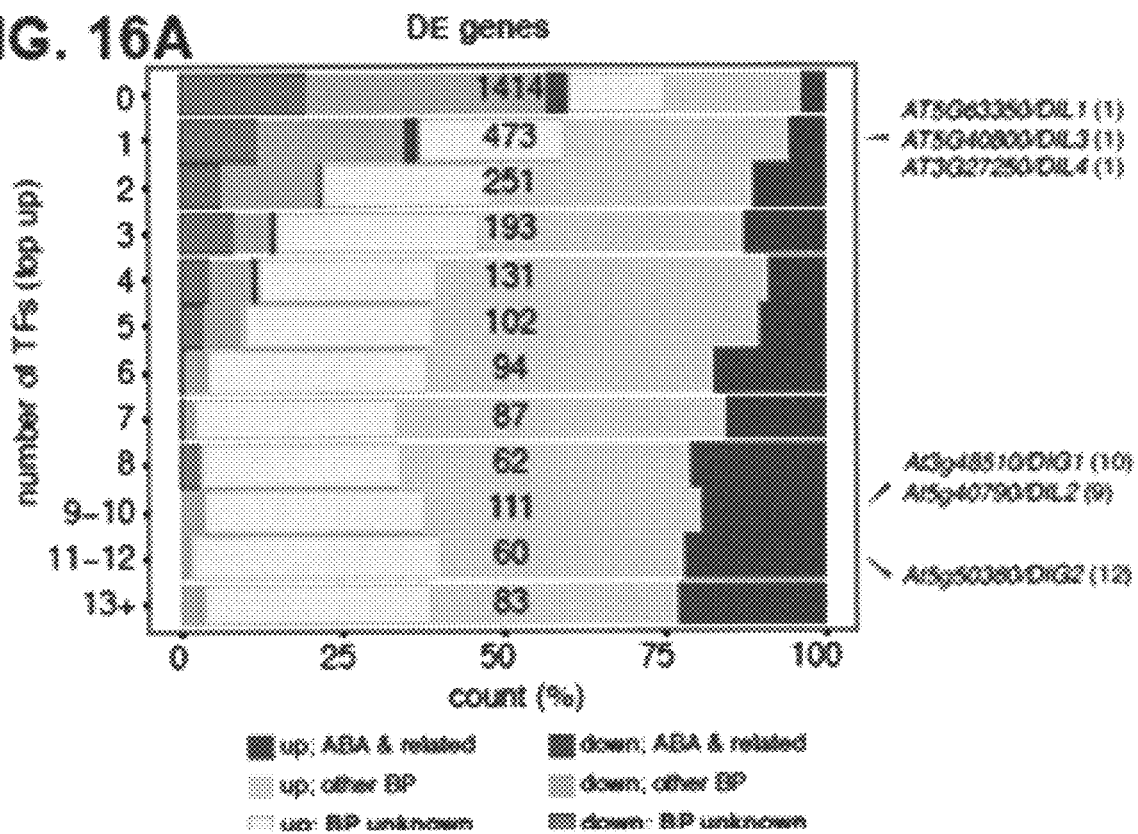
Figure 16B:
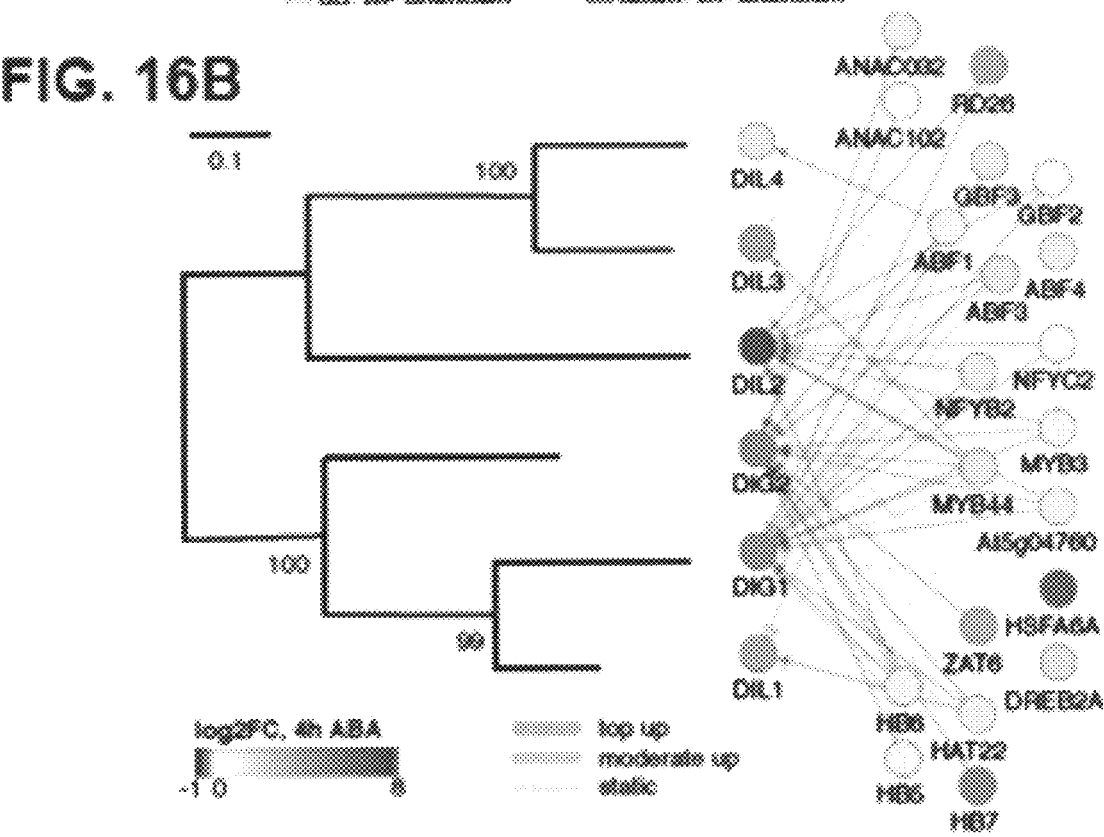

No GO term besides the ABA-related ones was enriched in DE genes heavily targeted by the 21 TFs through "top-up" binding. This is partially because more than one third (12136/33601) of the genes in the genome of *Arabidopsis thaliana* still have no information regarding their biological processes (BP) (FIG. 16A, see Table 4 of U.S. Provisional Application No. 62/413,349 and Table S4 of Song et al., "A transcription factor hierarchy defines an environmental stress response network," Science, Vol. 354, Issue 6312, 4 Nov. 2016, both herein incorporated by reference). On the basis of a "guilt-by-association" paradigm (31), it is proposed that many BP-unknown genes in FIG. 16A are also involved in ABA responses (see Table 8 of U.S. Provisional Application No. 62/413,349 and Table S8 of Song et al., "A transcription factor hierarchy defines an environmental stress response network," Science, Vol. 354, Issue 6312, 4 Nov. 2016, both herein incorporated by reference). As a proof of principle, a family in which all the members are BP-unknown and DE in response to ABA were functionally characterized. In particular, three members in this family, At3g48510, At5g50360 and At5g40790 are heavily targeted by TFs through "top up" binding (FIGS. 16A-16B). Little is known about this family except that the proper expression of At3g48510 relies on core ABA signaling (32). In addition, predicted proteins of this family contain no known domains.

Dexamethasone (DEX)-inducible lines expressing GFP fusion of the two most heavily targeted genes, At3g48510 and At5g50360 were generated. Analysis by RNA-seq showed that a few hundred DE genes were consistently identified from both short-term (4 h) and long-term (10 d) DEX induction of the two genes (FIG. 16C, see Table 8 of U.S. Provisional Application No. 62/413,349 and Table S8 of Song et al., "A transcription factor hierarchy defines an environmental stress response network," Science, Vol. 354, Issue 6312, 4 Nov. 2016, both herein incorporated by reference). To reflect their regulation and function, these genes were named Dynamic Influencer of Gene expression 1 (DIG1) and DIG2 and their homologs were named DIG-likes (DILs).

Figures 16D, 16E:
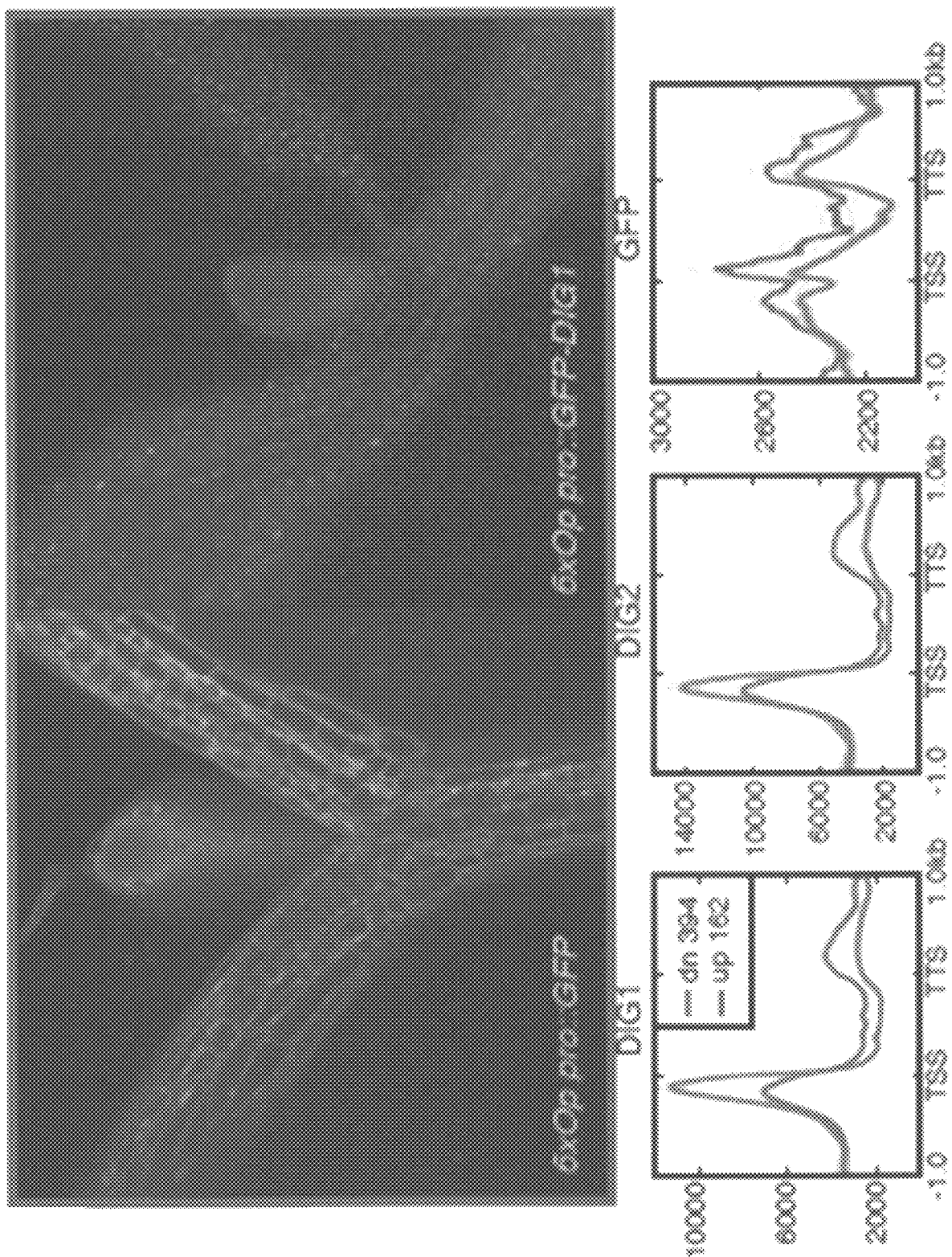
Figure 16F:
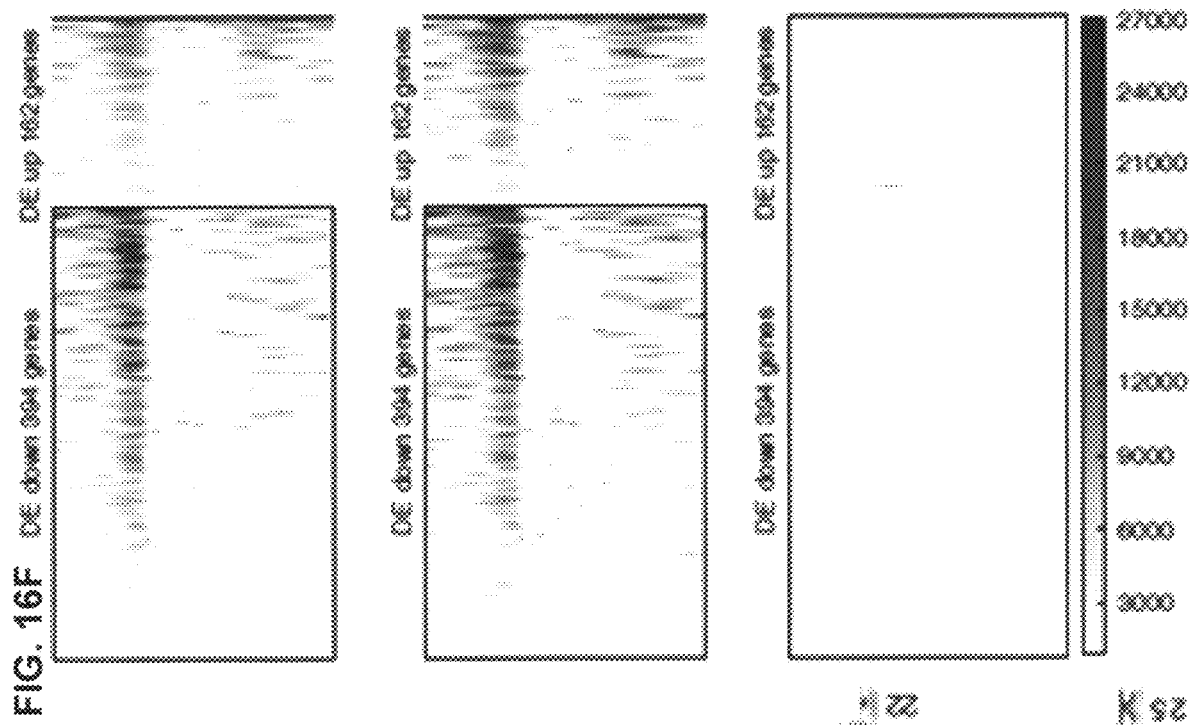
Figure 16G:
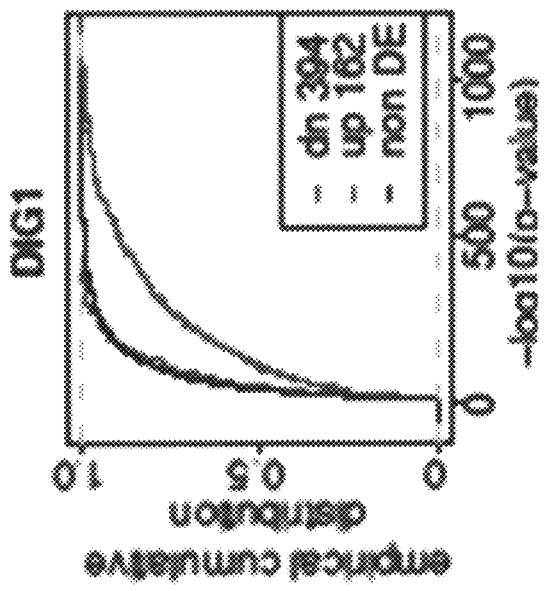
Figure 16H:
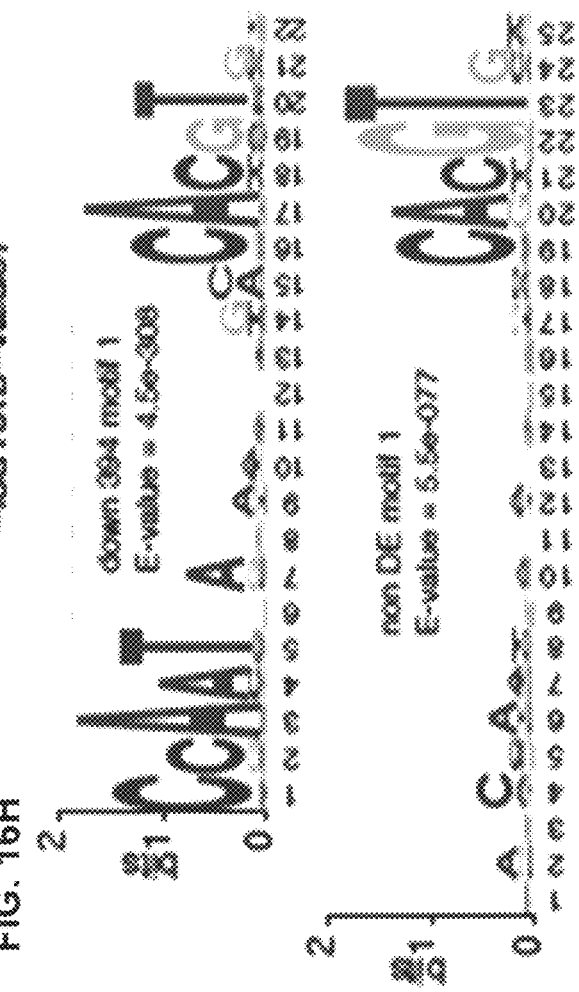
Figure 16I:
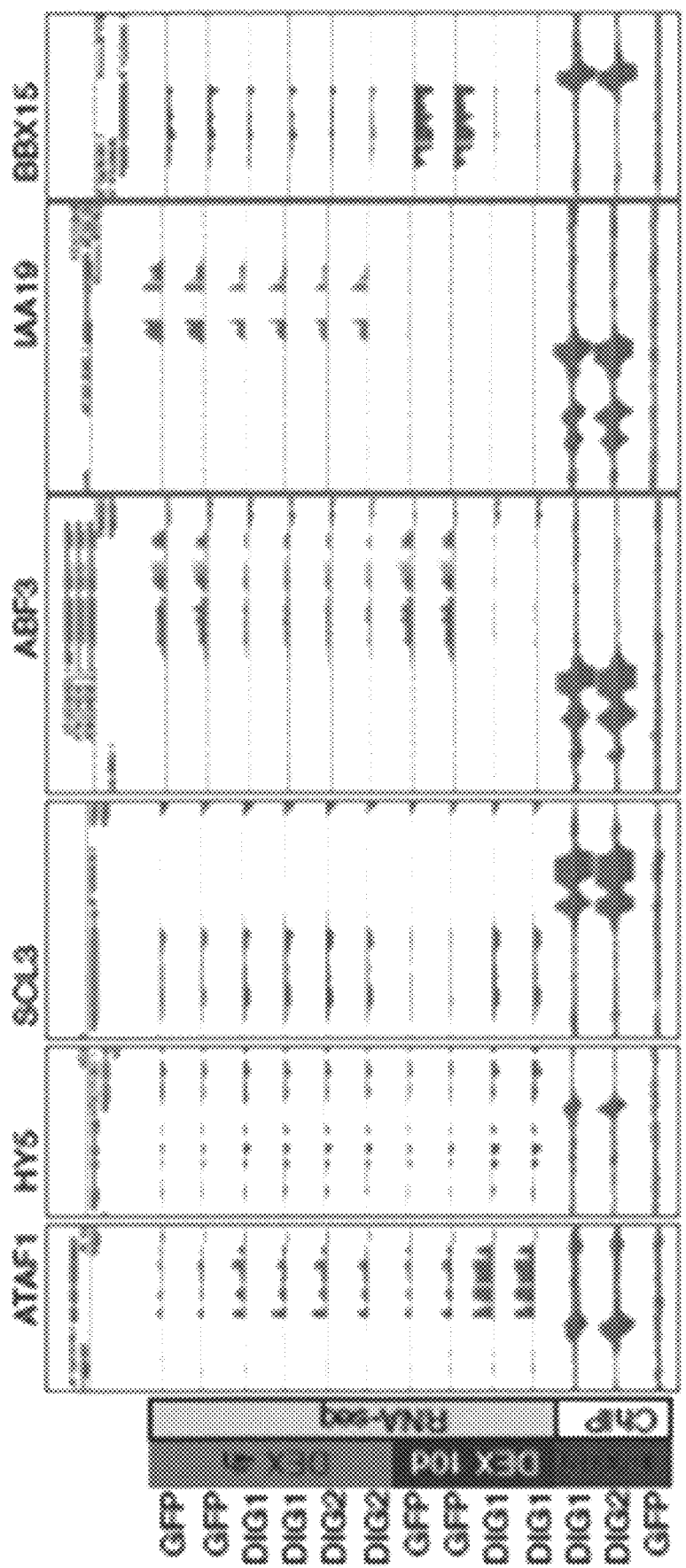
Figure 17:
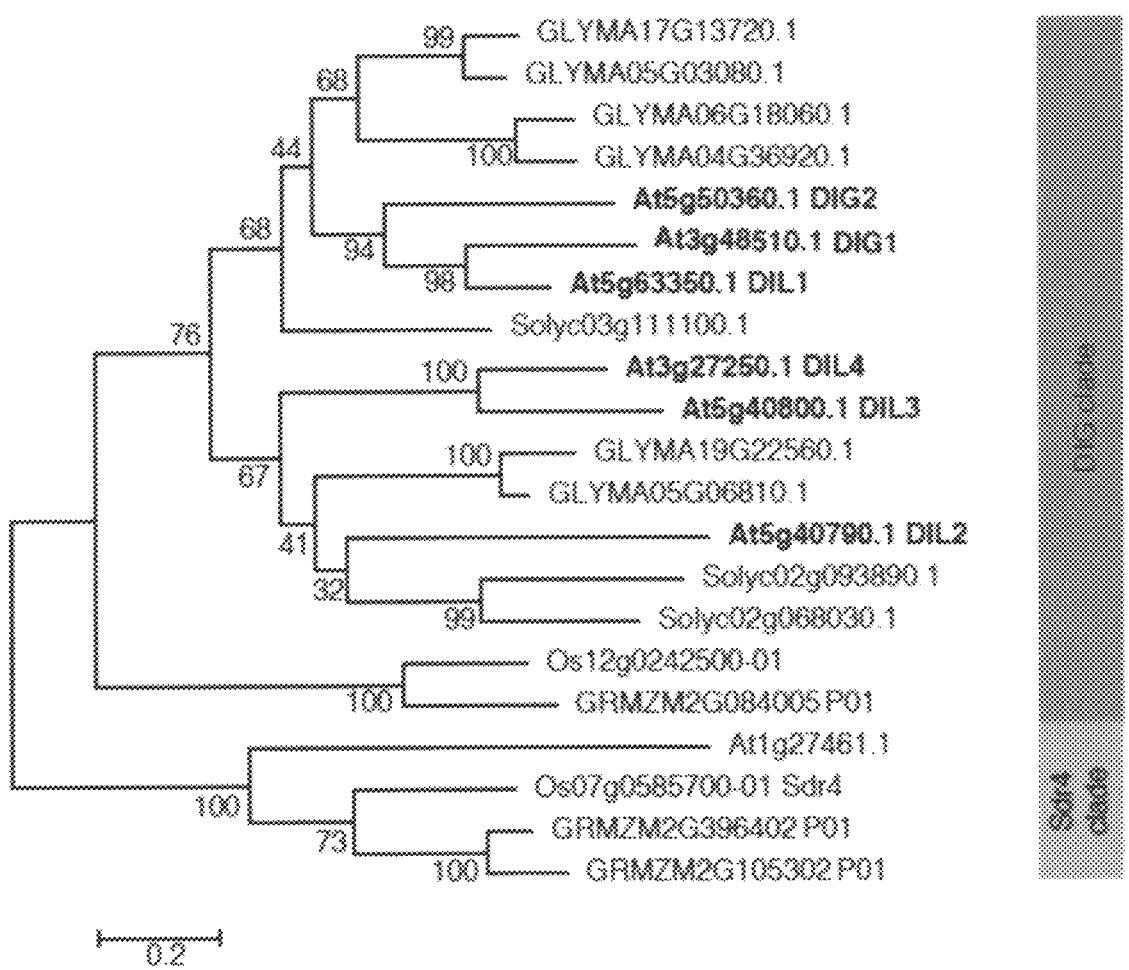
FIG. 17. DIG/DILs are evolutionarily conserved between monocots and dicots. The evolutionary history of DIG/DIL proteins was inferred by using the Maximum Likelihood method based on the JTT matrix-based model (68). The tree with the highest log likelihood (−6021.6483) is shown. The bootstrap values are shown next to the branches. Initial tree(s) for the heuristic search were obtained automatically by applying Neighbor-Joining and BioNJ algorithms to a matrix of pairwise distances estimated using a JTT model, and then selecting the topology with superior log likelihood value. The tree is drawn to scale, with branch lengths measured in the number of substitutions per site. The analysis involved 21 amino acid sequences. All positions containing gaps and missing data were eliminated. There were a total of 179 positions in the final dataset. Evolutionary analyses were conducted in MEGA6 (66). The clade containing DIGs and their homologs in representative dicot and monocot species is shown in mint, and a distantly-related clade containing the rice Sdr4 protein is shown in grey.
Figure 18:
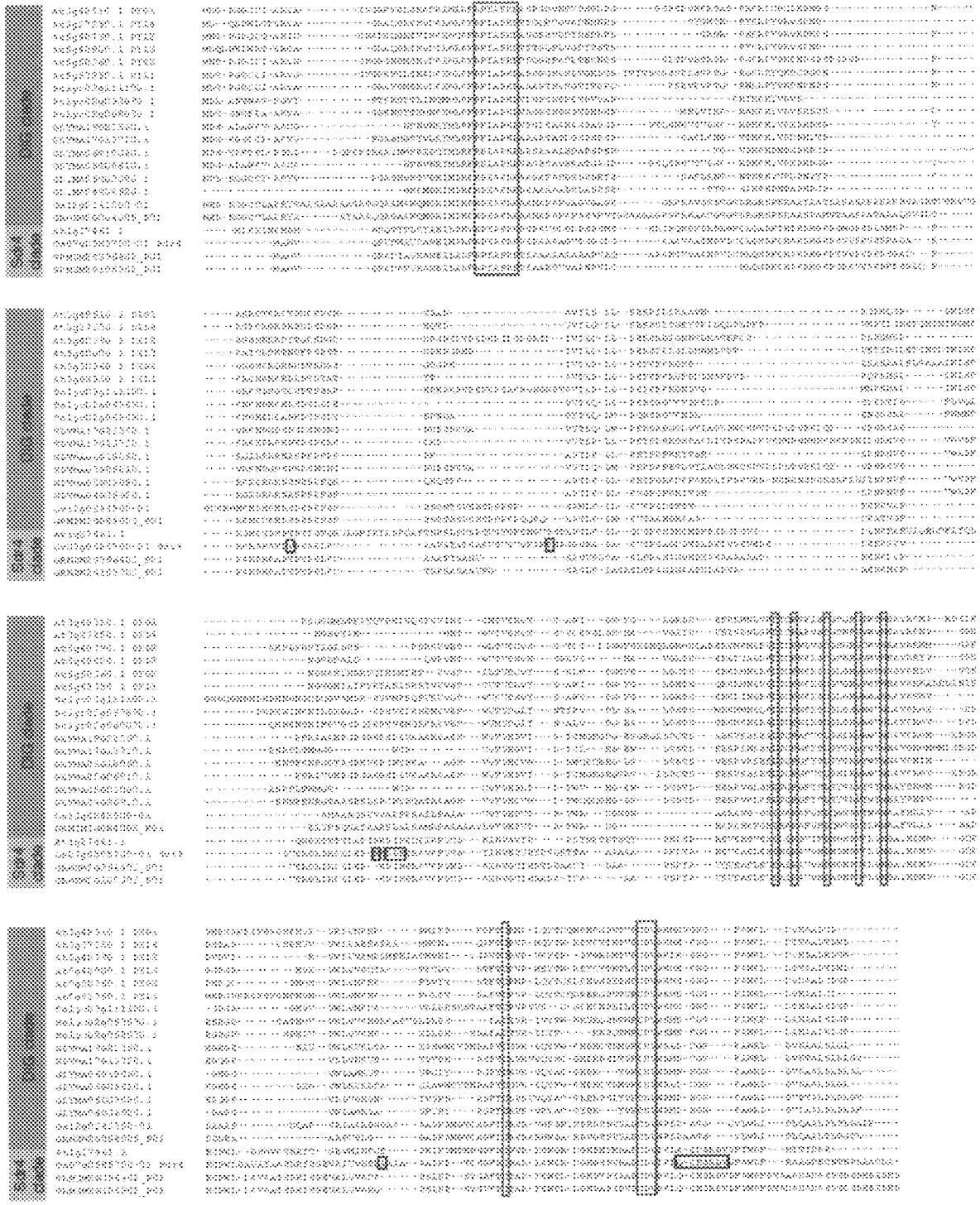
FIG. 18. DIGs and their homologs do not contain the functionally important motifs of Sdr4. Protein sequences of DIGs and related genes (from top to bottom SEQ ID NOS: 2, 12, 8, 10, 4, 6, 35, 36, 37, 38, 39, 40, 41, 42, 43, 44, 45, 46, 47, 48, and 49) were aligned by MUSCLE (69). Conserved amino acid between DIG clade and Sdr4 clade are highlighted in the red boxes. Previously reported amino acid motifs/sequences of potential functional importance (38) are highlighted in the green boxes.

ABA-related GO terms such as response to water deprivation were enriched in DIG down-regulated genes (FIG. 16C). Confocal imaging further showed DIGs were localized to the nucleus (FIG. 16D). Whether the DIGs are transcriptional regulators was determined. ChIP-seq of DEX inducible GFP-DIGs showed that the DIGs bind chromatin. Moreover, stronger binding was observed in the promoter of DIG down-regulated genes than up-regulated ones or non-DE genes (FIGS. 16E-16F). De novo motif discovery identified a $CCAAT(n)_8$ ABRE motif strongly enriched near the DIG1 binding sites within 1 kb of DIG down-regulated genes. By contrast, either a weaker motif or no similar motif was enriched near DIG binding sites in the corresponding regions of non-DE genes or DIG up-regulated genes (FIGS. 16G-16H). Several ABA-responsive or developmental TFs are targeted by DIGs and differentially expressed upon the induction of DIGs (see Table 9 of U.S. Provisional Application No. 62/413,349 and Table S9 of Song et al., "A transcription factor hierarchy defines an environmental stress response network," Science, Vol. 354, Issue 6312, 4 Nov. 2016, both herein incorporated by reference). Among these, ATAF1, HY5 and ABF3 have been linked to ABA sensitivity (33-35), whereas HY5, SCL3 and perhaps IAA19 have developmental roles (34, 36, 37). Sequence analysis revealed that DIGs are conserved between monocots and dicots (FIGS. 15A-15B). A remotely-related clade of DIG contains a gene Sdr4, which regulates seed dormancy in rice (38) (FIG. 17). The Sdr4 paralog in *Arabidopsis* is also dynamically targeted by multiple ABA-responsive TFs and differentially expressed in response to ABA (see Table 1 of U.S. Provisional Application No. 62/413,349 and Table 51 of Song et al., "A transcription factor hierarchy defines an environmental stress response network," Science, Vol. 354, Issue 6312, 4 Nov. 2016, both herein incorporated by reference). However, the functionally important amino acid residues of Sdr4 are not conserved in the DIGs and their homologs (FIG. 18) (38). Therefore, genes in the DIG and Sdr4 clades may exert ABA-related functions through distinct mechanisms.

Figure 19A:
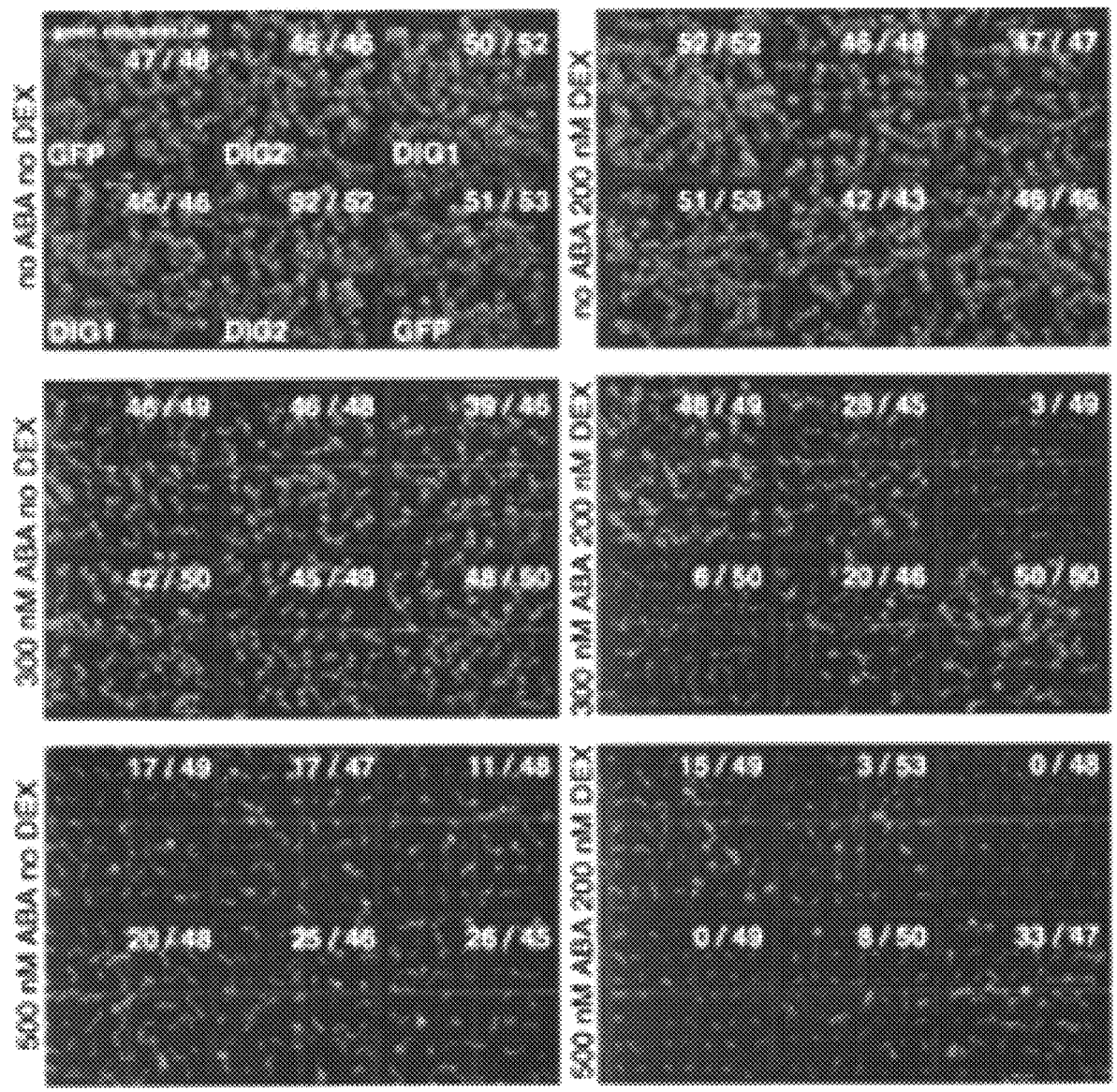
FIGS. 19A-19F. DIG inducible lines exhibit enhanced sensitivity to ABA and salt. (A-B) ABA-dependent delay of cotyledon greening in 8-day-old seedlings were further amplified upon DEX-mediated induction of DIG1 and DIG2 compared to GFP control quantified by count of green cotyledons (A) and measurement of relative chlorophyll content (B). Error bar reflects the 95% confidence interval around the mean estimate calculated from 3 biological replicates of ca. 50 eight-day-old seedlings each. (C) NaCl-dependent bleaching was observed in 4-week-old plants upon DEX-mediated induction of DIG1 and DIG2. (D-E) DEX-mediated induction of DIG1 (D1) and DIG2 (D2) resulted in more severe inhibition of lateral root growth than GFP (G) control plants on ABA (D) and NaCl (E) plates. (F) DEX-mediated induction of DIG1 and DIG2 led to over-accumulation of pigments in leaves. In D-F, seedlings were transferred to the indicated plates after grown on LS plates for seven days.
Figure 19B:
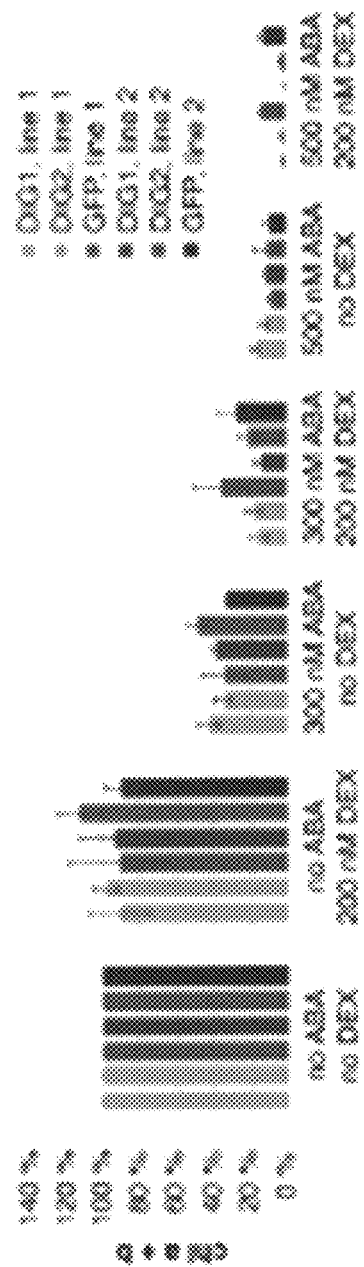
Figure 19C:
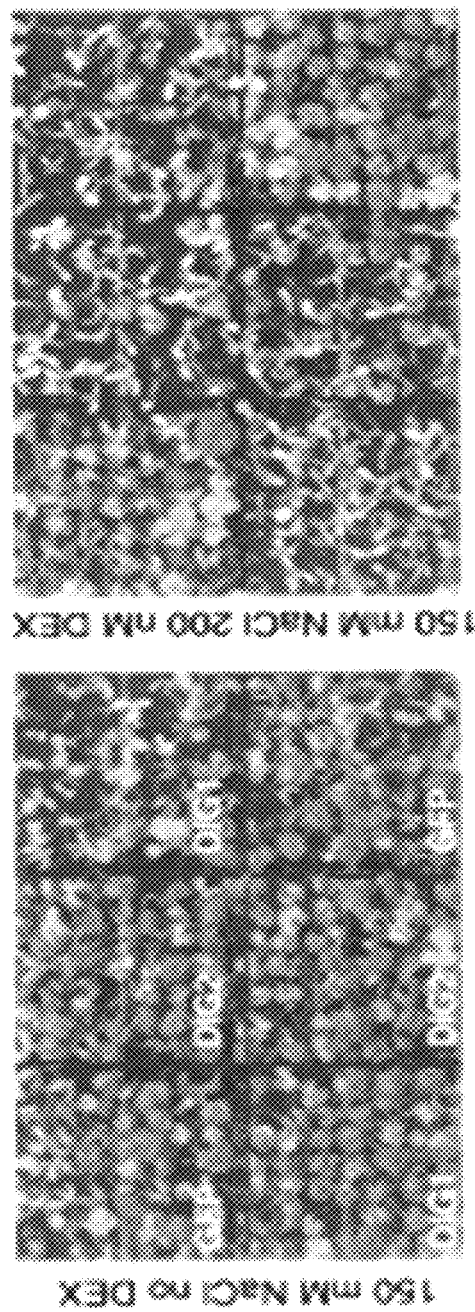
Figure 19E:
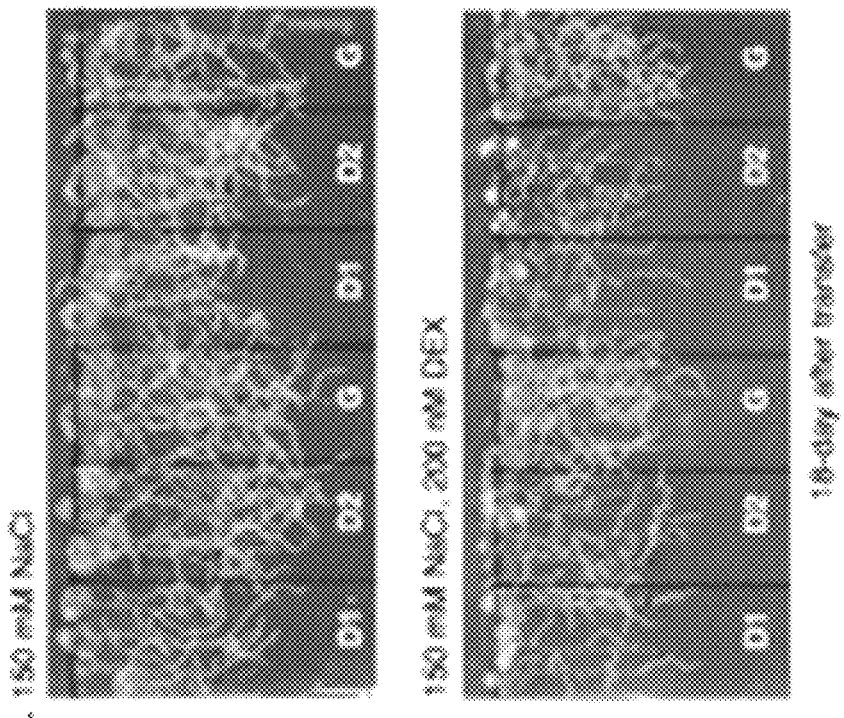
Figure 19D:
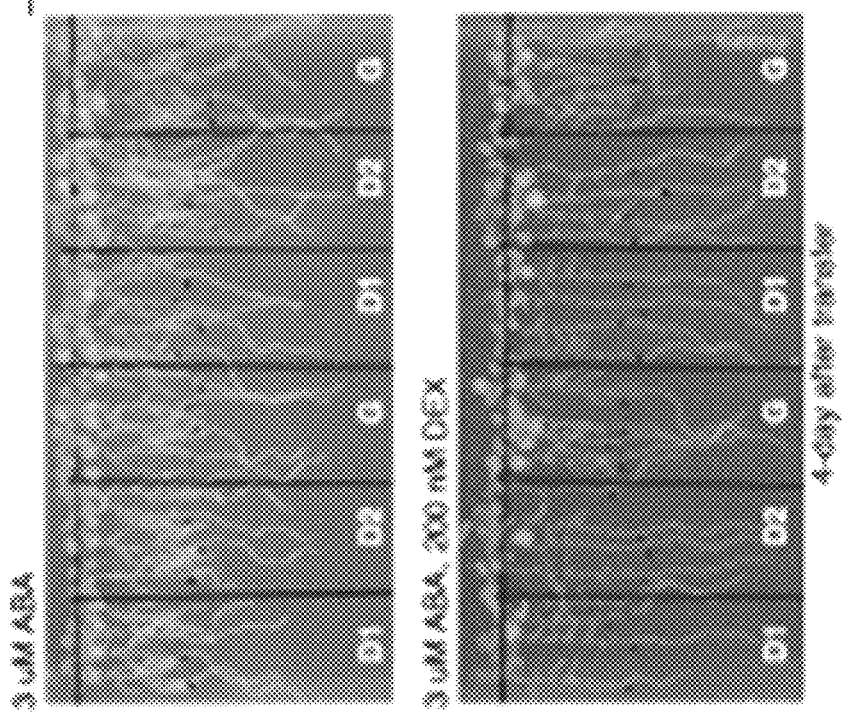
Figure 19F:
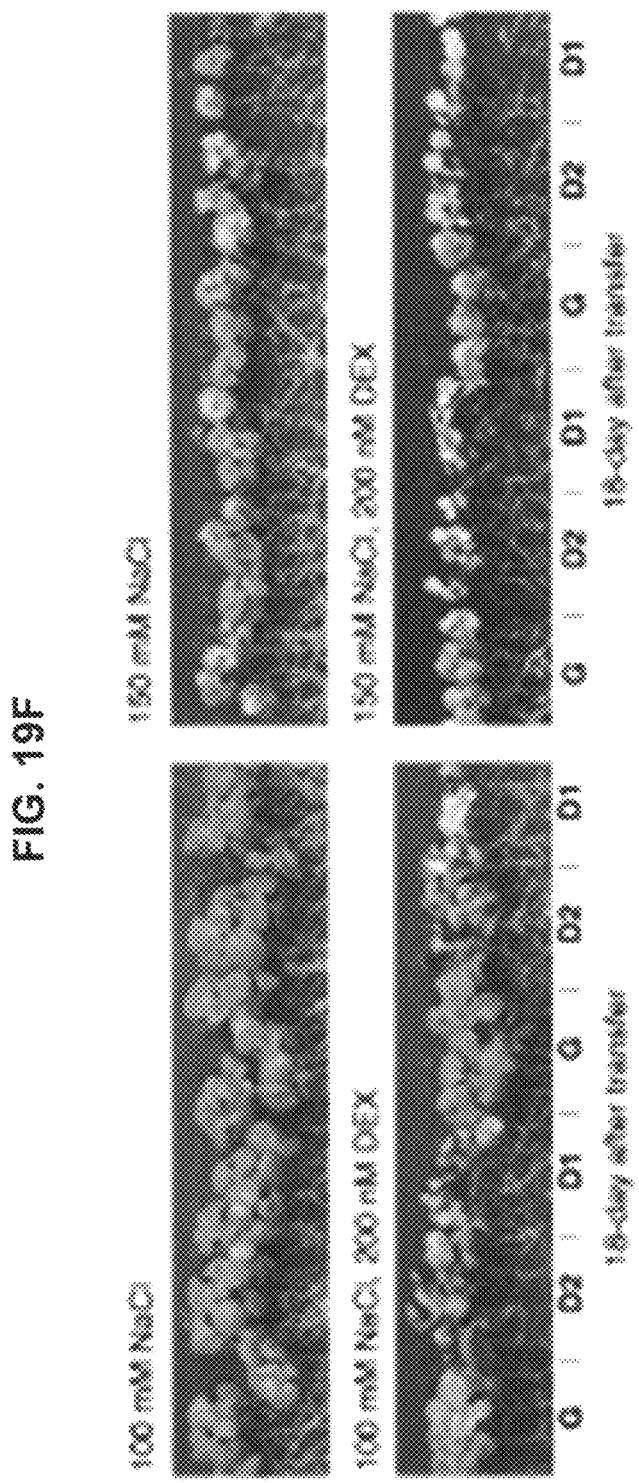

Inducible expression of DIGs enhances ABA sensitivity as assayed by cotyledon greening (FIGS. 19A-19B) and lateral root growth (FIG. 19D). Similarly, enhanced growth inhibition of DIG lines can also be observed after prolonged growth under high NaCl conditions (FIGS. 19C, 19E-19F). Combined, these results indicate that DIGs are a family of transcriptional regulators with broad roles that include regulating gene expression affecting ABA sensitivity and salt stress responses.

Example 6

Generating Loss-of-Function Mutants of DIG/DIL Genes in *Arabidopsis*

Single and high-order loss-of-function mutants of the DIG/DIL genes are generated in *Arabidopsis*. T-DNA mutants (Alonso, *Science* 301:653-7, 2003, herein incorporated by reference in its entirety) are available for three DIG/DIL family members: SALK_128578 for At3g48510 (DIG1), SALKseq_057406.2 for At5g50360 (DIG2) and SALK_130501 for At5g63350 (DIL1). CRISPR/Cas9 mutagenesis (Jinek et al., *Science* 337:816-22, 2012) can be used for the rest of the family, for example following the procedures described by Ma et al. (*Mol. Plant.* 8:1274-84, 2015).

A dig1dig2 double mutant can be created by crossing the T-DNA lines of dig1 and dig2 single mutants (SALK_128578, SALKseq_057406.2). Similar methods can be used to generate other double mutants. A dig1dig2dil1 triple mutant can be developed by knocking out the dil1 gene using a CRISPR-Cas9 system. Similar methods can be used to generate other higher order mutants.

In brief, guide RNA constructs targeting At5g40790 (DIL2), At5g40800 (DIL3), and At3g27250 (DIL4) can be made using pAtU6-sgRNA-SK. The resulting AtU6pro:: sgRNA cassette can be liberated by SpeI and NheI digestion, and inserted into the SpeI position in the pYAO:hSpCas9 plasmid. The pYAO:hSpCas9-pAtU6-sgRNA plasmid will be introduced into *Agrobacterium* for *Arabidopsis* transformation using the floral dip method (Clough and Bent, *Plant J.* 16:735-43, 1998). Wild-type Col-0 or a DIG/DIL mutant plant can be transformed to generate a single or a high-order mutant, respectively.

The resulting plants can be compared with wild-type controls for germination under salt stress. For example, seeds from the mutant generated (such as a dig1dig2dil1 triple mutant or dig1dig2 double mutant) are germinated along with wild-type Col-0 seeds either on a regular growth medium (1× Linsmaier & Skoog medium, 0.5% sucrose, 0.7% Phyto agar) or a medium supplemented with salt (1× Linsmaier & Skoog medium, 0.5% sucrose, 0.7% Phyto agar, 150 mM NaCl). Plants can be imaged about 12 days post seed imbibition.

Figure 21:
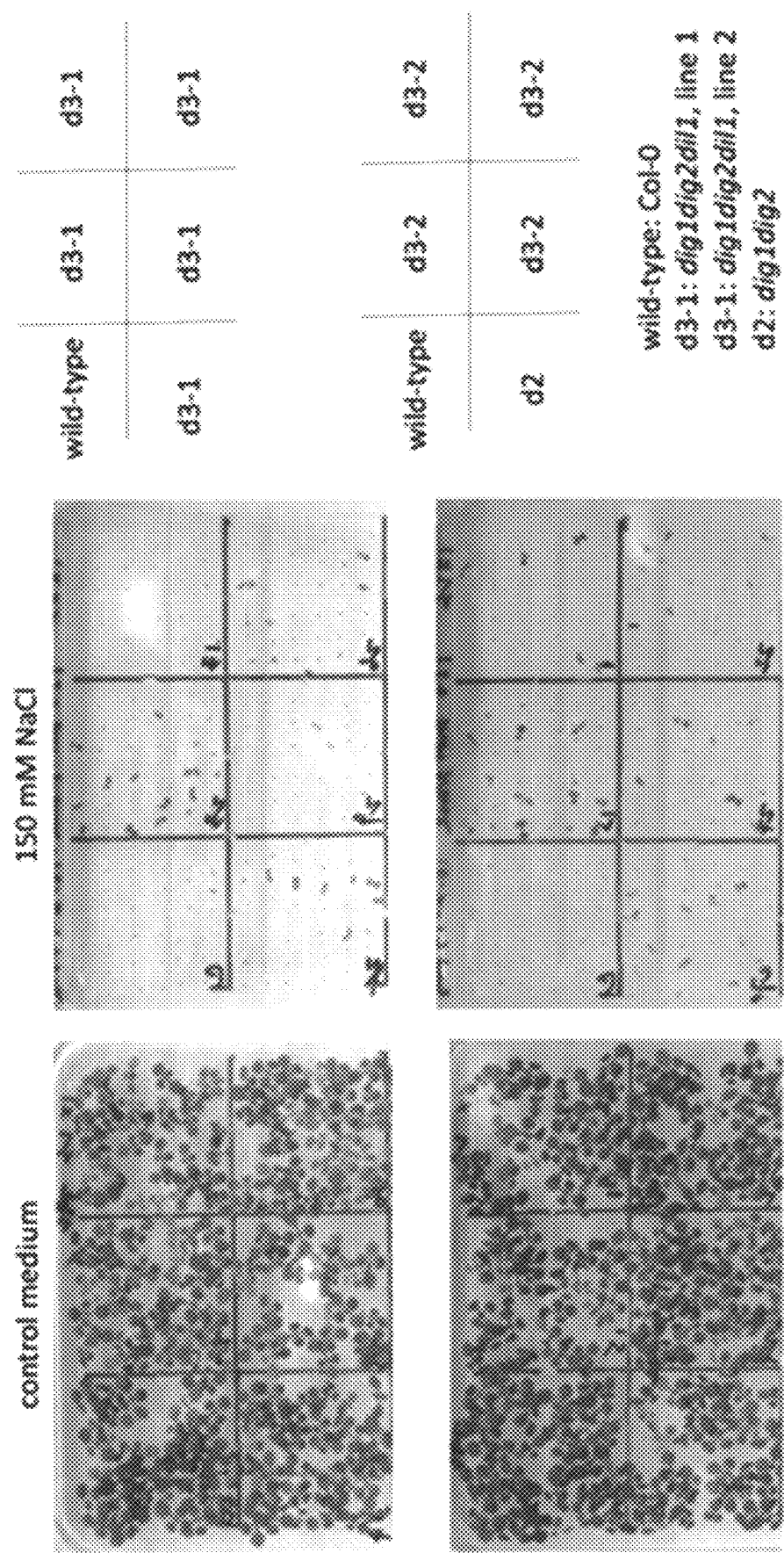
FIG. 21. Digital image showing that dig1dig2dil1 triple mutants germinate better than wild-type seeds under high salinity.

As shown in FIG. 21, the dig1dig2dil1 triple mutants germinate better than wild-type seeds under high salinity.

REFERENCES

1. Consortium et al., *Nature.* 447, 799-816 (2007).
2. Gerstein, *Science* (80-.). 47, 7-10 (2010).
3. Roy et al., *Science.* 330, 1787-97 (2010).
4. Yamaguchi-Shinozaki, Shinozaki, *Annu. Rev. Plant Biol.* 57, 781-803 (2006).
5. S. R. Cutler, P. L. Rodriguez, R. R. Finkelstein, S. R. Abrams, Abscisic acid: emergence of a core signaling network. (Annu Rev *Plant Biol.* 2010; 61:651-79).
6. Park et al., *Science.* 324, 1068-1071 (2009).
7. Ma et al., Regulators of PP2C phosphatase activity function as abscisic acid sensors. *Science.* 324, 1064-1068 (2009).
8. Santiago et al., *Nature.* 462, 665-668 (2009).
9. Santiago et al., *Plant J.* 60, 575-588 (2009).
10. Furihata et al., *Proc. Natl. Acad. Sci. U.S.A* 103, 1988-1993 (2006).
11. Fujii et al., *Nature.* 462, 660-664 (2009).
12. Fujita, M. Fujita, K. Shinozaki, K. *J. Plant Res.* 124, 509-25 (2011).
13. Weirauch et al., *Cell.* 158, 1431-1443 (2014).
14. Jolma et al., *Nature.* 527, 384-8 (2015).
15. O'Malley et al., Cistrome and Epicistrome Features Shape the Regulatory DNA Landscape. *Cell.* 165, 1280-1292 (2016).
16. Cumbie et al., *Plant Methods.* 11, 42 (2015).
17. Buenrostro et al., *Curr. Protoc. Mol. Biol.* 2015, 21.29.1-21.29.9 (2015).
18. Robinson et al., *Bioinformatics.* 26, 139-140 (2010).
19. Alonso and Stepanova, in *Bacterial artificial chromosomes* (2015), vol. 1227.
20. Lim et al., *Plant Sci.* 187, 83-8 (2012).
21. Okamoto et al., *Plant Physiol.* 141, 97-107 (2006).
22. Kumimoto et al., *PLoS One.* 8, e59481 (2013).
23. R. Stark, DiffBind: Differential binding analysis of ChIP-Seq peak data, 1-31 (2015).
24. Gene Ontology Consortium, Gene Ontology Consortium: going forward. *Nucleic Acids Res.* 43, D1049-56 (2015).
25. Schulz et al., DREM 2.0: Improved reconstruction of dynamic regulatory networks from time-series expression data. *BMC Syst. Biol.* 6 (2012), p. 104.
26. Celli et al., *F1000Research.* 4, 110 (2015).
27. Oldfield et al., *Mol. Cell.* 55, 708-722 (2014).
28. Bailey et al., *Nucleic Acids Res.* 43, W39-49 (2015).
29. Piskurewicz, L. Lopez-Molina, T *Plant Signal. Behav.* 4, 63-65 (2009).
30. Lee et al. *Plant Cell Physiol.* 52, 651-662 (2011).
31. Lee et al., *Genome Res.* 21, 1109-1121 (2011).
32. Lumba et al., *Dev. Cell.* 29, 360-372 (2014).
33. Yoshida et al., *Plant J.* 61, 672-685 (2010).
34. Lee et al., *Plant Cell.* 19, 731-49 (2007).
35. Jensen et al., *FEBS Open Bio.* 3, 321-327 (2013).
36. Zhang et al., *Proc. Natl. Acad. Sci. U.S.A* 108, 2160-2165 (2011).
37. Kohno, et al., *Mol. Biol. Rep.* 39, 911-917 (2012).
38. Sugimoto et al., Molecular cloning of Sdr4, a regulator involved in seed dormancy and domestication of rice. *Proc. Natl. Acad. Sci. U.S.A* 107, 5792-5797 (2010).
39. Yu, M. Gerstein, *Proc. Natl. Acad. Sci. U.S.A* 103, 14724-14731 (2006).
40. Gerstein et al., *Nature.* 489, 91-100 (2012).
41. Smaczniak et al., *Proc. Natl. Acad. Sci. U.S.A* 109, 1560-1565 (2012).
42. Moreno-Risueno et al., *Science* (80-.). 6, 1-20 (2015).
43. Park et al., Agrochemical control of plant water use using engineered abscisic acid receptors. *Nature.* 520, 545-8 (2015).
44. Bailey et al., *Nucleic Acids Res.* 43 (2015), pp. W39-49.
45. Shaner et al., *Nat. Methods.* 2, 905-9 (2005).
46. Song et al., *Curr. Protoc. plant Biol.* 293-306 (2016).
47. Lamesch et al., *Nucleic Acids Res.* 40 (2012), doi: 10.1093/nar/gkr1090.
48. Langmead, *Curr. Protoc. Bioinforma.* (2010), doi: 10.1002/0471250953.bi1107s32.
49. Landt et al., *Genome Res.* 22, 1813-31 (2012).
50. Ramírez et al., *Nucleic Acids Res.* 42, W187-91 (2014).
51. Zhu et al., *BMC Bioinformatics.* 11, 237 (2010).
52. Mahony et al., *PLoS Comput. Biol.* 3, 0578-0591 (2007).
53. E. Mercier, R. Gottardo, Motif Identification and Validation MotIV, 1-15 (2014).
54. Langfelder et al., *Bioinformatics.* 24, 719-720 (2008).
55. Grant et al., *Bioinformatics.* 27, 1017-1018 (2011).
56. Kim et al., *Genome Biol.* 14, R36 (2013).
57. Anders, P. T. Pyl, W. Huber, "HTSeq A Python framework to work with high-throughput sequencing data" (2014), doi:10.1101/002824.
58. Wise et al., *J. Comput. Biol.* 22, 324-333 (2015).
59. Fresno, E. a. Fernández, RDAVIDWebService: A versatile R interface to DAVID. *Bioinformatics.* 29, 2810-2811 (2013).
60. Jiao et al., *Bioinformatics.* 28, 1805-1806 (2012).

61. Ouyang et al., *Proc. Natl. Acad. Sci. U.S.A* 106, 21521-21526 (2009).
62. McLeay et al., *Bioinformatics*. 28, 2789-96 (2012).
63. Friedman et al., *J. Stat. Softw.* 33, 1-22 (2010).
64. Kuhn, *J. Stat. Softw.* 28, 1-26 (2008).
65. Kersey et al., *Nucleic Acids Res.* 42, D546-52 (2014).
66. Tamura et al., *Mol. Biol. Evol.* 30, 2725-2729 (2013).
67. E. Petrillo et al., *Science (80-.)*. 344, 427-30 (2014).
68. Jones et al., *Comput. Appl. Biosci.* 8, 275-282 (1992).
69. Edgar, *Nucleic Acids Res.* 32, 1792-7 (2004).
70. M. Fujita et al., *Plant J.* 39, 863-876 (2004).
71. Tran et al., *Plant Cell.* 16, 2481-2498 (2004).
72. Jensen et al., *Biochem. J.* 426, 183-196 (2010).
73. Liu et al., *Plant Cell.* 10, 1391-1406 (1998).
74. Narusaka et al., *Plant J.* 34, 137-148 (2003).
75. Lee et al., *Plant Physiol.* 153, 716-727 (2010).
76. Wang et al., *Proc. Natl. Acad. Sci. U.S.A* 110, 11205-10 (2013).
77. Takahashi et al., *Sci. Signal.* 6, ra48 (2013).
78. Liu et al., *New Phytol.* 201, 1192-1204 (2014).
79. Chen et al., *Plant J.* 75, 965-976 (2013).
80. Finkelstein et al., *Plant Mol. Biol.* 59, 253-267 (2005).
81. Kang et al., *Plant Cell.* 14, 343-357 (2002).
82. Lu et al., *Plant Cell.* 8, 847-57 (1996).
83. Ciftci-Yilmaz, R. Mittler, *Cell. Mol. Life Sci.* 65 (2008), pp. 1150-1160.
84. Liu et al., *Biochem. Biophys. Res. Commun.* 430, 1054-1059 (2013).
85. Mittler et al., *FEBS Lett.* 580, 6537-6542 (2006).
86. Conditions et al., *Society.* 136, 2734-2746 (2004).
87. Causier et al., *Plant Physiol.* 158, 423-438 (2012).
88. Kagale et al., *Plant Physiol.* 152, 1109-1134 (2010).
89. Ariel et al., *Trends Plant Sci.* 12 (2007), pp. 419-426.
90. Johannesson et al., *Plant Mol. Biol.* 45, 63-73 (2001).
91. Himmelbach et al., *EMBO J.* 21, 3029-3038 (2002).
92. Köllmer et al., *J. Plant Physiol.* 168, 1320-1327 (2011).
93. Rivero et al., *Proc. Natl. Acad. Sci. U.S.A* 104, 19631-6 (2007).
94. Hwang et al., *Plant. Cell Environ.* 37, 1202-22 (2014).
95. Chen et al., *J Biochem Mol Biol.* 40, 1083-1089 (2007).
96. Jung et al., *Plant Physiol.* 146, 623-635 (2008).

In view of the many possible embodiments to which the principles of the disclosure may be applied, it should be recognized that the illustrated embodiments are only examples of the invention and should not be taken as limiting the scope of the invention. Rather, the scope of the invention is defined by the following claims. We therefore claim as our invention all that comes within the scope and spirit of these claims.

We claim:

1. An expression cassette comprising:
   a nucleic acid sequence encoding a guide sequence 20 to 75 nucleotides in length, comprising the guide nucleic acid of SEQ ID NO: 13, 14, 15, 16, 17, 18, 19, 20, 21, 22, 23, 24, 25, 26, 27, 28, 29, 20, 57 or 58, wherein the encoding nucleic acid sequence is flanked by heterologous nucleic acid sequences and
   a promoter, wherein the nucleic acid sequence encoding the guide sequence is operably linked to the promoter.

2. The expression cassette of claim 1, wherein the promoter is a constitutive promoter, an inducible promoter, a tissue specific promoter, a ubiquitous promoter or a combination thereof.

3. A transgenic plant cell comprising heterologous nucleic acid sequences encoding a guide sequence specific for Dynamic Influencer of Gene expression (DIG1), a guide sequence specific for DIG2 and a guide sequence for DIG-like (DIL)1, wherein each heterologous nucleic acid sequence encoding a guide sequence is operably linked to a promoter and is present in a single expression cassette or in multiple different expression cassettes, wherein the cell has decreased expression of DIG1, DIG2 and DIL1 relative to a plant cell having native DIG1, DIG2, and DIL1 sequence, wherein the decreased expression of DIG1, DIG2 and DIL1 results from expression of the guide sequence specific for DIG1, the guide sequence specific for DIG2 and the guide sequence specific for DIL1, respectively.

4. The transgenic plant cell of claim 3, wherein the plant cell is a corn, wheat, soybean, canola, rice, or cotton plant cell.

5. The transgenic plant cell of claim 3, wherein the plant cell further comprises a transgenic nucleic acid molecule that confers a desired trait into the plant cell.

6. The transgenic plant cell of claim 3, wherein the plant cell has decreased abscisic acid (ABA) sensitivity, decreased salt sensitivity, or both as compared to a plant not expressing the guide sequences and grown in the same conditions.

7. A transgenic plant comprising the transgenic cell of claim 3.

8. The transgenic plant of claim 7, wherein the plant further comprises a transgenic nucleic acid molecule that confers a desired trait to the plant.

9. The transgenic plant cell of claim 5, wherein the desired trait is one or more of herbicide tolerance, drought tolerance, heat tolerance, low or high soil pH level tolerance, salt tolerance, resistance to an insect, resistance to a bacterial disease, resistance to a viral disease, resistance to a fungal disease, resistance to a nematode, resistance to a pest, male sterility, site-specific recombination; abiotic stress tolerance, modified phosphorus characteristics, modified antioxidant characteristics; modified essential seed amino acid characteristics, decreased phytate, modified fatty acid metabolism, and modified carbohydrate metabolism.

10. The transgenic plant of claim 7, wherein the plant has decreased abscisic acid (ABA) sensitivity, decreased salt sensitivity, or both as compared to a plant not expressing the guide sequences and grown in the same conditions.

11. The transgenic plant of claim 7, wherein the plant has accelerated cotyledon greening and increased lateral root growth as compared to a plant not expressing the guide sequences and grown in the same conditions.

12. The transgenic plant of claim 7, wherein the plant is an ornamental plant.

13. The transgenic plant of claim 7, wherein the plant is a crop plant.

14. The transgenic plant of claim 13, wherein the crop plant is a corn, wheat, soybean, canola, rice, or cotton plant.

15. A method of inhibiting or reducing expression of DIG1, DIG2, and DIL1 in a plant cell, comprising:
 introducing into the plant cell heterologous nucleic acid sequences encoding a guide sequence specific for Dynamic Influencer of Gene expression (DIG1), a guide sequence specific for DIG2 and a guide sequence for DIG-like (DIL)1, wherein each heterologous nucleic acid sequence encoding a guide sequence is operably linked to a promoter and is present in a single expression cassette or in multiple different expression cassettes;
 introducing a Cas9 protein or a Cas9 encoding nucleic acid into the cell; and
 expressing the guide sequence specific for DIG1, the guide sequence specific for DIG2 and the guide sequence specific for DIL1, thereby inhibiting or reducing expression of DIG1, DIG2, and DIL1, respectively, in the plant cell relative to a plant cell having native DIG1, DIG2, and DIL1 sequences.

16. The method of claim 15, wherein the method reduces abscisic acid (ABA) sensitivity, salt sensitivity, or both, in the plant cell as compared to a plant not expressing the guide sequences and grown in the same conditions.

17. The expression cassette of claim 1, wherein the guide sequence is 20 to 50 nucleotides in length.

18. The expression cassette of claim 1, wherein the guide sequence is 20 to 25 nucleotides in length.

19. The expression cassette of claim 1, wherein the guide sequence is 20 to 22 nucleotides in length.

20. The expression cassette of claim 1, wherein the guide sequence is 20 nucleotides in length.

21. The expression cassette of claim 1, wherein the promoter is U6.

22. The transgenic plant cell of claim 3, further comprising a Cas9 protein or a Cas9 encoding nucleic acid.

23. The transgenic plant cell of claim 3, wherein at least one of the promoters is U6.

24. The transgenic plant cell of claim 3, wherein the guide sequence specific for DIG1 comprises the guide nucleic acid of SEQ ID NO: 16, 17 or 18, the guide sequence specific for DIG2 comprises the guide nucleic acid of SEQ ID NO: 25, 26 or 27, and the guide sequence specific for DIL1 comprises the guide nucleic acid of SEQ ID NO: 28, 29 or 30, wherein each guide sequence is 20 to 75 nucleotides in length.

25. The method of claim 15, wherein at least one of the promoters is U6.

26. The method of claim 1, wherein the guide sequence specific for DIG1 comprises the guide nucleic acid of SEQ ID NO: 16, 17 or 18, the guide sequence specific for DIG2 comprises the guide nucleic acid of SEQ ID NO: 25, 26 or 27, and the guide sequence specific for DIL1 comprises the guide nucleic acid of SEQ ID NO: 28, 29 or 30, wherein each guide sequence is 20 to 75 nucleotides in length.

* * * * *

SEQUENCE LISTING

```
<160> NUMBER OF SEQ ID NOS: 58

<210> SEQ ID NO 1
<211> LENGTH: 885
<212> TYPE: DNA
<213> ORGANISM: Arabidopsis thaliana
<220> FEATURE:
<221> NAME/KEY: CDS
<222> LOCATION: (1)..(885)

<400> SEQUENCE: 1 atg gac ggt agg gga ggg tgt tgc ata gct agg tac gcc att ggc tct      48
Met Asp Gly Arg Gly Gly Cys Cys Ile Ala Arg Tyr Ala Ile Gly Ser
1               5                   10                  15 gga ccg tac gat ctt tcc aaa gca gat cgc atc atg ctt cga ttt cgt      96
Gly Pro Tyr Asp Leu Ser Lys Ala Asp Arg Ile Met Leu Arg Phe Arg
            20                  25                  30 ccc att gct cct aaa ccg gcc agc ccc ggc gga gta aat ccc gta tcc     144
Pro Ile Ala Pro Lys Pro Ala Ser Pro Gly Gly Val Asn Pro Val Ser
        35                  40                  45 agc gga gat agc ggc ggc gga agc tcc gac gtt tcc ttt aga tca gct     192
Ser Gly Asp Ser Gly Gly Gly Ser Ser Asp Val Ser Phe Arg Ser Ala
    50                  55                  60 agt aga aga aag agg aaa tgt cat cag ctg aag gag aat ggt ggt aac     240
Ser Arg Arg Lys Arg Lys Cys His Gln Leu Lys Glu Asn Gly Gly Asn
65                  70                  75                  80 gcc aag agg tgc acc cgg cgg aag acg tcg gat aaa ccc gtc gtt cac     288
Ala Lys Arg Cys Thr Arg Arg Lys Thr Ser Asp Lys Pro Val Val His
                85                  90                  95 ggc agt gct aat gcg gtg act ctt tct cta tta ccg gag aaa cct ata     336
Gly Ser Ala Asn Ala Val Thr Leu Ser Leu Leu Pro Glu Lys Pro Ile
            100                 105                 110 gat ctt aag gcg gcg gtg gag aag cag aag cgg cag ggt ccg tta tgg     384
Asp Leu Lys Ala Ala Val Glu Lys Gln Lys Arg Gln Gly Pro Leu Trp
        115                 120                 125 ttg agt ttc aaa gac ggc gga ggg atg ctc aca ccg gct tat cag aca     432
Leu Ser Phe Lys Asp Gly Gly Gly Met Leu Thr Pro Ala Tyr Gln Thr
```

```
              130                 135                 140
ccg gag att gtg cag agg acg gtg gtg att tcg tcg tgt atg acg gtg        480
Pro Glu Ile Val Gln Arg Thr Val Val Ile Ser Ser Cys Met Thr Val
145                 150                 155                 160 gag cgt gta acg gac gct tgg att gac ggt tac ggt tta ggg agg tca        528
Glu Arg Val Thr Asp Ala Trp Ile Asp Gly Tyr Gly Leu Gly Arg Ser
                165                 170                 175 gat gaa gaa agg aag atg aat ctt gtg aga gac acg tgt cct ggt ttc        576
Asp Glu Glu Arg Lys Met Asn Leu Val Arg Asp Thr Cys Pro Gly Phe
            180                 185                 190 ata tcc gac ggt tca ggg aga gtc acg tgg act aat gac gcg tat cgg        624
Ile Ser Asp Gly Ser Gly Arg Val Thr Trp Thr Asn Asp Ala Tyr Arg
        195                 200                 205 aag atg gct agg gat att att ccc gtg gaa gaa ggt gca ccg gag ata        672
Lys Met Ala Arg Asp Ile Ile Pro Val Glu Glu Gly Ala Pro Glu Ile
    210                 215                 220 act agc ggc gat agt ttt cac gtg atc gta cgg ttg gtg atg agg gag        720
Thr Ser Gly Asp Ser Phe His Val Ile Val Arg Leu Val Met Arg Glu
225                 230                 235                 240 agg ccg atg cta acg tcc cct gga ttc aca tgc aga atg aaa ctc cag        768
Arg Pro Met Leu Thr Ser Pro Gly Phe Thr Cys Arg Met Lys Leu Gln
                245                 250                 255 tac acg tgt caa aat cgt gag aga ggc tca gtc acg gtg cct tgc gac        816
Tyr Thr Cys Gln Asn Arg Glu Arg Gly Ser Val Thr Val Pro Cys Asp
            260                 265                 270 gtg tgg aga atg gac gtc ggt ggt ggt ttt gct tgg agg ctc gac gtt        864
Val Trp Arg Met Asp Val Gly Gly Gly Phe Ala Trp Arg Leu Asp Val
        275                 280                 285 aag gcc gct ttg tgc ctt tga                                            885
Lys Ala Ala Leu Cys Leu
    290

<210> SEQ ID NO 2
<211> LENGTH: 294
<212> TYPE: PRT
<213> ORGANISM: Arabidopsis thaliana

<400> SEQUENCE: 2

Met Asp Gly Arg Gly Gly Cys Cys Ile Ala Arg Tyr Ala Ile Gly Ser
1               5                   10                  15

Gly Pro Tyr Asp Leu Ser Lys Ala Asp Arg Ile Met Leu Arg Phe Arg
            20                  25                  30

Pro Ile Ala Pro Lys Pro Ala Ser Pro Gly Gly Val Asn Pro Val Ser
        35                  40                  45

Ser Gly Asp Ser Gly Gly Ser Ser Asp Val Ser Phe Arg Ser Ala
    50                  55                  60

Ser Arg Arg Lys Arg Lys Cys His Gln Leu Lys Glu Asn Gly Gly Asn
65                  70                  75                  80

Ala Lys Arg Cys Thr Arg Arg Lys Thr Ser Asp Lys Pro Val Val His
                85                  90                  95

Gly Ser Ala Asn Ala Val Thr Leu Ser Leu Leu Pro Glu Lys Pro Ile
            100                 105                 110

Asp Leu Lys Ala Ala Val Glu Lys Gln Lys Arg Gln Gly Pro Leu Trp
        115                 120                 125

Leu Ser Phe Lys Asp Gly Gly Gly Met Leu Thr Pro Ala Tyr Gln Thr
    130                 135                 140

Pro Glu Ile Val Gln Arg Thr Val Val Ile Ser Ser Cys Met Thr Val
145                 150                 155                 160
```

```
Glu Arg Val Thr Asp Ala Trp Ile Asp Gly Tyr Gly Leu Gly Arg Ser
                165                 170                 175

Asp Glu Glu Arg Lys Met Asn Leu Val Arg Asp Thr Cys Pro Gly Phe
            180                 185                 190

Ile Ser Asp Gly Ser Gly Arg Val Thr Trp Thr Asn Asp Ala Tyr Arg
        195                 200                 205

Lys Met Ala Arg Asp Ile Ile Pro Val Glu Glu Gly Ala Pro Glu Ile
    210                 215                 220

Thr Ser Gly Asp Ser Phe His Val Ile Val Arg Leu Val Met Arg Glu
225                 230                 235                 240

Arg Pro Met Leu Thr Ser Pro Gly Phe Thr Cys Arg Met Lys Leu Gln
                245                 250                 255

Tyr Thr Cys Gln Asn Arg Glu Arg Gly Ser Val Thr Val Pro Cys Asp
            260                 265                 270

Val Trp Arg Met Asp Val Gly Gly Phe Ala Trp Arg Leu Asp Val
        275                 280                 285

Lys Ala Ala Leu Cys Leu
    290

<210> SEQ ID NO 3
<211> LENGTH: 876
<212> TYPE: DNA
<213> ORGANISM: Arabidopsis thaliana
<220> FEATURE:
<221> NAME/KEY: CDS
<222> LOCATION: (1)..(876)

<400> SEQUENCE: 3 atg aat ttc cgg gga ggt tgt tgt att gcg agg tac ggt ggt agt ggt       48
Met Asn Phe Arg Gly Gly Cys Cys Ile Ala Arg Tyr Gly Gly Ser Gly
1               5                   10                  15 ggt gga aat gat atg tcg aag gtt gat cgg att atg ctc cgg tac cgt       96
Gly Gly Asn Asp Met Ser Lys Val Asp Arg Ile Met Leu Arg Tyr Arg
            20                  25                  30 ccg att gca ccg aga cct gat tct ggt gga tct cct gct tca ccg acg      144
Pro Ile Ala Pro Arg Pro Asp Ser Gly Gly Ser Pro Ala Ser Pro Thr
        35                  40                  45 gag aag aat gga tcg gtg ata act aac gtt tcg tcg aga tca cgg aga      192
Glu Lys Asn Gly Ser Val Ile Thr Asn Val Ser Ser Arg Ser Arg Arg
    50                  55                  60 ggt aag aga aaa tat tca aag gag aat aat agt agc agt acc gga tcc      240
Gly Lys Arg Lys Tyr Ser Lys Glu Asn Asn Ser Ser Ser Thr Gly Ser
65                  70                  75                  80 gtt aat agt aac ggt aac agc aaa cga cag aga aac gat gag acg aag      288
Val Asn Ser Asn Gly Asn Ser Lys Arg Gln Arg Asn Asp Glu Thr Lys
                85                  90                  95 aac gga tct ggt ggt ggt aga gag atc gtg acg ttg cct ctt ctt cca      336
Asn Gly Ser Gly Gly Gly Arg Glu Ile Val Thr Leu Pro Leu Leu Pro
            100                 105                 110 gag act cct gag aag aaa gac tcg ccg ttg aag gct aag gcg gcg ccg      384
Glu Thr Pro Glu Lys Lys Asp Ser Pro Leu Lys Ala Lys Ala Ala Pro
        115                 120                 125 gag tta ggt gcg gcg gcg ttg tgg ctg agt ttt aat gac gga gct agt      432
Glu Leu Gly Ala Ala Ala Leu Trp Leu Ser Phe Asn Asp Gly Ala Ser
    130                 135                 140 tat aac aga cgt tat cag aca gag tta atg acg gaa acg gtt gtg tcg      480
Tyr Asn Arg Arg Tyr Gln Thr Glu Leu Met Thr Glu Thr Val Val Ser
145                 150                 155                 160
```

```
tcg ttg ttg acg gtg gag tgt gta acg gag aga ttg atg gag gga gag        528
Ser Leu Leu Thr Val Glu Cys Val Thr Glu Arg Leu Met Glu Gly Glu
                165                 170                 175 tat gag tta ggg tgt acg gac gag gag agg aag atg aat ctt gag aga        576
Tyr Glu Leu Gly Cys Thr Asp Glu Glu Arg Lys Met Asn Leu Glu Arg
            180                 185                 190 gac acg tgt cct ggt ttt ata tcg gac ggt tta ggg aga gtc att tgg        624
Asp Thr Cys Pro Gly Phe Ile Ser Asp Gly Leu Gly Arg Val Ile Trp
        195                 200                 205 acg aac ggt tct tac aga gag ttg gtg gtt ggg aaa gat cat gag cag        672
Thr Asn Gly Ser Tyr Arg Glu Leu Val Val Gly Lys Asp His Glu Gln
    210                 215                 220 tgt agt aag atg agt gtg tgg ctt gtg atg aag gag aag cct ttg gta        720
Cys Ser Lys Met Ser Val Trp Leu Val Met Lys Glu Lys Pro Leu Val
225                 230                 235                 240 acg tac cgg act ttt acg tgt aga atg aga ttg cag tac acg tgt cgt        768
Thr Tyr Arg Thr Phe Thr Cys Arg Met Arg Leu Gln Tyr Thr Cys Arg
                245                 250                 255 gat aag gag gtg agt tcg att act tcg ttc tgt gat gtt tgg agg atg        816
Asp Lys Glu Val Ser Ser Ile Thr Ser Phe Cys Asp Val Trp Arg Met
            260                 265                 270 agt gac ggt ggc ttt gcg tgg cgg ctt gat gtt gat gct gca ctt tgc        864
Ser Asp Gly Gly Phe Ala Trp Arg Leu Asp Val Asp Ala Ala Leu Cys
        275                 280                 285 ctt gga cgg tga                                                        876
Leu Gly Arg
    290

<210> SEQ ID NO 4
<211> LENGTH: 291
<212> TYPE: PRT
<213> ORGANISM: Arabidopsis thaliana

<400> SEQUENCE: 4

Met Asn Phe Arg Gly Gly Cys Cys Ile Ala Arg Tyr Gly Gly Ser Gly
1               5                   10                  15

Gly Gly Asn Asp Met Ser Lys Val Asp Arg Ile Met Leu Arg Tyr Arg
            20                  25                  30

Pro Ile Ala Pro Arg Pro Asp Ser Gly Gly Ser Pro Ala Ser Pro Thr
        35                  40                  45

Glu Lys Asn Gly Ser Val Ile Thr Asn Val Ser Arg Ser Arg Arg
    50                  55                  60

Gly Lys Arg Lys Tyr Ser Lys Glu Asn Ser Ser Thr Gly Ser
65                  70                  75                  80

Val Asn Ser Asn Gly Asn Ser Lys Arg Gln Arg Asn Asp Glu Thr Lys
                85                  90                  95

Asn Gly Ser Gly Gly Gly Arg Glu Ile Val Thr Leu Pro Leu Leu Pro
            100                 105                 110

Glu Thr Pro Glu Lys Lys Asp Ser Pro Leu Lys Ala Lys Ala Ala Pro
        115                 120                 125

Glu Leu Gly Ala Ala Ala Leu Trp Leu Ser Phe Asn Asp Gly Ala Ser
    130                 135                 140

Tyr Asn Arg Arg Tyr Gln Thr Glu Leu Met Thr Glu Thr Val Val Ser
145                 150                 155                 160

Ser Leu Leu Thr Val Glu Cys Val Thr Glu Arg Leu Met Glu Gly Glu
                165                 170                 175

Tyr Glu Leu Gly Cys Thr Asp Glu Glu Arg Lys Met Asn Leu Glu Arg
            180                 185                 190
```

```
Asp Thr Cys Pro Gly Phe Ile Ser Asp Gly Leu Gly Arg Val Ile Trp
        195                 200                 205

Thr Asn Gly Ser Tyr Arg Glu Leu Val Val Gly Lys Asp His Glu Gln
    210                 215                 220

Cys Ser Lys Met Ser Val Trp Leu Val Met Lys Glu Lys Pro Leu Val
225                 230                 235                 240

Thr Tyr Arg Thr Phe Thr Cys Arg Met Arg Leu Gln Tyr Thr Cys Arg
                245                 250                 255

Asp Lys Glu Val Ser Ser Ile Thr Ser Phe Cys Asp Val Trp Arg Met
            260                 265                 270

Ser Asp Gly Gly Phe Ala Trp Arg Leu Asp Val Asp Ala Ala Leu Cys
        275                 280                 285

Leu Gly Arg
    290

<210> SEQ ID NO 5
<211> LENGTH: 909
<212> TYPE: DNA
<213> ORGANISM: Arabidopsis thaliana
<220> FEATURE:
<221> NAME/KEY: CDS
<222> LOCATION: (1)..(909)

<400> SEQUENCE: 5 atg gac ggt agg gga ggt tgt tgc ata gcc aga tat ggt ggt tac ggt    48
Met Asp Gly Arg Gly Gly Cys Cys Ile Ala Arg Tyr Gly Gly Tyr Gly
1               5                   10                  15 ggt cgc tac ggt ctc tcc aaa gca gat cga atc atg ctt cgt ttt cgt    96
Gly Arg Tyr Gly Leu Ser Lys Ala Asp Arg Ile Met Leu Arg Phe Arg
            20                  25                  30 ccc att gct cct aaa ccg gcc agc gac ggt gga agt gtc tct ctc acc   144
Pro Ile Ala Pro Lys Pro Ala Ser Asp Gly Gly Ser Val Ser Leu Thr
        35                  40                  45 ggg aag agc ggc tcc acc aca act aca agt ggt gga agc tcc gat ctc   192
Gly Lys Ser Gly Ser Thr Thr Thr Thr Ser Gly Gly Ser Ser Asp Leu
    50                  55                  60 tca ggt aaa tct ggg aga gga aag aga aag tat caa aaa gat tgt tcc   240
Ser Gly Lys Ser Gly Arg Gly Lys Arg Lys Tyr Gln Lys Asp Cys Ser
65                  70                  75                  80 ggt ggg aac tcc cga agg tgc aat aag aag aag aga gat cta agt gga   288
Gly Gly Asn Ser Arg Arg Cys Asn Lys Lys Lys Arg Asp Leu Ser Gly
                85                  90                  95 gac act gct act acc acg gcg gtt aca ttg tct ctt tta cca gag acg   336
Asp Thr Ala Thr Thr Thr Ala Val Thr Leu Ser Leu Leu Pro Glu Thr
            100                 105                 110 cct gag aaa cga gtt ttt cca gat ctg aat gct ttt ccg gtg gag aag   384
Pro Glu Lys Arg Val Phe Pro Asp Leu Asn Ala Phe Pro Val Glu Lys
        115                 120                 125 cag aag cga aac ggt cct tta tgg ctg agt ttc aac ggc ggt ggt gag   432
Gln Lys Arg Asn Gly Pro Leu Trp Leu Ser Phe Asn Gly Gly Gly Glu
    130                 135                 140 att tta acg ccg tac aaa acg gcg gag ata tca cga agg acg gtg gtg   480
Ile Leu Thr Pro Tyr Lys Thr Ala Glu Ile Ser Arg Arg Thr Val Val
145                 150                 155                 160 gtt tcg tcg tgt gtg acg gtt gag cgt gtg act gac gct tgg atc gac   528
Val Ser Ser Cys Val Thr Val Glu Arg Val Thr Asp Ala Trp Ile Asp
                165                 170                 175 ggt tat gga tta ggg gag aca aat cag gag agg aag atg aat cta gtg   576
Gly Tyr Gly Leu Gly Glu Thr Asn Gln Glu Arg Lys Met Asn Leu Val
```

```
                      180                 185                 190
gaa gac acg tgt cct ggt ttt ata tcg gac ggt gta ggg aga gtc acg      624
Glu Asp Thr Cys Pro Gly Phe Ile Ser Asp Gly Val Gly Arg Val Thr
            195                 200                 205 tgg acc aat gag gcg tat aag aag atg gct aga gaa gat att aat att      672
Trp Thr Asn Glu Ala Tyr Lys Lys Met Ala Arg Glu Asp Ile Asn Ile
210                 215                 220 ccg atg gag gaa ggt gta ccg gag gat att agt tac gat aat ttt cac      720
Pro Met Glu Glu Gly Val Pro Glu Asp Ile Ser Tyr Asp Asn Phe His
225                 230                 235                 240 gtg aac gta cgg tta gtg atg aag gag agg ccg atg cta acg tac cca      768
Val Asn Val Arg Leu Val Met Lys Glu Arg Pro Met Leu Thr Tyr Pro
                245                 250                 255 gct ttc aca tgc aga gtg aga tta cag tac acg tgt caa gat cga gaa      816
Ala Phe Thr Cys Arg Val Arg Leu Gln Tyr Thr Cys Gln Asp Arg Glu
            260                 265                 270 aga gga tcc gtc acg gtg cct tgt gac gtg tgg aga atg gac ggc ggt      864
Arg Gly Ser Val Thr Val Pro Cys Asp Val Trp Arg Met Asp Gly Gly
        275                 280                 285 ggt ttt gcg tgg agg ctt gac gtt aag gca gct ttg tgt ctg tga          909
Gly Phe Ala Trp Arg Leu Asp Val Lys Ala Ala Leu Cys Leu
290                 295                 300

<210> SEQ ID NO 6
<211> LENGTH: 302
<212> TYPE: PRT
<213> ORGANISM: Arabidopsis thaliana

<400> SEQUENCE: 6

Met Asp Gly Arg Gly Gly Cys Cys Ile Ala Arg Tyr Gly Gly Tyr Gly
1               5                   10                  15

Gly Arg Tyr Gly Leu Ser Lys Ala Asp Arg Ile Met Leu Arg Phe Arg
            20                  25                  30

Pro Ile Ala Pro Lys Pro Ala Ser Asp Gly Gly Ser Val Ser Leu Thr
        35                  40                  45

Gly Lys Ser Gly Ser Thr Thr Thr Ser Gly Gly Ser Ser Asp Leu
    50                  55                  60

Ser Gly Lys Ser Gly Arg Gly Lys Arg Lys Tyr Gln Lys Asp Cys Ser
65                  70                  75                  80

Gly Gly Asn Ser Arg Arg Cys Asn Lys Lys Arg Asp Leu Ser Gly
            85                  90                  95

Asp Thr Ala Thr Thr Thr Ala Val Thr Leu Ser Leu Leu Pro Glu Thr
        100                 105                 110

Pro Glu Lys Arg Val Phe Pro Asp Leu Asn Ala Phe Pro Val Glu Lys
    115                 120                 125

Gln Lys Arg Asn Gly Pro Leu Trp Leu Ser Phe Asn Gly Gly Glu
130                 135                 140

Ile Leu Thr Pro Tyr Lys Thr Ala Glu Ile Ser Arg Arg Thr Val Val
145                 150                 155                 160

Val Ser Ser Cys Val Thr Val Glu Arg Val Thr Asp Ala Trp Ile Asp
                165                 170                 175

Gly Tyr Gly Leu Gly Glu Thr Asn Gln Glu Arg Lys Met Asn Leu Val
            180                 185                 190

Glu Asp Thr Cys Pro Gly Phe Ile Ser Asp Gly Val Gly Arg Val Thr
        195                 200                 205

Trp Thr Asn Glu Ala Tyr Lys Lys Met Ala Arg Glu Asp Ile Asn Ile
    210                 215                 220
```

```
Pro Met Glu Gly Val Pro Glu Asp Ile Ser Tyr Asp Asn Phe His
225                 230                 235                 240

Val Asn Val Arg Leu Val Met Lys Glu Arg Pro Met Leu Thr Tyr Pro
                245                 250                 255

Ala Phe Thr Cys Arg Val Arg Leu Gln Tyr Thr Cys Gln Asp Arg Glu
            260                 265                 270

Arg Gly Ser Val Thr Val Pro Cys Asp Val Trp Arg Met Asp Gly Gly
        275                 280                 285

Gly Phe Ala Trp Arg Leu Asp Val Lys Ala Ala Leu Cys Leu
    290                 295                 300

<210> SEQ ID NO 7
<211> LENGTH: 912
<212> TYPE: DNA
<213> ORGANISM: Arabidopsis thaliana
<220> FEATURE:
<221> NAME/KEY: CDS
<222> LOCATION: (1)..(912)

<400> SEQUENCE: 7
```

| | | | | | | | | | | | | | | | | |
|---|---|---|---|---|---|---|---|---|---|---|---|---|---|---|---|---|
| atg | cat | ggc | aac | gga | aag | cag | tgt | caa | gct | tct | att | tgc | gac | ggt | gca | 48 |
| Met | His | Gly | Asn | Gly | Lys | Gln | Cys | Gln | Ala | Ser | Ile | Cys | Asp | Gly | Ala | |
| 1 | | | | 5 | | | | | 10 | | | | | 15 | | |
| aca | gat | cag | gac | aag | acc | gtt | ata | agc | aag | ata | atg | caa | cgg | ttc | cgt | 96 |
| Thr | Asp | Gln | Asp | Lys | Thr | Val | Ile | Ser | Lys | Ile | Met | Gln | Arg | Phe | Arg | |
| | | | 20 | | | | | 25 | | | | | 30 | | | |
| ccg | atc | gca | cca | aaa | cca | gct | gtc | ggc | gaa | tct | tca | gac | gat | aca | aat | 144 |
| Pro | Ile | Ala | Pro | Lys | Pro | Ala | Val | Gly | Glu | Ser | Ser | Asp | Asp | Thr | Asn | |
| | | 35 | | | | | 40 | | | | | 45 | | | | |
| agt | gat | aga | ttc | ctt | gga | aga | aac | aga | aga | tcg | aaa | cga | aag | tat | gtt | 192 |
| Ser | Asp | Arg | Phe | Leu | Gly | Arg | Asn | Arg | Arg | Ser | Lys | Arg | Lys | Tyr | Val | |
| 50 | | | | | 55 | | | | | 60 | | | | | | |
| agg | gtt | cgg | gac | aag | aaa | aat | agt | agt | ggt | agt | aat | aat | aag | aag | gat | 240 |
| Arg | Val | Arg | Asp | Lys | Lys | Asn | Ser | Ser | Gly | Ser | Asn | Asn | Lys | Lys | Asp | |
| 65 | | | | | 70 | | | | | 75 | | | | | 80 | |
| att | act | ggt | aaa | aag | aat | ggt | tgc | gat | aga | ggg | aac | ata | aag | acc | gat | 288 |
| Ile | Thr | Gly | Lys | Lys | Asn | Gly | Cys | Asp | Arg | Gly | Asn | Ile | Lys | Thr | Asp | |
| | | | | 85 | | | | | 90 | | | | | 95 | | |
| ctt | gat | aaa | aag | ata | gac | ggt | gat | gat | aga | acc | gat | atc | gtc | acg | ctt | 336 |
| Leu | Asp | Lys | Lys | Ile | Asp | Gly | Asp | Asp | Arg | Thr | Asp | Ile | Val | Thr | Leu | |
| | | | 100 | | | | | 105 | | | | | 110 | | | |
| cag | ctg | ctg | cca | gag | aag | gat | aga | gat | ata | gga | aac | aat | gga | gat | aaa | 384 |
| Gln | Leu | Leu | Pro | Glu | Lys | Asp | Arg | Asp | Ile | Gly | Asn | Asn | Gly | Asp | Lys | |
| | | 115 | | | | | 120 | | | | | 125 | | | | |
| gct | ggt | gag | ttt | tgt | tcg | gat | ctg | agt | gat | atg | gat | cca | aaa | aag | agc | 432 |
| Ala | Gly | Glu | Phe | Cys | Ser | Asp | Leu | Ser | Asp | Met | Asp | Pro | Lys | Lys | Ser | |
| 130 | | | | | 135 | | | | | 140 | | | | | | |
| ttg | tat | aat | tcg | atc | ata | ggg | cta | tcg | tca | tct | ttt | gat | cgg | aag | gtg | 480 |
| Leu | Tyr | Asn | Ser | Ile | Ile | Gly | Leu | Ser | Ser | Ser | Phe | Asp | Arg | Lys | Val | |
| 145 | | | | | 150 | | | | | 155 | | | | | 160 | |
| gtg | gag | tcg | tgg | ttg | acg | gtg | gag | tgt | gtg | agt | gac | acg | tgt | act | gac | 528 |
| Val | Glu | Ser | Trp | Leu | Thr | Val | Glu | Cys | Val | Ser | Asp | Thr | Cys | Thr | Asp | |
| | | | | 165 | | | | | 170 | | | | | 175 | | |
| ttg | gga | tgg | tat | cac | atc | ctg | gag | cag | cta | ggc | cgc | atg | gat | cag | gca | 576 |
| Leu | Gly | Trp | Tyr | His | Ile | Leu | Glu | Gln | Leu | Gly | Arg | Met | Asp | Gln | Ala | |
| | | | 180 | | | | | 185 | | | | | 190 | | | |
| gag | gag | aga | gtg | atg | agg | atg | tta | gag | gtt | gac | acg | tgt | cca | tgg | tta | 624 |
| Glu | Glu | Arg | Val | Met | Arg | Met | Leu | Glu | Val | Asp | Thr | Cys | Pro | Trp | Leu | |
| | | 195 | | | | | 200 | | | | | 205 | | | | |

| | | | | | | | | | | | | | | | | |
|---|---|---|---|---|---|---|---|---|---|---|---|---|---|---|---|---|
| gtg | tcg | gat | ggg | tca | aac | cgg | gtc | tgt | tgg | gta | aac | cgg | gcc | tac | cgg | 672 |
| Val | Ser | Asp | Gly | Ser | Asn | Arg | Val | Cys | Trp | Val | Asn | Arg | Ala | Tyr | Arg | |
| | 210 | | | | 215 | | | | 220 | | | | | | | |
| agg | atg | atg | gga | gct | ccc | gac | gtg | gat | gtt | atc | agg | gtg | tgg | ctg | gtg | 720 |
| Arg | Met | Met | Gly | Ala | Pro | Asp | Val | Asp | Val | Ile | Arg | Val | Trp | Leu | Val | |
| 225 | | | | | 230 | | | | | 235 | | | | | 240 | |
| gtg | gcc | atg | gac | ctt | atg | gag | gag | ata | gca | tgc | atg | gtg | gag | tta | tac | 768 |
| Val | Ala | Met | Asp | Leu | Met | Glu | Glu | Ile | Ala | Cys | Met | Val | Glu | Leu | Tyr | |
| | | | | 245 | | | | | 250 | | | | | 255 | | |
| ggt | gcg | gtg | acg | tgc | agg | gtt | agg | gtt | agg | tac | gag | ccg | tcc | acg | tgg | 816 |
| Gly | Ala | Val | Thr | Cys | Arg | Val | Arg | Val | Arg | Tyr | Glu | Pro | Ser | Thr | Trp | |
| | | | 260 | | | | | 265 | | | | | 270 | | | |
| agg | aag | atg | acg | gtg | ccg | tgt | gat | gta | tgg | agg | ata | aga | tca | ggt | ggg | 864 |
| Arg | Lys | Met | Thr | Val | Pro | Cys | Asp | Val | Trp | Arg | Ile | Arg | Ser | Gly | Gly | |
| | | | 275 | | | | | 280 | | | | | 285 | | | |
| ttt | gct | tgg | aga | ttg | gat | gtt | gaa | tca | gct | cta | agg | ctt | ggc | atg | tga | 912 |
| Phe | Ala | Trp | Arg | Leu | Asp | Val | Glu | Ser | Ala | Leu | Arg | Leu | Gly | Met | | |
| 290 | | | | | 295 | | | | | 300 | | | | | | |

<210> SEQ ID NO 8
<211> LENGTH: 303
<212> TYPE: PRT
<213> ORGANISM: Arabidopsis thaliana

<400> SEQUENCE: 8

Met His Gly Asn Gly Lys Gln Cys Gln Ala Ser Ile Cys Asp Gly Ala
1               5                   10                  15

Thr Asp Gln Asp Lys Thr Val Ile Ser Lys Ile Met Gln Arg Phe Arg
            20                  25                  30

Pro Ile Ala Pro Lys Pro Ala Val Gly Glu Ser Ser Asp Asp Thr Asn
        35                  40                  45

Ser Asp Arg Phe Leu Gly Arg Asn Arg Arg Ser Lys Arg Lys Tyr Val
    50                  55                  60

Arg Val Arg Asp Lys Lys Asn Ser Ser Gly Ser Asn Asn Lys Lys Asp
65                  70                  75                  80

Ile Thr Gly Lys Lys Asn Gly Cys Asp Arg Gly Asn Ile Lys Thr Asp
                85                  90                  95

Leu Asp Lys Lys Ile Asp Gly Asp Arg Thr Asp Ile Val Thr Leu
            100                 105                 110

Gln Leu Leu Pro Glu Lys Asp Arg Asp Ile Gly Asn Asn Gly Asp Lys
        115                 120                 125

Ala Gly Glu Phe Cys Ser Asp Leu Ser Asp Met Asp Pro Lys Lys Ser
    130                 135                 140

Leu Tyr Asn Ser Ile Ile Gly Leu Ser Ser Ser Phe Asp Arg Lys Val
145                 150                 155                 160

Val Glu Ser Trp Leu Thr Val Glu Cys Val Ser Asp Thr Cys Thr Asp
                165                 170                 175

Leu Gly Trp Tyr His Ile Leu Glu Gln Leu Gly Arg Met Asp Gln Ala
            180                 185                 190

Glu Glu Arg Val Met Arg Met Leu Glu Val Asp Thr Cys Pro Trp Leu
        195                 200                 205

Val Ser Asp Gly Ser Asn Arg Val Cys Trp Val Asn Arg Ala Tyr Arg
    210                 215                 220

Arg Met Met Gly Ala Pro Asp Val Asp Val Ile Arg Val Trp Leu Val
225                 230                 235                 240

Val Ala Met Asp Leu Met Glu Glu Ile Ala Cys Met Val Glu Leu Tyr
                245                 250                 255

```
Gly Ala Val Thr Cys Arg Val Arg Val Arg Tyr Glu Pro Ser Thr Trp
            260                 265                 270

Arg Lys Met Thr Val Pro Cys Asp Val Trp Arg Ile Arg Ser Gly Gly
        275                 280                 285

Phe Ala Trp Arg Leu Asp Val Glu Ser Ala Leu Arg Leu Gly Met
    290                 295                 300

<210> SEQ ID NO 9
<211> LENGTH: 819
<212> TYPE: DNA
<213> ORGANISM: Arabidopsis thaliana
<220> FEATURE:
<221> NAME/KEY: CDS
<222> LOCATION: (1)..(819)

<400> SEQUENCE: 9
```

| | | | | | | | | | | | | | | | | |
|---|---|---|---|---|---|---|---|---|---|---|---|---|---|---|---|---|
| atg | gat | caa | gat | cat | gag | tta | tgg | cgg | acg | cta | aga | tgc | gcc | ggt | aaa | 48 |
| Met | Asp | Gln | Asp | His | Glu | Leu | Trp | Arg | Thr | Leu | Arg | Cys | Ala | Gly | Lys | |
| 1 | | | | 5 | | | | | 10 | | | | | 15 | | |
| gcg | caa | gat | aag | acc | tct | gtt | gat | act | ctc | atg | ctt | aag | tac | cgt | ccg | 96 |
| Ala | Gln | Asp | Lys | Thr | Ser | Val | Asp | Thr | Leu | Met | Leu | Lys | Tyr | Arg | Pro | |
| | | | 20 | | | | | 25 | | | | | 30 | | | |
| atc | gct | cca | aag | ccg | acg | act | act | ggt | caa | cca | ttg | gtc | gga | gat | aca | 144 |
| Ile | Ala | Pro | Lys | Pro | Thr | Thr | Thr | Gly | Gln | Pro | Leu | Val | Gly | Asp | Thr | |
| | | 35 | | | | | 40 | | | | | 45 | | | | |
| agt | agc | acg | aga | agg | acg | aag | aga | aag | tac | gtt | agg | gtt | tca | aag | aat | 192 |
| Ser | Ser | Thr | Arg | Arg | Thr | Lys | Arg | Lys | Tyr | Val | Arg | Val | Ser | Lys | Asn | |
| | 50 | | | | | 55 | | | | | 60 | | | | | |
| aat | aaa | gcc | acg | tgt | cga | tca | aag | acg | aac | ggc | ttc | aga | tct | agc | tca | 240 |
| Asn | Lys | Ala | Thr | Cys | Arg | Ser | Lys | Thr | Asn | Gly | Phe | Arg | Ser | Ser | Ser | |
| 65 | | | | | 70 | | | | | 75 | | | | | 80 | |
| aca | gat | ccg | gag | aat | ggt | cgg | gaa | gat | atc | gtc | acg | cta | cag | ctc | tta | 288 |
| Thr | Asp | Pro | Glu | Asn | Gly | Arg | Glu | Asp | Ile | Val | Thr | Leu | Gln | Leu | Leu | |
| | | | | 85 | | | | | 90 | | | | | 95 | | |
| ccg | gag | aga | tct | acg | ccg | ttg | agt | tta | gat | cat | aat | aat | ctc | gat | cca | 336 |
| Pro | Glu | Arg | Ser | Thr | Pro | Leu | Ser | Leu | Asp | His | Asn | Asn | Leu | Asp | Pro | |
| | | | 100 | | | | | 105 | | | | | 110 | | | |
| acg | gtg | gaa | acg | ata | aac | gga | gat | gaa | act | tgt | aat | acc | gac | acg | tgg | 384 |
| Thr | Val | Glu | Thr | Ile | Asn | Gly | Asp | Glu | Thr | Cys | Asn | Thr | Asp | Thr | Trp | |
| | | 115 | | | | | 120 | | | | | 125 | | | | |
| ctc | aag | ttt | aac | ggc | ggt | gat | gac | gcg | ttg | caa | caa | gtt | ccg | gta | gag | 432 |
| Leu | Lys | Phe | Asn | Gly | Gly | Asp | Asp | Ala | Leu | Gln | Gln | Val | Pro | Val | Glu | |
| | 130 | | | | | 135 | | | | | 140 | | | | | |
| acg | tgg | gtg | acg | gtg | gag | tcc | gtt | aac | agt | ggc | ttg | gtt | tcc | cat | gcg | 480 |
| Thr | Trp | Val | Thr | Val | Glu | Ser | Val | Asn | Ser | Gly | Leu | Val | Ser | His | Ala | |
| 145 | | | | | 150 | | | | | 155 | | | | | 160 | |
| gta | ggg | tta | acg | gac | gaa | gag | ctc | aca | tat | gct | tta | gat | aaa | gac | acg | 528 |
| Val | Gly | Leu | Thr | Asp | Glu | Glu | Leu | Thr | Tyr | Ala | Leu | Asp | Lys | Asp | Thr | |
| | | | | 165 | | | | | 170 | | | | | 175 | | |
| tgt | cct | ggt | ttc | ata | tcg | gat | ggt | tcg | aac | cgt | gtg | gtg | atg | gtt | aac | 576 |
| Cys | Pro | Gly | Phe | Ile | Ser | Asp | Gly | Ser | Asn | Arg | Val | Val | Met | Val | Asn | |
| | | | 180 | | | | | 185 | | | | | 190 | | | |
| gag | gct | tac | cgg | agg | ata | gta | acc | gga | gac | ggc | gga | ttc | gga | aga | gag | 624 |
| Glu | Ala | Tyr | Arg | Arg | Ile | Val | Thr | Gly | Asp | Gly | Gly | Phe | Gly | Arg | Glu | |
| | | 195 | | | | | 200 | | | | | 205 | | | | |
| gtg | ata | gtg | tgg | ttg | gtg | gtt | gac | caa | acg | gcg | acg | ttt | tgt | gac | tac | 672 |
| Val | Ile | Val | Trp | Leu | Val | Val | Asp | Gln | Thr | Ala | Thr | Phe | Cys | Asp | Tyr | |
| | 210 | | | | | 215 | | | | | 220 | | | | | |
| cga | act | ttt | acg | tgt | aag | gtg | aga | atg | gaa | tac | acg | tgg | cga | gaa | acg | 720 |
| Arg | Thr | Phe | Thr | Cys | Lys | Val | Arg | Met | Glu | Tyr | Thr | Trp | Arg | Glu | Thr | |

| | | | | | | | | | | | | | | | |
|---|---|---|---|---|---|---|---|---|---|---|---|---|---|---|---|
| | | 225 | | | 230 | | | 235 | | | 240 | | | | |
| aag | tac | act | aaa | acg | ttg | ccg | tgt | gat | gtg | tgg | aag | atg | gag | ttt ggt | 768 |
| Lys | Tyr | Thr | Lys | Thr | Leu | Pro | Cys | Asp | Val | Trp | Lys | Met | Glu | Phe Gly | |
| | | 245 | | | | | 250 | | | | | 255 | | | |
| gga | ttt | gca | tgg | agg | ttg | gat | act | act | gca | gct | tta | act | ctt | tgg ctt | 816 |
| Gly | Phe | Ala | Trp | Arg | Leu | Asp | Thr | Thr | Ala | Ala | Leu | Thr | Leu | Trp Leu | |
| | | 260 | | | | | 265 | | | | | 270 | | | |
| tga | | | | | | | | | | | | | | | 819 |

<210> SEQ ID NO 10
<211> LENGTH: 272
<212> TYPE: PRT
<213> ORGANISM: Arabidopsis thaliana

<400> SEQUENCE: 10

Met Asp Gln Asp His Glu Leu Trp Arg Thr Leu Arg Cys Ala Gly Lys
1               5                   10                  15

Ala Gln Asp Lys Thr Ser Val Asp Thr Leu Met Leu Lys Tyr Arg Pro
            20                  25                  30

Ile Ala Pro Lys Pro Thr Thr Thr Gly Gln Pro Leu Val Gly Asp Thr
        35                  40                  45

Ser Ser Thr Arg Arg Thr Lys Arg Lys Tyr Val Arg Val Ser Lys Asn
50                  55                  60

Asn Lys Ala Thr Cys Arg Ser Lys Thr Asn Gly Phe Arg Ser Ser
65                  70                  75                  80

Thr Asp Pro Glu Asn Gly Arg Glu Asp Ile Val Thr Leu Gln Leu Leu
                85                  90                  95

Pro Glu Arg Ser Thr Pro Leu Ser Leu Asp His Asn Asn Leu Asp Pro
            100                 105                 110

Thr Val Glu Thr Ile Asn Gly Asp Glu Thr Cys Asn Thr Asp Thr Trp
        115                 120                 125

Leu Lys Phe Asn Gly Gly Asp Asp Ala Leu Gln Gln Val Pro Val Glu
130                 135                 140

Thr Trp Val Thr Val Glu Ser Val Asn Ser Gly Leu Val Ser His Ala
145                 150                 155                 160

Val Gly Leu Thr Asp Glu Glu Leu Thr Tyr Ala Leu Asp Lys Asp Thr
                165                 170                 175

Cys Pro Gly Phe Ile Ser Asp Gly Ser Asn Arg Val Val Met Val Asn
            180                 185                 190

Glu Ala Tyr Arg Arg Ile Val Thr Gly Asp Gly Gly Phe Gly Arg Glu
        195                 200                 205

Val Ile Val Trp Leu Val Val Asp Gln Thr Ala Thr Phe Cys Asp Tyr
210                 215                 220

Arg Thr Phe Thr Cys Lys Val Arg Met Glu Tyr Thr Trp Arg Glu Thr
225                 230                 235                 240

Lys Tyr Thr Lys Thr Leu Pro Cys Asp Val Trp Lys Met Glu Phe Gly
                245                 250                 255

Gly Phe Ala Trp Arg Leu Asp Thr Thr Ala Ala Leu Thr Leu Trp Leu
            260                 265                 270

<210> SEQ ID NO 11
<211> LENGTH: 849
<212> TYPE: DNA
<213> ORGANISM: Arabidopsis thaliana
<220> FEATURE:
<221> NAME/KEY: CDS
<222> LOCATION: (1)..(849)

<400> SEQUENCE: 11

| | | | | | | | | | | | | | | | | |
|---|---|---|---|---|---|---|---|---|---|---|---|---|---|---|---|---|
| atg | gat | caa | gat | gac | tgg | ttg | gga | acg | cta | aga | tac | gcc | ggt | aag | gcg | 48 |
| Met | Asp | Gln | Asp | Asp | Trp | Leu | Gly | Thr | Leu | Arg | Tyr | Ala | Gly | Lys | Ala | |
| 1 | | | | 5 | | | | | 10 | | | | | 15 | | |
| cag | gat | aaa | gtt | tcc | gtt | gac | gct | ctc | atg | ctc | cgg | tac | cgt | ccg | atc | 96 |
| Gln | Asp | Lys | Val | Ser | Val | Asp | Ala | Leu | Met | Leu | Arg | Tyr | Arg | Pro | Ile | |
| | | | 20 | | | | | 25 | | | | | 30 | | | |
| gct | cca | aag | ccg | acg | act | ggt | cag | cca | tgt | ggt | gtg | gca | gat | aac | aac | 144 |
| Ala | Pro | Lys | Pro | Thr | Thr | Gly | Gln | Pro | Cys | Gly | Val | Ala | Asp | Asn | Asn | |
| | | 35 | | | | | 40 | | | | | 45 | | | | |
| aac | aat | agc | tca | tac | ggt | atg | agc | aaa | cga | acc | aaa | cga | aag | tac | gtt | 192 |
| Asn | Asn | Ser | Ser | Tyr | Gly | Met | Ser | Lys | Arg | Thr | Lys | Arg | Lys | Tyr | Val | |
| | 50 | | | | | 55 | | | | | 60 | | | | | |
| agg | gtt | tcg | aag | aat | aat | aaa | ggc | acg | tgt | cga | ggt | aag | agc | aga | tct | 240 |
| Arg | Val | Ser | Lys | Asn | Asn | Lys | Gly | Thr | Cys | Arg | Gly | Lys | Ser | Arg | Ser | |
| 65 | | | | | 70 | | | | | 75 | | | | | 80 | |
| gac | ttg | tct | gat | gat | cgg | gaa | caa | act | gat | gtc | gtg | acg | ttg | caa | ctc | 288 |
| Asp | Leu | Ser | Asp | Asp | Arg | Glu | Gln | Thr | Asp | Val | Val | Thr | Leu | Gln | Leu | |
| | | | | 85 | | | | | 90 | | | | | 95 | | |
| ttg | ccg | gaa | aaa | tca | gat | att | tcc | ggt | gag | tac | tcg | ccg | ttg | gat | caa | 336 |
| Leu | Pro | Glu | Lys | Ser | Asp | Ile | Ser | Gly | Glu | Tyr | Ser | Pro | Leu | Asp | Gln | |
| | | | 100 | | | | | 105 | | | | | 110 | | | |
| gat | agt | ctc | gat | ccg | tcg | gtg | aaa | tcg | ata | atc | gga | gag | gaa | aca | caa | 384 |
| Asp | Ser | Leu | Asp | Pro | Ser | Val | Lys | Ser | Ile | Ile | Gly | Glu | Glu | Thr | Gln | |
| | | 115 | | | | | 120 | | | | | 125 | | | | |
| gaa | acc | aac | acg | tgg | ggt | atg | ttt | aac | ggc | agc | gtc | acg | gcg | gag | atg | 432 |
| Glu | Thr | Asn | Thr | Trp | Gly | Met | Phe | Asn | Gly | Ser | Val | Thr | Ala | Glu | Met | |
| | 130 | | | | | 135 | | | | | 140 | | | | | |
| gag | acg | tgg | gtg | acg | gtg | gag | tcc | gtc | aca | agc | gtg | tgt | gag | ggt | agt | 480 |
| Glu | Thr | Trp | Val | Thr | Val | Glu | Ser | Val | Thr | Ser | Val | Cys | Glu | Gly | Ser | |
| 145 | | | | | 150 | | | | | 155 | | | | | 160 | |
| ttg | agt | tcc | cat | gcg | gtg | ggg | att | acg | gac | gtt | gag | atc | gtt | gat | aat | 528 |
| Leu | Ser | Ser | His | Ala | Val | Gly | Ile | Thr | Asp | Val | Glu | Ile | Val | Asp | Asn | |
| | | | | 165 | | | | | 170 | | | | | 175 | | |
| ctt | ggt | aag | gac | acg | tgt | cca | gcg | ttc | gta | tcg | gat | ggc | tcg | aac | cgt | 576 |
| Leu | Gly | Lys | Asp | Thr | Cys | Pro | Ala | Phe | Val | Ser | Asp | Gly | Ser | Asn | Arg | |
| | | | 180 | | | | | 185 | | | | | 190 | | | |
| gtg | gtg | tgg | gtc | aac | gag | gct | tac | cgg | aga | aat | gtt | tcc | ggt | gat | gat | 624 |
| Val | Val | Trp | Val | Asn | Glu | Ala | Tyr | Arg | Arg | Asn | Val | Ser | Gly | Asp | Asp | |
| | | 195 | | | | | 200 | | | | | 205 | | | | |
| tca | acg | gcg | tca | gta | tcg | ccg | gaa | gtt | gtg | gtg | tgg | ttg | gtg | gcg | gag | 672 |
| Ser | Thr | Ala | Ser | Val | Ser | Pro | Glu | Val | Val | Val | Trp | Leu | Val | Ala | Glu | |
| | 210 | | | | | 215 | | | | | 220 | | | | | |
| gag | gca | acg | gcg | gcg | atg | cat | tgt | aac | tac | caa | gct | ttc | acg | tgt | agg | 720 |
| Glu | Ala | Thr | Ala | Ala | Met | His | Cys | Asn | Tyr | Gln | Ala | Phe | Thr | Cys | Arg | |
| 225 | | | | | 230 | | | | | 235 | | | | | 240 | |
| gtg | agg | atg | caa | tac | acg | tgg | aag | gaa | aca | aag | tat | acc | aaa | acg | gtg | 768 |
| Val | Arg | Met | Gln | Tyr | Thr | Trp | Lys | Glu | Thr | Lys | Tyr | Thr | Lys | Thr | Val | |
| | | | | 245 | | | | | 250 | | | | | 255 | | |
| ccg | tgt | gat | gtg | tgg | aaa | atg | gag | ttt | ggt | ggt | ttt | gca | tgg | agg | cta | 816 |
| Pro | Cys | Asp | Val | Trp | Lys | Met | Glu | Phe | Gly | Gly | Phe | Ala | Trp | Arg | Leu | |
| | | | 260 | | | | | 265 | | | | | 270 | | | |
| gac | aca | aca | gct | gct | ctg | act | ctc | tgg | ctt | tga | | | | | | 849 |
| Asp | Thr | Thr | Ala | Ala | Leu | Thr | Leu | Trp | Leu | | | | | | | |
| | | 275 | | | | | 280 | | | | | | | | | |

<210> SEQ ID NO 12
<211> LENGTH: 282
<212> TYPE: PRT
<213> ORGANISM: Arabidopsis thaliana

<400> SEQUENCE: 12

```
Met Asp Gln Asp Asp Trp Leu Gly Thr Leu Arg Tyr Ala Gly Lys Ala
1               5                   10                  15

Gln Asp Lys Val Ser Val Asp Ala Leu Met Leu Arg Tyr Arg Pro Ile
            20                  25                  30

Ala Pro Lys Pro Thr Thr Gly Gln Pro Cys Gly Val Ala Asp Asn Asn
        35                  40                  45

Asn Ser Ser Tyr Gly Met Ser Lys Arg Thr Lys Arg Lys Tyr Val
50                  55                  60

Arg Val Ser Lys Asn Asn Lys Gly Thr Cys Arg Gly Lys Ser Arg Ser
65                  70                  75                  80

Asp Leu Ser Asp Asp Arg Glu Gln Thr Asp Val Val Thr Leu Gln Leu
                85                  90                  95

Leu Pro Glu Lys Ser Asp Ile Ser Gly Glu Tyr Ser Pro Leu Asp Gln
            100                 105                 110

Asp Ser Leu Asp Pro Ser Val Lys Ser Ile Ile Gly Glu Thr Gln
        115                 120                 125

Glu Thr Asn Thr Trp Gly Met Phe Asn Gly Ser Val Thr Ala Glu Met
130                 135                 140

Glu Thr Trp Val Thr Val Glu Ser Val Thr Ser Val Cys Glu Gly Ser
145                 150                 155                 160

Leu Ser Ser His Ala Val Gly Ile Thr Asp Val Glu Ile Val Asp Asn
                165                 170                 175

Leu Gly Lys Asp Thr Cys Pro Ala Phe Val Ser Asp Gly Ser Asn Arg
            180                 185                 190

Val Val Trp Val Asn Glu Ala Tyr Arg Arg Asn Val Ser Gly Asp Asp
        195                 200                 205

Ser Thr Ala Ser Val Ser Pro Glu Val Val Trp Leu Val Ala Glu
210                 215                 220

Glu Ala Thr Ala Ala Met His Cys Asn Tyr Gln Ala Phe Thr Cys Arg
225                 230                 235                 240

Val Arg Met Gln Tyr Thr Trp Lys Glu Thr Lys Tyr Thr Lys Thr Val
                245                 250                 255

Pro Cys Asp Val Trp Lys Met Glu Phe Gly Gly Phe Ala Trp Arg Leu
            260                 265                 270

Asp Thr Thr Ala Ala Leu Thr Leu Trp Leu
        275                 280
```

<210> SEQ ID NO 13
<211> LENGTH: 20
<212> TYPE: DNA
<213> ORGANISM: Artificial Sequence
<220> FEATURE:
<223> OTHER INFORMATION: DlL4 guide RNA

<400> SEQUENCE: 13
atccaacggc gagtactcac                                           20

<210> SEQ ID NO 14
<211> LENGTH: 20
<212> TYPE: DNA
<213> ORGANISM: Artificial Sequence
<220> FEATURE:
<223> OTHER INFORMATION: DlL4 guide RNA

<400> SEQUENCE: 14
atggatcaag atgactggtt                                          20

<210> SEQ ID NO 15
<211> LENGTH: 20
<212> TYPE: DNA
<213> ORGANISM: Artificial Sequence
<220> FEATURE:
<223> OTHER INFORMATION: DIL4 guide RNA

<400> SEQUENCE: 15
aactttatcc tgcgccttac                                          20

<210> SEQ ID NO 16
<211> LENGTH: 20
<212> TYPE: DNA
<213> ORGANISM: Artificial Sequence
<220> FEATURE:
<223> OTHER INFORMATION: DIG1 guide RNA

<400> SEQUENCE: 16
ctatcgccgc tagttatctc                                          20

<210> SEQ ID NO 17
<211> LENGTH: 20
<212> TYPE: DNA
<213> ORGANISM: Artificial Sequence
<220> FEATURE:
<223> OTHER INFORMATION: DIG1 guide RNA

<400> SEQUENCE: 17
taatgacgcg tatcggaaga                                          20

<210> SEQ ID NO 18
<211> LENGTH: 20
<212> TYPE: DNA
<213> ORGANISM: Artificial Sequence
<220> FEATURE:
<223> OTHER INFORMATION: DIG1 guide RNA

<400> SEQUENCE: 18
attagcactg ccgtgaacga                                          20

<210> SEQ ID NO 19
<211> LENGTH: 20
<212> TYPE: DNA
<213> ORGANISM: Artificial Sequence
<220> FEATURE:
<223> OTHER INFORMATION: DIL2 guide RNA

<400> SEQUENCE: 19
tgcggtgacg tgcagggtta                                          20

<210> SEQ ID NO 20
<211> LENGTH: 20
<212> TYPE: DNA
<213> ORGANISM: Artificial Sequence
<220> FEATURE:
<223> OTHER INFORMATION: DIL2 guide RNA

<400> SEQUENCE: 20
ccatgcggcc tagctgctcc                                          20

<210> SEQ ID NO 21
<211> LENGTH: 20
<212> TYPE: DNA
<213> ORGANISM: Artificial Sequence

```
<220> FEATURE:
<223> OTHER INFORMATION: DIL2 guide RNA

<400> SEQUENCE: 21
ttataagcaa gataatgcaa                                          20

<210> SEQ ID NO 22
<211> LENGTH: 20
<212> TYPE: DNA
<213> ORGANISM: Artificial Sequence
<220> FEATURE:
<223> OTHER INFORMATION: DIL3 guide RNA

<400> SEQUENCE: 22
gacgactact ggtcaaccat                                          20

<210> SEQ ID NO 23
<211> LENGTH: 20
<212> TYPE: DNA
<213> ORGANISM: Artificial Sequence
<220> FEATURE:
<223> OTHER INFORMATION: DIL3 guide RNA

<400> SEQUENCE: 23
ctactgcagc tttaactctt                                          20

<210> SEQ ID NO 24
<211> LENGTH: 20
<212> TYPE: DNA
<213> ORGANISM: Artificial Sequence
<220> FEATURE:
<223> OTHER INFORMATION: DIL3 guide RNA

<400> SEQUENCE: 24
ttttacgtgt aaggtgagaa                                          20

<210> SEQ ID NO 25
<211> LENGTH: 20
<212> TYPE: DNA
<213> ORGANISM: Artificial Sequence
<220> FEATURE:
<223> OTHER INFORMATION: DIG2 guide RNA

<400> SEQUENCE: 25
tgagtgacgg tggctttgcg                                          20

<210> SEQ ID NO 26
<211> LENGTH: 20
<212> TYPE: DNA
<213> ORGANISM: Artificial Sequence
<220> FEATURE:
<223> OTHER INFORMATION: DIG2 guide RNA

<400> SEQUENCE: 26
tagggtgtac ggacgaggag                                          20

<210> SEQ ID NO 27
<211> LENGTH: 20
<212> TYPE: DNA
<213> ORGANISM: Artificial Sequence
<220> FEATURE:
<223> OTHER INFORMATION: DIG2 guide RNA

<400> SEQUENCE: 27
gttgaaggct aaggcggcgc                                          20
```

```
<210> SEQ ID NO 28
<211> LENGTH: 20
<212> TYPE: DNA
<213> ORGANISM: Artificial Sequence
<220> FEATURE:
<223> OTHER INFORMATION: DIL1 guide RNA

<400> SEQUENCE: 28
gatatcacga aggacggtgg                                               20

<210> SEQ ID NO 29
<211> LENGTH: 20
<212> TYPE: DNA
<213> ORGANISM: Artificial Sequence
<220> FEATURE:
<223> OTHER INFORMATION: DIL1 guide RNA

<400> SEQUENCE: 29
acgtgtcaag atcgagaaag                                               20

<210> SEQ ID NO 30
<211> LENGTH: 20
<212> TYPE: DNA
<213> ORGANISM: Artificial Sequence
<220> FEATURE:
<223> OTHER INFORMATION: DIL1 guide RNA

<400> SEQUENCE: 30
ccaccgtcgc tggccggttt                                               20

<210> SEQ ID NO 31
<211> LENGTH: 27
<212> TYPE: DNA
<213> ORGANISM: Artificial Sequence
<220> FEATURE:
<223> OTHER INFORMATION: primer sequence

<400> SEQUENCE: 31
atccttgaag agcttagact ggtaaga                                       27

<210> SEQ ID NO 32
<211> LENGTH: 27
<212> TYPE: DNA
<213> ORGANISM: Artificial Sequence
<220> FEATURE:
<223> OTHER INFORMATION: primer sequence

<400> SEQUENCE: 32
tcttaccagt ctaagctctt caaggat                                       27

<210> SEQ ID NO 33
<211> LENGTH: 21
<212> TYPE: DNA
<213> ORGANISM: Artificial Sequence
<220> FEATURE:
<223> OTHER INFORMATION: artificial micro RNA

<400> SEQUENCE: 33
tcacacatca cacggcgccg a                                             21

<210> SEQ ID NO 34
<211> LENGTH: 21
<212> TYPE: DNA
<213> ORGANISM: Artificial Sequence
<220> FEATURE:
<223> OTHER INFORMATION: artificial micro RNA
```

<400> SEQUENCE: 34
tgatataaaa ccaggacacg t                                                  21

<210> SEQ ID NO 35
<211> LENGTH: 310
<212> TYPE: PRT
<213> ORGANISM: Solanum lycopersicum

<400> SEQUENCE: 35

Met Asp Gly Arg Gly Gly Cys Cys Ile Ala Arg Tyr Ala Gly Gly Ala
1               5                   10                  15

Tyr Asp Met Ser Lys Val Asp Arg Ile Met Leu Lys Phe Arg Pro Ile
            20                  25                  30

Ala Pro Lys Pro Ala Ala Gly Thr Ser Val Ser Gly Thr Thr Thr
        35                  40                  45

Pro Pro Gln Lys Ser Glu Val Pro Val Arg Thr Gly Arg Trp Lys Arg
    50                  55                  60

Arg Tyr Val Lys Asp Asn Lys Asn Ser Asn Asn Lys Arg Ser Ser
65                  70                  75                  80

Ser Gly Gly Cys Ser Pro Thr Pro Ser Arg Arg Lys Lys Ala Arg
                85                  90                  95

Ser Val Glu Glu Asn Asp Ser Ser Ala Lys Ser Val Ser Gly Gly Glu
            100                 105                 110

Thr Ala Val Thr Leu Pro Leu Leu Ser Glu Ile Pro Glu Arg Lys Asp
        115                 120                 125

Asn Ser Val Asp Met Met Lys Lys Asn Ala Pro Ile Trp Leu Ser Phe
130                 135                 140

Gly Gly Asn Gln Gly Asn Asn Asn Asp Asn Ser Asn Asn Asn Asn Gly
145                 150                 155                 160

Gln Leu Gln Gly Val Ala Met Asp Arg Ser Val Val Met Phe Pro Gln
                165                 170                 175

Pro Val Arg Val Val Gly Ser Trp Val Lys Val Glu Ser Val Thr Asp
            180                 185                 190

Ala Trp Val Glu Gly Tyr Gly Leu Gly Arg Thr Asp Glu Glu Lys Leu
        195                 200                 205

Ile Asn Leu Glu Arg Asp Ser Cys Pro Gly Phe Ile Ser Asp Gly Leu
    210                 215                 220

Asn Arg Val Arg Trp Ala Asn Lys Ala Tyr Lys Gly Met Val Gly Asp
225                 230                 235                 240

Gly Ala Gly Glu Val Val Trp Leu Val Met Lys Asp Ala Val Arg
                245                 250                 255

Leu Pro Glu Ser Lys Ser Thr Ala Phe Thr Cys Arg Val Arg Val
            260                 265                 270

Val Arg Cys Gly Lys Glu Lys Asn Ser Leu Ile Leu Pro Cys Asp Val
        275                 280                 285

Trp Arg Met Asp Gly Gly Phe Ala Trp Arg Leu Asp Thr Glu Ala
    290                 295                 300

Ala Leu Ser Leu Gly Arg
305                 310

<210> SEQ ID NO 36
<211> LENGTH: 275
<212> TYPE: PRT
<213> ORGANISM: Solanum lycopersicum -continued

<400> SEQUENCE: 36

Met Asp Leu Ala Asn Thr Trp Ala Gly Pro Gly Tyr Thr Pro Thr Pro
1               5                   10                  15

Lys Asp Thr Thr Leu Ile Asn Gln Met Met Leu Arg Phe Arg Pro Ile
            20                  25                  30

Ala Pro Lys Pro Val Asp Asn Ser Gly Pro Pro Glu Thr His Val
        35                  40                  45

Val Ala Asn Arg Arg Thr Lys Arg Lys Tyr Val Arg Val Lys Lys Asn
    50                  55                  60

Lys Asn Asn Lys Lys Glu Lys Ser Asp Gly Leu Leu Asp Glu Val Val
65                  70                  75                  80

Thr Leu Gln Leu Leu Pro Glu Ser Ser Gly Val Lys Thr Ser Pro
                85                  90                  95

Glu Asp Arg Ser Tyr Pro Lys Thr Ile Asn Phe Leu Val Gln Leu Asp
            100                 105                 110

Arg Ser Ile Trp Ile Asn Lys Asn Ile Leu Ser Ile Gly Ala Pro Asp
        115                 120                 125

Pro Ser Val Glu Ile Arg Ser Pro Met Val Val Glu Ser Trp Val Thr
    130                 135                 140

Val Asp Gly Leu Thr Asn Thr Thr Phe Val Asp Leu Ser Ala Leu Gly
145                 150                 155                 160

Ser Thr Asp Met Glu Lys Met Met Asn Leu Gln Arg Asp Thr Cys Pro
                165                 170                 175

Gly Phe Ile Ser Asp Gly Leu Asp Ser Val Lys Trp Val Asn Leu Ala
            180                 185                 190

Tyr Arg Arg Met Ile Asp Pro Glu Glu Gly Gly Glu Ala Thr Glu
        195                 200                 205

Met Val Val Arg Leu Val Val Lys Glu Asp Lys Arg Ala Pro Val Leu
    210                 215                 220

Leu Leu Leu Pro Ser Phe Ala Cys Ile Val Arg Ile Val Tyr Thr Trp
225                 230                 235                 240

Asn Lys Val Lys Gln Ser Arg Thr Met Pro Cys Asp Val Trp Lys Met
                245                 250                 255

Asp Cys Gly Gly Phe Ala Trp Lys Phe Asp Ala Lys Ala Ala Leu Ser
            260                 265                 270

Leu Gly Arg
        275

<210> SEQ ID NO 37
<211> LENGTH: 280
<212> TYPE: PRT
<213> ORGANISM: Solanum lycopersicum

<400> SEQUENCE: 37

Met Asp Gly Gly Asn Gly Phe Pro Ala Ala Lys Tyr Ala Gly Gly Lys
1               5                   10                  15

Asn Asp Thr Thr Ile Met Asn Arg Ile Met Leu Arg Phe Arg Pro Ile
            20                  25                  30

Ala Pro Lys Pro Val Ala Gly Ser Ser Asp Gly Ser Thr Pro Glu
        35                  40                  45

Asn Asn Asn Met Glu Leu Val Thr Lys Arg Arg Ala Lys Arg Lys Tyr
    50                  55                  60

Val Arg Val Lys Lys Ser Ser Lys Cys Lys Ser Asn Lys Glu Asp Glu
65                  70                  75                  80

```
Ala Asn Lys Asp Gly Ser Ser Leu Tyr Glu Asp Asn Gly Ala Gly Ile
                85                  90                  95

Thr Leu Gln Leu Met Pro Gln Ser Ser Gly Val Arg Asn Ser Leu
            100                 105                 110

Glu Asn Ser Gly Ser Arg Pro Phe Trp Met Asn Phe Gln Lys Ser Glu
            115                 120                 125

Asn Ser Glu Ile Phe Pro Val Gly Ser Asp Gln Ile Asp Arg Thr Val
            130                 135                 140

Glu Met Gln Lys Lys Arg Val Val Glu Ser Trp Val Met Val Asp Gln
145                 150                 155                 160

Ile Thr Asn Ala Leu Val Asp Gly Glu Ala Leu Gly Ser Thr Asp Thr
                165                 170                 175

Glu Lys Met Lys Asn Leu Glu Ala Asp Thr Cys Pro Gly Leu Ile Ser
            180                 185                 190

Asp Gly Leu Asp Arg Val Arg Trp Val Asn Leu Ala Tyr Arg Arg Met
            195                 200                 205

Val Asp Pro Leu Glu Gly Ser Gly Asn Ser Pro Glu Leu Val Thr Trp
            210                 215                 220

Leu Val Val Lys Glu Lys Ile Leu Leu Pro Asn Ser Ser Ala Phe Ala
225                 230                 235                 240

Cys Thr Val Arg Ile Leu Tyr Thr Lys Asn Ser Gln Thr Met Pro Cys
                245                 250                 255

Asp Val Trp Lys Met Glu Phe Gly Gly Phe Ala Trp Arg Leu Asp Ala
            260                 265                 270

Lys Ala Ala Leu Arg Leu Gly Arg
            275                 280

<210> SEQ ID NO 38
<211> LENGTH: 309
<212> TYPE: PRT
<213> ORGANISM: Glycine max

<400> SEQUENCE: 38

Met Asp Ser Ala Asp Ala Trp Arg Val Ala Ala Cys Gly Asn Ser Asn
1               5                   10                  15

Val Asn Lys Ile Met Leu Arg Phe Arg Pro Ile Ala Pro Lys Pro Val
                20                  25                  30

Thr Gly Ile Ser Ala Ala Glu Ala Gly Ser Ala Val Gly Glu Val Thr
            35                  40                  45

Gln Asn Asn His Val Ser Val Leu Gly Lys Pro Lys Arg Lys Tyr
        50                  55                  60

Val Arg Ile Arg Arg Asn Ser Gly Tyr Val Arg Lys Asn Asn Gly Asp
65                  70                  75                  80

Ser Asn Gly Lys Ser Asn Gly Asn Gly Asn Asp Glu Ser Ser Asp Val
                85                  90                  95

Ala Val Val Thr Leu Gln Leu Met Pro Glu Lys Asp Ala Pro Gly Gly
            100                 105                 110

Asp Val Thr Leu Ala Gly Asp Ser Trp Cys Lys Asn Val Asp Leu Asp
            115                 120                 125

Leu Thr Val Glu Lys Ile Gln Ile Val Glu Asn Arg Ser Ala Pro Pro
            130                 135                 140

Pro Arg Ala Ala Ala Glu Glu Gly Gly Gly Lys Arg Ser Asp Leu
145                 150                 155                 160

Val Ala Ala Ala Lys Val Ala Glu Ser Trp Val Thr Val Glu Ser Val
                165                 170                 175
```

```
Thr Gly Thr Cys Met Gly Glu Gly Asp Gly Glu Gly Arg Gly Leu
            180                 185                 190

Leu Asp Cys Thr Asp Ala Glu Lys Val Lys Ser Leu Glu Ala Asp Thr
        195                 200                 205

Cys Pro Ala Phe Val Cys Asp Gly Ser Leu Arg Val Arg Trp Val Asn
210                 215                 220

Asp Ala Tyr Lys Arg Met Met Leu Glu Gly Arg Glu Gly Glu Gly Glu
225                 230                 235                 240

Asn Ile Val Val Trp Leu Lys Val Lys Asp Ser Ala Ile Ala Ser Trp
                245                 250                 255

Trp Cys Tyr Ser His Pro Ala Phe Thr Cys Gly Val Arg Leu Gln Tyr
            260                 265                 270

Thr Trp Arg Asn Glu Lys Cys Thr Lys Met Val Pro Cys Asp Val Trp
        275                 280                 285

Arg Leu Asp Cys Gly Gly Phe Ala Trp Arg Leu Asp Val Lys Ala Ala
    290                 295                 300

Leu Ser Leu Gly Leu
305

<210> SEQ ID NO 39
<211> LENGTH: 290
<212> TYPE: PRT
<213> ORGANISM: Glycine max

<400> SEQUENCE: 39

Met Asp Gly Arg Gly Gly Cys Cys Ile Ala Arg Tyr Val Pro Gly Ala
1               5                   10                  15

Ser His Gly Ser Thr Val Asp Lys Ile Met Leu Arg Phe Arg Pro Ile
            20                  25                  30

Ala Pro Lys Pro Ala Ala Ala Thr Ala Ser Asp Gly Ser Ser Ser
        35                  40                  45

Glu Ser Ser Asp Ala Phe Leu Lys Asn Gly Thr Thr Lys Arg Lys Tyr
    50                  55                  60

Val Arg Asp Asn Asn Tyr Thr Ser Lys Arg Arg Ile Arg Arg Arg Lys
65                  70                  75                  80

Asn Thr Ser Ser Pro Glu Lys Lys Gln Lys Pro Val Val Thr Leu Pro
                85                  90                  95

Leu Leu Pro Glu Thr Pro Asp Arg Lys Asp Ser Arg Ala Lys Asp Leu
            100                 105                 110

Thr Pro Ser Pro Ala Lys Pro Val Arg Asn Asn Asn Asn Asn Asn
        115                 120                 125

Lys Ser Lys Asn Leu Asn Ile Ile Asn Lys Asn Val Pro Val Trp Val
130                 135                 140

Ser Phe Glu Asn Arg Ser Leu Thr Met Met Gly Gly Trp Cys Ser Cys
145                 150                 155                 160

Val Thr Val Glu Gly Val Thr Asp Thr Cys Leu Glu Ser Glu Trp Leu
                165                 170                 175

Gly Ser Thr Asp Glu Glu Arg Arg Leu Asn Leu Ser Asn Asp Thr Cys
            180                 185                 190

Pro Gly Phe Ile Ser Asp Gly Tyr Gly Arg Val Thr Trp Thr Asn Glu
        195                 200                 205

Ala Tyr Gly Lys Met Met Met Met Lys Gly Glu Gly Asp Glu Gly Gln
    210                 215                 220

Gly Pro Val Leu Leu Val Asn Lys Val Asn Thr Val Val Pro His Ala
```

```
                225                 230                 235                 240

Ser Phe Thr Cys Leu Val Arg Val Val Gln Tyr Ser Cys Gly Lys Glu
                            245                 250                 255

Arg Asn Ser Leu Thr Val Pro Cys Asp Val Trp Arg Met Asp Cys Gly
                            260                 265                 270

Gly Phe Ala Trp Arg Leu Asp Val Lys Thr Ala Leu Ser Leu Arg Leu
                            275                 280                 285

Gly Tyr
                290

<210> SEQ ID NO 40
<211> LENGTH: 270
<212> TYPE: PRT
<213> ORGANISM: Glycine max

<400> SEQUENCE: 40

Met Ser Ser Tyr Lys Pro Thr Pro Leu Pro Ser Leu Leu Gln Pro
1               5                   10                  15

Pro Ser Thr Arg Ala Ala Tyr Asn Met Ser Lys Ile Asp Gln Ile Met
                20                  25                  30

Leu Arg Phe Arg Pro Ile Ala Pro Lys Pro Leu Pro Ser Ala Ala Ala
            35                  40                  45

Leu Ser Asp Ala Phe Ser Ser Glu Asn Thr Gly Val Ser Lys Arg Lys
50                  55                  60

Asp Asn Thr Gly Ser Lys Arg Cys Ser Arg Gly Ile Arg Arg Arg Arg
65                  70                  75                  80

Asn Ala Pro Pro Pro Pro Pro Pro Pro Ala Val Thr Leu Pro
                85                  90                  95

Leu Leu Pro Glu Thr Pro Asp Pro Lys Lys Thr Thr Ser Glu Leu Lys
            100                 105                 110

Asn Lys Asn Val Pro Val Trp Leu Ser Phe Glu Asn Ser Phe Lys Asn
        115                 120                 125

Arg Gly Gly Thr Ala Ser Glu Lys Val Asp Pro Cys Trp Tyr Ser Pro
    130                 135                 140

Ala Ala Gly Ser Val Val Thr Val Glu Cys Val Met Asp Arg Trp Gln
145                 150                 155                 160

Pro Gln Glu Glu Gly Leu Gly Leu Gly Arg Gly Asp Val Glu Arg Lys
                165                 170                 175

Val Lys Leu Glu Glu Asp Thr Cys Pro Gly Phe Ile Ser Asp Gly Tyr
            180                 185                 190

Gly Arg Val Thr Trp Thr Asn Gly Ala Tyr Arg Glu Ile Met Gly Glu
        195                 200                 205

Gly Gly Val Trp Leu Ala Met Lys Val Thr Val Pro Cys Leu Tyr Arg
    210                 215                 220

Gly Phe Thr Cys Arg Val Arg Val Gln Tyr Ala Cys Gly Lys Glu Arg
225                 230                 235                 240

Thr Val Pro Cys Asp Val Trp Arg Met Asn Ser Gly Gly Phe Ala Trp
                245                 250                 255

Arg Leu Asp Val Lys Ala Ala Leu Ser Leu Ser Leu Ala Leu
            260                 265                 270

<210> SEQ ID NO 41
<211> LENGTH: 307
<212> TYPE: PRT
<213> ORGANISM: Glycine max
```

```
<400> SEQUENCE: 41

Met Asp Gly Ala Asp Ala Trp Arg Val Ala Cys Ala Asn Thr Asn
1               5                   10                  15

Val Asn Arg Ile Met Leu Arg Phe Arg Pro Ile Ala Pro Lys Pro Val
            20                  25                  30

Ala Gly Ser Ser Ala Val Ser Arg Ala Thr Gly Ala Gly Asp Gly Ser
        35                  40                  45

Gln Ser Ser His Val Ser Val Leu Gly Lys Arg Pro Lys Arg Lys Tyr
    50                  55                  60

Val Arg Ile Arg Arg Asn Gly Gly Tyr Val Lys Asn Asn Gly Asn
65              70                  75                  80

Ser Asn Arg Lys Ser Asn Cys Asn Cys Asn Asp Glu Ser Ser Asp Val
                85                  90                  95

Ala Val Val Thr Leu Gln Leu Met Pro Glu Lys Asp Ala Pro Glu Gly
            100                 105                 110

Asp Val Thr Leu Ala Gly Asp Ser Trp Cys Lys Asn Val Asp Leu Asp
            115                 120                 125

Leu Thr Val Glu Lys Ile Gln Ile Val Glu Asn Arg Ser Val Pro Pro
    130                 135                 140

Pro Arg Leu Val Val Glu Gly Glu Gly Ala Lys Gly Ser Asp Leu
145             150                 155                 160

Val Pro Ala Ala Lys Ala Ala Glu Ser Trp Val Thr Val Glu Ser Val
                165                 170                 175

Thr Gly Thr Cys Met Gly Glu Gly Gly Arg Gly Leu Leu Ser
            180                 185                 190

Cys Thr Asp Glu Glu Arg Val Lys Ser Leu Glu Thr Asp Thr Cys Pro
    195                 200                 205

Gly Phe Val Cys Asp Gly Ser Leu Arg Val Arg Trp Val Asn Asp Ala
210                 215                 220

Tyr Lys Arg Met Val Leu Glu Gly Arg Lys Gly Glu Gly Glu Asp Ile
225             230                 235                 240

Met Val Trp Leu Lys Val Lys Asp Ser Ala Cys Ala Ala Trp Trp Cys
            245                 250                 255

Tyr Ser His Pro Ala Phe Thr Cys Gly Val Arg Leu Gln Tyr Thr Trp
            260                 265                 270

Arg Asn Glu Lys Cys Thr Lys Met Val Pro Cys Asp Val Trp Arg Leu
            275                 280                 285

Asp Cys Gly Gly Phe Ala Trp Arg Leu Asp Val Lys Ala Ala Leu Ser
    290                 295                 300

Leu Gly Leu
305

<210> SEQ ID NO 42
<211> LENGTH: 289
<212> TYPE: PRT
<213> ORGANISM: Glycine max

<400> SEQUENCE: 42

Met Asp Leu Arg Gly Gly Cys Cys Ile Ala Arg Tyr Val Pro Gly Ala
1               5                   10                  15

Ser His Val Ser Thr Val Asp Lys Ile Met Leu Arg Phe Arg Pro Ile
            20                  25                  30

Ala Pro Lys Pro Ala Ala Gly Ala Thr Ala Ser Asp Gly Ser Ser Ser
        35                  40                  45
```

Glu Thr Ser Asp Ala Phe Leu Arg Asn Gly Asn Thr Lys Arg Lys Tyr
 50                  55                  60

Val Arg Asp Ser Asn Tyr Thr Ser Lys Arg Arg Ile Cys Arg Arg Lys
 65                  70                  75                  80

Asn Ser Asn Ser Pro Glu Gln Lys Gln Lys Gln Thr Thr Pro Ala
                 85                  90                  95

Val Thr Leu Pro Leu Leu Pro Glu Thr Pro Asp Arg Lys Asp Phe Pro
                100                 105                 110

Ala Lys Asp Leu Thr Pro Ser Pro Val Arg Asn Asn Asn Asn Asn
             115                 120                 125

Ser Ser Asn Lys Ser Lys Lys Leu Asn Ile Ile Asn Lys Asn Val Pro
     130                 135                 140

Val Trp Val Ser Phe Ala Asn Arg Ser Leu Thr Met Met Gly Gly Trp
145                 150                 155                 160

Cys Ser Cys Val Thr Val Glu Ser Leu Thr Asp Thr Trp Val Glu Gly
                 165                 170                 175

Glu Trp Leu Gly Ser Thr Asp Glu Glu Arg Arg Val Asn Leu Ser Lys
             180                 185                 190

Asp Thr Cys Pro Gly Phe Ile Ser Asp Gly Tyr Gly Arg Val Thr Gly
     195                 200                 205

Thr Asn Glu Ala Tyr Glu Lys Met Met Glu Gly Asp Glu Gly Gln Gly
210                 215                 220

Pro Val Leu Leu Val Asn Lys Val Asn Thr Val Val Pro His Ala Ser
225                 230                 235                 240

Phe Thr Cys Leu Val Arg Val Val Gln Tyr Ala Cys Gly Arg Glu Arg
                 245                 250                 255

Ser Ser Leu Thr Val Pro Cys Asp Val Trp Arg Met Asp Ser Gly Gly
             260                 265                 270

Phe Ala Trp Arg Leu Asp Val Glu Thr Ala Leu Ser Leu Arg Leu Gly
     275                 280                 285

Tyr

<210> SEQ ID NO 43
<211> LENGTH: 248
<212> TYPE: PRT
<213> ORGANISM: Glycine max

<400> SEQUENCE: 43

Met Ser Lys Met Asp Lys Ile Met Leu Arg Phe Arg Pro Ile Ala Pro
  1               5                  10                  15

Lys Pro Leu Pro Ala Ala Ala Ala Leu Ser Asp Ala Ser Ser Ser
                 20                  25                  30

Glu Ser Thr Gly Ser Ala Lys Arg Lys Asp Asn Thr Ala Ser Lys Arg
             35                  40                  45

Cys Ser Arg Gly Ile Arg Arg Arg Asn Ala Pro Pro Pro Pro
 50                  55                  60

Ser Pro Ala Val Thr Leu Pro Leu Leu Pro Gly Ser Pro Gly Pro Lys
 65                  70                  75                  80

Lys Ile Thr Ser Glu Leu Lys Asn Lys Asn Val Pro Val Trp Leu Ser
                 85                  90                  95

Phe Glu Asn Asn Phe Glu Asn Arg Gly Gly Ala Ala Ser Glu Lys Leu
                100                 105                 110

Asp Pro Cys Trp Tyr Ser Gln Ala Thr Ala Ala Gly Ser Val Val
             115                 120                 125

```
Thr Val Glu Cys Val Met Asp Thr Trp Gln Gln Asp Glu Gly Leu
        130                 135                 140

Gly Leu Gly Ser Gly Asp Glu Arg Lys Val Lys Leu Lys Glu Asp
145                 150                 155                 160

Thr Cys Pro Gly Phe Ile Ser Asp Gly Tyr Gly Arg Val Thr Trp Thr
                165                 170                 175

Asn Glu Ala Tyr Arg Glu Thr Val Gly Ala Gly Val Trp Leu Ala
                180                 185                 190

Met Lys Val Ala Val Pro Tyr Pro Tyr Arg Gly Phe Thr Cys Arg Val
                195                 200                 205

Arg Val Arg Tyr Ala Cys Gly Ile Glu Arg Thr Val Pro Cys Asp Val
        210                 215                 220

Trp Arg Met Asp Ser Gly Gly Phe Ala Trp Arg Leu Asp Val Lys Ala
225                 230                 235                 240

Ala Leu Ser Leu Ser Leu Ala Phe
                245

<210> SEQ ID NO 44
<211> LENGTH: 329
<212> TYPE: PRT
<213> ORGANISM: Oryza sativa

<400> SEQUENCE: 44

Met Glu Arg Lys Gly Gly Cys Cys Leu Ala Pro Arg Tyr Gly Ala Ala
1               5                   10                  15

Ser Ala Ala Ala Ala Gly Ala Gly Gly Gln Ala Ala Met Ala Trp
                20                  25                  30

Gln Met Gly Arg Ile Met Leu Lys Phe Arg Pro Ile Ala Pro Lys Pro
            35                  40                  45

Ala Ala Met Ala Pro Ala Pro Val Ala Gly Val Gly Ala Gly Lys Gly
        50                  55                  60

Lys Arg Lys Ala Val Ser Gly Ser Gly Gly Arg Arg Gly Arg Lys
65                  70                  75                  80

Pro Lys Lys Ala Ala Thr Ala Ala Thr Leu Ala Pro Ala His Ala Pro
                85                  90                  95

Ala Pro Ala Pro Ser Val Ala Gly Lys Thr Val Pro Lys Val Val Gly
                100                 105                 110

Asp Cys Lys Glu Met Glu Arg Glu Lys Glu Lys Glu Lys Ser Leu Ser
            115                 120                 125

Ser Pro Ser Ser Ser Ser Ser Gly Met Thr Ser Val Glu Ser Ser Pro
        130                 135                 140

Pro Pro Pro Pro Ser Ala Met Leu Pro Leu Leu Pro Val Arg Pro Leu
145                 150                 155                 160

Asp Thr Thr Thr Thr Thr Pro Pro Pro Val Ala Pro Ala His Ala Ala
                165                 170                 175

Ala Gln Ser Val Val Val Ala Pro Pro Arg Ala Leu Leu Pro Ala
            180                 185                 190

Ala Ala Val Val Thr Val Glu Asp Val Thr Ser Val Trp Arg Asp Gly
        195                 200                 205

Gly Ser Gly Ala Ala Arg Ala Gly Asp Asp Gly Asp Gly Ala Pro Ala
        210                 215                 220

Phe Val Ser Asp Gln Trp Gly Arg Val Thr Trp Lys Asn Ala Ala Phe
225                 230                 235                 240

His Arg Ala Val Ala Pro Asp Ala Ala Pro Asp Gln Ala Arg Val
            245                 250                 255
```

```
Ala Leu Ala Ala Arg Asp Gly Asp Ala Ala Ala Val Pro Ala Trp
            260                 265                 270

Gly Thr Cys Ala Gly Phe Thr Cys Arg Val Arg Val His Pro Ser Pro
            275                 280                 285

Tyr Ser Pro Arg Ser Ser Val Val Ala Pro Cys Asp Val Trp Arg
            290                 295                 300

Leu Asp Ala Gly Gly Cys Tyr Leu Trp Arg Leu Asp Leu Gln Ala Ala
305                 310                 315                 320

Leu Ser Leu Ser Leu Gly Ala Leu Pro
                325

<210> SEQ ID NO 45
<211> LENGTH: 318
<212> TYPE: PRT
<213> ORGANISM: Zea mays

<400> SEQUENCE: 45

Met Glu Arg Lys Gly Gly Cys Cys Leu Ala Pro Arg Tyr Ala Ala Thr
1               5                   10                  15

Ala Ala Ala Gln Gln Ala Gly Ala Ala Trp Gln Met Gly Arg Ile Met
            20                  25                  30

Leu Lys Phe Arg Pro Ile Ala Pro Lys Pro Ala Ala Met Ala Pro Ala
            35                  40                  45

Pro Ala Pro Ala Ser Ala Pro Val Thr Gly Ser Ala Ala Gly Ala Gly
    50                  55                  60

Arg Gly Lys Arg Lys Ala Ala Cys Gly Gly Gly Arg Arg Gly Arg
65                  70                  75                  80

Lys Pro Lys Lys Ala Ala Lys Val Ala Met Val Thr Ala Ala Pro Ala
            85                  90                  95

Ala Thr Ala Ala Ala Gln Asp Val Gly Asp Cys Arg Glu His Cys Asp
            100                 105                 110

Lys Glu Lys Ser Ser Ser Ser Pro Ser Ser Ser Ser Gly Thr Ser
            115                 120                 125

Ser Val Asp Ser Ser Pro Pro Pro Arg Pro Gln Gln Arg Gln Leu Ala
    130                 135                 140

Thr Leu Pro Leu Met Pro Val Thr Ala Ala Glu Asp Lys Ala Ala Ala
145                 150                 155                 160

Cys Pro Ala Thr Val Gly Pro Glu Leu Val Pro Ser Gln Val Ala Thr
                165                 170                 175

Ala Ala Arg Pro Leu Ala Pro Arg Ala Met Arg Pro Ala Ala Ala Ala
            180                 185                 190

Ala Tyr Leu Val Thr Val Glu Glu Val Thr Ala Thr Trp Arg Asp Gly
            195                 200                 205

Glu Ala Pro Ala Ser Ala Thr Gly His Asp Glu Ala Pro Ala Phe Val
    210                 215                 220

Ser Asp Gln Trp Gly Arg Val Thr Leu Trp Asn Ala Ala Phe Val Arg
225                 230                 235                 240

Ala Ala Ser Ala Asp Asp Gly Asp Glu Ala Ala Ala Pro Val Val Leu
                245                 250                 255

Gly Gly Ala Leu Pro Ala Trp Gly Thr Cys Ala Gly Phe Thr Cys Arg
            260                 265                 270

Val Arg Ala Arg His Trp Ser Ala Arg Arg Val Gly Ser Pro Val Val
            275                 280                 285

Ala Pro Cys Asp Val Trp Arg Leu Asp Ala Ala Gly Ser Tyr Leu Trp
```

```
            290                 295                 300
Arg Leu Asp Leu Gln Ala Ala Leu Thr Leu Gly Gly Cys Leu
305                 310                 315

<210> SEQ ID NO 46
<211> LENGTH: 354
<212> TYPE: PRT
<213> ORGANISM: Arabidopsis thaliana

<400> SEQUENCE: 46

Met Ile Lys Ile Leu Asn Pro His Ser His Ser Gln Thr Thr Thr
1               5                   10                  15

Leu Lys Thr Ala Glu Ile Leu Ser Lys Tyr Arg Pro Ile Ala Pro Lys
                20                  25                  30

Pro Gly Thr Pro Arg Val Asn Asp Asp Pro Ser Ser Met Ser
            35                  40                  45

His Lys Ile Ser Gln Ser Pro Tyr Leu Arg Asn Leu Trp Pro Gln Leu
        50                  55                  60

Gln Ala Arg Pro Thr Arg Thr Arg Lys Arg Gly Arg Gly Gly Met Gly
65                  70                  75                  80

Pro Ser Ser Leu Ala Met Lys Arg Pro Lys Ser Ser Cys Gly Ser Ser
                85                  90                  95

Ser Thr Ser Thr Ile Ser Thr Gln Arg Val Leu Gly Pro Ile Lys Thr
                100                 105                 110

Leu Ser Phe Gln Ala Phe Thr His His Arg Leu Pro Asn Leu Pro Gln
            115                 120                 125

Val Gly Tyr Gly Phe Glu Asn Gly Val Ser Ser Thr Leu Val Thr Leu
        130                 135                 140

Pro Leu Leu Gln Cys Ser Pro Pro Ser Ser Lys Cys Met Glu Pro Glu
145                 150                 155                 160

Ile Lys Gly Lys Gly Val Ile Asp Leu Asn Lys Thr Ala Glu Val Ile
                165                 170                 175

Gln Glu Arg Asp Phe Leu Thr Gln Leu Gln Gly Pro Ile Thr Thr Thr
            180                 185                 190

Thr Thr Ala Thr Thr Ser Arg Val Ile Ser Pro Gln Pro Ile Arg Pro
        195                 200                 205

Val Cys Ser Lys Ile Asn Val Ala Tyr Ile Asn Pro Leu Thr Asn Pro
210                 215                 220

Ser Pro Thr Ser Gln Thr Ser Lys Lys Ser Pro Arg Glu Val Glu Glu
225                 230                 235                 240

Asp Val Glu Ser Asp Asp Leu Pro Ser Val Ile Thr Asp Ser Asn Ser
                245                 250                 255

Arg Val Arg Leu Val Asn Ser Ala Tyr Lys Glu Met Met Gly Gln Pro
            260                 265                 270

Glu Cys Ser Trp Leu Asp Ser Met Val Arg Gly Lys Arg Ile Cys Gly
        275                 280                 285

Glu Val Met Ile Asn Phe Cys Glu Ser Lys Ile Pro Val Met Thr Glu
    290                 295                 300

Asn Asn Gly Phe Ser Cys Trp Val Arg Ile Asp Trp Gly Arg Asp Gly
305                 310                 315                 320

Lys Glu Glu Tyr Met His Ala Phe Cys Asp Val Thr Lys Leu Ala Cys
                325                 330                 335

Asp Ser Lys Asp Tyr Val Phe Thr Trp Arg Phe His Thr Thr Asp
            340                 345                 350
```

Arg Arg

<210> SEQ ID NO 47
<211> LENGTH: 343
<212> TYPE: PRT
<213> ORGANISM: Oryza sativa

<400> SEQUENCE: 47

```
Met Ala Met Val Gln Pro Val Asp Met Ala Val Lys Ala Asn Glu Ile
1               5                   10                  15

Met Ala Arg Phe Arg Pro Ile Ala Pro Lys Pro Val Leu Pro Ala Ala
                20                  25                  30

Ala Ala Gly Val Thr Gly Gly Asp Gly Ala Ala Val Ala Ala
            35                  40                  45

Thr Asn Arg Val Leu Cys Gln Leu Gln Ser Arg Pro Cys Arg Ala Arg
        50                  55                  60

Lys Arg Gly Arg Pro Ser Val Val Pro Val Ser Pro Ala Gly
65                  70                  75                  80

Ala Lys Arg Lys Arg Ala Pro Ala Tyr Pro Val Pro Val Ala Pro Leu
                85                  90                  95

Arg Cys Ala Ala Val Ala Thr Ala Thr Arg Ala Arg Val Ser Val Val
            100                 105                 110

Val Val Pro Ala Pro Glu Ser Ala Gly Gly Val Ser Ala Leu Ala Pro
        115                 120                 125

Val Ser Pro Ser Ala Gly Asp Ser Thr Arg Leu Ser Pro Thr Val Val
130                 135                 140

Glu Val Glu Asp Glu Asp Glu Glu Arg Gly Val Val Leu Val Glu Arg
145                 150                 155                 160

Asp Leu Leu Arg Lys Leu Leu Glu Pro Arg Lys Leu Leu Glu Pro Arg
                165                 170                 175

Ala Val Arg Pro Val Gly Ser Thr Ile His Val Glu Ser Val His Ile
            180                 185                 190

Asp Val Gly Arg Thr Thr Ala Ala Ala Ala Ala Ala Pro Lys Thr
        195                 200                 205

Ala Glu Glu Val Glu Ala Glu Leu Glu Ser Asp Ser Leu Pro Ala Val
210                 215                 220

Val Ser Asp Ser Ser Asn Arg Val Arg Leu Val Asn Asp Ala Tyr Lys
225                 230                 235                 240

Arg Met Val Gly Gln Pro Glu Cys Pro Trp Leu Asp Ala Val Ala Thr
                245                 250                 255

Ala Ala Ser Arg Arg Ile Ser Gly Glu Val Ala Leu Val Val Ser Glu
            260                 265                 270

Pro Ala Ala Ala Ala Ala Leu Pro Glu Thr Cys Lys Gly Phe Ser
        275                 280                 285

Cys Ser Ala Lys Ile Ala Trp Glu Arg Asp Gly Lys Trp Ser Ser Val
    290                 295                 300

His Ala Pro Cys Asp Val Thr Arg Leu Gln Cys Glu Ser Arg Asp Tyr
305                 310                 315                 320

Val Phe Ala Trp Arg Phe Arg Ala Ala Gly Asp Glu Cys Asn Thr His
                325                 330                 335

Arg Arg Ala Ala Gly Asp Ala
            340
```

<210> SEQ ID NO 48
<211> LENGTH: 327

<212> TYPE: PRT
<213> ORGANISM: Zea mays

<400> SEQUENCE: 48

```
Met Ala Met Val Gln Pro Ala Asp Thr Ala Val Lys Ala Asn Glu Ile
1               5                   10                  15

Leu Ala Arg Phe Arg Pro Ile Ala Pro Lys Pro Thr Leu Ala Ala Ala
            20                  25                  30

Ala Ala Ala Ala Ala Pro Val Ala Gln Ala Ala Glu Gly Val
        35                  40                  45

Val Ala Ala Asn Arg Val Leu Cys His Leu Gln Ser Arg Pro Cys Arg
    50                  55                  60

Ala Arg Lys Arg Gly Arg Pro Thr Val Val Pro Val Ser Pro Lys Ser
65                  70                  75                  80

Gly Ala Gln Pro Pro Ala Lys Arg Arg Ala Ser Thr Pro Tyr Pro
                85                  90                  95

Pro Leu Arg Cys Ala Ala Ala Thr Thr Gly Ala His Val Ser Ala Val
                100                 105                 110

Val Pro Gly Ser Ala Arg Leu Pro Pro Ala Ser Ala Gly Val Glu Asp
            115                 120                 125

Ile Ala Lys Ala Ala Ala Ala Ala Thr Glu Glu Gly Arg Asp Val
    130                 135                 140

Pro Val Glu Arg Asp Leu Leu Arg Lys Leu Leu Glu Pro Arg Val Ile
145                 150                 155                 160

Ser Pro Arg Ala Val Arg Pro Val Trp Ser Ala Ile His Val Gly Cys
                165                 170                 175

Ile His Arg Thr Asp Asp Ala Ala Cys Thr Asp Ala Ala Val Ser Lys
            180                 185                 190

Thr Ala Val Gln Val Glu Ala Glu Leu Glu Val Asp Ala Leu Pro Ala
        195                 200                 205

Val Val Ser Asp Ser Gly Asn Arg Val Arg Leu Val Asn Asp Ala Tyr
    210                 215                 220

Lys Glu Met Val Gly Gln Pro Glu Cys Pro Trp Leu Asp Ala Val Ala
225                 230                 235                 240

Ala Thr Ser Arg Arg Ile Ser Gly Glu Val Ala Leu Val Val Ala Asp
                245                 250                 255

Arg Ser Ser Leu Pro Asp Ser Tyr Gly Ala Phe Thr Cys Thr Ala Lys
            260                 265                 270

Ile Glu Trp Glu Asp Asp Gly Lys Val Thr Ser Ile Ala Ala Pro Cys
        275                 280                 285

Asp Val Ser Arg Leu Gln Cys Glu Ser Arg Asp Tyr Leu Phe Ala Trp
    290                 295                 300

Arg Phe Arg Thr Ala Ala Ala Asp Ala Asp Ala Ser Val Gly His Ser
305                 310                 315                 320

Ser Glu Glu Ile Ser Glu Ser
                325
```

<210> SEQ ID NO 49
<211> LENGTH: 312
<212> TYPE: PRT
<213> ORGANISM: Zea mays

<400> SEQUENCE: 49

```
Met Ala Met Val Gln Pro Ala Asp Ala Thr Val Lys Ala Asn Glu Ile
1               5                   10                  15
```

Leu Ala Arg Phe Arg Pro Ile Ala Pro Lys Pro Thr Leu Ala Ala Glu
            20                  25                  30

Gly Val Ala Ala Asn Arg Val Leu Cys His Leu Gln Gly Arg Pro
        35                  40                  45

Cys Arg Ala Arg Lys Arg Gly Arg Pro Gly Pro Ala Val Val Ala Pro
 50                  55                  60

Ser Pro Glu Ser Gly Leu Gln Pro Pro Ala Lys Arg Lys Arg Ala Thr
 65                  70                  75                  80

Thr Pro Tyr Pro Pro Leu Arg Cys Thr Gly Pro Arg Ala Ser Ala Ala
            85                  90                  95

Val Pro Gly Ser Ala Gly Leu Pro Leu Ala Ser Ala Ser Leu Pro Pro
            100                 105                 110

Ala Gly Ala Gly Ala Ala Glu Asp Leu Ala Lys Val Ala Ala Glu Gly
            115                 120                 125

Arg His Val Pro Val Glu Arg Asp Leu Leu Arg Lys Leu Leu Glu Pro
    130                 135                 140

Lys Val Ile Ser Pro Arg Ala Val Arg Pro Val Cys Ser Ala Ile His
145                 150                 155                 160

Val Gly Cys Ile His Arg Ala Asp Ala Thr Cys Ala Ala Ala Val Ser
                165                 170                 175

Lys Thr Ala Val Arg Val Glu Ala Glu Leu Glu Val Asp Ala Leu Pro
            180                 185                 190

Ala Val Val Ser Asp Ala Ser Asn Arg Val Arg Leu Val Asn Asp Ala
            195                 200                 205

Tyr Lys Glu Met Val Gly Gln Pro Glu Cys Pro Trp Leu Asp Ala Val
    210                 215                 220

Ala Ala Thr Ser Arg Arg Ile Ser Gly Glu Val Ala Leu Val Val Ala
225                 230                 235                 240

Asn Gln Ser Ser Leu Pro Glu Ser Tyr Gly Val Phe Thr Cys Thr Ala
                245                 250                 255

Lys Ile Glu Trp Glu Asp Asp Gly Lys Val Ala Ser Ile Asp Val Pro
            260                 265                 270

Cys Asp Val Ser Arg Leu Gln Cys Glu Ser Arg Glu Tyr Leu Phe Val
            275                 280                 285

Trp Arg Phe Arg Thr Ala Asp Ala Asp Ala Asp Ala Ser Val Gly Cys
    290                 295                 300

Ser Ser Glu Glu Ile Ser Glu Ser
305                 310

<210> SEQ ID NO 50
<211> LENGTH: 415
<212> TYPE: DNA
<213> ORGANISM: Artificial Sequence
<220> FEATURE:
<223> OTHER INFORMATION: TDNA junction sequence for SALK_128578

<400> SEQUENCE: 50
tgaagatagg aagatgactc ttgtgagaga cacgtgtcct ggtttcatat ccgacggttc     60
agggagagtc acgtggacta atgacgcgta tcggaagatg gctagggata ttattcccgt    120
ggaagaaggt gcaccggaga taactagcgg cgatagtttt cacgtgatcg tacggttggt    180
gatggaggga gacgcctatg ctaacgtccc ctggattcac atgcagaatg aaactcctgt    240
acacgtgtca aaatcctgag agaggctcag tcactgtgcc ttgcgatatg tggacaatga    300
acgtcagtgg cgtctctgct tctaggcgcg atatgagcac tgctacgagc tctaacatga    360
tgcgatctgc tttggaaata tcgtacggac catagcccat ggtgtatcta cctat         415

<210> SEQ ID NO 51
<211> LENGTH: 455
<212> TYPE: DNA
<213> ORGANISM: Artificial Sequence
<220> FEATURE:
<223> OTHER INFORMATION: T-DNA junction sequence for SALK_128578

<400> SEQUENCE: 51
ttacttgcac cgcgttatta ctatgtcgag tcgtaatggg tgaagatagg aagatgactc    60
ttgtgagaga cacgtgtcct ggtttcatat ccgacggttc agggagagtc acgtggacta   120
atgacgcgta tcggaagatg gctagggata ttattcccgt ggaagaaggt gcaccggaga   180
taactagcgg cgatagtttt cacgtgatcg tacggttggt gatggaggga gacgcctatg   240
ctaacgtccc ctggattcac atgcagaatg aaactcctgt acacgtgtca aaatcctgag   300
agaggctcag tcactgtgcc ttgcgatatg tggacaatga acgtcagtgg cgtctctgct   360
tctaggcgcg atatgagcac tgctacgagc tctaacatga tgcgatctgc tttggaaata   420
tcgtacggac catagcccat ggtgtatcta cctat                              455

<210> SEQ ID NO 52
<211> LENGTH: 78
<212> TYPE: DNA
<213> ORGANISM: Artificial Sequence
<220> FEATURE:
<223> OTHER INFORMATION: T-DNA junction sequence for SALKseq_057406.2

<400> SEQUENCE: 52
ggagctagtt ataacagacg ttatcagaca gagttaatga cggaaacggt tgtgtcgtcg    60
taaacaaatt gacgctta                                                  78

<210> SEQ ID NO 53
<211> LENGTH: 369
<212> TYPE: DNA
<213> ORGANISM: Artificial Sequence
<220> FEATURE:
<223> OTHER INFORMATION: T-DNA junction sequence for SALK_130501

<400> SEQUENCE: 53
gatactctat aatgatttga taacacgtgg accaatgagg cgtataagaa gatggctaga    60
gaagatatta ttcacacatta caccacgtgg ggcgtcaaga gggtcgcatt agaccccatc   120
gtgccctatt tgcttcctaa tacccccgt ttgccttata ttgtaggcga gcgcgctgcg    180
tatgggccca cccacccctcg cgcggaggaa gccccattg cgtctcgatg tagcttcacc    240
gccctggtag ttcgggccgg gcgggccgta tagggagggt gttcggcgcg atcgggccgc   300
tggcactgtt agcgcagtag tgcgggaggg ttttaatcgc agtgatatag tccgattttc   360
cgcctttt                                                            369

<210> SEQ ID NO 54
<211> LENGTH: 12883
<212> TYPE: DNA
<213> ORGANISM: Artificial Sequence
<220> FEATURE:
<223> OTHER INFORMATION: pROK2 vector

<400> SEQUENCE: 54 ccggggctggt tgccctcgcc gctgggctgg cggccgtcta tggccctgca aacgcgccag    60
aaacgccgtc gaagccgtgt gcgagacacc gcggccgccg gcgttgtgga tacctcgcgg   120

-continued

```
aaaacttggc cctcactgac agatgagggg cggacgttga cacttgaggg gccgactcac    180
ccggcgcggc gttgacagat gaggggcagg ctcgatttcg gccggcgacg tggagctggc    240
cagcctcgca aatcggcgaa aacgcctgat tttacgcgag tttcccacag atgatgtgga    300
caagcctggg gataagtgcc ctgcggtatt gacacttgag gggcgcgact actgacagat    360
gaggggcgcg atccttgaca cttgaggggc agagtgctga cagatgaggg gcgcacctat    420
tgacatttga ggggctgtcc acaggcagaa aatccagcat ttgcaagggt ttccgcccgt    480
ttttcggcca ccgctaacct gtcttttaac ctgcttttaa accaatattt ataaaccttg    540
tttttaacca gggctgcgcc ctgtgcgcgt gaccgcgcac gccgaagggg ggtgccccccc   600 cttctcgaac cctcccggcc cgctaacgcg ggcctcccat cccccagggg gctgcgcccc    660
tcggccgcga acggcctcac cccaaaaatg gcagcgctgg cagtccttgc cattgccggg    720
atcggggcag taacgggatg ggcgatcagc ccgagcgcga cgcccggaag cattgacgtg    780
ccgcaggtgc tggcatcgac attcagcgac caggtgccgg gcagtgaggg cggcggcctg    840
ggtggcggcc tgcccttcac ttcggccgtc ggggcattca cggacttcat ggcggggccg    900
gcaattttta ccttgggcat tcttggcata gtggtcgcgg gtgccgtgct cgtgttcggg    960
ggtgcgataa acccagcgaa ccatttgagg tgataggtaa gattataccg aggtatgaaa   1020
acgagaattg gacctttaca gaattactct atgaagcgcc atatttaaaa agctaccaag   1080
acgaagagga tgaagaggat gaggaggcag attgccttga atatattgac aatactgata   1140
agataatata tcttttatat agaagatatc gccgtatgta aggatttcag ggggcaaggc   1200
ataggcagcg cgcttatcaa tatatctata gaatgggcaa agcataaaaa cttgcatgga   1260
ctaatgcttg aaacccagga caataacctt atagcttgta aattctatca taattgggta   1320
atgactccaa cttattgata gtgttttatg ttcagataat gcccgatgac tttgtcatgc   1380
agctccaccg attttgagaa cgacagcgac ttccgtccca gccgtgccag gtgctgcctc   1440
agattcaggt tatgccgctc aattcgctgc gtatatcgct tgctgattac gtgcagcttt   1500
cccttcaggc gggattcata cagcggccag ccatccgtca tccatatcac cacgtcaaag   1560
ggtgacagca ggctcataag acgccccagc gtcgccatag tgcgttcacc gaatacgtgc   1620
gcaacaaccg tcttccggag actgtcatac gcgtaaaaca gccagcgctg gcgcgattta   1680
gccccgacat agccccactg ttcgtccatt tccgcgcaga cgatgacgtc actgcccggc   1740
tgtatgcgcg aggttaccga ctgcggcctg agttttttaa gtgacgtaaa atcgtgttga   1800
ggccaacgcc cataatgcgg gctgttgccc ggcatccaac gccattcatg gccatatcaa   1860
tgattttctg gtgcgtaccg ggttgagaag cggtgtaagt gaactgcagt tgccatgttt   1920
tacggcagtg agagcagaga tagcgctgat gtccggcggt gcttttgccg ttacgcacca   1980
ccccgtcagt agctgaacag gagggacagc tgatagacac agaagccact ggagcacctc   2040
aaaaacacca tcatacacta aatcagtaag ttggcagcat cacccataat tgtggtttca   2100
aaatcggctc cgtcgatact atgttatacg ccaactttga aaacaacttt gaaaaagctg   2160
ttttctggta tttaaggttt tagaatgcaa ggaacagtga attggagttc gtcttgttat   2220
aattagcttc ttggggtatc tttaaatact gtagaaaaga ggaaggaaat aataaatggc   2280
taaaatgaga atatcaccgg aattgaaaaa actgatcgaa aaataccgct gcgtaaaaga   2340
tacgaaagga atgtctcctg ctaaggtata taagctggtg ggagaaaatg aaaacctata   2400
tttaaaaatg acggacagcc ggtataaagg gaccaccctat gatgtggaac gggaaaagga   2460
```

```
catgatgcta tggctggaag gaaagctgcc tgttccaaag gtcctgcact ttgaacggca    2520
tgatggctgg agcaatctgc tcatgagtga ggccgatggc gtcctttgct cggaagagta    2580
tgaagatgaa caaagccctg aaaagattat cgagctgtat gcggagtgca tcaggctctt    2640
tcactccatc gacatatcgg attgtcccta tacgaatagc ttagcagcc gcttagccga     2700
attggattac ttactgaata cgatctggc cgatgtggat tgcgaaaact gggaagaaga     2760
cactccattt aaagatccgc gcgagctgta tgattttta aagacggaaa agcccgaaga     2820
ggaacttgtc ttttcccacg gcgacctggg agacagcaac atctttgtga agatggcaa     2880
agtaagtggc tttattgatc ttgggagaag cggcagggcg acaagtggt atgacattgc     2940
cttctgcgtc cggtcgatca gggaggatat cggggaagaa cagtatgtcg agctatttt     3000
tgacttactg gggatcaagc ctgattggga gaaataaaa tattatattt tactggatga    3060
attgttttag tacctagatg tggcgcaacg atgccggcga caagcaggag cgcaccgact   3120
tcttccgcat caagtgtttt ggctctcagg ccgaggccca cggcaagtat ttgggcaagg   3180
ggtcgctggt attcgtgcag ggcaagattc ggaataccaa gtacgagaag gacggccaga   3240
cggtctacgg gaccgacttc attgccgata aggtggatta tctggacacc aaggcaccag   3300
gcgggtcaaa tcaggaataa gggcacattg ccccggcgtg agtcggggca atcccgcaag   3360
gagggtgaat gaatcggacg tttgaccgga aggcatacag gcaagaactg atcgacgcgg   3420
ggttttccgc cgaggatgcc gaaaccatcg caagccgcac cgtcatgcgt gcgccccgcg   3480
aaaccttcca gtccgtcggc tcgatggtcc agcaagctac ggccaagatc gagcgcgaca   3540
gcgtgcaact ggctcccct gccctgcccg cgccatcggc cgccgtggag cgttcgcgtc     3600
gtctcgaaca ggaggcggca ggtttggcga agtcgatgac catcgacacg cgaggaacta   3660
tgacgaccaa gaagcgaaaa accgccggcg aggacctggc aaaacaggtc agcgaggcca   3720
agcaggccgc gttgctgaaa cacacgaagc agcagatcaa ggaaatgcag cttccttgt    3780
tcgatattgc gccgtggccg gacacgatgc gagcgatgcc aaacgacacg gcccgctctg   3840
ccctgttcac cacgcgcaac aagaaaatcc cgcgcgaggc gctgcaaaac aaggtcattt   3900
tccacgtcaa caaggacgtg aagatcacct acaccggcgt cgagctgcgg gccgacgatg   3960
acgaactggt gtggcagcag gtgttggagt acgcgaagcg caccctatc ggcgagccga     4020
tcaccttcac gttctacgag cttgccagg acctgggctg gtcgatcaat ggccggtatt    4080
acacgaaggc cgaggaatgc ctgtcgcgcc tacaggcgac ggcgatgggc ttcacgtccg   4140
accgcgttgg gcacctggaa tcggtgtcgc tgctgcaccg cttccgcgtc ctggaccgtg   4200
gcaagaaaac gtcccgttgc caggtcctga tcgacgagga aatcgtcgtg ctgtttgctg   4260
gcgaccacta cacgaaattc atatgggaga agtaccgcaa gctgtcgccg acggcccgac   4320
ggatgttcga ctatttcagc tcgcaccggg agccgtaccc gctcaagctg gaaaccttcc   4380
gcctcatgtg cggatcggat ccacccgcg tgaagaagtg gcgcgagcag gtcggcgaag    4440
cctgcgaaga gttgcgaggc agcggcctgg tggaacacgc tgggtcaat gatgacctgg    4500
tgcattgcaa acgctagggc cttgtggggt cagttccggc tgggggttca gcagccagcg   4560
ctttactggc atttcaggaa caagcggca ctgctcgacg cacttgcttc gctcagtatc    4620
gctcgggacg cacggcgcgc tctacgaact gccgataaac agaggattaa aattgacaat   4680
tgtgattaag gctcagattc gacggcttgg agcggccgac gtgcaggatt ccgcgagat    4740
ccgattgtcg gccctgaaga aagctccaga gatgttcggg tccgtttacg agcacgagga   4800
gaaaaagccc atggaggcgt tcgctgaacg gttgcgagat gccgtggcat tcggcgccta   4860
```

```
catcgacggc gagatcattg ggctgtcggt cttcaaacag gaggacggcc ccaaggacgc      4920
tcacaaggcg catctgtccg gcgttttcgt ggagcccgaa cagcgaggcc gagggtcgc       4980 cggtatgctg ctgcgggcgt tgccggcggg tttattgctc gtgatgatcg tccgacagat     5040
tccaacggga atctggtgga tgcgcatctt catcctcggc gcacttaata tttcgctatt     5100
ctggagcttg ttgtttattt cggtctaccg cctgccgggc ggggtcgcgg cgacggtagg     5160
cgctgtgcag ccgctgatgg tcgtgttcat ctctgccgct ctgctaggta gcccgatacg     5220
attgatggcg gtcctggggg ctatttgcgg aactgcgggc gtggcgctgt tggtgttgac     5280
accaaacgca gcgctagatc ctgtcggcgt cgcagcgggc ctggcggggg cggtttccat     5340
ggcgttcgga accgtgctga cccgcaagtg gcaacctccc gtgcctctgc tcacctttac     5400
cgcctggcaa ctggcggccg gaggacttct gctcgttcca gtagctttag tgtttgatcc     5460
gccaatcccg atgcctacag gaaccaatgt tctcggcctg gcgtggctcg gcctgatcgg     5520
agcgggttta acctacttcc tttggttccg ggggatctcg cgactcgaac ctacagttgt     5580
ttccttactg ggctttctca gccccagatc tggggtcgat cagccgggga tgcatcaggc     5640
cgacagtcgg aacttcgggt ccccgacctg taccattcgg tgagcaatgg ataggggagt     5700
tgatatcgtc aacgttcact tctaaagaaa tagcgccact cagcttcctc agcggcttta     5760
tccagcgatt tcctattatg tcggcatagt tctcaagatc gacagcctgt cacggttaag     5820
cgagaaatga ataagaaggc tgataattcg gatctctgcg agggagatga tatttgatca     5880
caggcagcaa cgctctgtca tcgttacaat caacatgcta ccctccgcga gatcatccgt     5940
gtttcaaacc cggcagctta gttgccgttc ttccgaatag catcggtaac atgagcaaag     6000
tctgccgcct tacaacggct ctcccgctga cgccgtcccg gactgatggg ctgcctgtat     6060
cgagtggtga ttttgtgccg agctgccggt cggggagctg ttggctggct ggtggcagga     6120
tatattgtgg tgtaaacaaa ttgacgctta gacaacttaa taacacattg cggacgtttt     6180
taatgtactg gggtggtttt tcttttcacc agtgagacgg gcaacagctg attgcccttc     6240
accgcctggc cctgagagag ttgcagcaag cggtccacgc tggtttgccc cagcaggcga     6300
aaatcctgtt tgatggtggt tccgaaatcg gcaaaatccc ttataaatca aaagaatagc     6360
ccgagatagg gttgagtgtt gttccagttt ggaacaagag tccactatta agaacgtgg      6420 actccaacgt caaagggcga aaaaccgtct atcagggcga tggcccacta cgtgaaccat     6480
cacccaaatc aagttttttg gggtcgaggt gccgtaaagc actaaatcgg aaccctaaag     6540 ggagccccg atttagagct tgacggggaa agccggcgaa cgtggcgaga aaggaaggga      6600
agaaagcgaa aggagcgggc gccattcagg ctgcgcaact gttgggaagg gcgatcggtg     6660
cgggcctctt cgctattacg ccagctggcg aaagggggat gtgctgcaag gcgattaagt     6720
tgggtaacgc cagggttttc ccagtcacga cgttgtaaaa cgacggccag tgaattcccg     6780
atctagtaac atagatgaca ccgcgcgcga taatttatcc tagtttgcgc gctatatttt     6840
gttttctatc gcgtattaaa tgtataattg cgggactcta atcataaaaa cccatctcat     6900
aaataacgtc atgcattaca tgttaattat tacatgctta acgtaattca acagaaatta     6960
tatgataatc atcgcaagac cggcaacagg attcaatctt aagaaacttt attgccaaat     7020
gtttgaacga tcggggaaat tcgagctcgg tacccgggga tcctctagag tccccgtgt      7080 tctctccaaa tgaaatgaac ttccttatat agaggaaggg tcttgcgaag gatagtggga     7140
ttgtgcgtca tcccttacgt cagtgggaga tcacatcaa tccacttgct ttgaagacgt      7200
```

```
ggttggaacg tcttctttt  ccacgatgct  cctcgtgggt  ggggtccat   ctttgggacc   7260
actgtcggca gaggcatctt caacgatggc  ctttccttta  tcgcaatgat  ggcatttgta   7320
ggagccacct tccttttcca ctatcttcac  aataaagtga  cagatagctg  gcaatggaa    7380
tccgaggagg tttccggata ttacccttg   ttgaaaagtc  tcaattgccc  tttggtcttc   7440
tgagactgta tctttgatat ttttggagta  gacaagtgtg  tcgtgctcca  ccatgttgac   7500
gaagattttc ttcttgtcat tgagtcgtaa  gagactctgt  atgaactgtt  cgccagtctt   7560
tacggcgagt tctgttaggt cctctatttg  aatctttgac  tccatggcct  ttgattcagt   7620
gggaactacc ttttagaga  ctccaatctc  tattacttgc  cttggtttgt  gaagcaagcc   7680
ttgaatcgtc catactggaa tagtacttct  gatcttgaga  aatatatctt  tctctgtgtt   7740
cttgatgcag ttagtcctga atcttttgac  tgcatcttta  accttcttgg  gaaggtattt   7800
gatttcctgg agattattgc tcgggtagat  cgtcttgatg  agacctgctg  cgtaagcctc   7860
tctaaccatc tgtgggttag cattctttct  gaaattgaaa  aggctaatct  ggggacctgc   7920
aggcatgcaa gcttggcgta atcatggtca  tagctgtttc  ctgtgtgaaa  ttgttatccg   7980
ctcacaattc cacacaacat acgagccgga  agcataaagt  gtaaagcctg  ggtgcctaa    8040
tgagtgagct aactcacatt aattgcgttg  cgctcactgc  ccgctttcca  gtcgggaaac   8100
ctgtcgtgcc agctgcatta tgaatcggc   caacgcgcgg  ggagaggcgg  tttgcgtatt   8160
gggccaaaga caaagggcg  acattcaacc  gattgaggga  gggaaggtaa  atattgacgg   8220
aaattattca ttaaaggtga attatcaccg  tcaccgactt  gagccatttg  ggaattagag   8280
ccagcaaaat caccagtagc accattacca  ttagcaaggc  cggaaacgtc  accaatgaaa   8340
ccatcgatag cagcaccgta atcagtagcg  acagaatcaa  gtttgccttt  agcgtcagac   8400
tgtagcgcgt tttcatcggc attttcggtc  atagccccct  tattagcgtt  tgccatcttt   8460
tcataatcaa aatcaccgga accagagcca  ccaccggaac  cgcctccctc  agagccgcca   8520
ccctcagaac cgccaccctc agagccacca  ccctcagagc  cgccaccaga  accaccacca   8580
gagccgccgc cagcattgac aggaggcccg  atctagtaac  atagatgaca  ccgcgcgcga   8640
taatttatcc tagtttgcgc gctatatttt  gttttctatc  gcgtattaaa  tgtataattg   8700
cgggactcta atcataaaaa cccatctcat  aaataacgtc  atgcattaca  tgttaattat   8760
tacatgctta acgtaattca acagaaatta  tatgataatc  atcgcaagac  cggcaacagg   8820
attcaatctt aagaaacttt attgccaaat  gtttgaacga  tcgggatca   tccgggtctg   8880
tggcgggaac tccacgaaaa tatccgaacg  cagcaagata  tcgcggtgca  tctcggtctt   8940
gcctgggcag tcgccgccga cgccgttgat  gtggacgccg  gcccgatca   tattgtcgct   9000
caggatcgtg gcgttgtgct tgtcggccgt  tgctgtcgta  atgatatcgg  caccttcgac   9060
cgcctgttcc gcagagatcc cgtgggcgaa  gaactccagc  atgagatccc  cgcgctggag   9120
gatcatccag ccggcgtccc ggaaaacgat  tccgaagccc  aacctttcat  agaaggcggc   9180
ggtggaatcg aaatctcgtg atggcaggtt  gggcgtcgct  tggtcggtca  tttcgaaccc   9240
cagagtcccg ctcagaagaa ctcgtcaaga  aggcgataga  aggcgatgcg  ctgcgaatcg   9300
ggagcggcga taccgtaaag cacgaggaag  cggtcagccc  attcgccgcc  aagctcttca   9360
gcaatatcac gggtagccaa cgctatgtcc  tgatagcggt  ccgccacacc  cagccggcca   9420
cagtcgatga atccagaaaa gcggccattt  tccaccatga  tattcggcaa  gcaggcatcg   9480
ccatgggtca cgacgagatc atcgccgtcg  ggcatgcgcg  ccttgagcct  ggcgaacagt   9540
tcggctggcg cgagcccctg atgctcttcg  tccagatcat  cctgatcgac  aagaccggct   9600
```

```
tccatccgag tacgtgctcg ctcgatgcga tgtttcgctt ggtggtcgaa tgggcaggta    9660
gccggatcaa gcgtatgcag ccgccgcatt gcatcagcca tgatggatac tttctcggca    9720
ggagcaaggt gagatgacag gagatcctgc cccggcactt cgcccaatag cagccagtcc    9780
cttcccgctt cagtgacaac gtcgagcaca gctgcgcaag gaacgccgt cgtggccagc     9840
cacgatagcc gcgctgcctc gtcctgcagt tcattcaggg caccggacag gtcggtcttg    9900
acaaaaagaa ccgggcgccc ctgcgctgac agccggaaca cggcggcatc agagcagccg    9960
attgtctgtt gtgcccagtc atagccgaat agcctctcca cccaagcggc cggagaacct   10020
gcgtgcaatc catcttgttc aatcatgcga aacgatccag atccggtgca gattatttgg   10080
attgagagtg aatatgagac tctaattgga taccgagggg aatttatgga acgtcagtgg   10140
agcattttg acaagaaata tttgctagct gatagtgacc ttaggcgact tttgaacgcg    10200
caataatggt ttctgacgta tgtgcttagc tcattaaact ccagaaaccc gcggctgagt   10260
ggctccttca acgttgcggt tctgtcagtt ccaaacgtaa aacggcttgt cccgcgtcat   10320
cggcggggt cataacgtga ctcccttaat tctccgctca tgatcagatt gtcgtttccc   10380
gccttcagtt taaactatca gtgtttgaca ggatatattg gcgggtaaac ctaagagaaa   10440
agagcgttta ttagaataat cggatattta aagggcgtg aaaaggttta tccgttcgtc    10500
catttgtatg tgcatgccaa ccacagggtt ccccagatct ggcgccggcc agcgagacga   10560
gcaagattgg ccgccgcccg aaacgatccg acagcgcgcc cagcacaggt gcgcaggcaa   10620
attgcaccaa cgcatacagc gccagcagaa tgccatagtg ggcggtgacg tcgttcgagt   10680
gaaccagatc gcgcaggagg cccggcagca ccggcataat caggccgatg ccgacagcgt   10740
cgagcgcgac agtgctcaga attacgatca ggggtatgtt gggtttcacg tctggcctcc   10800
ggaccagcct ccgctggtcc gattgaacgc gcggattctt tatcactgat aagttggtgg   10860
acatattatg tttatcagtg ataaagtgtc aagcatgaca aagttgcagc cgaatacagt   10920
gatccgtgcc gccctggacc tgttgaacga ggtcggcgta gacggtctga cgacacgcaa   10980
actggcggaa cggttggggg ttcagcagcc ggcgctttac tggcacttca ggaacaagcg   11040
ggcgctgctc gacgcactgg ccgaagccat gctggcggag aatcatacgc attcggtgcc   11100
gagagccgac gacgactggc gctcatttct gatcgggaat gcccgcagct tcaggcaggc   11160
gctgctcgcc taccgcgatg gcgcgcgcat ccatgccggc acgcgaccgg gcgcaccgca   11220
gatgaaaacg gccgacgcgc agcttcgctt cctctgcgag gcgggttttt cggccgggga   11280
cgccgtcaat gcgctgatga caatcagcta cttcactgtt ggggccgtgc ttgaggagca   11340
ggccggcgac agcgatgccg gcgagcgcgg cggcaccgtt gaacaggctc cgctctcgcc   11400
gctgttgcgg gccgcgatag acgccttcga cgaagccggt ccgacgcag cgttcgagca    11460
gggactcgcg gtgattgtcg atggattggc gaaaaggagg ctcgttgtca ggaacgttga   11520
aggaccgaga aagggtgacg attgatcagg accgctgccg gagcgcaacc cactcactac   11580
agcagagcca tgtagacaac atcccctccc cctttccacc gcgtcagacg cccgtagcag   11640
cccgctacgg gcttttttcat gccctgccct agcgtccaag cctcacggcc gcgctcggcc   11700
tctctggcgg ccttctggcg ctcttccgct tcctcgctca ctgactcgct gcgctcggtc   11760
gttcggctgc ggcgagcggt atcagctcac tcaaaggcgg taatacggtt atccacagaa   11820
tcaggggata acgcaggaaa gaacatgtga gcaaaaggcc agcaaaaggc caggaaccgt   11880
aaaaaggccg cgttgctggc gttttccat aggctccgcc cccctgacga gcatcacaaa    11940
```

```
aatcgacgct caagtcagag gtggcgaaac ccgacaggac tataaagata ccaggcgttt    12000
ccccctggaa gctccctcgt gcgctctcct gttccgaccc tgccgcttac cggatacctg    12060
tccgcctttc tcccttcggg aagcgtggcg cttttccgct gcataaccct gcttcgggt     12120 cattatagcg atttttcgg tatatccatc ctttttcgca cgatatacag gattttgcca     12180
aagggttcgt gtagactttc cttggtgtat ccaacggcgt cagccgggca ggataggtga    12240
agtaggccca cccgcgagcg ggtgttcctt cttcactgtc ccttattcgc acctggcggt    12300
gctcaacggg aatcctgctc tgcgaggctg gccggctacc gccggcgtaa cagatgaggg    12360
caagcggatg gctgatgaaa ccaagccaac caggaagggc agcccaccta tcaaggtgta    12420
ctgccttcca gacgaacgaa gagcgattga ggaaaaggcg gcggcggccg gcatgagcct    12480
gtcggcctac ctgctggccg tcggccaggg ctacaaaatc acgggcgtcg tggactatga    12540
gcacgtccgc gagctggccc gcatcaatgg cgacctgggc cgcctgggcg gctgctgaa     12600 actctggctc accgacgacc cgcgcacggc gcggttcggt gatgccacga tcctcgccct    12660
gctggcgaag atcgaagaga agcaggacga gcttggcaag gtcatgatgg gcgtggtccg    12720
cccgagggca gagccatgac tttttttagcc gctaaaacgg ccgggggtg cgcgtgattg     12780 ccaagcacgt ccccatgcgc tccatcaaga gagcgactt cgcggagctg gtgaagtaca    12840
tcaccgacga gcaaggcaag accgagcgcc tttgcgacgc tca                      12883
```

<210> SEQ ID NO 55
<211> LENGTH: 858
<212> TYPE: DNA
<213> ORGANISM: Artificial Sequence
<220> FEATURE:
<223> OTHER INFORMATION: 3xFLAG-YPet

<400> SEQUENCE: 55

```
gactacaaag accatgacgg tgattataaa gatcatgata tcgattacaa ggatgacgat      60
gacaagctgg aagttctgtt ccaggggcca atgtctaagg gtgaagagtt gttcactggt     120
gttgttccta tccttgtgga gcttgatggt gatgttaacg gacacaagtt ctctgtttct     180
ggtgaaggtg aaggtgatgc tacttacgga aagcttactc ttaagctcct ctgcactact     240
ggaaagcttc cagttccttg gcctactctt gttactactc tcggatacgg acttcaatgt     300
ttcgctagat accctgatca tatgaagcag cacgatttct tcaagtctgc tatgcctgaa     360
ggatacgtgc aagagagaac catcttcttc aaggatgatg gaaactacaa gactagagct     420
gaggttaagt tcgagggtga tactctcgtt aacaggatcg agcttaaggg aatcgatttc     480
aaagaggatg gaaacatcct tggacataag ctcgagtaca actacaactc tcacaacgtg     540
tacatcactg ctgataagca gaagaacggt atcaaggcta acttcaagat cagacacaac     600
attgaggatg gtggagttca acttgctgat cactaccaac agaacactcc tattggagat     660
ggacctgttc ttctccctga taaccactac ctttcttacc agtctaagct cttcaaggat     720
cctaacgaga gagggatca tatggttctt ctcgagttcc ttactgctgc tggaattact     780
gagggaatga acgagcttta aaggggaag ttcctatact ttctagagaa taggaacttc      840
ggtgctgctg gcgcggct                                                   858
```

<210> SEQ ID NO 56
<211> LENGTH: 912
<212> TYPE: DNA
<213> ORGANISM: Artificial Sequence
<220> FEATURE:
<223> OTHER INFORMATION: YPet-6xHis-3xFLAG

```
<400> SEQUENCE: 56
ggaggtggag gtggagctat gtctaagggt gaagagttgt tcactggtgt tgttcctatc      60
cttgtggagc ttgatggtga tgttaacgga cacaagttct ctgtttctgg tgaaggtgaa     120
ggtgatgcta cttacggaaa gcttactctt aagctcctct gcactactgg aaagcttcca     180
gttccttggc ctactcttgt tactactctc ggatacggac ttcaatgttt cgctagatac     240
cctgatcata tgaagcagca cgatttcttc aagtctgcta tgcctgaagg atacgtgcaa     300
gagagaacca tcttcttcaa ggatgatgga aactacaaga ctagagctga ggttaagttc     360
gagggtgata ctctcgttaa caggatcgag cttaagggaa tcgatttcaa agaggatgga     420
aacatccttg gacataagct cgagtacaac tacaactctc acaacgtgta catcactgct     480
gataagcaga agaacggtat caaggctaac ttcaagatca gacacaacat tgaggatggt     540
ggagttcaac ttgctgatca ctaccaacag aacactccta ttggagatgg acctgttctt     600
ctccctgata accactacct ttcttaccag tctaagctct tcaaggatcc taacgagaag     660
agggatcata tggttcttct cgagttcctt actgctgctg gaattactga gggaatgaac     720
gagctttata aggggaagtt cctatacttt ctagagaata ggaacttcgg tgctgctggc     780
gcgcctcatc accatcacca tcacctggaa gttctgttcc aggggccaga ctacaaagac     840
catgacggtg attataaaga tcatgatatc gattacaagg atgacgatga caaggctggc     900
gcgcctgggg cc                                                         912

<210> SEQ ID NO 57
<211> LENGTH: 20
<212> TYPE: DNA
<213> ORGANISM: Artificial Sequence
<220> FEATURE:
<223> OTHER INFORMATION: DIL1 guide RNA

<400> SEQUENCE: 57
gctcctaaac cggccagcga                                                  20

<210> SEQ ID NO 58
<211> LENGTH: 20
<212> TYPE: DNA
<213> ORGANISM: Artificial Sequence
<220> FEATURE:
<223> OTHER INFORMATION: DIL1 guide RNA

<400> SEQUENCE: 58
gttccggtgg gaactcccga                                                  20
```